US009908897B2

(12) United States Patent
Cremonesi et al.

(10) Patent No.: US 9,908,897 B2
(45) Date of Patent: Mar. 6, 2018

(54) SPIROCYCLIC DERIVATIVES

(71) Applicant: CHRONOS THERAPEUTICS LIMITED, Oxford (GB)

(72) Inventors: Susanna Cremonesi, Verona (IT); Tim Luker, Nottingham (GB); Teresa Semeraro, Verona (IT); Fabrizio Micheli, Verona (IT)

(73) Assignee: CHRONOS THERAPEUTICS LIMITED, Oxford (GB)

( * ) Notice: Subject to any disclaimer, the term of this patent is extended or adjusted under 35 U.S.C. 154(b) by 0 days.

(21) Appl. No.: 15/511,443

(22) PCT Filed: Sep. 14, 2015

(86) PCT No.: PCT/IB2015/057030
§ 371 (c)(1),
(2) Date: Mar. 15, 2017

(87) PCT Pub. No.: WO2016/042452
PCT Pub. Date: Mar. 24, 2016

(65) Prior Publication Data
US 2017/0253615 A1    Sep. 7, 2017

(30) Foreign Application Priority Data

Sep. 16, 2014  (GB) .................... 1416352.1

(51) Int. Cl.
| C07D 513/10 | (2006.01) |
| C07D 498/10 | (2006.01) |
| C07D 471/10 | (2006.01) |
| C07D 491/20 | (2006.01) |
| A61K 31/438 | (2006.01) |
| A61K 31/499 | (2006.01) |
| A61K 31/5386 | (2006.01) |
| A61K 31/547 | (2006.01) |
| A61K 31/551 | (2006.01) |
| C07D 493/20 | (2006.01) |

(52) U.S. Cl.
CPC .......... *C07D 498/10* (2013.01); *A61K 31/438* (2013.01); *A61K 31/499* (2013.01); *A61K 31/5386* (2013.01); *A61K 31/547* (2013.01); *A61K 31/551* (2013.01); *C07D 471/10* (2013.01); *C07D 491/20* (2013.01); *C07D 493/20* (2013.01); *C07D 513/10* (2013.01)

(58) Field of Classification Search
CPC .. C07D 498/10; C07D 471/10; C07D 491/20; C07D 513/10
See application file for complete search history.

(56) References Cited

U.S. PATENT DOCUMENTS

| 5,698,567 | A  | 12/1997 | Guillonneau et al. |
| 6,835,371 | B1 | 12/2004 | Elmaleh et al. |

FOREIGN PATENT DOCUMENTS

| EP | 1 683 797 A1 | 7/2006 |
| WO | WO-01/49677 A1 | 7/2001 |
| WO | WO-02/18437 A2 | 3/2002 |
| WO | WO-2004/005293 A2 | 1/2004 |
| WO | WO-2006/023630 A2 | 3/2006 |
| WO | WO-2007/050348 A2 | 5/2007 |
| WO | WO-2012/024397 A2 | 2/2012 |
| WO | WO-2015/031036 A1 | 3/2015 |
| WO | WO-2015/140132 A1 | 9/2015 |

OTHER PUBLICATIONS

Database Registry [Online] Chemical Abstracts Service, Columbus, Ohio, US; Jun. 17, 2005, "2,7-Diazaspiro[4.5]decan-1-one, 2-(4-phenoxyphenyl)-," XP002750359, Database accession No. 852432-89-4.
Database Registry [Online] Chemical Abstracts Service, Columbus, Ohio, US; Mar. 30, 2010, "I,7-Diazaspiro[4.4]nonane, 1-methyl-7-(5-phenoxy-3-pyridinyl)-," XP002750360, Database accession No. 1215074-56-8.
Database Registry [Online] Chemical Abstracts Service, Columbus, Ohio, US; Jun. 5, 2013, "2,7-Diazaspiro[4.5]decan-6-one, 2-[5-methyl-6-[(2-methyl-3-pyridinyl)-oxy]-" XP002750362, Database accession No. 1434891-71-0.
Database Registry [Online] Chemical Abstracts Service, Columbus, Ohio, US; Jan. 6, 2014, "2,7-Diazaspiro[4.4]nonane, 2[I-(phenylmethyl)-IH-pyrazol-4-yl]-," XP002750363, Database accession No. 1512788-53-2.
Database Registry [Online] Chemical Abstracts Service, Columbus, Ohio, US; Mar. 7, 2012, "1-0xa-3,8-diazaspiro[4.6]undecanone, 3-methyl-8-[5-methyl-6-[(2-methyl-3-pyridinyl)oxy]-4-pyrimidinyl]-", XP002750361, Database accession No. 1360173-11-0.

(Continued)

*Primary Examiner* — Kahsay Habte
(74) *Attorney, Agent, or Firm* — Foley & Lardner LLP

(57) ABSTRACT

The present invention provides compounds of formula (I): compositions comprising such compounds; the use of such compounds in therapy (for example in the treatment or prevention of a disease, disorder or condition ameliorated by inhibition of a dopamine transporter); and methods of treating patients with such compounds; wherein $R^1$, $R^2$, $R^3$, $R^4$, $R^5$, $R^6$, $R^9$, $R^{10}$, Q, X, Y, Z, A, L, B, m, n and p are as defined herein.

16 Claims, No Drawings

(56) References Cited

OTHER PUBLICATIONS

Fritch, Paul C. et al, "Design, syntheses, and SAR of 2,8-diazaspiro[4.5]decanones as T-type calcium channel antagonists," Bioorganic & Medicinal Chemistry Letters, vol. 20, No. 22, 2010, pp. 6375-6378.
International Search Report & Written Opinion in International Application No. PCT/IB2015/057029, dated Mar. 24, 2016. (11 pages).
International Search Report & Written Opinion in International Application No. PCT/IB2015/057030, dated Mar. 24, 2016. (13 pages).
International Search Report & Written Opinion in International Application No. PCT/IB2015/057031, dated Mar. 24, 2016. (8 pages).
Michela Bettati et al: "Oxa-azaspiro Derivatives: a Novel Class of Triple Re-uptake Inhibitors," Chemmedchem, vol. 5, No. 3, Mar. 1, 2010, pp. 361-366.
Motel, William C et al, "Chlorophenylpiperazine analogues as high affinity dopamine transporter ligands," Bioorganic & Medicinal Chemistry Letters, vol. 23, No. 24, 2013, pp. 6920-6922.
Abler B et al., "Neural Correlates of Antidepressant-Related Sexual Dysfunction: A Placebo-Controlled fMRI Study on Healthy Males Under Subchronic Paroxetine and Bupropion," Neuropsychopharmacology. 2011; 36(9): 1837-1847.
Amsterdam et al., "Greater Striatal Dopamine Transporter Density May Be Associated With Major Depressive Episode," J Affect Disord. 2012; 141(2-3): 425-431.
Auriel et al., "Effects of Methylphenidate on Cognitive Function and Gain in Patients With Parkinson's Disease," Clin Neuropharmacol. 2006; 29(1): 15-17.
Baldwin DS et al., "Antidepressant drugs and sexual dysfunction," Br J Psychiatry. 2013; 202: 396-397.
Baumann MH et al., "GBR12909 Attenuates Cocaine-Induced Activation of Mesolimbic Dopamine Neurons in the Rat," J Pharmacol Exp Ther. 1994; 271(3): 1216-1222.
Bello et al., "Acute methylphenidate treatments reduce sucrose intake in restricted-fed bingeing rats," Brain Res Bull. 2006; 70(4-6): 422-429.
Berrios GE, "Feelings of Fatigue and Psychopathology: A Conceptual History," Compr Psychiatry 1990; 31(2): 140-151.
Campbell VC et al., "Assessment of the Influence of Histaminergic Actions on Cocaine-Like Effects of 3α-Diphenylmethoxytropane Analogs," J Pharmacol Exp Ther. 2005; 315(2): 631-640.
Cheon et al., "Dopamine transporter density of the basal ganglia assessed with [123I]IPT SPECT in drug-naive children with Tourette's disorder," Psychiatry Res. 2004; 130(1): 85-95.
Cohen NJ et al., "The Effect of Methylphenidate on Attentive Behavior and Autonomic Activity in Hyperactive Children," Psychopharmacologia. 1971; 22(3): 282-294.
Cook EH Jr et al., "Association of Attention-Deficit Disorder and the Dopamine Transporter Gene," Am J Hum Genet. 1995; 56(4): 993-998.
Cornish RS et al., "Pharmacodynamic Assessment of the Benztropine Analogues AHN-1055 and AHN-2005 Using Intracerebral Microdialysis to Evaluate Brain Dopamine Levels and Pharmacokinetic/Pharmacodynamic Modeling," Pharm Res. 2005; 22(4): 603-612.
Database Registry [Online] Chemical Abstracts Service, Columbus, Ohio, US; Jun. 13, 2011, "Pyrrolo[3,4-c]pyrazole-1(4H)-ethanol, 5,6-dihydro-5-[5-methyl-6-[(2-methyl-3-pyridinyl)oxy]-4-pyrimidinyl]," Database accession No. 1309141-55-6.
Denolle T et al., "Hemodynamic effects of reboxetine in healthy male volunteers," Clin Pharmacol Ther. 1999; 66(3): 282-287.
Devos D et al., "Improvement of gait by chronic, high doses of methylphenidate in patients with advanced Parkinson's disease," J Neurol Neurosurg Psychiatry. 2007; 78(5): 470-475.

Dworkin N, "Letters to the Editor: Increased Blood Pressure and Atomoxetine," J Am Acad Child Adolesc Psychiatry. 2005; 44(6): 510.
Espay et al., "Methylphenidate for gait impairment in Parkinson disease," Neurology. 2011; 76(14): 1256-1262.
Grigorenko EL et al., "Aggressive Behavior, Related Conduct Problems, and Variation in Genes Affecting Dopamine Turnover," Aggress Behav. 2010; 36(3): 158-176.
Harris JD, "Fatigue in chronically ill patients," Curr Opin Support Palliat Care 2008; 2(3): 180-186.
Hartmann E et al.,"Sleep: Effects of d- and l-Amphetamine in Man and in Rat," Psychopharmacology (Berl). 1976 10; 50(2): 171-175.
Hsiao et al., "The interaction between dopamine transporter function, gender differences,and possible laterality in depression," Psychiatry Res. 2013; 211(1): 72-77.
Kim CH et al., "Dopamine transporter density of basal ganglia assessed with [123I]IPT SPET in obsessive-compulsive disorder," Eur J Nucl Med Mol Imaging. 2003; 30(12): 1637-1643.
Lacerda et al., "Vanoxerine: Cellular Mechanism of a New Antiarrhythmic," J Cardiovasc Electrophysiol. 2010; 21(3): 301-310.
Lader MH, "Tolerability and Safety: Essentials in Antidepressant Pharmacotherapy," J Clin Psychiatry. 1996; 57 Suppl 2: 39-44.
Leibowitz SF et al., "Amphetamine: Effects on Meal Patterns and Macronutrient Selection," Brain Res Bull. 1986; 17(5): 681-689.
Li SM et al., "N-Substituted Benztropine Analogs: Selective Dopamine Transporter Ligands with a Fast Onset of Action and Minimal Cocaine-Like Behavioral Effects," J Pharmacol Exp Ther. 2011; 336(2): 575-585.
Michaelides M et al., "Dopamine-related frontostriatal abnormalities in obesity and binge-eating disorder: Emerging evidence for developmental psychopathology," Int Rev Psychiatry. 2012; 24(3): 211-218.
Montejo-González AL et al., "SSRI-Induced Sexual Dysfunction: Fluoxetine, Paroxetine, Sertraline, and Fluvoxamine in a Prospective, Multicenter, and Descriptive Clinical Study of 344 Patients," J Sex Marital Ther. 1997; 23(3): 176-194.
Nieoullon A, "Dopamine and the regulation of cognition and attention," Prog Neurobiol. 2002; 67(1): 53-83.
Olfson M et al., "Antidepressant Drug Therapy and Suicide in Severely Depressed Children and Adults," Arch Gen Psychiatry. Aug. 2006; 63(8): 865-872.
Remy P et al., "The role of dopamine in cognition," Curr Opin Neurol. 2003; 16 Suppl 2: S37-41.
Rothman RB et al., "GBR12909 Antagonizes the Ability of Cocaine to Elevate Extracellular Levels of Dopamine," Pharmacol Biochem Behav. 1991; 40(2): 387-397.
Segman et al., "Association between the dopamine transporter gene and posttraumatic stress disorder," Mol Psychiatry. 2002; 7(8): 903-7.
Shinohara M et al., "Eating disorders with binge-eating behaviour are associated with the s allele of the 3'-UTR VNTR polymorphism of the dopamine transporter gene," J Psychiatry Neurosci. 2004; 29(2): 134-137.
Slama et al., "Double Blind Clinical Trial of Mazindol on Weight Loss Blood Glucose, Plasma Insulin and Serum Lipids in Overweight Diabetic Patients," Diabete Metab. 1978; 4(3): 193-199.
Van Gaalen MM et al., "Critical Involvement of Dopaminergic Neurotransmission in Impulsive Decision Making," Biol Psychiatry. 2006; 60(1): 66-73.
Wang GJ et al., "Enhanced Striatal Dopamine Release During Food Stimulation in Binge Eating Disorder," Obesity (Silver Spring) 2011; 19(8): 1601-1608.
Wise RA, "Addictive Drugs and Brain Stimulation Reward," Annu Rev Neurosci. 1996; 19: 319-340.
Yoon et al., "Frontal dopaminergic abnormality in Tourette syndrome: A postmortem analysis," J Neurol Sci. 2007; 255(1-2): 50-56.
Zou MF et al., "Structure-Activity Relationship Studies on a Novel Series of (S)-2β-Substituted 3α-[Bis(4-fluoro- or 4-chlorophenyl)methoxy]tropane Analogues for in Vivo Investigation," J Med Chem. 2006; 49(21): 6391-6399.

SPIROCYCLIC DERIVATIVES

CROSS-REFERENCE TO RELATED APPLICATIONS

This application is a U.S. National Stage Application under 35 U.S.C. § 371 of International Application No. PCT/IB2015/057030, filed on Sep. 14, 2015, which claims priority to GB Application No. 1416352.1, filed on Sep. 16, 2014, the contents of which are incorporated herein by reference in their entirety.

This invention relates to spirocyclic derivatives that are inhibitors of dopamine active transporter protein (DAT) and to pharmaceutical compositions containing, and the uses of, such derivatives.

BACKGROUND TO THE INVENTION

The spirocyclic derivatives of the present invention are inhibitors of human dopamine active transporter protein (DAT) and have a number of therapeutic applications, particularly in the treatment of sexual dysfunction, affective disorders, anxiety, depression, chronic fatigue, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including smoking cessation), eating disorders, and impulse control disorders.

Dopamine (DA) is a neurotransmitter which has a fundamental role in cognitive, affective, motor, motivational and reward-related functions. Following evoked action potentials DA is released into the synaptic cleft and this DA signal is extinguished by reuptake of DA into pre-synaptic neurons by DAT and by amine diffusion and local metabolism via enzymatic degradation. Dysfunction of the dopaminergic system is implicated in numerous CNS disorders and consequently DAT has been the focus of research into a number of these conditions and strong associations exist between abnormal DAT expression and/or function and disease.

Several marketed drugs have pharmacological activity at DAT, but none are selective and potent DAT inhibitors. Stimulants such as amphetamine and methylphenidate have multiple pharmacological activities including effects on synaptic levels of DA, noradrenaline (NE) and serotonin (5-HT). Despite their therapeutic potential in conditions such as ADHD, they also carry unwanted side effects such as abuse potential (1), cardiovascular effects (2), appetite suppression (3) and sleep disturbance (4).

Other non-selective DAT inhibitors are also used to treat CNS disorders. Bupropion which is prescribed as an antidepressant and a smoking cessation aid has a significant DAT component to its pharmacological activity, although it carries an increased seizure risk. Similarly Modafinil which is prescribed as a treatment for narcolepsy, excessive daytime sleepiness and shift work sleep disorder has been shown to inhibit DAT as part of its pharmacological mechanism of action. Multiple compounds have been developed that target the other monoamine transporters either selectively as inhibitors of the serotonin transporter (SERT) (Citalopram, Fluoxetine) or noradrenaline transporter (NET) inhibitors (Atomoxetine, Reboxetine) as well as dual serotonin/noradrenaline reuptake inhibitors (Venlafaxine). Drugs that inhibit SERT and NET have been burdened with multiple adverse side effects such as nausea (5), sexual dysfunction (6), increased suicide risk (7) for drugs that elevate 5-HT levels and elevated heart rate and blood pressure (8, 9) for drugs that increase noradrenaline levels. This makes a selective and potent DAT inhibitor, with a neurochemical profile distinct from that of stimulants, a highly desirable compound for the treatment of CNS disorders.

ADD and ADHD are neurodevelopmental psychiatric, behavioural and cognitive disorders characterised by concentration deficits, inner restlessness/hyperactivity, and impulsivity. These are the most common behavioural disorders amongst children, with a prevalence of 5-10% of the general population. It is widely believed that the symptoms of these disorders result from a dopaminergic and/or noradrenergic hypofunction. There is a wealth of information showing that the core symptoms of ADHD are influenced by changes in dopaminergic function (10) and hence a DAT inhibitor which would raise synaptic DA levels, should be efficacious. Current treatments for ADD/ADHD include the stimulants amphetamine and methylphenidate. These compounds have pharmacological activity for DAT, amongst other activities, and it is believed that their efficacy is derived from the elevation of corticostriatal DA and NE. These drugs are not selective DAT inhibitors however, and as such cause rapid, transient and marked release of DA from synaptic terminals which has been associated with their unwanted side effects, such as abuse potential. This neurochemical profile is distinct from that of a selective and potent DAT inhibitor which causes a slower increase in dopamine which is sustained for a much longer duration. This different neurochemical profile has been associated with less reinforcing effects and subsequently lower abuse potential (11). In addition to the neurochemical evidence for a likely therapeutic benefit of DAT inhibitors in ADHD, several studies have shown associations between DAT polymorphisms and overexpression of DAT in ADHD (12). Preclinical models of ADHD symptoms have shown that like amphetamine and methylphenidate a selective DAT inhibitor will decrease impulsive behaviour in rodents (13) further supporting the potential for efficacy of DAT inhibitors. Collectively this evidence provides compelling data to believe that selective DAT inhibitors will be efficacious in ADD/ADHD and other disorders characterised by poor impulse control (such as Trichotillomania, pathological gambling, Kleptomania and disorders with comorbid impulse control such as Parkinson's disease) or inattention.

Tourette's syndrome is a neuropsychiatric disorder characterised by motor and/or phonic tics. It normally presents during childhood and is poorly treated with drugs. Studies have postulated that one aspect underlying Tourette's is dopaminergic dysfunction whereby tonic/phasic dysfunction results in reduced synaptic DA levels and consequently higher levels in axon terminals leading to increased stimulus dependent release. Further studies have shown that postmortem tissue from Tourette's patients showed elevated levels of DAT in the frontal lobe (14) and that polymorphisms in DAT are associated with the occurrence of Tourette's. This was further supported in a clinical study of drug naïve children which showed and increased specific/non-specific DAT binding ratio in those with Tourette's (15). These findings suggest that a selective DAT inhibitor may provide symptomatic relief for Tourette's patients.

Other neuropsychiatric disorders such as obsessive compulsive disorder (OCD), oppositional defiant disorder (ODD) and conduct disorder have also been associated with DAT. OCD patients have been shown to have an increased specific/non-specific DAT binding ratio (16) and this ratio was altered following treatment with SSRIs which are commonly used to treat OCD. Similarly abnormal dopamine function and/or dopamine turnover have been implicated in ODD, conduct disorder and other related behavioural disorders (17) and polymorphisms in DAT have been implicated as a risk factor for externalising behaviour in children. Studies showing that children with conduct disorder display disrupted reinforcement signalling and a response to reward have also suggested that modulation of synaptic dopamine levels could be a therapeutic option for these disorders presenting the opportunity to use a selective DAT inhibitor to treat these behavioural disorders.

Sleep disorders such as narcolepsy, cataplexy, excessive daytime sleepiness and shift work sleep disorder can interfere with an individual's normal mental and physical well-being. Several of these disorders are treated with drugs that have pharmacological activity at DAT. Modafinil is widely used to treat narcolepsy and its therapeutic potential has been related to occupancy of DAT). Other treatments for sleep disorders include amphetamine, methamphetamine and methylphenidate, all of which have pharmacological actions at DAT. Preclinical studies have shown that the wake promoting effects of several of these compounds and a selective DAT inhibitor are abolished in DAT knockout mice. Together these data support the use of a selective DAT inhibitor in the treatment of sleep disorders.

Mood disorders such as major depressive disorder, bipolar depression, seasonal affective disorder, melancholic depression, catatonic depression, postpartum depression and dysthymia represent a major medical and social burden on society and are amongst the most common of all CNS disorders. Treatment for these disorders is currently inadequate with low levels of efficacy and poor responder rates to currently available therapies. In addition many of the drugs that are the current standard of care carry unwanted side effects. SPECT studies in patients suffering from major depressive disorder have shown that there is an increased binding of DAT in depressed patients and that this was reversed following successful antidepressant treatment (18, 19). In addition to this marketed antidepressants such as Nomifensine have a significant DAT inhibitory component to their mechanism of action. Preclinical studies investigating the behavioural phenotype of DAT knockout mice in tests for antidepressant activity have shown that genetic removal of DAT function results in antidepressant-like behaviour. This evidence is supportive for a therapeutic benefit for DAT inhibitors in mood disorders.

A comorbid symptom of depression and an unwanted side effect of many commonly used antidepressants is sexual dysfunction (20). Bupropion a commonly prescribed antidepressant with a significant DAT inhibitory component to its mechanism of action has been shown to result in fewer sexual dysfunction related side effects than other antidepressants (21). Furthermore Bupropion has been shown to reverse the sexual dysfunction caused by SSRIs. Preclinical studies have shown an effect of Bupropion on sexual behaviour in rats which is supported by clinical evidence that the drug is effective in treating women suffering from hypoactive sexual desire disorder. Amphetamine has also been shown to increase sexual behaviour in male and female rats and has also been shown to reverse sexual impairment in female rats. This evidence for drugs that have pharmacological activity at DAT is an indicator that a selective and potent DAT inhibitor would be a suitable therapy for antidepressant induced sexual dysfunction as well as for treating sexual dysfunction in non-depressed patients.

DAT polymorphisms have been implicated in anxiety disorders such as post traumatic stress disorder (PTSD) (22). The non-selective monoamine oxidase inhibitor Phenelzine which elevates dopamine levels in the brain amongst its actions has been shown to reduce the symptoms of PTSD. Bupropion which has a significant DAT inhibitory component to its mechanism of action is also prescribed for patients with anxiety disorders and has been shown to be efficacious in patients with panic disorder, further supporting the potential of DAT inhibitors in these conditions.

Movement disorders such as Parkinson's disease (PD) and Restless Leg Syndrome (RLS) are common neurological disorders which have been treated with therapies that result in elevated brain dopamine. PD is characterised by a loss of dopaminergic neurones in the nigrostriatal pathway and a subsequent loss of dopamine. Drugs such as L-DOPA which is converted to dopamine in the brain have been shown to alleviate the motor symptoms of both PD and RLS. Given that DAT inhibitors also increase dopamine levels it is reasonable to assume that they would also provide therapeutic benefit in movement disorders which have been shown to have a dopaminergic component. Further support for this hypothesis is given by the fact that methylphenidate, a stimulant which has DAT inhibition amongst its pharmacological activities has shown to be clinically efficacious in PD patients, both in motor (23) and non-motor symptoms (24,25).

Addiction and substance abuse are closely linked to dopamine and reward circuits in the brain. These substance dependencies include alcohol dependence, opioid dependence, cocaine dependence, *cannabis* dependence, amphetamine dependence (or amphetamine-like), hallucinogen dependence, inhalant dependence, polysubstance dependence, phencyclidine (or phencyclidine-like) dependence, and nicotine dependence. Preclinical studies using the selective DAT inhibitor GBR12909 and other benztropines have shown that these compounds can block the rewarding effects of drugs of abuse, such as cocaine. GBR12909 has been shown to block the neurochemical effects of cocaine (26, 27) as well as that of amphetamine. Furthermore compounds which have been demonstrated to be DAT inhibitors are effective in smoking cessation. This provides evidence that a high affinity, selective DAT inhibitor could block the rewarding effects of drugs of abuse and be an effective medication to treat addiction.

Dopamine is also known to have a role in eating disorders such as Binge Eating Disorder (BED). Eating disorders such as BED are known to have multiple components including impulse control, reward circuits and cognition, all of which are under the influence of dopaminergic signalling. It has been shown that BED sufferers have abnormal brain dopamine responses, which regulates motivation for food intake (28). In addition BED and obese patients show an abnormal frontostriatal dopamine signalling as compared to healthy controls (29). Preclinical models have shown that stimulation of the nucleus accumbens, which receives major dopaminergic input, attenuates binge eating behaviour in rats and that this effect is blocked by dopaminergic antagonists. This indicates that increased synaptic dopamine is a potential therapeutic opportunity for eating disorders such as binge eating disorder. Preclinical data has shown that food intake is modulated by drugs which modulate synaptic dopamine levels and specifically by compounds with affinity at DAT (30). DAT has been specifically implicated in BED and other eating disorders due to polymorphisms in DAT being associated with eating disorders (31). This hypothesis is further supported by the efficacy of drugs with DAT inhibition as part of their mechanism of action in clinical trials of BED and other eating disorders (32). Together this is supportive for the therapeutic potential of a selective DAT inhibitor in eating disorders such as BED.

Dopamine has a well-documented role in cognition and particularly in cognitive deficits seen in patients suffering from diseases characterised by abnormal dopaminergic signalling such as Parkinson's disease and schizophrenia (33). This coupled with the fact that cortical dopamine D1 receptor function is linked to NMDA mediated glutamate signalling implies that cognitive processes would be expected to be enhanced by DAT inhibitors.

Chronic or persistent fatigue is a symptom which is common to several diseases and can be persisting or relapsing (34). Disease states that are associated with fatigue include chronic fatigue syndrome, post-viral fatigue syndrome, HIV, multiple sclerosis, amyotrophic lateral sclerosis (ALS), myasthenia gravis, sarcoidosis, cancer, chemotherapy treatment, celiac disease, irritable bowel syndrome, spondyloarthropathy, fibromyalgia, arthritis, infectious diseases, diabetes, eating disorders, Parkinson's disease, sleep disorders, stroke, mood disorders, drug and alcohol abuse. Clinical studies have shown that multiple drugs with DAT inhibition as part of their mechanism of action are effective in combating fatigue in chronically ill patients (35). Drugs such as modafinil, methylphenidate and bupropion which share DAT inhibition as a common pharmacological mechanism of action have been shown to be efficacious in fatigue associated with cancer, chemotherapy, sarcoidosis, ALS, depression, bipolar disorder, multiple sclerosis, Parkinson's disease, HIV and chronic fatigue syndrome. This evidence is supportive of likely efficacy for a selective and potent DAT inhibitor in fatigue associated with the diseases mentioned above.

The multiple potential applications for a selective and potent DAT inhibitor have resulted in numerous chemical series being described in the literature. A particular issue has been pharmacological selectivity, with many previously described structural classes of DAT inhibitors suffering from significant off target pharmacology, which has limited their development. A particular issue is the affinity of DAT inhibitors described in the literature for ion channels. Vanoxerine has been shown to have significant activity at multiple ion channels resulting in a cardiovascular safety risk that has hampered its development (36). The compound showed potent functional activity at multiple sodium, calcium and potassium channels which would be an undesirable profile for a drug to treat CNS disorders. In addition to off target ion channel pharmacology DAT inhibitors (particularly those of the benztropine class) have been shown to have pharmacological activity at multiple other receptors such as the serotonin receptor 5-HT2, the muscarinic receptor M1 and the histamine receptor H1 (37,38,39). These significant secondary pharmacological activities may introduce unwanted side effects to potentially therapeutically beneficial DAT inhibitors. This makes the selectivity profile of DAT inhibitors of particular importance.

Therefore there remains a need to develop new DAT inhibitors, especially inhibitors that are selective over noradrenaline and serotonin, that will have utility to treat a wide range of disorders, in particular to treat depression, ADHD and eating disorders. Preferred compounds will possess a good pharmacokinetic profile and in particular will be suitable as drugs for oral delivery. Particularly preferred compounds will additionally display selectivity over noradrenaline and serotonin.

SUMMARY OF THE INVENTION

The present invention relates to a series of spirocyclic derivatives that are inhibitors of DAT. Many of these compounds demonstrate good selectivity for DAT and are potentially useful in the treatment of sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including cocaine abuse and smoking cessation), eating disorders, chronic fatigue and impulse control disorders. The invention further relates to pharmaceutical compositions of the inhibitors, to the use of the compositions as therapeutic agents, and to methods of treatment using these compositions.

In an aspect, the invention provides a compound according to formula I,

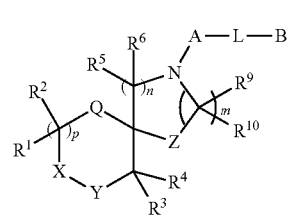

I wherein:
Q is selected from $CR^7R^8$, C=O, C=N—OH, C=N—O-alkyl, $S(O)_q$, O, NH, N-cycloalkyl and N-alkyl;
X is selected from C=O, $CR^{11}R^{12}$, NH, N-cycloalkyl and N-alkyl;
Y is selected from $CR^{11}R^{12}$, NH, N-cycloalkyl or N-alkyl, $S(O)_q$ and O;
wherein:
  X is C=O or $CR^{11}R^{12}$ when Y is O, $S(O)_q$, NH, N-alkyl or N-cycloalkyl;
  X is C=O or $CR^{11}R^{12}$ when p is 0 and Q is $S(O)_q$, O, NH, N-cycloalkyl or N-alkyl;
  Y is $CR^{11}R^{12}$ when X is NH, N-cycloalkyl or N-alkyl;
  Q is selected from $CR^7R^8$, C=O, C=N—OH and C=N—O-alkyl when n is 0;
  Q is $CR^7R^8$ when p is 0 and X is NH, N-cycloalkyl or N-alkyl;
  Q is $CR^7R^8$, O, NH, N-cycloalkyl or N-alkyl when p is 0 and X is C=O;
  Q is NH, N-cycloalkyl or N-alkyl and X is $CR^{11}R^{12}$ when Y is O or $S(O)_q$, and
  at least one of Q, X and Y is NH, N-cycloalkyl or N-alkyl;
Z is selected from $CR^{11}R^{12}$, O and S; wherein Z is $CR^{11}R^{12}$ when Q is O, $S(O)_q$, NH, N-cycloalkyl or N-alkyl, or when m is 0, or when n is 0;
A is selected from phenyl and heteroaryl;
B is selected from phenyl and heteroaryl;
L is a linker selected from alkylene and O;
$R^1$ is selected from H, OH, alkyl, F, Cl, and alkoxy;
$R^2$ is selected from H, OH, alkyl, F, Cl, and alkoxy;
  or $R^1$ and $R^2$ may together form =O;
$R^3$ and $R^4$ are independently selected from H, OH, alkoxy and alkyl; or
  $R^3$ and $R^4$ may both be O, wherein said O atoms are linked by an alkylene group to form a straight chain or branched alkylenedioxy group; or
  $R^3$ and $R^4$ may together form =O;
$R^5$ and $R^6$ are independently selected from H and alkyl;
  or $R^5$ and $R^6$ may together form =O;
$R^7$ is selected from H, F, Cl, OH, alkoxy, and alkyl;

$R^8$ is selected from H, F, Cl, OH, alkoxy and alkyl;
or $R^7$ and $R^8$ may both be O, wherein said O atoms are linked by an alkylene group to form a straight chain or branched alkylenedioxy group;
$R^9$ is H or alkyl;
$R^{10}$ is H or alkyl;
$R^{11}$ and $R^{12}$ are independently selected from H and alkyl;
$R^{13}$ and $R^{14}$ are independently selected from H and alkyl;
q is 0, 1 or 2;
n is 0, 1 or 2, wherein n is 0 or 1 when m is 2 and n is 1 or 2 when m is 0;
m is 0, 1 or 2, wherein m is 0 or 1 when n is 2 and m is 1 or 2 when n is 0;
p is 0, 1 or 2, wherein p is 1 or 2 when m is 1 and n is 1 or when n is 2 and m is 0;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents independently selected from S-alkyl, S(O)alkyl, S(O)$_2$alkyl, cycloalkyl, heterocyclyl, alkoxy, OH, —CN, $CF_3$, $COOR^{13}$, $CONR^{13}R^{14}$, F, Cl, $NR^{13}COR^{14}$ and $NR^{13}R^{14}$;
alkylene is a bivalent $C_{1-3}$ straight-chained alkyl radical or a bivalent $C_{3-4}$ branched alkyl radical, wherein alkylene may optionally be substituted with 1 or 2 substituents selected from S-alkyl, S(O)alkyl, S(O)$_2$alkyl, heterocyclyl, alkoxy, OH, —CN, $CF_3$, $COOR^{13}$, $CONR^{13}R^{14}$, F, Cl, $NR^{13}COR^{14}$ and $NR^{13}R^{14}$;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from S-alkyl, S(O)alkyl, S(O)$_2$alkyl, alkyl, OH, —CN, $CF_3$, $COOR^{13}$, $CONR^{13}R^{14}$, F, Cl, $NR^{13}COR^{14}$ and $NR^{13}R^{14}$;
cycloalkyl is a monocyclic saturated hydrocarbon of between 3 and 7 carbon atoms; cycloalkyl may optionally be substituted with 1, 2, 3, 4 or 5 substituents independently selected from S-alkyl, S(O)alkyl, S(O)$_2$alkyl, alkyl, alkoxy, OH, —CN, $CF_3$, $COOR^{13}$, $CONR^{13}R^{14}$, F, Cl, $NR^{13}COR^{14}$ and $NR^{13}R^{14}$;
phenyl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$;
heteroaryl is a 5 or 6 membered aromatic ring, containing, where possible, 1, 2 or 3 ring members independently selected from N, $NR^{13}$, S and O; heteroaryl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$;
heterocyclyl is a monocyclic ring which is saturated or partially unsaturated, containing, where possible, 1 or 2 ring members independently selected from N, S, O and $NR^{13}$ and 2 to 5 carbon atoms; heterocyclyl may optionally be substituted with 1, 2 or 3 substituents independently selected from alkyl, cycloalkyl, alkoxy, S-alkyl, S(O)alkyl, S(O)$_2$alkyl, oxo, OH, F, Cl, —CN, $OCF_3$, $CF_3$, $NR^{13}COR^{14}$ and $NR^{13}R^{14}$;
and tautomers, stereoisomers (including enantiomers, diastereoisomers and racemic and scalemic mixtures thereof), pharmaceutically acceptable salts and solvates thereof;
wherein:
$R^1$ is not OH or alkoxy when Q is NH,N-alkyl or N-cycloalkyl, or when X is NH, N-alkyl, N-cycloalkyl; and
$R^2$ is not OH or alkoxy when Q is NH,N-alkyl or N-cycloalkyl, or when X is NH, N-alkyl or N-cycloalkyl; and
$R^3$ is not OH or alkoxy when Y is O, NH, N-alkyl or N-cycloalkyl; and
$R^4$ is not OH or alkoxy when Y is O, NH, N-alkyl or N-cycloalkyl;
and wherein the compound of formula I is not:

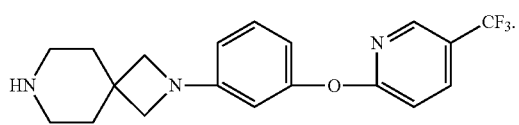

In an aspect, the invention comprises a compound of formula I, wherein m is 1 or 2 and n is 1 or 2, wherein n is 1 when m is 2; and m is 1 when n is 2.

In an aspect, the invention comprises a compound of formula I, wherein L is O.

In an aspect, the invention comprises a compound of formula I, wherein Q is selected from C=O, O, S, $SO_2$ and $CR^7R^8$.

In an aspect, the invention comprises a compound of formula I, wherein $R^1$, $R^2$, $R^5$ and $R^6$ are all H; and $R^3$ and $R^4$ are H, or $R^3$ and $R^4$ may both be O, wherein said O atoms are linked by an ethylene group to form an ethylenedioxy group.

In an aspect, the invention comprises a compound of formula I, wherein A is phenyl, pyridyl or pyrimidinyl, optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$.

In an aspect, the invention comprises a compound of formula I, wherein A is phenyl, 2-pyridyl or 1,3-pyrimidinyl, optionally substituted with 1, 2 or 3 substituents independently selected from alkyl, F, Cl, —CN and $CF_3$.

In an aspect, the invention comprises a compound of formula I, wherein A is selected from the group consisting of:

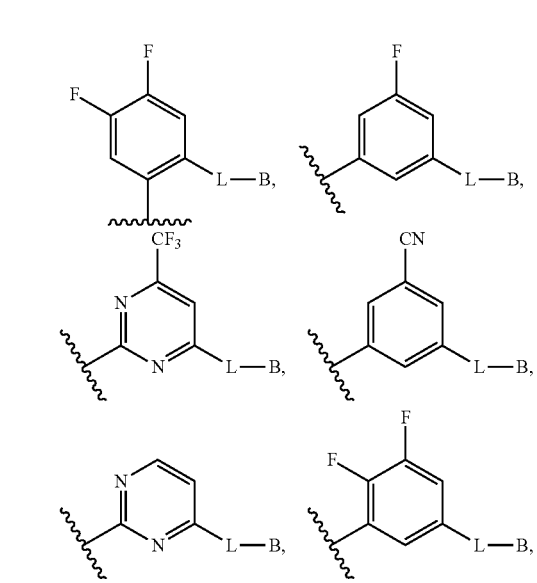

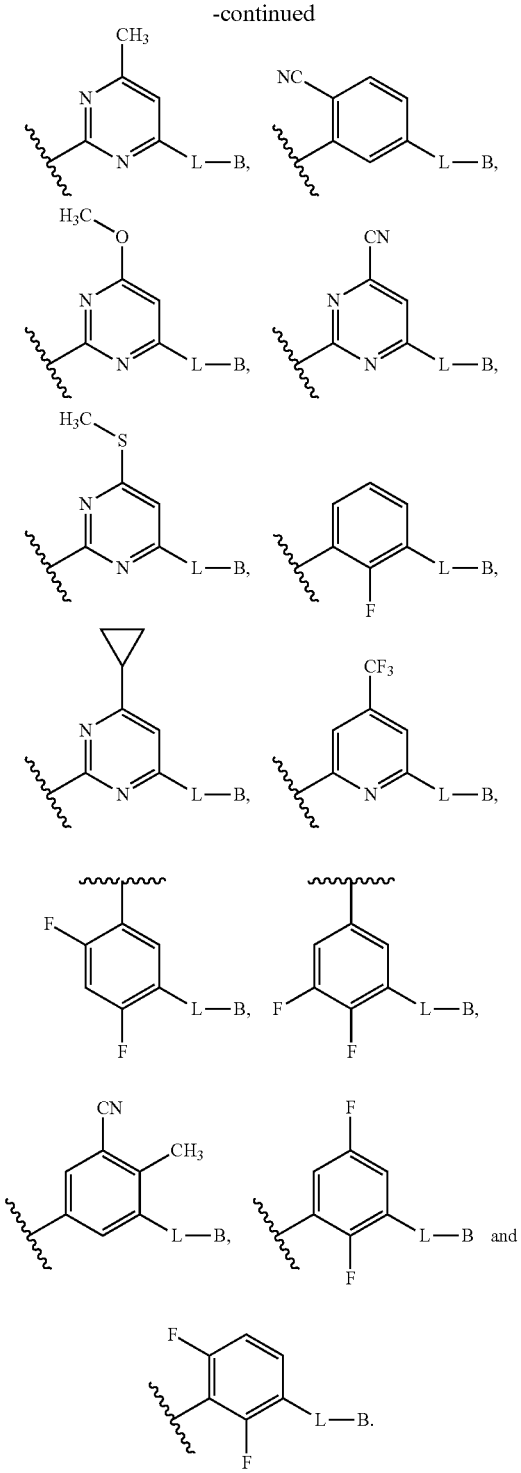

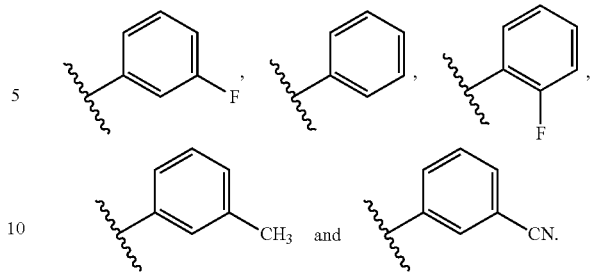

In an aspect, the invention comprises a compound of formula I, wherein B is phenyl, optionally substituted with 1, 2 or 3 substituents independently selected from alkyl, cycloalkyl, heterocyclyl, alkoxy, S-alkyl, S(O)alkyl, S(O)$_2$ alkyl, OH, F, Cl, —CN, OCF$_3$, CF$_3$, NR$^{13}$COR$^{14}$ and NR$^{13}$R$^{14}$.

In an aspect, the invention comprises a compound of formula I, wherein B is selected from the group consisting of:

In an aspect, the invention comprises a compound selected from Examples 1 to 102.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

DETAILED DESCRIPTION

In an aspect, the invention comprises a subset of the compounds of formula I, as defined by formula IA,

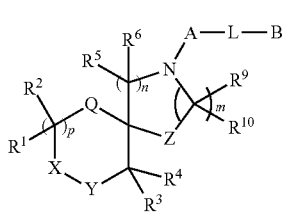

IA wherein:
X is selected from C=O, CH$_2$ and NH;
Y is selected from CH$_2$ and NH;
Q is selected from CR$^7$R$^8$, C=O, S(O)$_q$, O and NH;
wherein:
 X is C=O or CH$_2$ when Y is NH;
 Y is CH$_2$ when X is NH;
 Q is CR$^7$R$^8$ when p is 0 and X is NH;
 Q is CR$^7$R$^8$, O or NH when p is 0 and X is C=O; and
 wherein at least one of Q, X and Y is NH;
Z is selected from CH$_2$ and O; wherein Z is CH$_2$ when Q is O;
A is selected from phenyl, pyrazinyl, pyridyl, pyrimidinyl and 1,2,4-triazinyl; A may optionally be substituted with 1, 2 or 3 substituents independently selected from alkyl, cycloalkyl, heterocyclyl, alkoxy, S-alkyl, S(O)alkyl, S(O)$_2$ alkyl, OH, F, Cl, —CN, OCF$_3$, CF$_3$, NR$^{13}$COR$^{14}$ and NR$^{13}$R$^{14}$;
B is selected from phenyl and pyridyl; B may optionally be substituted with 1, 2 or 3 substituents independently selected from alkyl, cycloalkyl, heterocyclyl, alkoxy, S-alkyl, S(O) alkyl, S(O)$_2$alkyl, OH, F, Cl, —CN, OCF$_3$, CF$_3$, NR$^{13}$COR$^{14}$ and NR$^{13}$R$^{14}$;
L is a linker selected from alkylene and O;
R$^1$ is selected from H, OH, alkyl, alkoxy, F and Cl;
R$^2$ is selected from H, OH, alkyl, alkoxy, F and Cl;

$R^3$ and $R^4$ are independently selected from H, OH, alkoxy and alkyl; or $R^3$ and $R^4$ may both be O, wherein said O atoms are linked by an alkylene group to form a straight chain or branched alkylenedioxy group;

$R^5$ and $R^6$ are independently selected from H and alkyl;

$R^7$ is selected from H, OH, alkoxy, F and Cl;

$R^8$ is selected from H, OH and alkoxy;

or $R^7$ and $R^8$ may both be O, wherein said O atoms are linked by an alkylene group to form a straight chain or branched alkylenedioxy group;

$R^9$ is H or alkyl;

$R^{10}$ is H or alkyl;

$R^{11}$ and $R^{12}$ are independently selected from H and alkyl;

$R^{13}$ and $R^{14}$ are independently selected from H and alkyl;

q is 0 or 2;

n is 1 or 2, wherein n is 1 when m is 2;

m is 1 or 2, wherein m is 1 when n is 2;

p is 0 or 1, wherein p is 1 when m and n are 1;

alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents independently selected from alkoxy, OH, —CN, $CF_3$, $COOR^{13}$, $CONR^{13}R^{14}$, F, Cl and $NR^{13}R^{14}$;

alkylene is a bivalent $C_{1-3}$ straight-chained alkyl radical or a bivalent $C_{3-4}$ branched alkyl radical, wherein alkylene may optionally be substituted with 1 or 2 substituents selected from S-alkyl, S(O)alkyl, $S(O)_2$alkyl, heterocyclyl, alkoxy, OH, —CN, $CF_3$, $COOR^{13}$, $CONR^{13}R^{14}$, F, Cl, $NR^{13}COR^4$ and $NR^{13}R^{14}$; alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from alkyl, OH, —CN, $CF_3$, $COOR^{13}$, $CONR^{13}R^{14}$, F, Cl and $NR^{13}R^{14}$;

cycloalkyl is a monocyclic saturated hydrocarbon of between 3 and 7 carbon atoms; cycloalkyl may optionally be substituted with 1, 2, 3, 4 or 5 substituents independently selected from alkyl, alkoxy, OH, —CN, $CF_3$, $COOR^{13}$, $CONR^{13}R^{14}$, F, Cl and $NR^{13}R^{14}$;

heterocyclyl is a monocyclic ring which is saturated or partially unsaturated, containing, where possible, 1 or 2 ring members independently selected from N, S, O and $NR^{13}$ and 2 to 5 carbon atoms; heterocyclyl may optionally be substituted with 1, 2 or 3 substituents independently selected from alkyl, cycloalkyl, alkoxy, S-alkyl, S(O)alkyl, $S(O)_2$alkyl, oxo, OH, F, Cl, —CN, $OCF_3$, $CF_3$, $NR^{13}COR^4$ and $NR^{13}R^{14}$; and tautomers, stereoisomers (including enantiomers, diastereoisomers and racemic and scalemic mixtures thereof), pharmaceutically acceptable salts and solvates thereof;

wherein:

$R^1$ is not OH or alkoxy when Q is NH, or when X is NH; and $R^2$ is not OH or alkoxy when Q is NH, or when X is NH; and $R^3$ is not OH or alkoxy when Y is NH; and $R^4$ is not OH or alkoxy when Y is NH.

In an aspect, the invention comprises a subset of the compounds of formula I, as defined by formula IB,

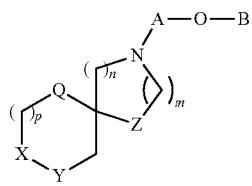

IB

X is selected from C=O, $CH_2$, and NH and Y is selected from $CH_2$ and NH, wherein:

X is C=O or $CH_2$ when Y is NH, and

Y is $CH_2$ when X is NH;

Q is $CR^7R^8$ when p is 0 and X is NH;

Q is $CR^7R^8$ or O when p is 0 and X is C=O; and one of X or Y is NH;

Q is selected from C=O, O, $SO_2$ and $CR^7R^8$,

Z is selected from 0 and $CH_2$; wherein Z is $CH_2$ when Q is O;

A is phenyl, optionally substituted with 1 or 2 substituents selected from $CF_3$, F, —CN, $OCH_3$, and $CH_3$, or heteroaryl selected from pyridyl and pyrimidinyl, optionally substituted with 1 or 2 substituents selected from $CF_3$, F, —CN, $OCH_3$, $SCH_3$, $CH_3$;

B is phenyl, optionally substituted with 1 substituent selected from F, —CN and $CH_3$;

or $R^3$ and $R^4$ may both be O, wherein said O atoms are linked by an ethylene group to form an ethylenedioxy group;

$R^7$ and $R^8$ are both H, or one of $R^7$ and $R^8$ is H and one of $R^7$ and $R^8$ is OH, or $R^7$ and $R^8$ are O, wherein said O atoms are linked by an ethylene group to form an ethylenedioxy group.

n is 1 or 2, wherein n is 1 when m is 2;

m is 1 or 2, wherein m is 1 when n is 2;

p is 0 or 1, wherein p is 1 when m and n are 1;

alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents independently selected from alkoxy, OH, —CN, $CF_3$, $COOR^{13}$, $CONR^{13}R^{14}$, F, Cl and $NR^{13}R^{14}$;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from alkyl, OH, —CN, $CF_3$, $COOR^{13}$, $CONR^{13}R^{14}$, F, Cl and $NR^{13}R^{14}$;

$R^{11}$ and $R^{12}$ are independently selected from H and alkyl;

$R^{13}$ and $R^{14}$ are independently selected from H and alkyl;

and tautomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula 1C

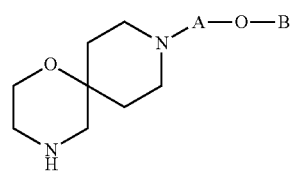

IC

A is phenyl, optionally substituted with 1 or 2 substituents selected from $CF_3$, F, —CN, $OCH_3$, and $CH_3$; or heteroaryl selected from pyridyl and pyrimidinyl, optionally substituted with 1 or 2 substituents selected from $CF_3$, F, —CN, $OCH_3$, $SCH_3$, $CH_3$;

B is phenyl, optionally substituted with 1 substituent selected from F, —CN and $CH_3$;

and tautomers, stereoisomers (including enantiomers, diastereoisomers and racemic and scalemic mixtures thereof), pharmaceutically acceptable salts and solvates thereof.

The present invention also comprises the following aspects and combinations thereof.

In an aspect X is selected from C=O, $CR^{11}R^{12}$, NH and N-alkyl. In an aspect X is selected from C=O, $CR^{11}R^{12}$ and NH. In an aspect X is $CR^{11}R^{12}$. In an aspect X is $CH_2$.

In an aspect Y is selected from $CR^{11}R^{12}$, NH, N-cycloalkyl or N-alkyl, $S(O)_q$ and O. In an aspect Y is O, $CR^{11}R^{12}$ or NH. In an aspect Y is $CR^{11}R^{12}$ or NH. In an aspect Y is $CH_2$ or NH. In an aspect Y is NH.

In an aspect Q is selected from $CR^7R^8$, C=O, C=N—OH, C=N—O-alkyl, $S(O)_q$, O, NH and N-alkyl. In an aspect Q is selected from C=O, NH, O, S, $SO_2$ and $CR^7R^8$. In an aspect, Q is selected from C=O, O, S, $SO_2$ and $CR^7R^8$. In an aspect Q is selected from C=O, O, $SO_2$ and $CR^7R^8$. In an aspect Q is O, CHOH or $CH_2$. In an aspect Q is O or $CH_2$. In an aspect Q is O. In an aspect X is $CH_2$, Y is O and Q is NH.

In an aspect Z is O or $CR^{11}R^{12}$. In an embodiment Z is O or $CH_2$. In an aspect Z is $CH_2$.

In an aspect A is selected from phenyl, pyrazinyl, pyridyl, pyrimidinyl and 1,2,4-triazinyl, optionally substituted with 1, 2 or 3 substituents independently selected from alkyl, cycloalkyl, alkoxy, S-alkyl, OH, F, Cl, —CN, $OCF_3$, $CF_3$ and $NR^{13}R^{14}$.

In an aspect, X is $CH_2$, Y is O and Q is NH.
In an aspect, X is $CH_2$, Y is NH and Q is O.
In an aspect A is selected from phenyl, pyrazinyl, pyridyl and pyrimidinyl, optionally substituted with 1, 2 or 3 substituents independently selected from alkyl, cycloalkyl, alkoxy, S-alkyl, OH, F, Cl, —CN, $OCF_3$, $CF_3$ and $NR^{13}R^{14}$.

In an aspect A is selected from phenyl, pyridyl and pyrimidinyl, optionally substituted with 1, 2 or 3 substituents independently selected from alkyl, cycloalkyl, alkoxy, S-alkyl, F, —CN and $CF_3$.

In an aspect A is selected from phenyl, 2-pyridyl and 1,3-pyrimidinyl, optionally substituted with 1, 2 or 3 substituents independently selected from alkyl, cycloalkyl, alkoxy, S-alkyl, F, —CN and $CF_3$.

In an aspect A is phenyl or pyrimidinyl, optionally substituted with 1, 2 or 3 substituents independently selected from alkyl, cycloalkyl, alkoxy, S-alkyl, F, —CN and $CF_3$.

In an aspect B is phenyl or pyridyl, optionally substituted with 1, 2 or 3 substituents independently selected from alkyl, cycloalkyl, alkoxy, S-alkyl, OH, F, Cl, —CN, $OCF_3$, $CF_3$ and $NR^{13}R^{14}$.

In an aspect B is phenyl, optionally substituted with 1, 2 or 3 substituents independently selected from alkyl, alkoxy, OH, F, Cl, —CN, $OCF_3$, and $CF_3$.

In an aspect B is selected from unsubstituted phenyl or phenyl substituted with 1 or 2 groups selected from F, —CN and $CH_3$.

In an aspect B is phenyl substituted with one F substituent. In an aspect B is meta-fluoro-phenyl.

In an aspect L is selected from methylene, ethylene or O. In an aspect L is O or methylene. In an aspect L is O.

In an aspect $R^1$ is selected from H, F, OH and alkoxy. In an aspect $R^2$ is selected from H, F, OH and alkoxy.

In an aspect $R^3$ and $R^4$ are independently selected from H, OH, alkoxy and alkyl; or $R^3$ and $R^4$ may both be O, wherein said O atoms are linked by an alkylene group to form a straight chain or branched alkylenedioxy group.

In an aspect $R^3$ is H. In an embodiment $R^4$ is H. In an aspect $R^3$ is H and $R^4$ is H.

In an aspect $R^5$ is H. In an embodiment $R^6$ is H. In an aspect $R^5$ is H and $R^6$ is H.

In an aspect $R^7$ and $R^8$ are selected from H and OH, or are O linked by an alkylene group to form an alkylenedioxy group.

In an aspect $R^7$ and $R^8$ are both H, or one of $R^7$ and $R^8$ is H and one of $R^7$ and $R^8$ is OH, or $R^7$ and $R^8$ are O linked by an ethylene group to form an ethylenedioxy group.

In an aspect $R^9$ and $R^{10}$ are both H.

In an aspect n is 1 or 2, wherein n is 1 when m is 2; and m is 1 or 2, wherein m is 1 when n is 2.

In an aspect n is 1 and m is 2. In an aspect m is 1 and n is 2.

In an aspect p is 0 or 1, wherein p is 1 when m is 1 and n is 1 or when n is 2 and m is 0.

In an aspect p is 1.

In an aspect p is 1, m is 1 and n is 2.

In an aspect, the invention comprises a subset of the compounds of formula I selected from:

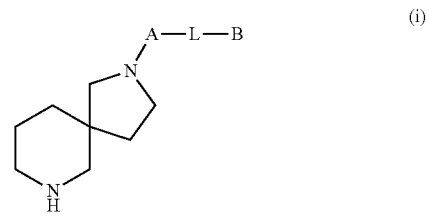

(i)

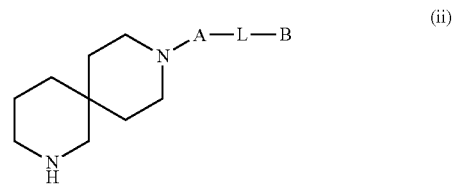

(ii)

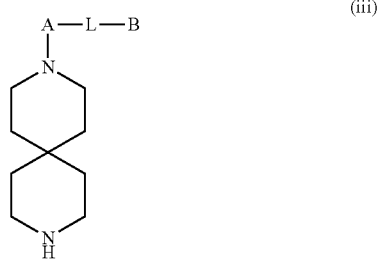

(iii)

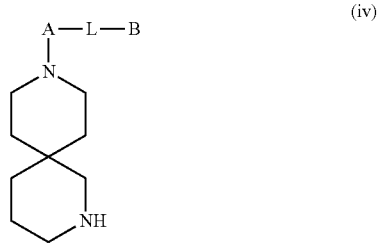

(iv)

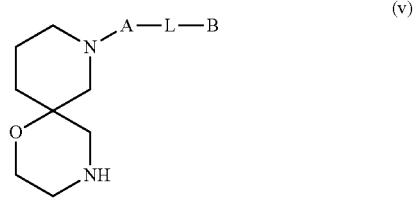

(v)

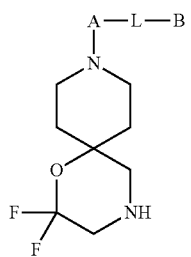
(vi)
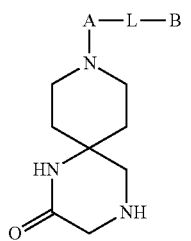
(vii)
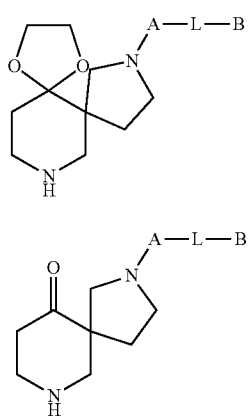
(viii)
(ix)
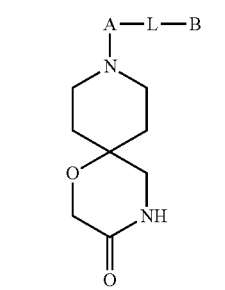
(x)
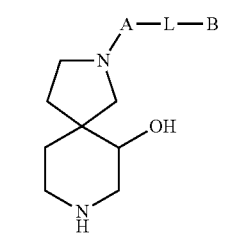
(xi)
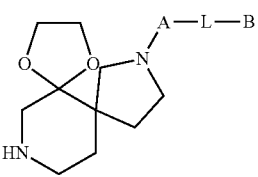
(xii)
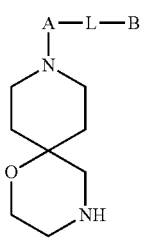
(xiii)
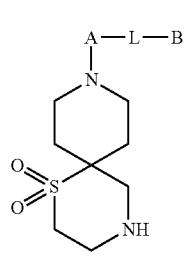
(xiv)
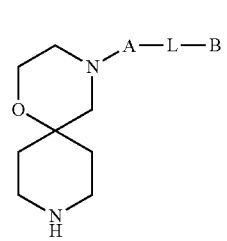
(xv)
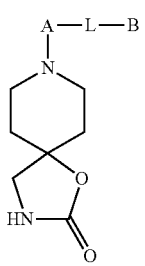
(xvi)
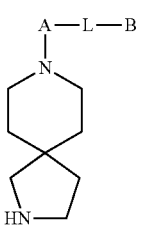
(xvii)
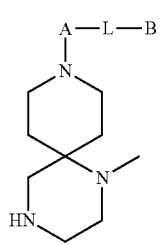
(xviii)

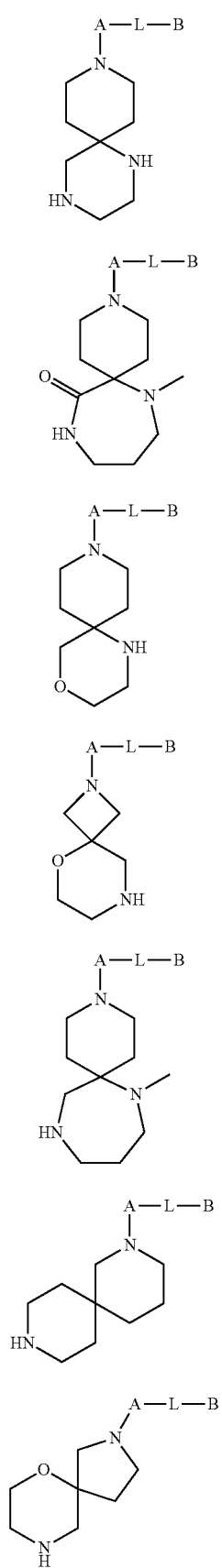
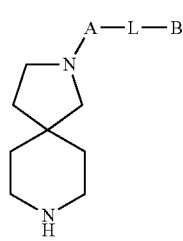
Preferably the compound of Formula I is selected from the group consisting of (viii), (ix), (x), (xi), (xii), (xiii), (xiv), (xv), (xvi), (xvii), (xviii), (xix), (xx), (xxi), (xxii), (xxiii) and (xxvi).
In an aspect A-L-B is selected from:
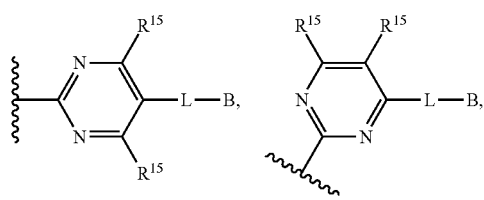
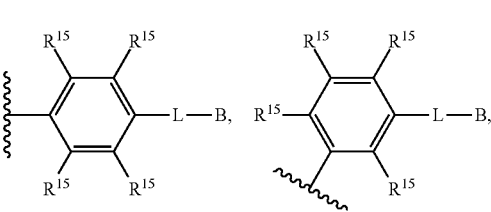
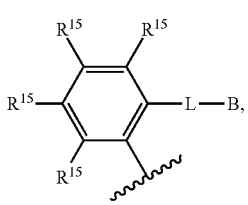
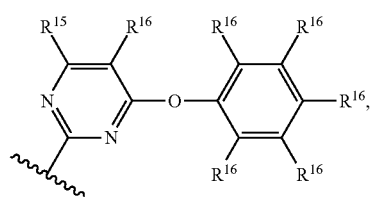
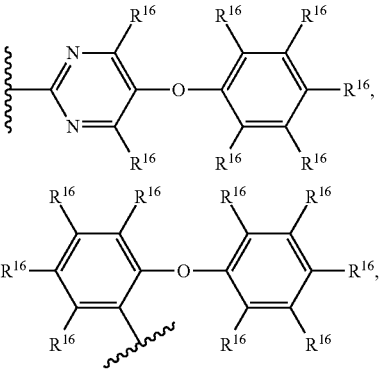

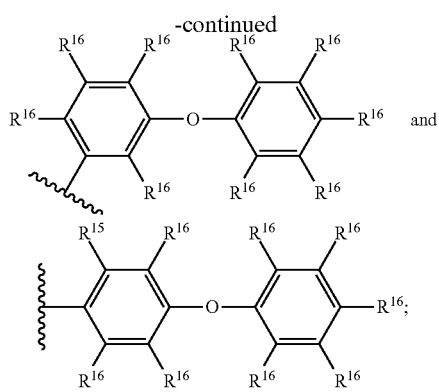
wherein
each $R^{15}$ is independently selected from H and $R^{17}$, wherein 0, 1, 2 or 3 $R^{15}$ are $R^{17}$;
each $R^{16}$ is independently selected from H and $R^{17}$, wherein 0, 1, 2 or 3 $R^{16}$ are $R^{17}$; and
each $R^{17}$ is independently selected from alkyl, cycloalkyl, heterocyclyl, alkoxy, S-alkyl, S-alkyl, S(O)alkyl, S(O)$_2$alkyl, OH, F, Cl, —CN, OCF$_3$, CF$_3$, $NR^{13}COR^{14}$ and $NR^{13}R^{14}$.
In an aspect A is selected from:
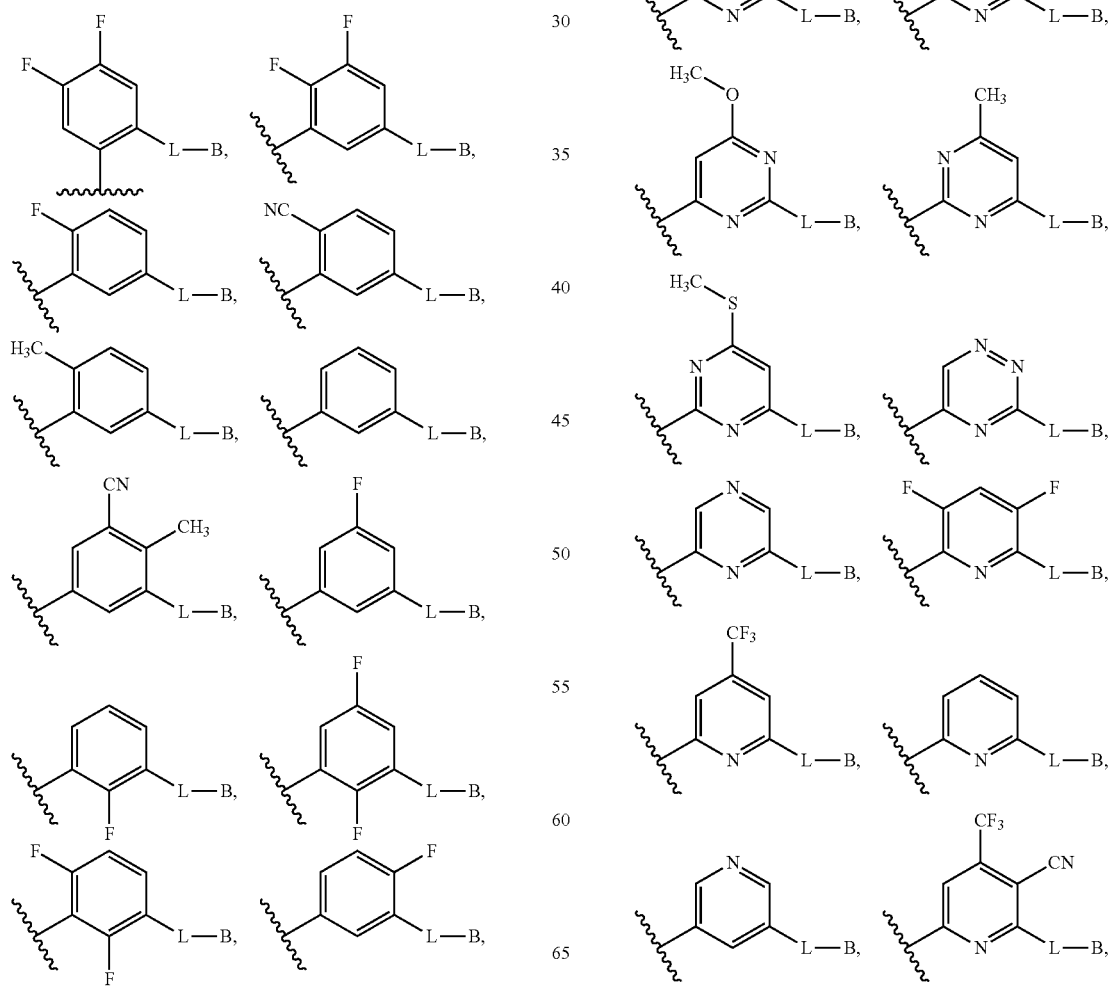

-continued
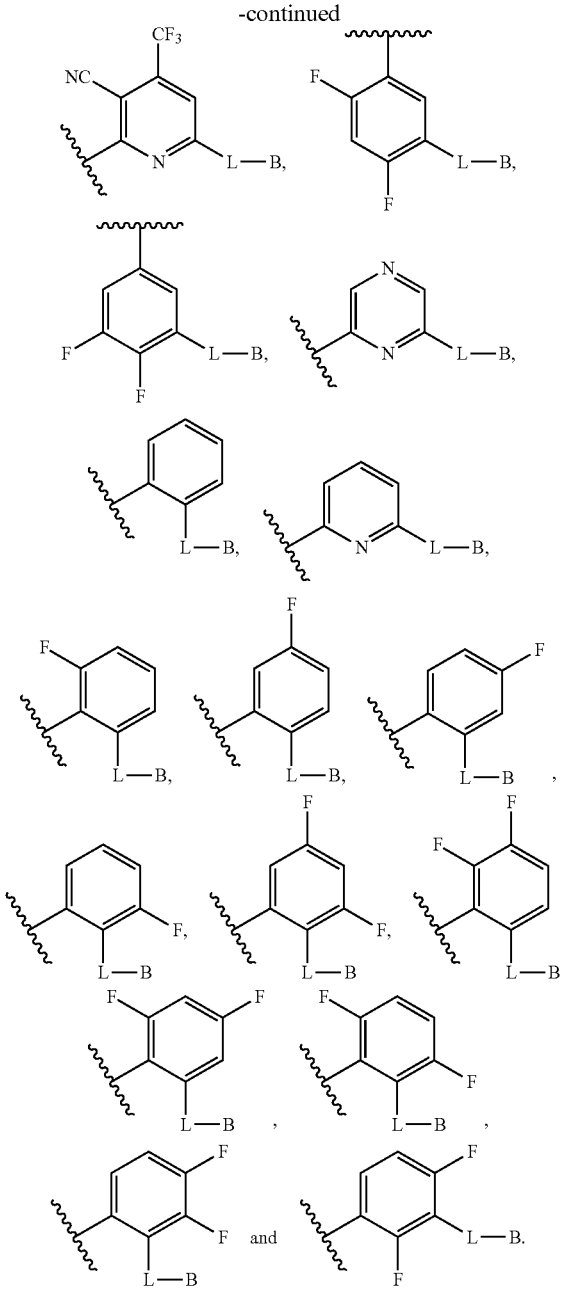
In an aspect B is selected from:
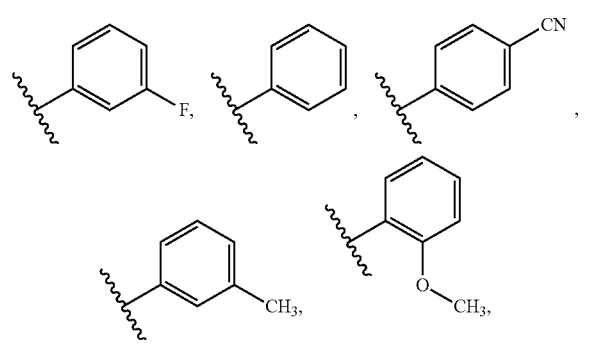
-continued
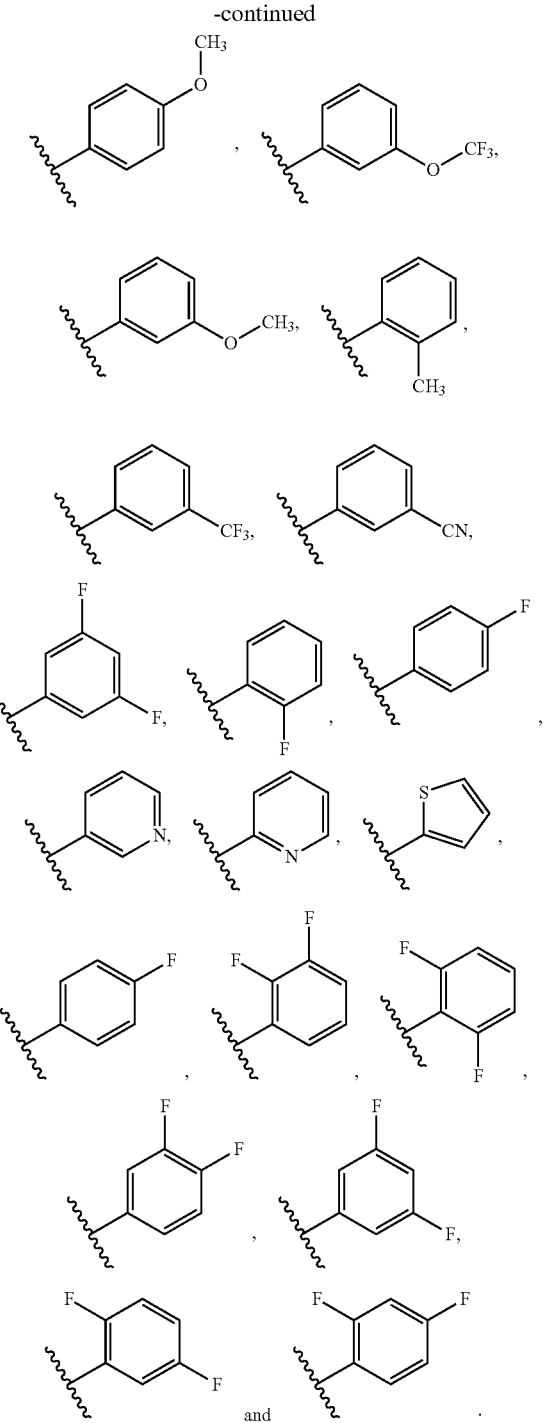
In an aspect A-L-B is selected from:
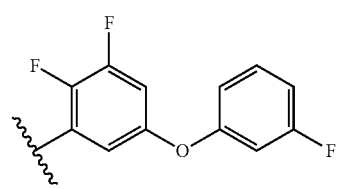
(a)

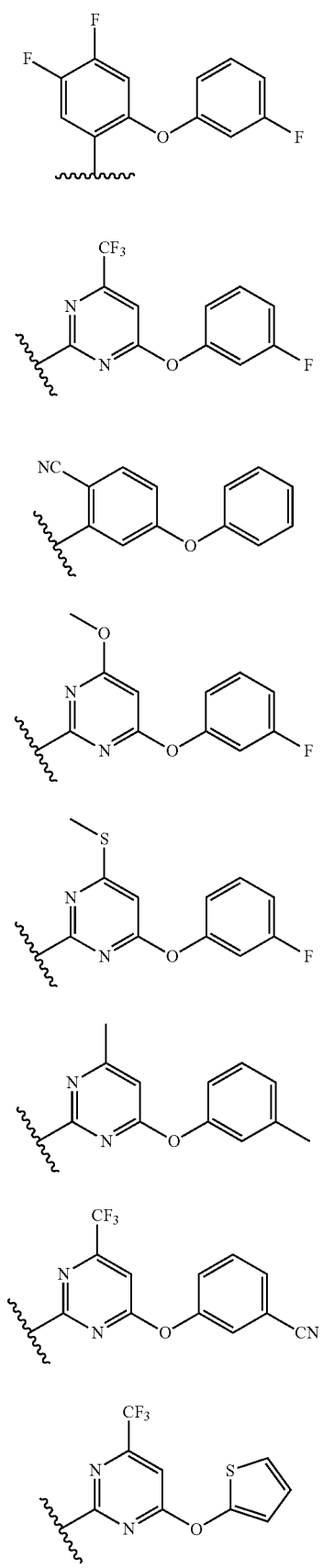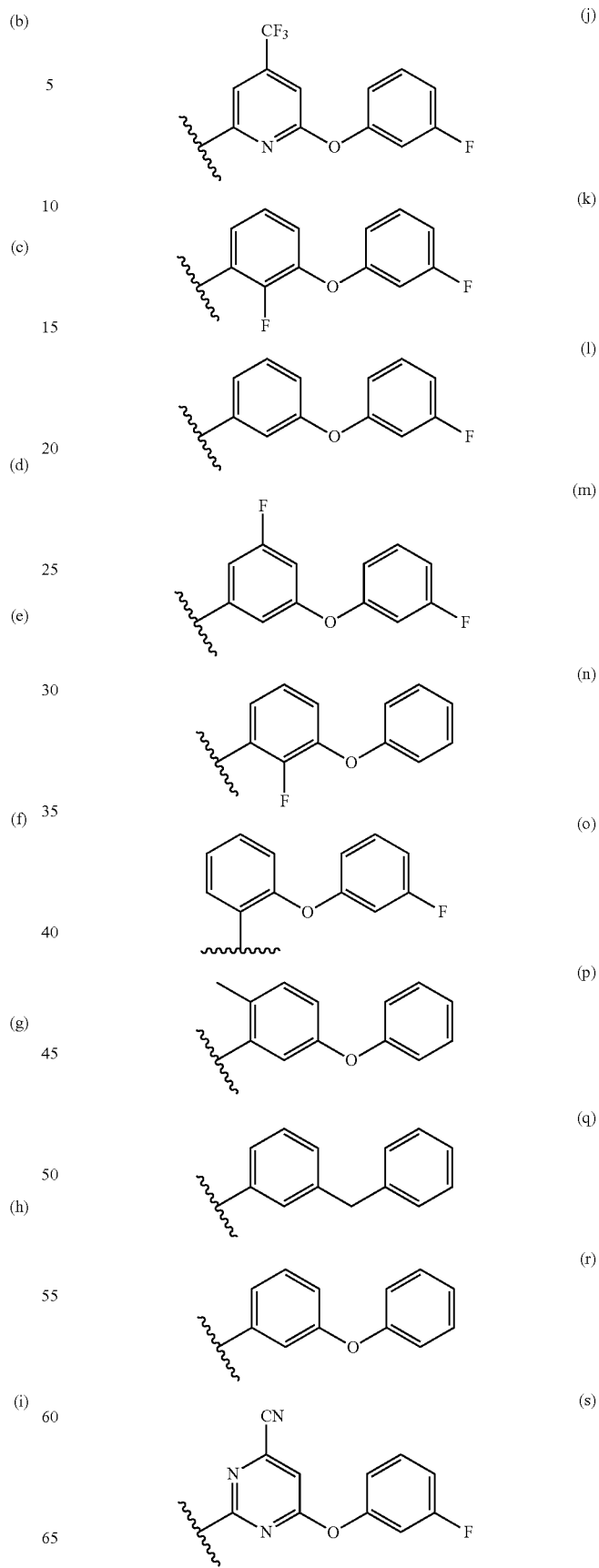

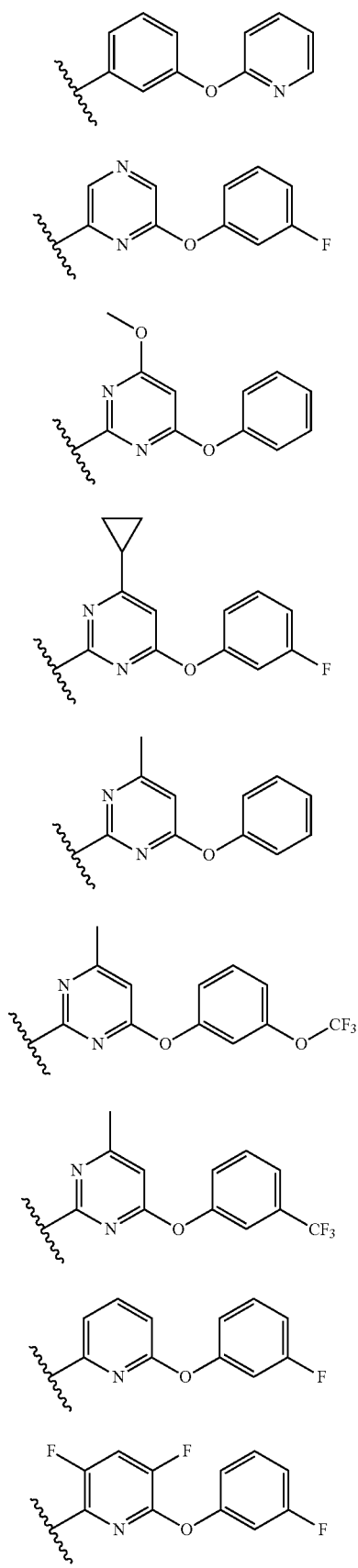
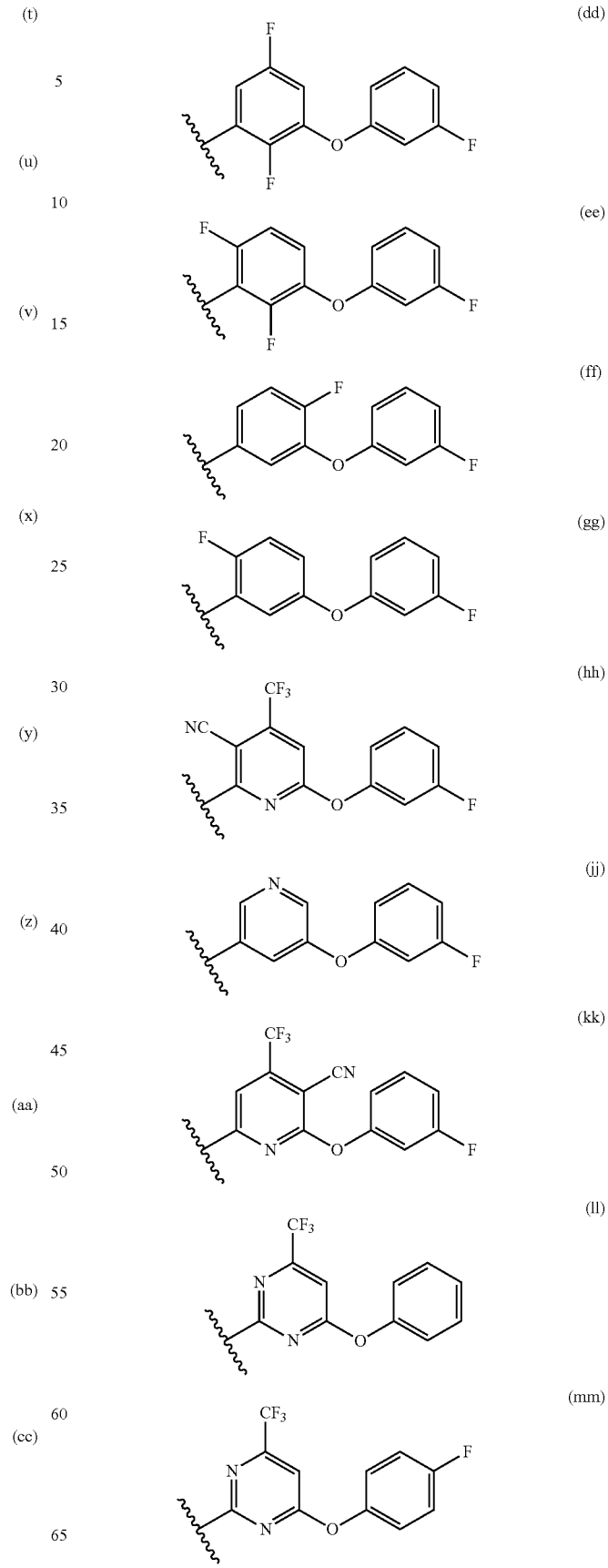

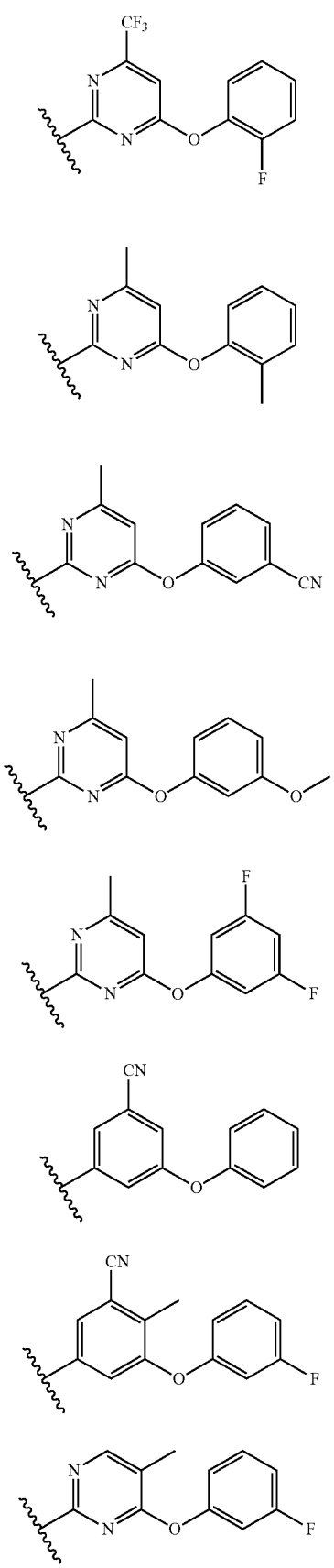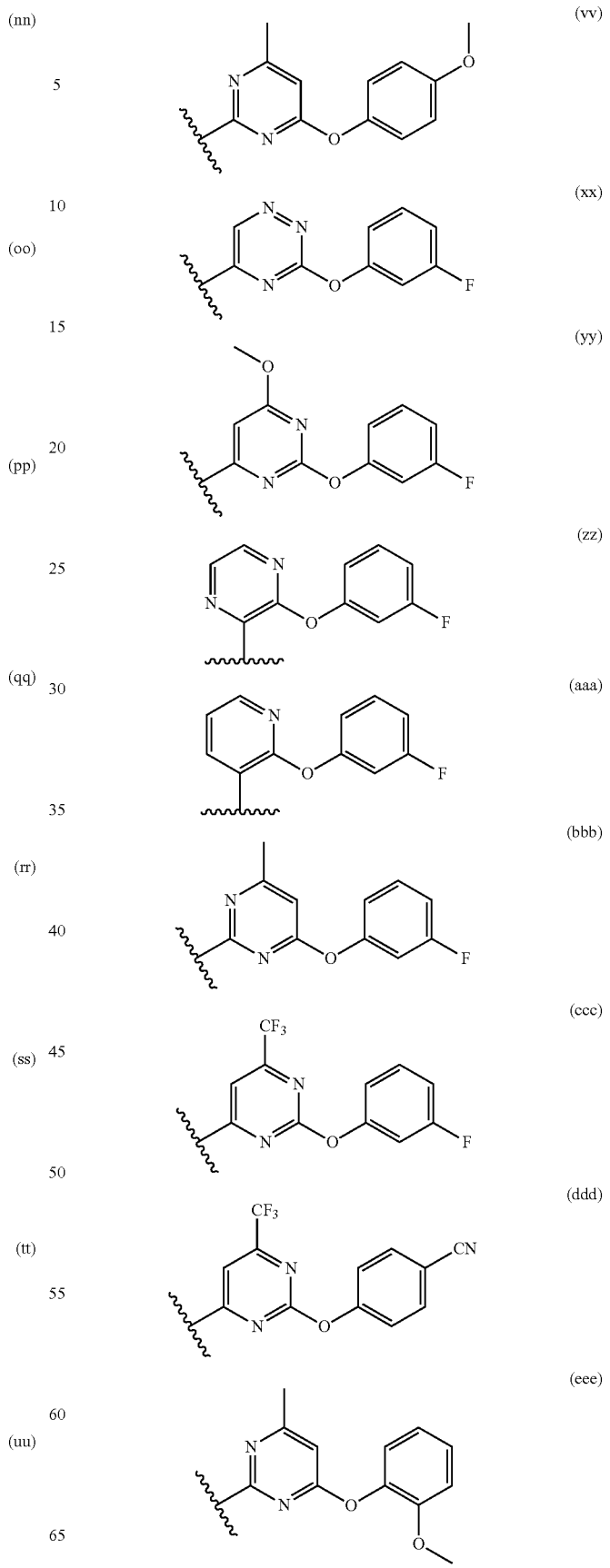

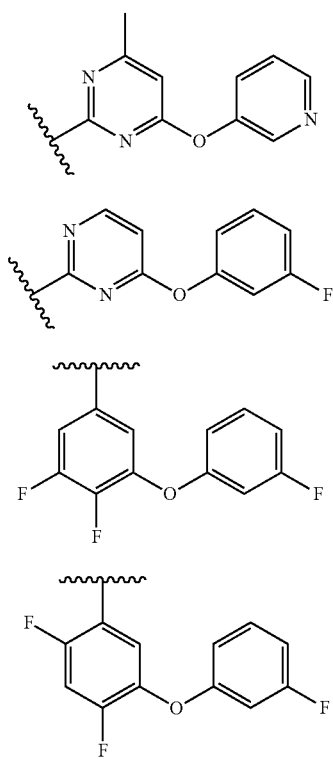

Preferably A-L-B is selected from the group consisting of (a), (b), (c), (d), (e), (f), (g), (j), (k), (m), (n), (s), (x), (y), (dd), (ee), (ll), (nn), (pp), (ss), (bbb), (ggg), (hhh) and (jjj).

More preferably A-L-B is selected from the group consisting of (a), (b), (c), (k), (n) and (dd).

In an aspect, the invention comprises a compound of formula I selected from:

9-[4,5-difluoro-2-(3-fluorophenoxy)phenyl]-1-oxa-4,9-diazaspiro[5.5]undecane;
9-(2-phenoxyphenyl)-1-oxa-4,9-diazaspiro[5.5]undecane;
9-[2-(3-fluorophenoxy)phenyl]-1-oxa-4,9-diazaspiro[5.5]undecane;
3-{1-oxa-4,9-diazaspiro[5.5]undecan-9-yl}-4-phenoxybenzonitrile;
9-(3-phenoxyphenyl)-1-oxa-4,9-diazaspiro[5.5]undecane;
9-[3-(3-fluorophenoxy)phenyl]-1-oxa-4,9-diazaspiro[5.5]undecane;
9-[3-fluoro-5-(3-fluorophenoxy)phenyl]-1-oxa-4,9-diazaspiro[5.5]undecane;
9-[2-fluoro-5-(3-fluorophenoxy)phenyl]-1-oxa-4,9-diazaspiro[5.5]undecane;
9-[4-fluoro-3-(3-fluorophenoxy)phenyl]-1-oxa-4,9-diazaspiro[5.5]undecane;
9-[2,4-difluoro-5-(3-fluorophenoxy)phenyl]-1-oxa-4,9-diazaspiro[5.5]undecane;
9-[2,3-difluoro-5-(3-fluorophenoxy)phenyl]-1-oxa-4,9-diazaspiro[5.5]undecane;
9-[3,4-difluoro-5-(3-fluorophenoxy)phenyl]-1-oxa-4,9-diazaspiro[5.5]undecane;
9-(2-fluoro-3-phenoxyphenyl)-1-oxa-4,9-diazaspiro[5.5]undecane;
9-[2-fluoro-3-(3-fluorophenoxy)phenyl]-1-oxa-4,9-diazaspiro[5.5]undecane;
9-[2,5-difluoro-3-(3-fluorophenoxy)phenyl]-1-oxa-4,9-diazaspiro[5.5]undecane;
9-[2,6-difluoro-3-(3-fluorophenoxy)phenyl]-1-oxa-4,9-diazaspiro[5.5]undecane;
3-{1-oxa-4,9-diazaspiro[5.5]undecan-9-yl}-5-phenoxybenzonitrile;
2-{1-oxa-4,9-diazaspiro[5.5]undecan-9-yl}-4-phenoxybenzonitrile;
9-(2-methyl-5-phenoxyphenyl)-1-oxa-4,9-diazaspiro[5.5]undecane;
9-[5-(3-fluorophenoxy)pyridin-3-yl]-1-oxa-4,9-diazaspiro[5.5]undecane;
9-(3-benzylphenyl)-1-oxa-4,9-diazaspiro[5.5]undecane;
3-(3-fluorophenoxy)-2-methyl-5-{1-oxa-4,9-diazaspiro[5.5]undecan-9-yl}benzonitrile;
9-[6-(3-fluorophenoxy)pyridin-2-yl]-1-oxa-4,9-diazaspiro[5.5]undecane;
9-[6-(3-fluorophenoxy)-4-(trifluoromethyl)pyridin-2-yl]-1-oxa-4,9-diazaspiro[5.5]undecane;
2-(3-fluorophenoxy)-6-{1-oxa-4,9-diazaspiro[5.5]undecan-9-yl}pyridine-4-carbonitrile;
2-(3-fluorophenoxy)-6-{1-oxa-4,9-diazaspiro[5.5]undecan-9-yl}-4-(trifluoromethyl)pyridine-3-carbonitrile;
6-(3-fluorophenoxy)-2-{1-oxa-4,9-diazaspiro[5.5]undecan-9-yl}-4-(trifluoromethyl)pyridine-3-carbonitrile;
9-[6-(3-fluorophenoxy)pyrazin-2-yl]-1-oxa-4,9-diazaspiro[5.5]undecane;
9-[4-(3-fluorophenoxy)pyrimidin-2-yl]-1-oxa-4,9-diazaspiro[5.5]undecane;
9-(4-methyl-6-phenoxypyrimidin-2-yl)-1-oxa-4,9-diazaspiro[5.5]undecane;
9-[4-(3-fluorophenoxy)-6-methylpyrimidin-2-yl]-1-oxa-4,9-diazaspiro[5.5]undecane;
9-[4-methyl-6-(3-methylphenoxy)pyrimidin-2-yl]-1-oxa-4,9-diazaspiro[5.5]undecane;
3-[(6-methyl-2-{1-oxa-4,9-diazaspiro[5.5]undecan-9-yl}pyrimidin-4-yl)oxy]benzonitrile;
9-{4-methyl-6-[3-(trifluoromethoxy)phenoxy]pyrimidin-2-yl}-1-oxa-4,9-diazaspiro[5.5]undecane;
9-{4-methyl-6-[3-(trifluoromethyl) phenoxy]pyrimidin-2-yl}-1-oxa-4,9-diazaspiro[5.5]undecane;
9-[4-(3-methoxyphenoxy)-6-methylpyrimidin-2-yl]-1-oxa-4,9-diazaspiro[5.5]undecane;
9-[4-(3,5-difluorophenoxy)-6-methylpyrimidin-2-yl]-1-oxa-4,9-diazaspiro[5.5]undecane;
9-[4-methyl-6-(2-methylphenoxy)pyrimidin-2-yl]-1-oxa-4,9-diazaspiro[5.5]undecane;
9-[4-(2-methoxyphenoxy)-6-methylpyrimidin-2-yl]-1-oxa-4,9-diazaspiro[5.5]undecane;
9-[4-methyl-6-(pyridin-3-yloxy)pyrimidin-2-yl]-1-oxa-4,9-diazaspiro[5.5]undecane;
9-[4-(3-fluorophenoxy)-5-methylpyrimidin-2-yl]-1-oxa-4,9-diazaspiro[5.5]undecane;
9-[4-phenoxy-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecane;
9-[4-(2-fluorophenoxy)-6-(trifluoromethyl)pyrimidin-2-yl]-1-oxa-4,9-diazaspiro[5.5]undecane;
9-[4-(4-fluorophenoxy)-6-(trifluoromethyl)pyrimidin-2-yl]-1-oxa-4,9-diazaspiro[5.5]undecane;
3-[(2-{1-oxa-4,9-diazaspiro[5.5]undecan-9-yl}-6-(trifluoromethyl)pyrimidin-4-yl)oxy]benzonitrile;
9-[4-(thiophen-2-yloxy)-6-(trifluoromethyl)pyrimidin-2-yl]-1-oxa-4,9-diazaspiro[5.5]undecane;
9-(4-benzyl-6-methoxypyrimidin-2-yl)-1-oxa-4,9-diazaspiro[5.5]undecane;
6-(3-fluorophenoxy)-2-{1-oxa-4,9-diazaspiro[5.5]undecan-9-yl}pyrimidine-4-carbonitrile;

9-[4-(3-fluorophenoxy)-6-(methylsulfanyl)pyrimidin-2-yl]-1-oxa-4,9-diazaspiro[5.5]undecane;
9-[2-(3-fluorophenoxy)-6-(methylsulfanyl)pyrimidin-4-yl]-1-oxa-4,9-diazaspiro[5.5]undecane;
9-[4-cyclopropyl-6-(3-fluorophenoxy)pyrimidin-2-yl]-1-oxa-4,9-diazaspiro[5.5]undecane;
9-[4-(3-fluorophenoxy)-6-methoxypyrimidin-2-yl]-1-oxa-4,9 diazaspiro[5.5]undecane;
4-[4-(3-fluorophenoxy)-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecan-3-one;
9-[4,5-difluoro-2-(3-fluorophenoxy)phenyl]-2,2-difluoro-1-oxa-4,9-diazaspiro[5.5]undecane;
2,2-difluoro-9-[4-(3-fluorophenoxy)-6-(trifluoromethyl)pyrimidin-2-yl]-1-oxa-4,9-diazaspiro[5.5]undecane;
9-[4,5-difluoro-2-(3-fluorophenoxy)phenyl]-1λ6-thia-4,9-diazaspiro[5.5]undecane-1, 1-dione;
9-[4-(3-fluorophenoxy)-6-(trifluoromethyl)pyrimidin-2-yl]-1λ6-thia-4,9-diazaspiro[5.5]undecane-1, 1-dione;
9-[4-(3-fluorophenoxy)-6-(trifluoromethyl)pyrimidin-2-yl]-1,4,9-triazaspiro[5.5]undecan-2-one;
9-[4-(3-fluorophenoxy)-6-(trifluoromethyl)pyrimidin-2-yl]-1-methyl-1,4,9-triazaspiro[5.5]undecane;
9-[4-(3-fluorophenoxy)-6-(trifluoromethyl)pyrimidin-2-yl]-1,4,9-triazaspiro[5.5]undecane;
3-[4-(3-fluorophenoxy)-6-(trifluoromethyl)pyrimidin-2-yl]-7-methyl-3,7,11-triazaspiro[5.6]dodecan-12-one;
3-[4-(3-fluorophenoxy)-6-(trifluoromethyl)pyrimidin-2-yl]-7-methyl-3,7,11-triazaspiro[5.6]dodecane;
9-[4-(3-fluorophenoxy)-6-(trifluoromethyl)pyrimidin-2-yl]-4-oxa-1,9-diazaspiro[5.5]undecane;
9-[4,5-difluoro-2-(3-fluorophenoxy)phenyl]-2,9-diazaspiro[5.5]undecane;
2-[4,5-difluoro-2-(3-fluorophenoxy)phenyl]-2,9-diazaspiro[5.5]undecane;
2-[4,5-difluoro-2-(3-fluorophenoxy)phenyl]-2,8-diazaspiro[5.5]undecane;
3-[4,5-difluoro-2-(3-fluorophenoxy)phenyl]-3,9-diazaspiro[5.5]undecane;
2-[4,5-difluoro-2-(3-fluorophenoxy)phenyl]-6-oxa-2,9-diazaspiro[4.5]decane;
2-[4,5-difluoro-2-(3-fluorophenoxy)phenyl]-2,7-diazaspiro[4.5]decane;
8-[4,5-difluoro-2-(3-fluorophenoxy)phenyl]-1,4-dioxa-8,12-diazadispiro[4.0.4⁶.4⁵]tetradecane;
2-[4,5-difluoro-2-(3-fluorophenoxy)phenyl]-2,7-diazaspiro[4.5]decan-10-one;
8-[4-(3-fluorophenoxy)-6-(trifluoromethyl)pyrimidin-2-yl]-1,4-dioxa-8,12-diazadispiro[4.0.4⁶.4⁵]tetradecane;
2-[4-(3-fluorophenoxy)-6-(trifluoromethyl)pyrimidin-2-yl]-2,7-diazaspiro[4.5]decan-10-one;
8-[4-(3-fluorophenoxy)-6-(trifluoromethyl)pyrimidin-2-yl]-1-oxa-3,8-diazaspiro[4.5]decan-2-one;
2-[4,5-difluoro-2-(3-fluorophenoxy)phenyl]-2,8-diazaspiro[4.5]decane;
8-[4,5-difluoro-2-(3-fluorophenoxy)phenyl]-2,8-diazaspiro[4.5]decane;
8-[3-fluoro-5-(3-fluorophenoxy)phenyl]-2,8-diazaspiro[4.5]decane;
8-[4,5-difluoro-2-(3-fluorophenoxy)phenyl]-1,4-dioxa-8,13-diazadispiro[4.0.4⁶.4⁵]tetradecane;
8-[4-(3-fluorophenoxy)-6-(trifluoromethyl)pyrimidin-2-yl]-1,4-dioxa-8,13-diazadispiro[4.0.4⁶.4⁵]tetradecane;
2-[4-(3-fluorophenoxy)-6-(trifluoromethyl)pyrimidin-2-yl]-2,8-diazaspiro[4.5]decan-6-ol;
2-[4-(3-fluorophenoxy)-6-(trifluoromethyl)pyrimidin-2-yl]-5-oxa-2,8-diazaspiro[3.5]nonane;

and pharmaceutically acceptable salts and solvates thereof.
Preferably, the invention comprises a compound of formula I selected from:
9-[4,5-difluoro-2-(3-fluorophenoxy)phenyl]-1-oxa-4,9-diazaspiro[5.5]undecane;
9-[3-fluoro-5-(3-fluorophenoxy)phenyl]-1-oxa-4,9-diazaspiro[5.5]undecane;
9-[2,3-difluoro-5-(3-fluorophenoxy)phenyl]-1-oxa-4,9-diazaspiro[5.5]undecane;
9-(2-fluoro-3-phenoxyphenyl)-1-oxa-4,9-diazaspiro[5.5]undecane;
9-[2-fluoro-3-(3-fluorophenoxy)phenyl]-1-oxa-4,9-diazaspiro[5.5]undecane;
9-[2,5-difluoro-3-(3-fluorophenoxy)phenyl]-1-oxa-4,9-diazaspiro[5.5]undecane;
9-[2,6-difluoro-3-(3-fluorophenoxy)phenyl]-1-oxa-4,9-diazaspiro[5.5]undecane;
3-{1-oxa-4,9-diazaspiro[5.5]undecan-9-yl}-5-phenoxybenzonitrile;
2-{1-oxa-4,9-diazaspiro[5.5]undecan-9-yl}-4-phenoxybenzonitrile;
3-(3-fluorophenoxy)-2-methyl-5-{1-oxa-4,9-diazaspiro[5.5]undecan-9-yl}benzonitrile;
9-[6-(3-fluorophenoxy)-4-(trifluoromethyl)pyridin-2-yl]-1-oxa-4,9-diazaspiro[5.5]undecane;
2-(3-fluorophenoxy)-6-{1-oxa-4,9-diazaspiro[5.5]undecan-9-yl}pyridine-4-carbonitrile;
9-[4-(3-fluorophenoxy)pyrimidin-2-yl]-1-oxa-4,9-diazaspiro[5.5]undecane;
9-(4-methyl-6-phenoxypyrimidin-2-yl)-1-oxa-4,9-diazaspiro[5.5]undecane;
9-[4-(3-fluorophenoxy)-6-methylpyrimidin-2-yl]-1-oxa-4,9-diazaspiro[5.5]undecane;
9-[4-methyl-6-(3-methylphenoxy)pyrimidin-2-yl]-1-oxa-4,9-diazaspiro[5.5]undecane;
3-[(6-methyl-2-{1-oxa-4,9-diazaspiro[5.5]undecan-9-yl}pyrimidin-4-yl)oxy]benzonitrile;
9-[4-(3,5-difluorophenoxy)-6-methylpyrimidin-2-yl]-1-oxa-4,9-diazaspiro[5.5]undecane;
9-[4-phenoxy-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecane;
9-[4-(2-fluorophenoxy)-6-(trifluoromethyl)pyrimidin-2-yl]-1-oxa-4,9-diazaspiro[5.5]undecane;
3-[(2-{1-oxa-4,9-diazaspiro[5.5]undecan-9-yl}-6-(trifluoromethyl)pyrimidin-4-yl)oxy]benzonitrile;
6-(3-fluorophenoxy)-2-{1-oxa-4,9-diazaspiro[5.5]undecan-9-yl}pyrimidine-4-carbonitrile;
9-[4-(3-fluorophenoxy)-6-(methylsulfanyl)pyrimidin-2-yl]-1-oxa-4,9-diazaspiro[5.5]undecane;
9-[4-cyclopropyl-6-(3-fluorophenoxy)pyrimidin-2-yl]-1-oxa-4,9-diazaspiro[5.5]undecane;
9-[4-(3-fluorophenoxy)-6-methoxypyrimidin-2-yl]-1-oxa-4,9 diazaspiro[5.5]undecane;
4-[4-(3-fluorophenoxy)-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecan-3-one;
9-[4-(3-fluorophenoxy)-6-(trifluoromethyl)pyrimidin-2-yl]-1λ6-thia-4,9-diazaspiro[5.5]undecane-1,1-dione;
9-[4-(3-fluorophenoxy)-6-(trifluoromethyl)pyrimidin-2-yl]-1-methyl-1,4,9-triazaspiro[5.5]undecane;
9-[4-(3-fluorophenoxy)-6-(trifluoromethyl)pyrimidin-2-yl]-1,4,9-triazaspiro[5.5]undecane; one;

3-[4-(3-fluorophenoxy)-6-(trifluoromethyl)pyrimidin-2-yl]-7-methyl-3,7,11-triazaspiro[5.6]dodecane;
9-[4-(3-fluorophenoxy)-6-(trifluoromethyl)pyrimidin-2-yl]-4-oxa-1,9-diazaspiro[5.5]undecane;
9-[4,5-difluoro-2-(3-fluorophenoxy)phenyl]-2,9-diazaspiro[5.5]undecane;
3-[4,5-difluoro-2-(3-fluorophenoxy)phenyl]-3,9-diazaspiro[5.5]undecane;
8-[4-(3-fluorophenoxy)-6-(trifluoromethyl)pyrimidin-2-yl]-1,4-dioxa-8,12-diazadispiro[4.0.4$^6$.4$^5$]tetradecane;
2-[4-(3-fluorophenoxy)-6-(trifluoromethyl)pyrimidin-2-yl]-2,7-diazaspiro[4.5]decan-10-one;
8-[4-(3-fluorophenoxy)-6-(trifluoromethyl)pyrimidin-2-yl]-1-oxa-3,8-diazaspiro[4.5]decan-2-one;
2-[4,5-difluoro-2-(3-fluorophenoxy)phenyl]-2,8-diazaspiro[4.5]decane;
8-[4,5-difluoro-2-(3-fluorophenoxy)phenyl]-2,8-diazaspiro[4.5]decane;
8-[3-fluoro-5-(3-fluorophenoxy)phenyl]-2,8-diazaspiro[4.5]decane;
8-[4,5-difluoro-2-(3-fluorophenoxy)phenyl]-1,4-dioxa-8,13-diazadispiro[4.0.4$^6$.4$^5$]tetradecane;
8-[4-(3-fluorophenoxy)-6-(trifluoromethyl)pyrimidin-2-yl]-1,4-dioxa-8,13-diazadispiro[4.0.4$^6$.4$^5$]tetradecane;
2-[4-(3-fluorophenoxy)-6-(trifluoromethyl)pyrimidin-2-yl]-2,8-diazaspiro[4.5]decan-6-ol;
2-[4-(3-fluorophenoxy)-6-(trifluoromethyl)pyrimidin-2-yl]-5-oxa-2,8-diazaspiro[3.5]nonane;
and pharmaceutically acceptable salts and solvates thereof.

Therapeutic Applications

As previously mentioned, the compounds of the present invention are potent inhibitors of dopamine transporters. They are therefore useful in the treatment of disease conditions for which over-activity of a dopamine transporter is a causative factor.

The compounds of the present invention are preferably selective for dopamine transporters over noradrenaline and serotonin transporters. In the present context, the word "selective" means the compound has an IC50 value that is at least 10-fold selective for the dopamine transporter than for each of the noradrenaline and serotonin transporters, preferably at least 20-fold, more preferably at least 30-fold, even more preferably 50-fold, most preferably 100-fold higher for the dopamine transporter than for each of the noradrenaline and serotonin transporters.

Accordingly, the present invention provides a compound of formula (I) for use in therapy.

The present invention also provides for the use of a compound of formula (I) in the manufacture of a medicament for the treatment or prevention of a condition, disease or disorder ameliorated by inhibition of a dopamine transporter.

The present invention also provides a compound of formula (I) for use in the treatment or prevention of a condition, disease or disorder ameliorated by inhibition of a dopamine transporter.

The present invention also provides a method of treatment of a condition, disease or disorder ameliorated by inhibition of a dopamine transporter comprising administration to a subject in need thereof a therapeutically effective amount of a compound of formula (I).

In one aspect, the condition, disease or disorder ameliorated by inhibition of a dopamine transporter includes sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including smoking cessation), eating disorders, chronic fatigue and impulse control disorders.

In a particular aspect, the condition, disease or disorder is selected from ADD, ADHD and binge eating disorder.

In the context of the present invention, references herein to "treatment" include references to curative, palliative and prophylactic treatment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Combination Therapy

When combination therapy is employed, the compounds of the present invention and said combination agents may exist in the same or different pharmaceutical compositions, and may be administered separately, sequentially or simultaneously.

The compounds of the invention may be administered as a combination with at least one other active pharmaceutical ingredient for the treatment of mood disorders, disorders such as depression, refractory depression, bipolar depression, and psychotic depression. Such a pharmaceutical combination may be in the form of a unit dosage form or it may be in the form of a package comprising the at least two active components separately. In a further aspect, the invention relates to such pharmaceutical combinations. In a further aspect, the invention therefore relates to a pharmaceutical combination comprising a therapeutically effective amount of an compound of the invention and a second active substance, for simultaneous or sequential administration.

In an aspect the invention relates to a compound of the invention in combination with another therapeutic agent wherein the other therapeutic agent is selected from:
a tricyclic antidepressant (Amitriptyline, Clomipramine, Doxepin, Imipramine, Trimipramine Desipramine, Nortriptyline, Protriptyline),
tetracyclic antidepressant (Amoxapine, Maprotiline, Mazindol, Mianserin, Mirtazapine, Setiptiline), selective serotonin reuptake inhibitor (Citalopram, Escitalopram, Paroxetine, Fluoxetine, Fluvoxamine, Sertraline),
serotonin antagonist and reuptake inhibitors (Etoperidone, Nefazodone, Trazodone), selective norepinephrine reuptake inhibitor (Atomoxetine, Reboxetine, Viloxazine),
serotonin and norepinephrine reuptake inhibitor (Desvenlafaxine, Duloxetine, Milnacipran, Venlafaxine),
monoamine oxidase inhibitor (Isocarboxazid, Phenelzine, Selegiline, Tranylcypromine, Moclobemide, Pirlindole),
mood stabilisers (Lithium, Valproic Acid, Lamotrigine, Carbamazepine, Oxcarbazepine)
and/or antipsychotics (Clozapine, Olanzapine, Risperidone, Quetiapine, Ziprasidone, Amisulpride, Asenapine, Paliperidone, Iloperidone, Zotepine, Sertindole, Lurasidone, Aripiprazole, Haloperidol, Droperidol, Chlorpromazine, Fluphenazine Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol).

In addition to treating the primary disease symptoms or the therapeutic lag phase, DAT inhibitors may be used adjunctively to treat medication induced sedation, common in diseases such as bipolar depression as well as sexual dysfunction which is a common side effect of antidepressant treatment, particularly SSRIs.

The compounds of the invention may be administered as a combination with at least one other active pharmaceutical ingredient for the treatment of smoking cessation and mitigation of nicotine withdrawal and weight gain. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of a compound of the invention and a second active substance, for simultaneous or sequential administration.

In an aspect, the invention relates to a compound of the invention in combination with another therapeutic agent wherein the other therapeutic agent is selected from:

Nicotine replacement therapies (nicotine patches, nicotine gum, nicotine sprays, nicotine sublingual tablets, nicotine lozenges and nicotine inhalers), nicotinic full/partial agonists (Nicotine, Varenicline, Lobeline), opioid antagonists/inverse agonists (Naloxone, Naltrexone, Buprenorphine).

The compounds of the invention may be administered as a combination with at least one other active pharmaceutical ingredient for the treatment of ADHD. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of a compound of the invention and a second active substance, for simultaneous or sequential administration.

In an aspect, the invention relates to a compound of the invention in combination with another therapeutic agent wherein the other therapeutic agent is selected from:
Norepinephrine reuptake inhibitors (Atomoxetine, Reboxetine, Viloxazine), alpha-adrenoceptor agonists (Guanfacine, Clonidine).

The compounds of the invention may be administered as a combination with at least one other active pharmaceutical ingredient for the treatment of movement disorders such as Parkinson's disease and Restless Leg Syndrome. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of a compound of the invention and a second active substance, for simultaneous or sequential administration.

In an aspect, the invention relates to a compound of the invention in combination with another therapeutic agent wherein the other therapeutic agent is selected from:
A dopamine precursor (L-dopa) a dopaminergic agent (Levodopa-carbidopa, Levodopa-benzerazide), a dopaminergic and anti-cholinergic agent (amantadine), an anti-cholinergic agent (trihexyphenidyl, benztropine, ethoproprazine, or procyclidine), a dopamine agonist (apomorphine, bromocriptine, cabergoline, lisuride, pergolide, pramipexole, or ropinirole), a MAO-B (monoamine oxidase B) inhibitor (selegiline, rasageline or deprenyl0, a COMT (catechol O-methyltransferase) inhibitor (tolcapone or entacapone.
Definitions "Alkyl" is as defined above and includes saturated hydrocarbon residues including:
linear groups of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.
branched groups of between 3 and 6 carbon atoms ($C_3$-$C_6$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.
each optionally substituted as stated above.

"Cycloalkyl" is as defined above and includes monocyclic saturated hydrocarbon of between 3 and 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl. Cycloalkyl is optionally substituted as stated above.

"Alkylene" is a bivalent $C_{1-3}$ straight-chained alkyl radical, such as —$(CH_2)$—, —$(CH_2)_2$—, —$(CH_2)_3$— or a bivalent $C_{3-4}$ branched alkyl radical such as —$CH(CH_3)CH$, $CH_2CH(CH_3)$—, —$CH(CH_3)CH(CH_3)$—. Alkylene is optionally substituted as stated above.

"Alkoxy" is as defined above and includes O-linked hydrocarbon residues including:
linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.
branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.
each optionally substituted as stated above.

"Heteroaryl" is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, pyridinyl, pyridazinyl, pyrimidinyl and pyrazinyl (optionally substituted as stated above). Preferably heteroaryl is selected from pyridyl, pyrazinyl, pyrimidinyl and 1,2,4-triazinyl optionally substituted as stated above. Unless otherwise stated pyrimidinyl refers to 1,3-pyrimidinyl. Unless otherwise stated (e.g. by a chemical formula) when A is pyrimidinyl it is attached to the spiro backbone at the 2-position. Unless other stated when B is pyrimidinyl it is attached to L at the 2-position.

"Heterocyclyl" is defined above. Examples of suitable heterocyclyl groups include aziridinyl, azetidinyl, pyrrolidinyl, imidazolidinyl, imidazolyl, morpholine, thiomorpholine pyrazolidinyl, piperidinyl and piperazinyl (optionally substituted as stated above).

The term "O-linked", such as in "O-linked hydrocarbon residue", means that the hydrocarbon residue is joined to the remainder of the molecule via an oxygen atom.

In groups such as —CN and —$CH_2CH(CH_3)$—, "-" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Compounds of the invention may exist in one or more geometrical, optical, enantiomeric, diastereomeric, conformational and tautomeric forms, including but not limited to cis- and trans-forms, E- and Z-forms, R-, S- and meso-forms, keto- and enol-forms, and conformers. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

An example of a compound of the invention that exhibits diastereoisomerism is 2-[4-(3-fluorophenoxy)-6-(trifluoromethyl)pyrimidin-2-yl]-2,8-diazaspiro[4.5]decan-6-ol. The present invention therefore encompasses all diastereomeric forms of this compound, as illustrated below.

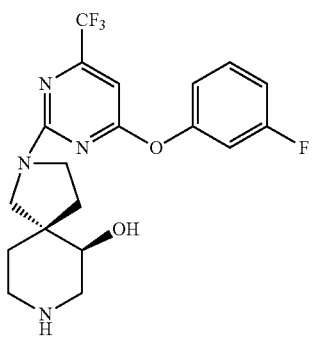

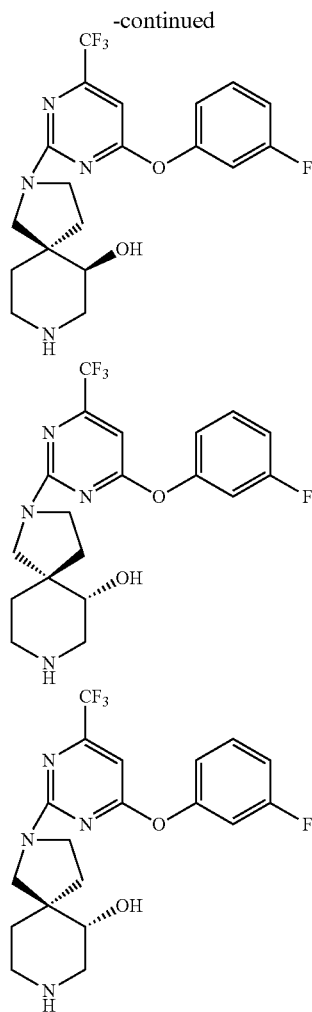

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one aspect, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the routes outlined in the schemes below.

i) Synthesis of Spirocyclic Systems

Scheme A

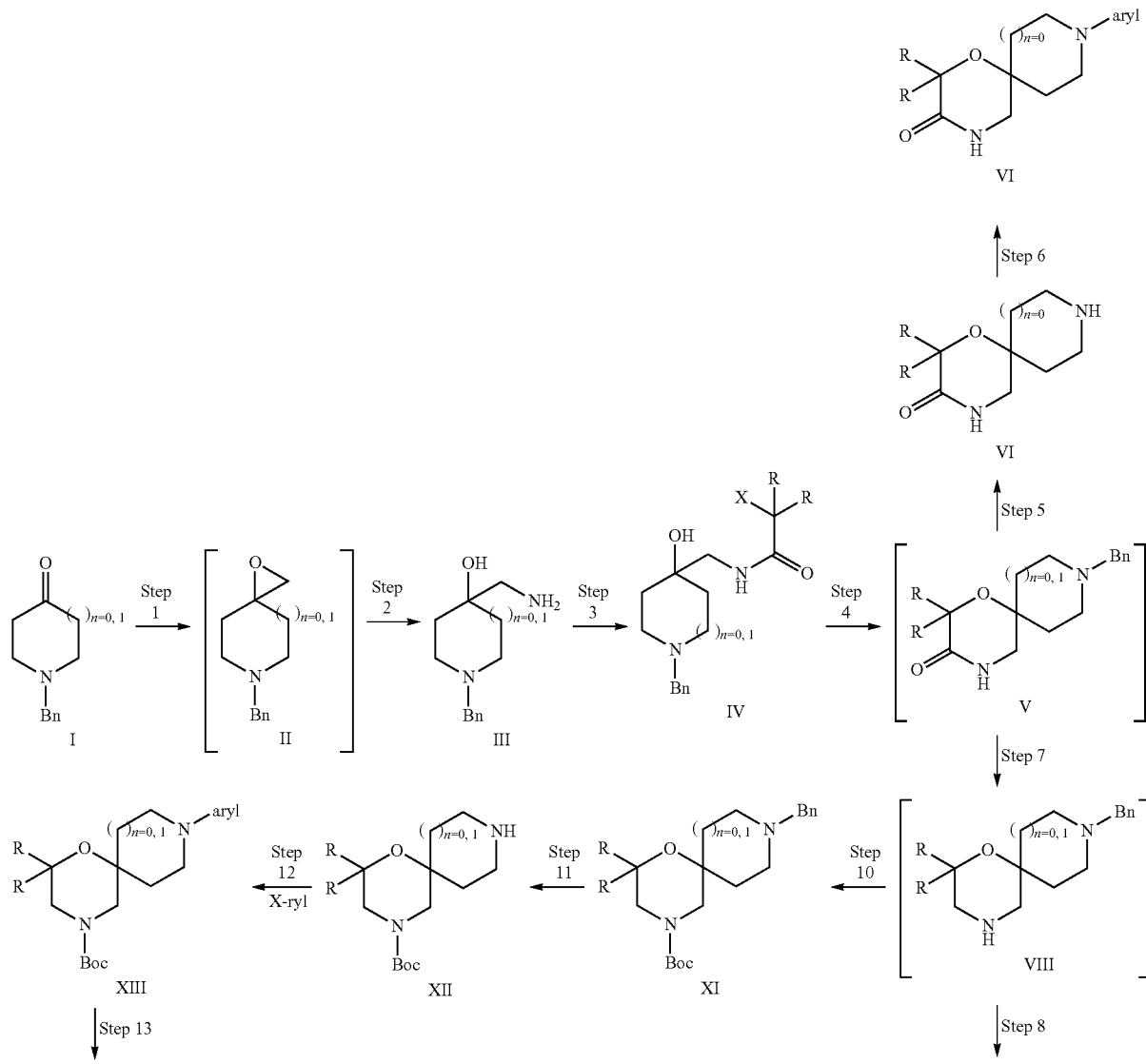

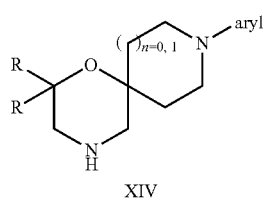

XIV

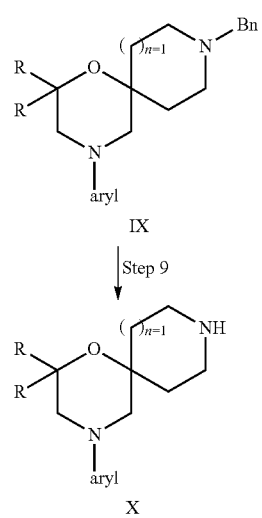

IX

Step 9

X

Step 1

Compound of formula II may be obtained by Corey-Chaykovsky epoxidation of compound I (commercially available from Sigma-Aldrich) using trimethylsulfoxonium iodide and an inorganic base, e.g. NaH, carrying out the reaction in a suitable solvent, such as DMSO, at room temperature. The reaction takes about 1 to about 2 hours to complete.

Step 2

Compound of formula III may be obtained by epoxide opening of compound II using primary amines, such as ammonium hydroxide, carrying out the reaction in a mixture of MeOH/water, at room temperature. The reaction takes about 16 hours to complete.

Step 3 Compound IV may be obtained by acylation of compound III by reaction with an appropriate acylating agent (e.g. chloroacetyl chloride or 2-bromo-2,2-difluoroacetate), with or without a base such as triethylamine, in a suitable solvent, such as dichloromethane or dimethyformamide, at a temperature between 0° C. and room temperature. The reaction takes from 10 min to 12 hours to complete.

Step 4

Compound of formula V can be obtained by ring closure of compound IV in an aprotic solvent, such as THF, in presence of a suitable base, e.g. NaH or tBuOK, at a temperature between room temperature and 70° C. The reaction takes from about 40 min to about 2 hours to complete.

Step 5

Compound of formula VI may be obtained from compound V by removing the benzyl group by hydrogenolysis, e.g. using ammonium formate and palladium on carbon, in a suitable solvent such as methanol under reflux. The reaction takes about 1.5 hour.

Step 6

Compound VII can be obtained from compound V by SnAr substitution with the appropriate aryl halide in a suitable aprotic solvent, e.g. DMSO, in presence of an inorganic base, such as $K_2CO_3$. The reaction proceeds in a temperature of about 50° C. and takes about 1.5 hour.

Step 7

Compound of formula VIII may be obtained by reduction of compound V using a suitable reducing agent, e.g. $LiAlH_4$ or $BH_3Me_2S$ complex in THF, carrying out the reaction in a suitable solvent, such as THF, and at elevate temperature (preferably around 60° C. or reflux). The reaction takes about from 40 min to around 2 hours to complete.

Step 8

Compound IX can be obtained from compound VIII by SnAr substitution with the appropriate aryl halide in a suitable aprotic solvent, e.g. DMSO, in presence of an inorganic base, such as $K_2CO_3$. The reaction proceeds in a temperature to about 90° C. and takes about 2 hours.

Step 9

Compound of formula X may be obtained from compound IXI by removing the benzyl group by hydrogenolysis, e.g. using ammonium formate and palladium on carbon, in a suitable solvent such as methanol under reflux. The reaction takes about 1 hour.

Step 10

Compound of formula XI may be obtained by N-protection of compound VIII under standard literature conditions such as by reaction with Di-tert-butyl dicarbonate, with or without the presence of a suitable base such as triethylamine, carrying out the reaction in a suitable solvent, e.g. DCM, typically at room temperature. Alternatively the reaction can be performed by reaction with Di-tert-butyl dicarbonate in a mixture of THF/water, in presence of a suitable base, such as $Na_2CO_3$, at a temperature between 0° C. and room temperature. The reaction takes about 1 to about 16 hours to complete.

Step 11

Compound of formula XII may be obtained from compound XI by removing the benzyl group by hydrogenolysis, e.g. using ammonium formate and palladium on carbon, in a suitable solvent such as methanol under reflux. The reaction takes from about 1 hour to about 1.5 hour.

Step 12

Compound XIII can be obtained from compound XII by SnAr substitution with the appropriate aryl halide in a suitable aprotic solvent, e.g. DMSO, in presence of an inorganic base, such as $K_2CO_3$. The reaction proceeds in a temperature range of about 80 to about 100° C. and takes about 1 to about 18 hours. Alternatively the compound XIII can be obtained via Buchwald reaction with the appropriate aryl halide in presence of suitable transition metal catalyst, e.g. Pd$_2$(dba)$_3$, a suitable ligand such as BINAP, a suitable base, such as tBuONa and like, in a suitable solvent, e.g. toluene. The reaction is carrying out at a temperature around 100° C. and takes from about 12 hours to about 18 hours to complete.

Step 13

Compound XIV can be obtained from compound XIII by removing the Boc group under acidic conditions, e.g. TFA in dichloromethane solution, typically at room temperature. The reaction takes about 1 hour.

e.g. using ammonium formate and palladium on carbon, in a suitable solvent such as methanol under reflux. The reaction takes about 1 hour.

Step 6

Compound VII can be obtained from compound VI by SnAr substitution with the appropriate aryl halide in a suitable aprotic solvent, e.g. DMSO, in presence of an inorganic base, such as K$_2$CO$_3$. The reaction proceeds in a temperature range of about 80 to about 100° C. and takes about 1 to about 18 hours. Alternatively the compound XIII Scheme B

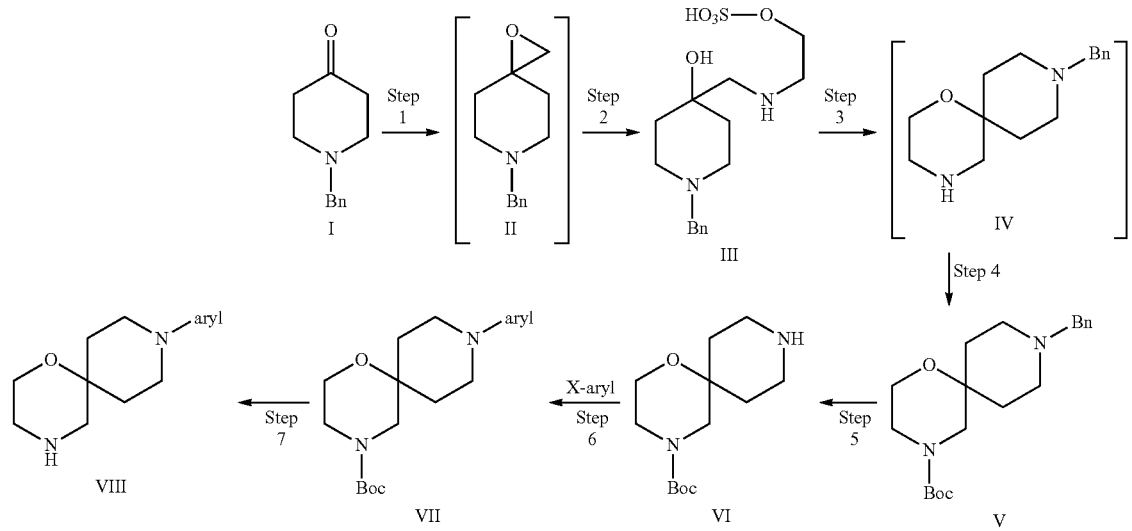

Step 1

Compound of formula II may be obtained by Corey-Chaykovsky epoxidation of compound I (commercially available from Sigma-Aldrich) using trimethylsulfoxonium iodide and a inorganic base, e.g. NaH, carrying out the reaction in a suitable solvent, such as DMSO, at room temperature. The reaction takes about 1 to about 2 hours to complete.

Step 2

Compound of formula III may be obtained by epoxide opening of compound II using 2-aminoethylhydrogensulfate carrying out the reaction in a mixture of MeOH/water in presence of an organic base, such as triethylamine, typically at a temperature of about 50° C. The reaction takes about 36 hours to complete.

Step 3

Compound of formula IV may be obtained by ring closure of compound III in presence of a suitable base, e.g. NaOH, carrying out the reaction in a mixture of THF/EtOH, typically at a temperature of about 50° C. The reaction takes about 5 hours to complete.

Step 4

Compound of formula V may be obtained by N-protection of compound IV under standard literature conditions such as by reaction with Di-tert-butyl dicarbonate, carrying out the reaction in a suitable solvent, e.g. dichloromethane. The reaction proceeds typically at room temperature and takes about 1.5 hour to complete.

Step 5

Compound of formula VI may be obtained from compound V by removing the benzyl group by hydrogenolysis, can be obtained via Buchwald reaction with the appropriate aryl halide in presence of suitable transition metal catalyst, e.g. Pd$_2$(dba)$_3$, a suitable ligand such as BINAP, a suitable base, such as tBuONa and like, in a suitable solvent, e.g. toluene. The reaction is carrying out at a temperature about 100° C. and takes from about 12 hours to about 18 hours to complete.

Step 7

Compound VIII can be obtained from compound VII by removing the Boc group under acidic conditions, e.g. TFA in dichloromethane solution. The reaction takes about 1 hour to complete.

Scheme C1

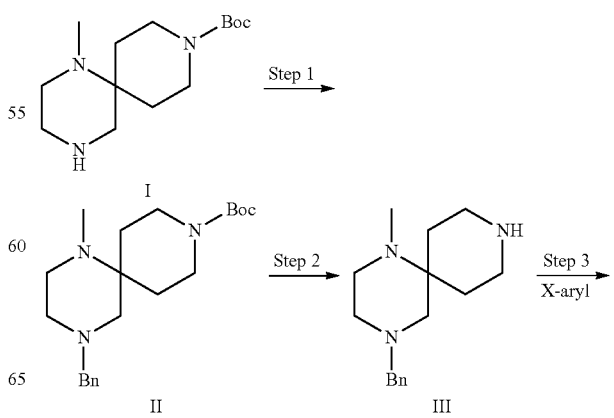

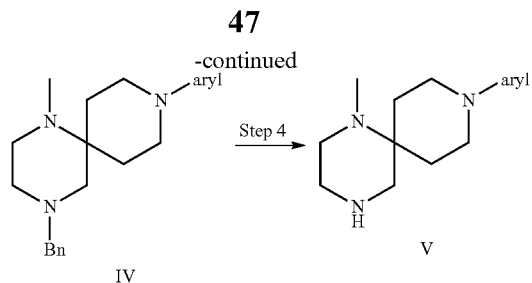

Step 1

Compound of formula II may be obtained by reductive amination of compound I (commercially available from Sigma-Aldrich) using benzaldehyde, carrying out the reaction in a suitable solvent, such as dichloromethane, in presence of an acid, such as $CH_3COOH$, and a suitable reducing agent, e.g. $Na(AcO)_3BH$, generally at room temperature. The reaction takes about 12 hours to complete.

Step 2

Compound III can be obtained from compound II by removing the Boc group under acidic conditions, e.g. TFA in dichloromethane solution, typically at room temperature. The reaction takes about 2 hours.

Step 3

Compound VII can be obtained from compound V by SnAr substitution with the appropriate aryl halide in a suitable aprotic solvent, e.g. DMSO, in presence of an inorganic base, such as $K_2CO_3$. The reaction proceeds at a temperature of about 90° C. and takes about 1.5 hour.

Step 4

Compound of formula V may be obtained from compound IV by removing the benzyl group by hydrogenolysis, e.g. using ammonium formate and palladium on carbon, in a suitable solvent such as methanol under reflux. The reaction takes about 2 hours.

Step 1

Compound of formula II may be obtained by reduction of compound I (commercially available from Activate Scientific) using a suitable reducing agent, e.g. $LiAlH_4$, carrying out the reaction in a suitable solvent, such as THF under reflux. The reaction takes about 2 hours to complete.

Step 2

Compound III may be obtained by acylation of compound II by reaction with an appropriate acylating agent (e.g. chloroacetyl chloride), under Schotten-Baumann conditions, e.g. in a mixture of dichloromethane and aqueous solution of NaOH at a temperature between 0° C. and room temperature. The reaction takes about 2 hours to complete.

Step 3

Compound of formula IV can be obtained by ring closure of compound III carrying out the reaction in an aprotic solvent, such as THF, in presence of a suitable base, e.g. tBuOK, at room temperature. The reaction takes about 1.5 hour to complete.

Step 4

Compound of formula V may be obtained by reduction of compound IV using a suitable reducing agent, e.g. $LiAlH_4$, carrying out the reaction in a suitable solvent, such as THF at reflux temperature. The reaction takes around 2 hours to complete.

Step 5

Compound of formula VI may be obtained by N-protection of compound V under standard literature conditions such as by reaction with Di-tert-butyl dicarbonate, carrying out the reaction in a suitable solvent, e.g. dichloromethane, typically at room temperature. The reaction takes about 12 hours.

Step 6

Compound of formula VII may be obtained from compound VI by removing the benzyl group by hydrogenolysis, Scheme C2

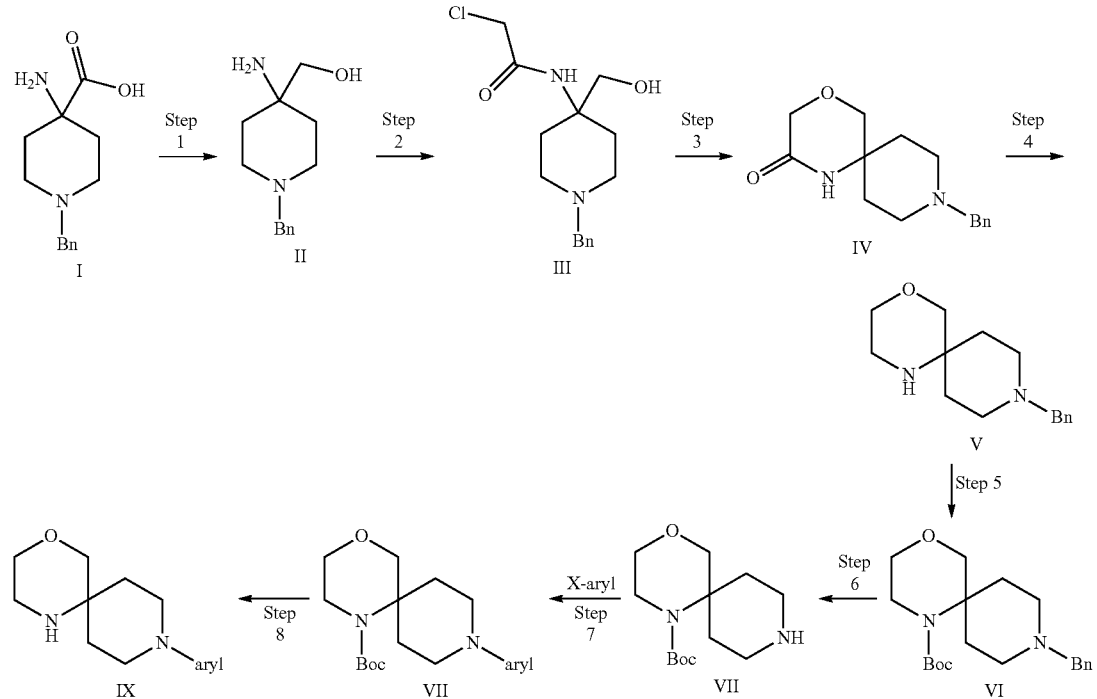

e.g. using ammonium formate and palladium on carbon, in a suitable solvent such as methanol under reflux. The reaction takes about 1 hour.

Step 7

Compound VIII can be obtained from compound VII by SnAr substitution with the appropriate aryl halide in a suitable aprotic solvent, e.g. DMSO, in presence of an inorganic base, such as $K_2CO_3$. The reaction proceeds at a temperature of about 90° C. and takes about 2 hours.

Step 8

Compound IX can be obtained from compound VIII by removing the Boc group under acidic conditions, e.g. TFA in dichloromethane solution, typically at room temperature. The reaction takes about 1 hour.

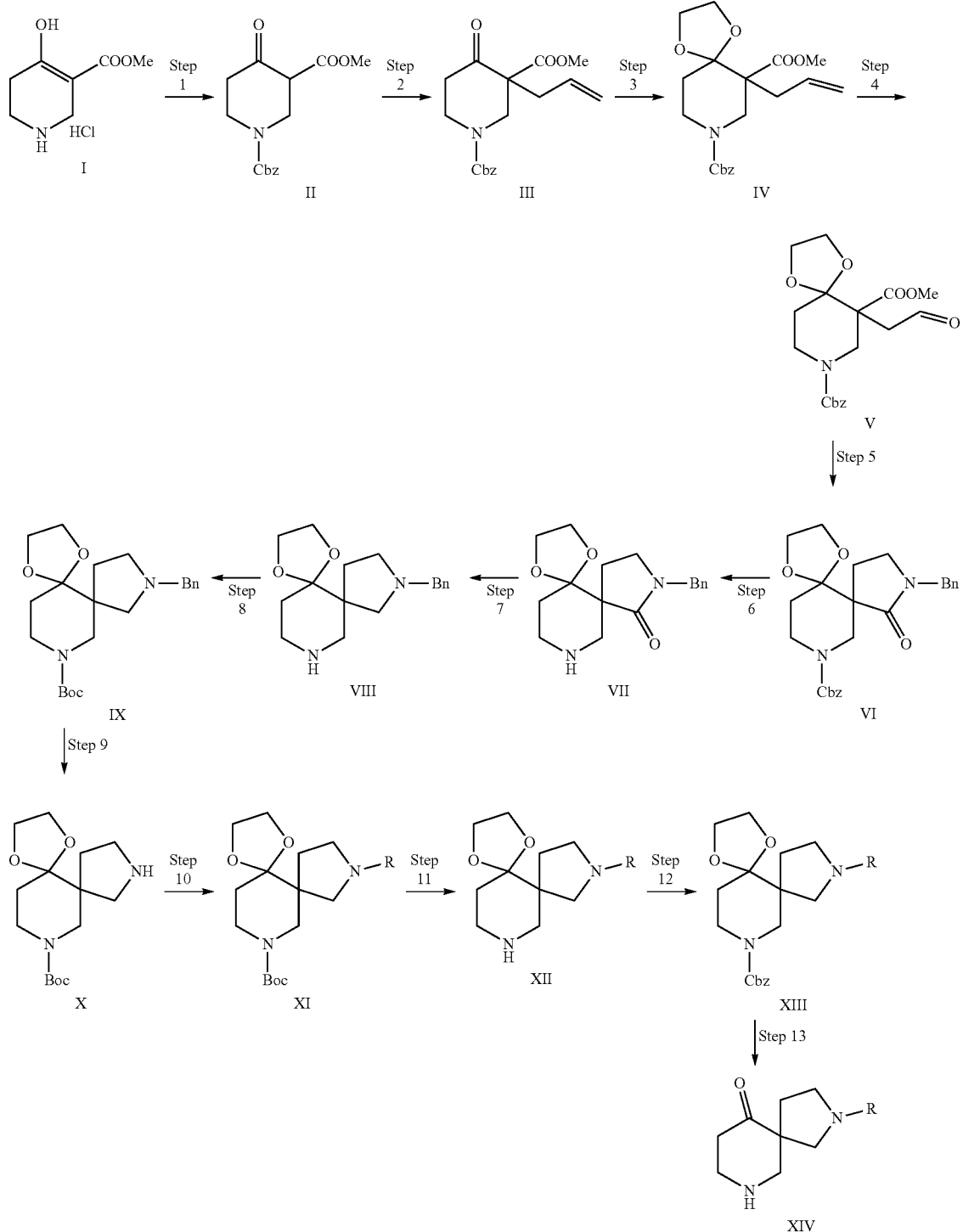

Scheme D

Step 1

Compound of formula II may be obtained by N-protection of compound I (commercially available from Sigma-Aldrich) under standard literature conditions such as by reaction with benzyl chloroformate, with the presence of a suitable base such as triethylamine, carrying out the reaction in a suitable solvent, e.g. DCM, typically at room temperature. The reaction takes about 12 hours to complete.

Step 2

Compound of formula III may be obtained by alkylation of compound II with allyl bromide, after deprotonation using a suitable base, such as NaH, in a suitable solvent, e.g. DMF, carrying out the reaction at a temperature between 0° C. and room temperature. The reaction takes about 4 hours to complete.

Step 3

Compound of formula IV may be obtained by ketone protection of compound III by reaction with ethylene glycol, in presence of catalytic amount of p-Toluensulfonic in a suitable solvent, such as toluene, using Dean Stark apparatus, typically at reflux temperature. The reaction takes about 16 hours to complete.

Step 4

Compound of formula V may be obtained by oxidation of compound IV using an aqueous solution of $OsO_4$ in a mixture of THF/water, in presence of $NaIO_4$, carrying out the reaction typically at room temperature. The reaction takes about 1 hour to complete.

Step 5

Compound of formula VI may be obtained by reductive amination and of compound V with a suitable primary amine, such as benzylamine, in a suitable solvent, such as THF, in presence of a reducing agent like $Na(AcO)_3BH$, followed by spontaneous lactam ring closure. The reaction is carried out typically at room temperature and takes about 12 hours to complete.

Step 6

Compound of formula VII can be obtained by N-deprotection of compound VI with a suitable reducing system, such as hydrogenation over palladium catalyst on carbon, and the like, in a suitable solvent, e.g. MeOH at a temperature of about 25° C., over a period of about 0.5 hour.

Step 7

Compound of formula VIII may be obtained by reduction of compound VII using a suitable reducing agent, e.g. $LiAlH_4$, carrying out the reaction in a suitable solvent, such as THF at elevate temperature (preferably around 65° C.). The reaction takes about 4 hours to complete.

Step 8

Compound of formula IX may be obtained by N-protection of compound VIII under standard literature conditions such as by reaction with Di-tert-butyl dicarbonate in a mixture of THF/water, in presence of a suitable base, such as $Na_2CO_3$, at a temperature around 0° C. The reaction takes about 1 hour to complete.

Step 9

Compound of formula X may be obtained from compound IX by removing the benzyl group by hydrogenolysis, e.g. using ammonium formate and palladium on carbon, in a suitable solvent such as methanol under reflux. The reaction takes about 1 hour.

Step 10

Compound XI can be obtained from compound X by SnAr substitution with the appropriate aryl halide in a suitable aprotic solvent, e.g. DMSO, in presence of an inorganic base, such as $K_2CO_3$. The reaction proceeds in a temperature range of about 80 to about 100° C. and takes about 1 hour. Alternatively the compound X can be obtained from Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes about 12 hours to complete.

Step 11

Compound XII can be obtained from compound XI by removing the Boc group under acidic conditions, e.g. TFA in dichloromethane solution, typically at room temperature. The reaction takes about 1 hour.

Step 12

Compound of formula XIII may be obtained by N-protection of compound XII under standard literature conditions such as by reaction with benzyl chloroformate, with the presence of a suitable base such as triethylamine, carrying out the reaction in a suitable solvent, e.g. DCM, typically at room temperature. The reaction takes about 1 to about 3 hours to complete.

Step 13

Compound XIV can be obtained from compound XIII by ketal cleavage under acidic conditions, e.g. $HClO_4$ in dichloromethane solution, typically at room temperature. The reaction takes about 2 to 3 hours to complete.

Scheme E

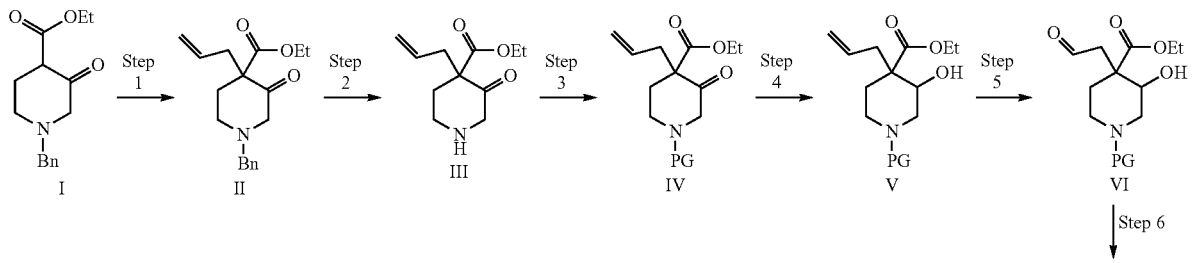

Step 6

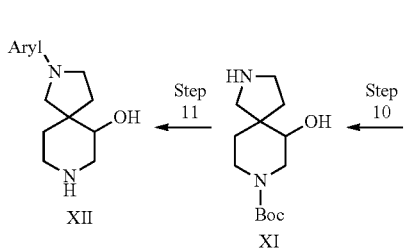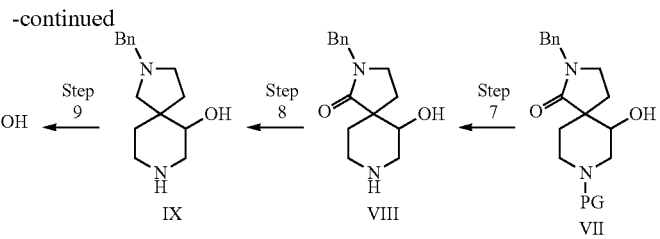

Step 1
Compound of formula II may be obtained by alkylation of compound I (commercially available from Sigma-Aldrich) with allyl bromide, after deprotonation using a suitable base, such as tBuOK, in a suitable aprotic solvent, e.g. THF, carrying out the reaction at a temperature between 0° C. and room temperature. The reaction takes about 12 hours to complete.

Step 2
Compound of formula III may be obtained by removing the benzyl group treating compound II with 1-chloroethyl chloroformate in a suitable solvent, such as dichloroethane, typically at reflux temperature for about 14 hours, followed by reflux in MeOH for about 1.5 hour.

Step 3
Compound of formula IV may be obtained by N-protection of compound III under standard literature conditions such as by reaction with a suitable protecting agent (e.g. as benzyl chloroformate or Di-tert-butyl dicarbonate), with the presence of a suitable base, such as triethylamine or diisopropylamine, carrying out the reaction in a suitable solvent, e.g. DCM, typically at room temperature. The reaction takes about 2 hours to complete.

Step 4
Compound of formula V may be obtained by reduction of compound IV using a suitable reducing agent, e.g. NaBH$_4$, carrying out the reaction in a suitable solvent, such as MeOH at room. The reaction takes about 1 hour to complete.

Step 5
Compound of formula VI may be obtained by oxidation of compound V using a solution of OsO$_4$, in water or tBuOH, in a mixture of THF/water, in presence of NaIO$_4$, carrying out the reaction typically at room temperature. The reaction takes about 1 hour to complete.

Step 6
Compound of formula VII may be obtained by reductive amination and of compound VI with a suitable primary amine, such as benzylamine, in a suitable solvent, such as THF, in presence of a reducing agent like Na(AcO)$_3$BH, followed by spontaneous lactam ring closure. The reaction is carried out typically at room temperature and takes about 12 to 48 hours to complete.

Step 7
Compound of formula VIII can be obtained by N-deprotection of compound VII with an appropriate method, e.g. with a reducing system when PG is Cbz (such as hydrogenation over palladium catalyst on carbon, and the like, in a suitable solvent, e.g. MeOH at a temperature of about 25° C., over a period of about 12 hours), or under acidic conditions when PG is Boc (e.g. TFA in dichloromethane solution, typically at room temperature, the reaction takes about 1 hour).

Step 8
Compound of formula IX may be obtained by reduction of compound VIII using a suitable reducing agent, e.g. LiAlH$_4$, carrying out the reaction in a suitable solvent, such as THF at reflux temperature. The reaction takes from about 1 to about 3 hours to complete.

Step 9
Compound of formula X may be obtained by N-protection of compound IX under standard literature conditions such as by reaction with Di-tert-butyl dicarbonate, with or without the presence of a suitable base such as triethylamine, carrying out the reaction in a suitable solvent, e.g. DCM, typically at room temperature. The reaction takes about 2 hours.

Step 10
Compound of formula XI may be obtained from compound X by removing the benzyl group by hydrogenolysis, e.g. using ammonium formate and palladium on carbon, in a suitable solvent such as methanol under reflux. The reaction takes about 1 hour.

Step 11
Compound XII can be obtained from compound XI by SnAr substitution with the appropriate aryl halide in a suitable aprotic solvent, e.g. DMSO, in presence of an inorganic base, such as K$_2$CO$_3$ (the reaction proceeds in a temperature range of about 25 to about 100° C. and takes about 1 to 2 hours), and followed by Boc removal under acidic conditions, e.g. TFA in dichloromethane solution, typically at room temperature. The reaction takes about 1 hour.

Scheme F

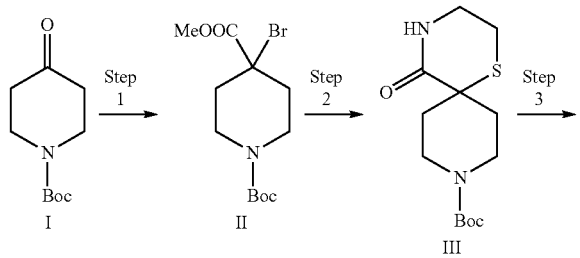

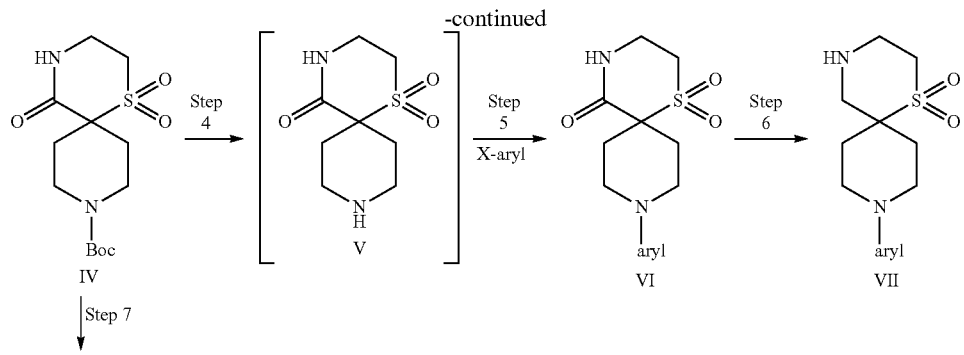

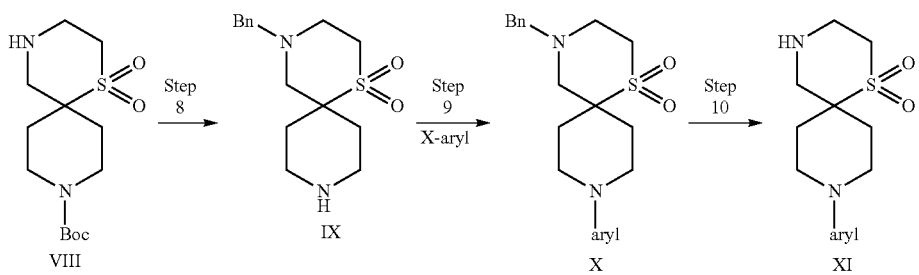

Step 1

Compound of formula II may be obtained from compound I (commercially available from Sigma-Aldrich) by reaction with bromoform, in a mixture of t-BuOH/water, in presence of a suitable base, such as LiOH $H_2O$ and a phase transfer catalyst, e.g. benzyltriethylammonium chloride. The reaction is carried out at room temperature and takes about 72 hours to complete.

Step 2

Compound of formula III may be obtained by esterification of compound II, e.g. by reaction with Trimethylsilyldiazomethane in a mixture toluene/methanol at room temperature for 3 hours, followed by cyclisation with 2-aminoethanthiol in basic conditions, such as KOH in n-butanol. The reaction proceeds at reflux temperature and takes about 48 hours to complete.

Step 3

Compound of formula IV may be obtained by oxidation of compound III with a suitable oxidant, such as 3-chloroperbenzoic acid, in a suitable solvent, such as dichloromethane, at a temperature between 0° C. and room temperature. The reaction takes about 2 hours to complete.

Step 4

Compound V can be obtained from compound IV by removing the Boc group under acidic conditions, e.g. TFA in dichloromethane solution, typically at room temperature. The reaction takes about 1 hour.

Step 5

Compound VI can be obtained from compound V by SnAr substitution with the appropriate aryl halide in a suitable aprotic solvent, e.g. DMSO, in presence of an inorganic base, such as $K_2CO_3$. The reaction proceeds at a temperature of about 100° C. and takes about 1 hour.

Step 6

Compound of formula VII may be obtained by reduction of compound VI using a suitable reducing agent, e.g. Borane THF complex, carrying out the reaction in a suitable solvent, such as THF, at elevate temperature (preferably to reflux temperature) for about 16 hours, followed by treatment with methanol at a temperature of 50° C. for about 2 hours and treatment with $NaBH_4$ in methanol for 12 hours.

Step 7

Compound of formula VIII may be obtained by reduction of compound IV using a suitable reducing agent, e.g. Borane THF complex, carrying out the reaction in a suitable solvent, such as THF, at elevate temperature (preferably around 50° C.) for about 2 hours, followed by treatment with methanol at a temperature of 40° C. for about 2 hours.

Step 8

Compound of formula IX may be obtained by reductive amination of compound VIII using benzaldehyde, carrying out the reaction in a suitable solvent, such as dichloromethane, and with a suitable reducing agent, e.g. $Na(AcO)_3BH$ at room temperature for 16 hours, followed by removing the Boc group under acidic conditions, e.g. TFA in dichloromethane solution, typically at room temperature. The reaction takes about 1 hour.

Step 9

Compound X can be obtained from compound IX by Buchwald reaction with the appropriate aryl halide in presence of suitable transition metal catalyst, e.g. $Pd_2(dba)_3$, a suitable ligand such as BINAP, a suitable base, such as t-BuONa and like, in a suitable solvent, e.g. toluene. The reaction is carrying out at a temperature about 100° C. and takes about 12 hours to complete.

Step 10

Compound XI can be obtained from compound X by removing the benzyl group by hydrogenolysis with a suitable reducing system, such as hydrogenation over palladium catalyst on carbon, and the like, in a suitable solvent, e.g. MeOH at a temperature of about 25° C., over a period of about 2.5 hours.

Scheme G

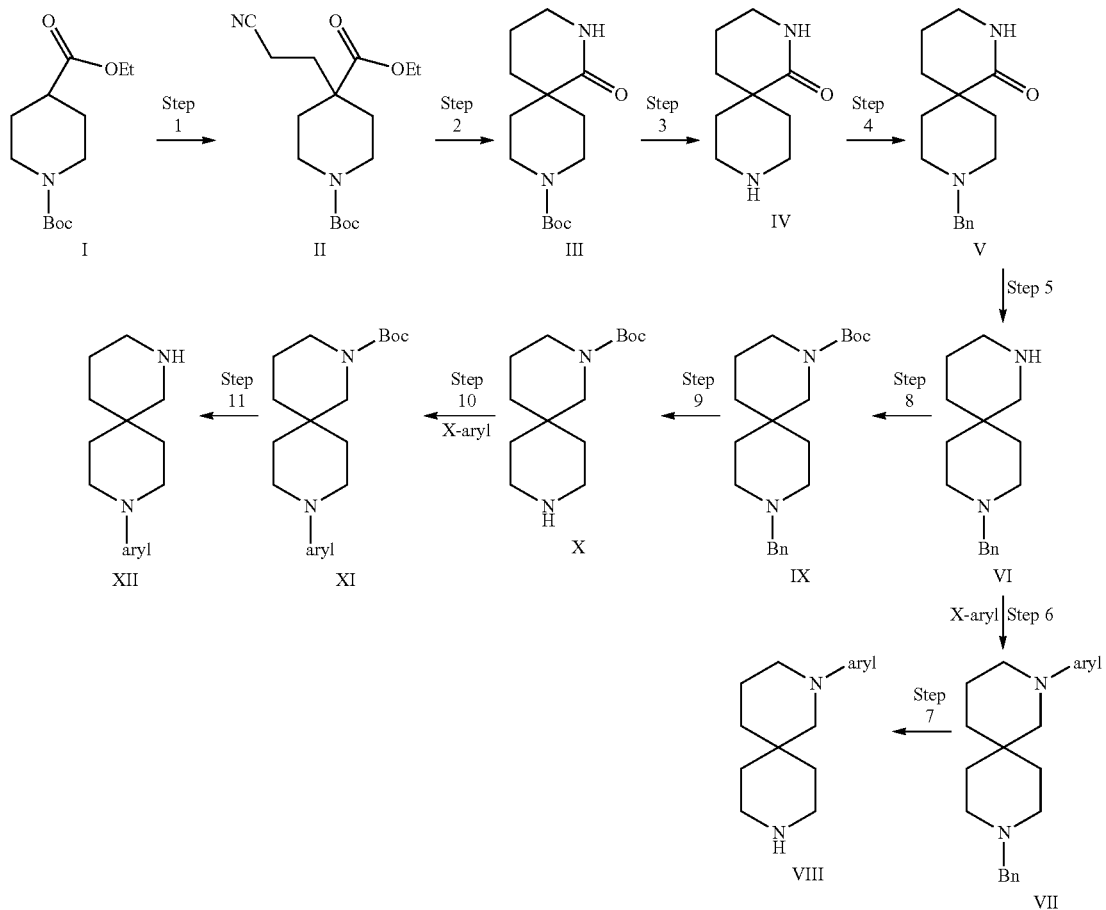

Step 1
Compound of formula II may be obtained by alkylation of compound I (commercially available from Sigma-Aldrich) with 3-bromopropanenitrile, after deprotonation using a suitable base, such as LDA, in a suitable solvent, e.g. THF, carrying out the reaction at a temperature between −78° C. and −30° C. The reaction takes about 4.5 hours to complete.

Step 2
Compound of formula III may be obtained by nitrile reduction of compound II with a suitable reducing system, such as high pressure hydrogenation over $PtO_2$, in acid condition, such as a solution in $CH_3COOH$, typically for 12 hours at room temperature, followed by unusual lactam ring closure in a mixture of MeOH/THF in presence of LiOH $H_2O$. The reaction is carried out at 50° C. and takes about 12 hours to complete.

Step 3
Compound IV can be obtained from compound III by removing the Boc group under acidic conditions, e.g. HCl in dioxane solution, typically at room temperature. The reaction takes about 6 hours.

Step 4
Compound of formula V may be obtained by reductive amination of compound IV using benzaldehyde, carrying out the reaction in a suitable solvent, such as DCM, and a suitable reducing agent, e.g. $Na(AcO)_3BH$ at room temperature. The reaction takes about 16 hours to complete.

Step 5
Compound of formula VI may be obtained by reduction of compound V using a suitable reducing agent, e.g. $LiAlH_4$, carrying out the reaction in a suitable solvent, such as THF at reflux temperature. The reaction takes about 1 hour to complete.

Step 6
Compound VII can be obtained from compound VI by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 115° C. and takes about 12 hours to complete.

Step 7
Compound of formula VIII may be obtained by removing the benzyl group treating compound VII with 1-chloroethyl chloroformate in a suitable solvent, such as dichloromethane, in presence of a suitable base, e.g. diisopropylamine, typically at reflux temperature for about 2 hours, followed by reflux in MeOH for about 12 hours.

Step 8
Compound of formula IX may be obtained by N-protection of compound VI under standard literature conditions such as by reaction with Di-tert-butyl dicarbonate in a mixture of THF/water, in presence of a suitable base, such as $Na_2CO_3$, at a temperature around 0° C. The reaction takes about 1 hour to complete.

Step 9

Compound of formula X can be obtained by N-deprotection of compound IX with a suitable reducing system, such as hydrogenation over palladium catalyst on carbon, and the like, in a suitable solvent, e.g. MeOH at a temperature of about 25° C., over a period of about 7 hours.

Step 10

Compound XI can be obtained from compound X by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 115° C. and takes about 12 hours to complete.

Step 11

Compound XII can be obtained from compound XI by removing the Boc group under acidic conditions, e.g. TFA in dichloromethane solution, typically at room temperature. The reaction takes about 1 hour.

Scheme H1

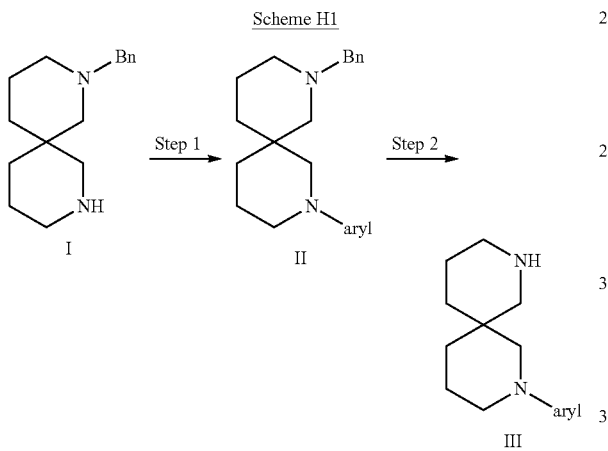

Step 1

The compound II can be obtained from compound I (commercially available from ChemBridge) by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes about 12 hours to complete.

Step 2

Compound of formula III may be obtained by removing the benzyl group treating compound II with 1-chloroethyl chloroformate in a suitable solvent, such as dichloromethane, in presence of a suitable base, e.g. diisopropylamine, typically at reflux temperature for about 2 hours, followed by overnight reflux in MeOH.

Scheme H2

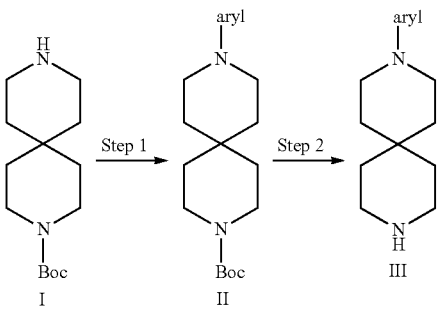

Step 1

The compound II can be obtained from compound I (commercially available from ChemBridge) by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes about 12 hours to complete.

Step 2

Compound III can be obtained from compound II by removing the Boc group under acidic conditions, e.g. TFA in dichloromethane solution, typically at room temperature, usually for 1 hour, and following treatment with a reducing agent, such as $NaBH_4$, in a suitable solvent, such as methanol, for about 12 hours.

Scheme I

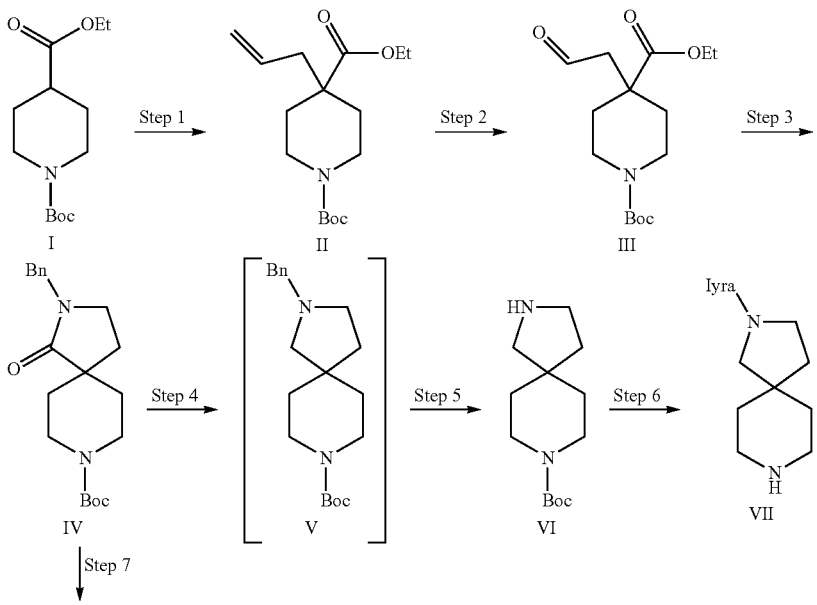

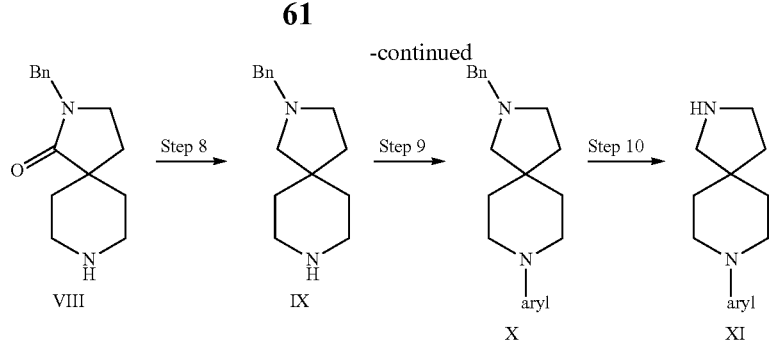

Step 1
Compound of formula II may be obtained by alkylation of compound I (commercially available from Sigma-Aldrich) with allyl bromide, after deprotonation using a suitable base, such as LiHMDS, in a suitable aprotic solvent, e.g. THF, carrying out the reaction at a temperature between −78° C. and room temperature. The reaction takes about 12 hours to complete.

Step 2
Compound of formula III may be obtained by oxidation of compound II using an aqueous solution of $OsO_4$, in a mixture of THF/water, in presence of $NaIO_4$, carrying out the reaction typically at room temperature. The reaction takes about 3 hours to complete.

Step 3
Compound of formula IV may be obtained by reductive amination and of compound III with a suitable primary amine, such as benzylamine, in a suitable solvent, such as THF, in presence of a reducing agent like $Na(AcO)_3BH$, followed by spontaneous lactam ring closure. The reaction is carried out typically at room temperature and takes about 12 to complete.

Step 4
Compound of formula V may be obtained by reduction of compound IV using a suitable reducing agent, e.g. $LiAlH_4$, carrying out the reaction in a suitable solvent, such as THF at a temperature between −20° C. to room temperature. The reaction takes about 2 hours to complete.

Step 5
Compound of formula VI may be obtained from compound V by removing the benzyl group by hydrogenolysis, e.g. using ammonium formate and palladium on carbon, in a suitable solvent such as methanol under reflux. The reaction takes about 1 hour.

Step 6
Compound VII can be obtained from compound VI by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes from about 12 hours to complete.

Step 7
Compound VIII can be obtained from compound IV by removing the Boc group under acidic conditions, e.g. TFA in dichloromethane solution, typically at room temperature. The reaction takes about 1 hour.

Step 8
Compound of formula IX may be obtained by reduction of compound VIII using a suitable reducing agent, e.g. $LiAlH_4$, carrying out the reaction in a suitable solvent, such as THF at reflux temperature. The reaction takes to about 2 hours to complete.

Step 9
Compound X can be obtained from compound IX via Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes about 12 hours to complete.

Step 10
Compound of formula XI can be obtained by N-deprotection of compound X by removing the benzyl group by hydrogenolysis, e.g. in hydrogen atmosphere or with ammonium formate in presence of palladium on carbon, in a suitable solvent such as methanol. The reaction is carried out at a temperature between about 25° C. to about 60° C. The reaction takes from about 1 to about 12 hours.

Scheme L1

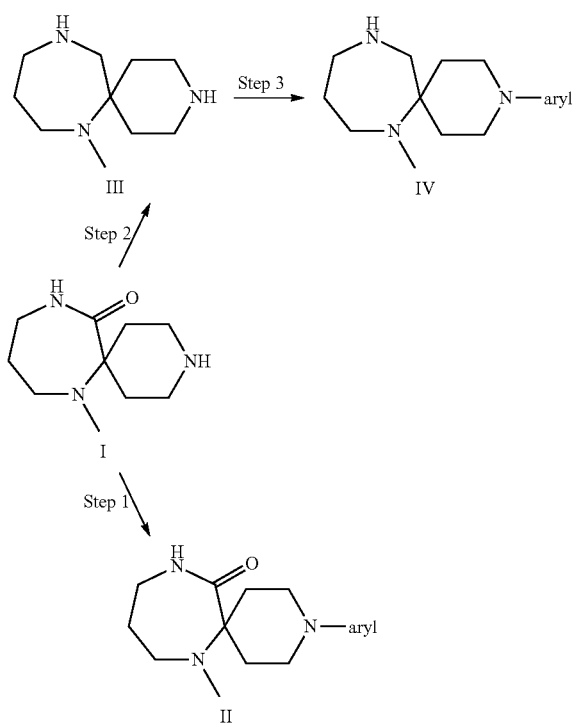

Step 1
Compound II can be obtained from compound I (commercially available from Sigma-Aldrich) by SnAr substitution with the appropriate aryl halide in a suitable aprotic solvent, e.g. DMSO, in presence of an inorganic base, such as K₂CO₃. The reaction proceeds in a temperature of about 60° C. and takes about 12 hours.

Step 2

Compound of formula III may be obtained by reduction of compound I (commercially available from Sigma-Aldrich) using a suitable reducing agent, e.g. LiAlH₄, carrying out the reaction in a suitable solvent, such as THF under reflux. The reaction takes about 52 hours to complete.

Step 3

Compound II can be obtained from compound IV by SnAr substitution with the appropriate aryl halide in a suitable aprotic solvent, e.g. DMSO, in presence of an inorganic base, such as K₂CO₃. The reaction proceeds in a temperature of about 70° C. and takes about 2 hours

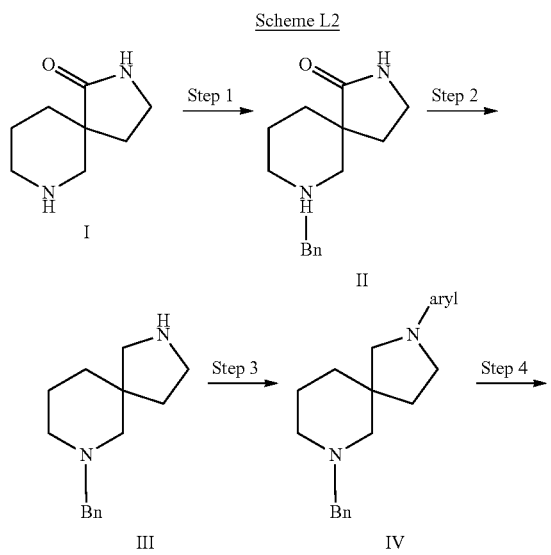

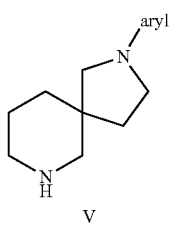

Step 1

Compound of formula II may be obtained by reductive amination of compound I (commercially available from Bepharm Limited) using benzaldehyde, carrying out the reaction in a suitable solvent, such as DCM, in presence a suitable reducing agent, e.g. Na(AcO)₃BH at room temperature. The reaction takes about 12 hours to complete.

Step 2

Compound of formula III may be obtained by reduction of compound II using a suitable reducing agent, e.g. LiAlH₄, carrying out the reaction in a suitable solvent, such as THF under reflux. The reaction takes about 1 hour to complete.

Step 3

The compound IV can be obtained from compound III via Buchwald reaction with the appropriate aryl halide in the presence of suitable transition metal catalyst, e.g. Pd₂(dba)₃, a suitable ligand such as BINAP, a suitable base, such as tBuONa and like, in a suitable solvent, e.g. toluene. The reaction is carrying out at a temperature about 115° C. and takes about 12 hours to complete.

Step 4

Compound of formula V may be obtained from compound IV by removing the benzyl group by hydrogenolysis, e.g. using ammonium formate and palladium on carbon, in a suitable solvent such as methanol under reflux. The reaction takes about 1 hour.

Scheme M

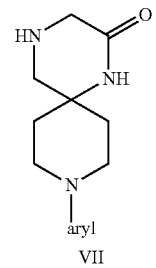

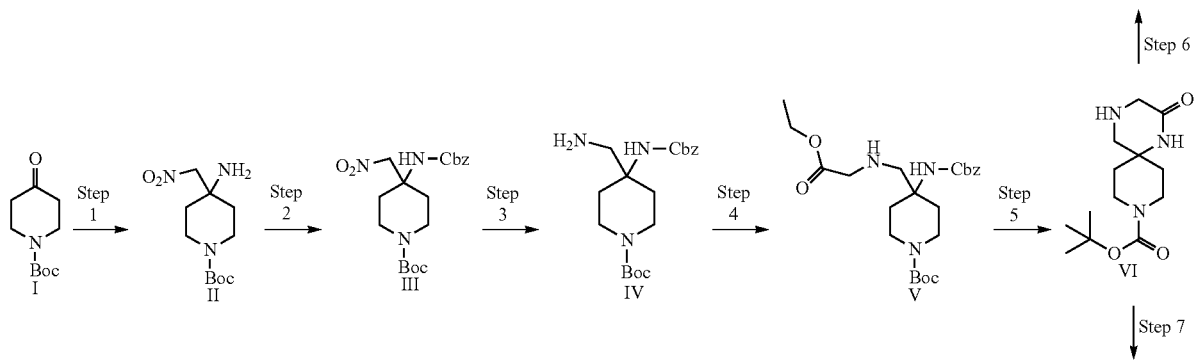

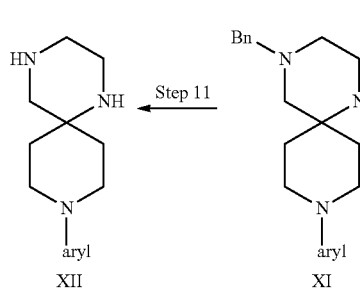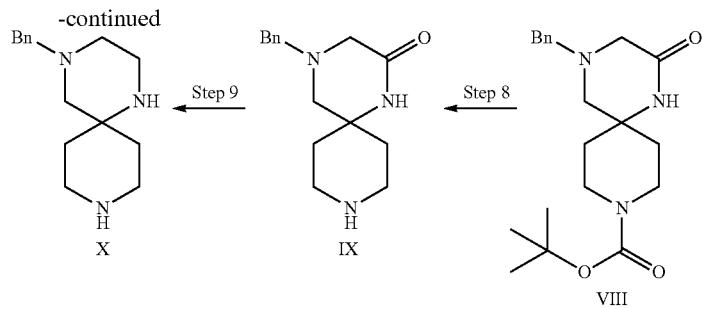

Step 1

Compound of formula II may be obtained from compound I (commercially available from Sigma-Aldrich) by reaction with nitromethane in a solution of ammonium hydroxide, carrying out the reaction typically at room temperature. The reaction takes about 3 hours to complete.

Step 2

Compound of formula III may be obtained by N-protection of compound II by reaction with benzyl chloroformate in presence of a suitable base, such as NaOH, carrying out the reaction under Schotten-Baumann conditions, e.g. in a mixture DCM/water, typically at room temperature. The reaction takes about 3 hours to complete.

Step 3

Compound of formula IV may be obtained by reduction of compound III using a suitable reducing system, e.g. $NaBH_4$ in presence of $NiCl_2 \cdot 6H_2O$, carrying out the reaction in a suitable solvent, such as MeOH at room temperature. The reaction takes about 1 hour to complete.

Step 4

Compound V may be obtained by acylation of compound IV by reaction with ethyl 2-bromoacetate, with a base such as triethylamine, in a suitable solvent, such as THF, at a temperature between 0° C. and room temperature. The reaction takes about 2 hours to complete.

Step 5

Compound of formula VI may be obtained from compound V by Cbz removal by hydrogenolysis, e.g. using ammonium formate and palladium on carbon, in a suitable solvent, such as isopropanol, under reflux, followed by spontaneous lactam ring closure. The reaction takes about 2 hours to complete.

Step 6

Compound VII can be obtained from compound VI by SnAr substitution with the appropriate aryl halide in a suitable aprotic solvent, e.g. DMSO, in presence of an inorganic base, such as $K_2CO_3$. The reaction proceeds at a temperature of about 100° C. and takes about 3 hours.

Step 7

Compound of formula VIII may be obtained by reductive amination of compound VI using benzaldehyde, carrying out the reaction in a suitable solvent, such as DCM, in presence of CH3COOH and a suitable reducing agent, e.g. $Na(AcO)_3BH$ at room temperature. The reaction takes about 3 hours to complete.

Step 8

Compound IX can be obtained from compound VIII by removing the Boc group under acidic conditions, e.g. TFA in dichloromethane solution, typically at room temperature. The reaction takes about 2 hours.

Step 9

Compound of formula X may be obtained by reduction of compound IX using a suitable reducing agent, e.g. $LiAlH_4$, carrying out the reaction in a suitable solvent, such as THF at reflux temperature. The reaction takes about 8 hours to complete.

Step 10

Compound XI can be obtained from compound X by SnAr substitution with the appropriate aryl halide in a suitable aprotic solvent, e.g. DMSO, in presence of an inorganic base, such as $K_2CO_3$. The reaction proceeds at a temperature of about 70° C. and takes about 2.5 hours.

Step 11

Compound of formula XII may be obtained from compound XI by removing the benzyl group by hydrogenolysis, e.g. using ammonium formate and palladium on carbon, in a suitable solvent such as methanol under reflux. The reaction takes 45 minute to complete.

Scheme N

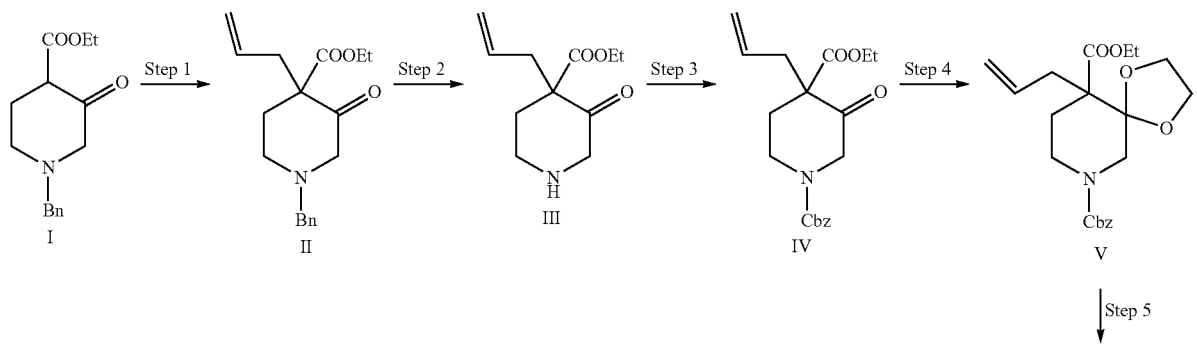

-continued

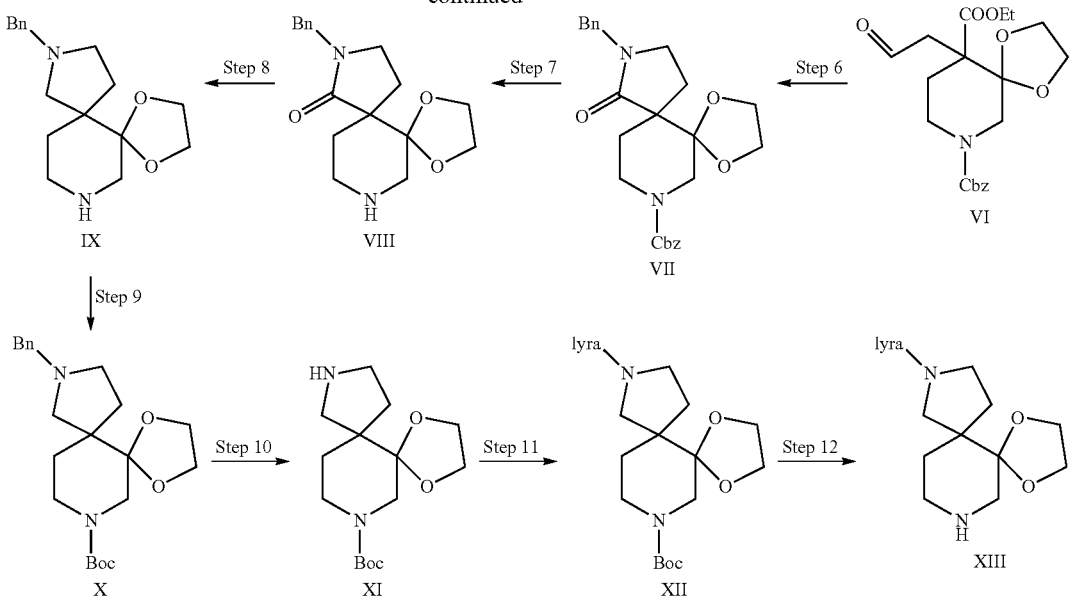

Step 1
Compound of formula II may be obtained by alkylation of compound I (commercially available from Sigma-Aldrich) with allyl bromide, after deprotonation using a suitable base, such as tBuOK, in a suitable aprotic solvent, e.g. THF, carrying out the reaction at a temperature between 0° C. and room temperature. The reaction takes about 12 hours to complete.

Step 2
Compound of formula III may be obtained by removing the benzyl group treating compound II with 1-chloroethyl chloroformate in a suitable solvent, such as dichloroethane, typically at reflux temperature for about 14 hours, followed by reflux in MeOH for about 1.5 hour.

Step 3
Compound of formula IV may be obtained by N-protection of compound III under standard literature conditions such as by reaction with a suitable protecting agent (e.g. as benzyl chloroformate), with the presence of a suitable base, such as diisopropylamine, carrying out the reaction in a suitable solvent, e.g. DCM, typically at room temperature. The reaction takes about 2 hours to complete.

Step 4
Compound of formula V may be obtained by ketone protection of compound IV by reaction with ethylene glycol, in presence of catalytic amount of p-Toluensulfonic in a suitable solvent, such as toluene, using Dean Stark apparatus, typically at reflux temperature. The reaction takes about 16 hours to complete.

Step 5
Compound of formula VI may be obtained by oxidation of compound V using an aqueous solution of $OsO_4$ in a mixture of THF/water, in presence of $NaIO_4$, carrying out the reaction typically at room temperature. The reaction takes about 2 hour to complete.

Step 6
Compound of formula VII may be obtained by reductive amination and of compound VI with a suitable primary amine, such as benzylamine, in a suitable solvent, such as THF, in presence of a reducing agent like $Na(AcO)_3BH$, followed by spontaneous lactam ring closure. The reaction is carried out typically at room temperature and takes about 16 to complete.

Step 7
Compound of formula VIII can be obtained by N-deprotection of compound VII by removing the benzyl group by hydrogenolysis, e.g. in hydrogen atmosphere with palladium on carbon, in a suitable solvent such as methanol. The reaction is carried out at a temperature about 25° C. The reaction takes from about 12 hours.

Step 8
Compound of formula IX may be obtained by reduction of compound VIII using a suitable reducing agent, e.g. $LiAlH_4$, carrying out the reaction in a suitable solvent, such as THF at reflux temperature. The reaction takes to about 1.5 hour to complete.

Step 9
Compound of formula X may be obtained by N-protection of compound IX under standard literature conditions such as by reaction with Di-tert-butyl dicarbonate in a mixture of THF/water, in presence of a suitable base, such as $Na_2CO_3$, at a temperature around 0° C. The reaction takes about 1 hour to complete.

Step 10
Compound of formula XI may be obtained from compound X by removing the benzyl group by hydrogenolysis, e.g. using ammonium formate and palladium on carbon, in a suitable solvent such as methanol under reflux. The reaction takes about 2 hours.

Step 11
Compound XII can be obtained from compound XI by Buchwald reaction with the appropriate aryl halide in the presence of suitable transition metal catalyst, e.g. $Pd_2(dba)_3$, a suitable ligand such as BINAP, a suitable base, such as tBuONa and like, in a suitable solvent, e.g. toluene. The reaction is carrying out at a temperature about 100° C. and takes from about 12 hours to complete. Alternatively compound XII may be obtained by SnAr substitution with the appropriate aryl halide in a suitable aprotic solvent, e.g. DMSO, in presence of an inorganic base, such as $K_2CO_3$. The reaction proceeds at a temperature of 100° C. and takes 2 hours.

Step 12

Compound XIII can be obtained from compound XII by removing the Boc group under acidic conditions, e.g. TFA in dichloromethane solution, typically at room temperature. The reaction takes about 1 hour.

aqueous NaOH, at a temperature between 0° C. and room temperature. The reaction takes 2 hours to complete.

Step 4

Compound of formula V can be obtained by ring closure of compound IV in an aprotic solvent, such as THF, in

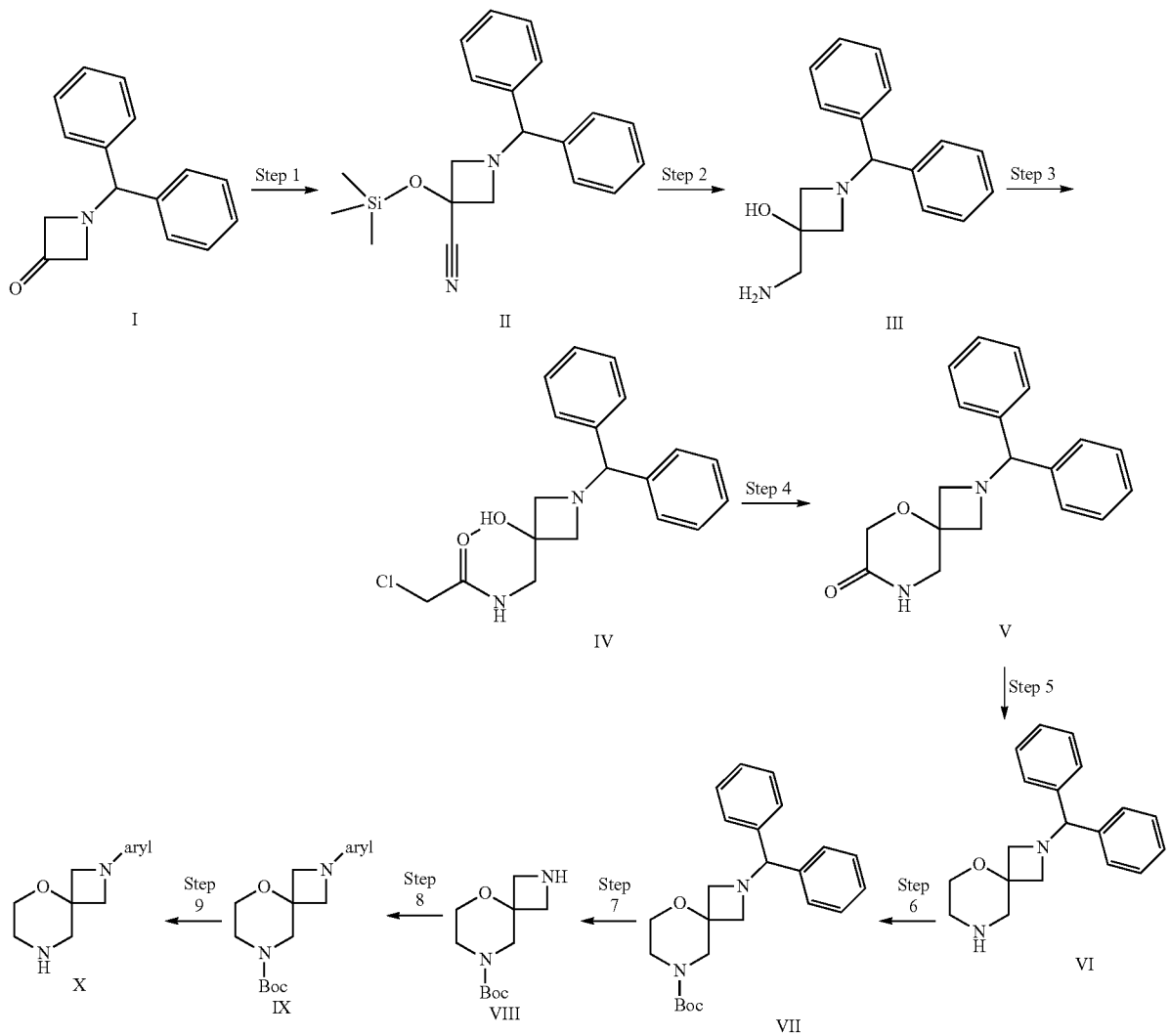

Scheme O

Step 1

Compound II can be obtained from compound I (commercially available from Alfa-Aesar) by reaction with trimethylsilanecarbonitrile in presence of tetrabutylammonium cyanide. The reaction is carried out in dichloromethane and proceeds typically at room temperature. The reaction takes about 1 hour to complete.

Step 2

Compound of formula III may be obtained by reduction of compound II using a suitable reducing system, e.g. $NaBH_4$ in presence of $NiCl_2 \cdot 6H_2O$, carrying out the reaction in a suitable solvent, such as MeOH at room temperature. The reaction takes about 1 hour to complete.

Step 3

Compound IV may be obtained by acylation of compound III by reaction with chloroacetyl chloride under Schotten-Baumann conditions, e.g. in a mixture dichloromethane/ presence of a suitable base, e.g. tBuOK, at room temperature. The reaction takes from about 1.5 hour to complete.

Step 5

Compound of formula VI may be obtained by reduction of compound V using a suitable reducing agent, e.g. $LiAlH_4$, carrying out the reaction in a suitable solvent, such as THF at reflux temperature. The reaction takes about 2 hours to complete.

Step 6

Compound of formula VII may be obtained by N-protection of compound VI under standard literature conditions such as by reaction with Di-tert-butyl dicarbonate, carrying out the reaction in a suitable solvent, e.g. DCM, typically at room temperature. The reaction takes 12 hours to complete.

Step 7

Compound of formula VIII may be obtained from compound VII by removing the benzyl group by hydrogenolysis, e.g. using ammonium formate and palladium on carbon, in a suitable solvent such as ethanol under reflux. The reaction takes about 0.5 hour.

Step 8

Compound IX can be obtained from compound VIII by SnAr substitution with the appropriate aryl halide in a suitable aprotic solvent, e.g. DMSO, in presence of an inorganic base, such as $K_2CO_3$. The reaction proceeds at a temperature of about 70° C. and takes about 1.5 hour to complete.

Step 9

Compound X can be obtained from compound IX by removing the Boc group under acidic conditions, e.g. TFA in dichloromethane solution, typically at room temperature. The reaction takes about 1 hour.

ii) Synthesis of A-L-B Systems

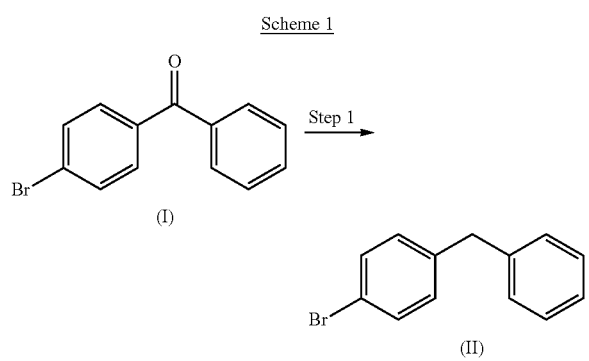

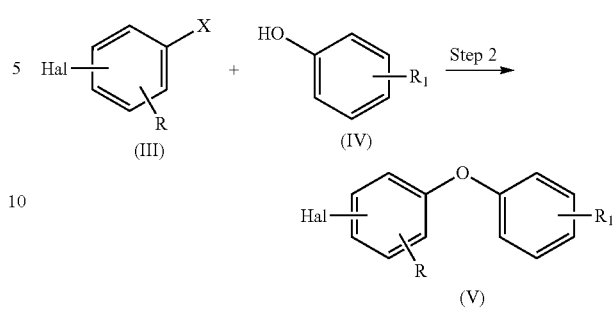

Step 2

Compound V can be obtained by Ullmann condensation between compounds III, the desired di-halogen benzene, such as 1,2-dibromo-4,5-difluorobenzene, and compound IV, the appropriate phenol, such as 3-fluorophenol, (both commercially available from Alfa-Aesar and Sigma-Aldrich respectively) in presence of a suitable catalyst, such as Cu, and a suitable base, e. g. KOH, typically at high temperature, from about 100 to about 150° C. The reaction takes about 14 hours to complete. Alternatively compound V may be obtained by SnAr reaction between compounds III and IV in presence of an inorganic base, such as $K_2CO_3$, a suitable solvent, e. g. DMSO, at a temperature between 25° C. and about 160° C., the reaction takes from about 20 to around 12 hours to complete.

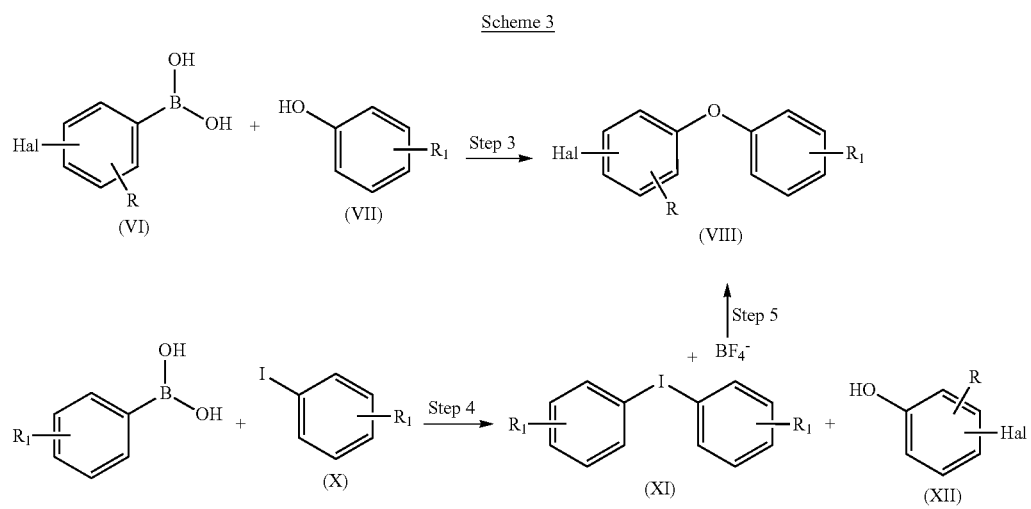

Step 1

Compound of formula II can be obtained by reduction of compound I, (3-bromophenyl)(phenyl)methanone, (commercially available from Sigma-Aldrich) with a suitable reducing system, such as $NaBH_4$ in presence of TFA, carrying out the reaction in a suitable solvent, e. g. dichloromethane, typically at room temperature. The reaction takes about 12 hours to complete.

Step 3

Compound of formula VIII may be obtained via Chan-Lam coupling between compound VI, the desired boronic acid, such as phenyl boronic acid, and compound VII, the appropriate phenol, e. g. 3-bromo-2-fluorophenol (both commercially available from Sigma-Aldrich and Zentek respectively), in presence of a suitable catalyst, such as $Cu(OAc)_2$, a suitable base, e. g. triethylamine, typically at room temperature. The reaction takes about 16 hours to complete.

Step 4

Compound XI can be obtained by reaction between compound IX, the desired boronic acid, e. g. phenyl boronic acid, and compound X, the appropriate benzene iodide, such as iodobenzene, (both commercially available from Sigma-Aldrich), in presence of a suitable oxidant, such as m-CPBA, and $BF_3Et_2O$, carrying out the reaction in a suitable solvent, such as dichloromethane. The reaction proceeds at a temperature between 0° C. and room temperature and takes about 45 minutes to complete.

Step 5

Compound VIII may be obtained from compound XI by reaction with compound XII, a suitable phenol such as 3-fluorophenol, in presence of a suitable base, such as tBuOK, in a suitable solvent, usually THF, at a temperature between 0° C. and 40° C. The reaction takes about 1 hour.

Scheme 4

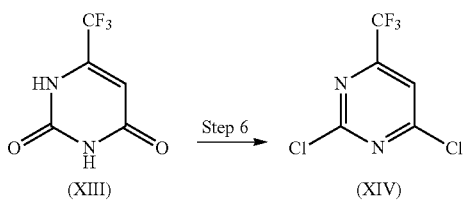

(XIII)     (XIV)

Step 6

Compound XIV can be obtained by chlorination of the commercially available (from Sigma-Aldrich) compound XIII, 6-(Trifluoromethyl)uracil, by treatment with a suitable chlorinating agent, such as $SOCl_2$ in a suitable solvent, e. g. DMF, carrying out the reaction usually at 80° C. for about 4 hours.

Scheme 5

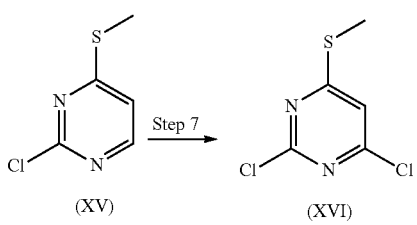

(XV)     (XVI)

Step 7

Compound of formula XVI can be obtained by chlorination of compound XV, 2-chloro-4-(methylthio)pyrimidine (commercially available from Sigma-Aldrich), with N-chlorosuccinimide in presence of 2,2,6,6-Tetramethylpiperidinylmagnesium chloride lithium chloride complex solution in THF/Toluene, in a suitable solvent, such as THF, typically at room temperature. The reaction takes 4 hours to complete.

Scheme 6

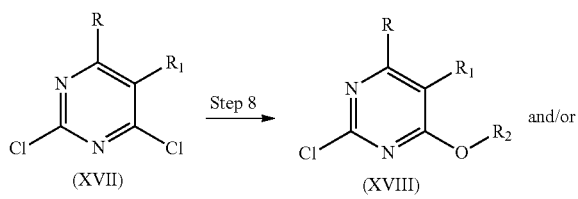

(XVII)     (XVIII)

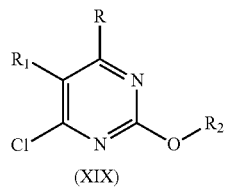

(XIX)

Step 8

Compounds of structure XVIII and XIX can be obtained via SnAr reaction between compound XVII, e. g. 2,4-dichloro-6-methylpyrimidine (commercially available from Sigma-Aldrich), or ad hoc prepared, and a suitable partner, such as 3-fluorophenol (commercially available from Sigma-Aldrich), the reaction typically proceeds in aprotic solvent, such as DMSO, in presence of a suitable base, such as $K_2CO_3$, at a temperature between 25° C. and 110° C. The reaction takes from about 20 min to about 12 hours to complete.

Scheme 7

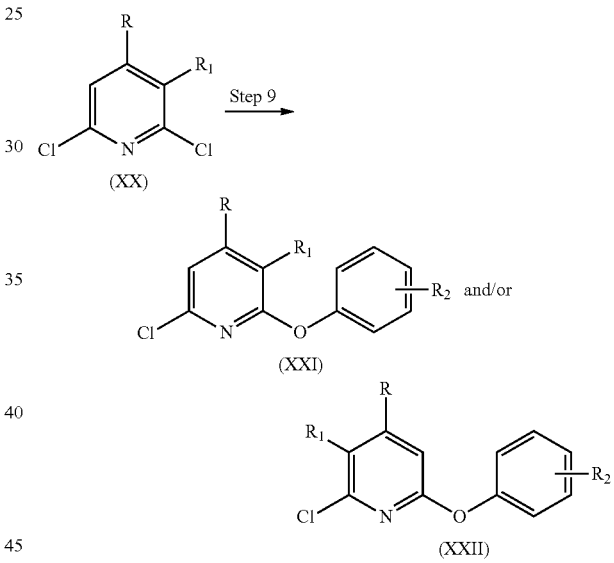

(XX)

(XXI)

(XXII)

Step 9

Compounds of structure XXI and XXII can be obtained via SnAr reaction between compound XX, e. g. 2,6-dichloropyridine (commercially available from Sigma-Aldrich), and a suitable phenol, such as 3-fluorophenol (commercially available from Sigma-Aldrich). The reaction typically proceeds in aprotic solvent, such as DMSO, in presence of a suitable base, such as $K_2CO_3$, at a temperature between 25° C. and 103° C. The reaction takes from about 2 hours to about 48 hours to complete.

Scheme 8

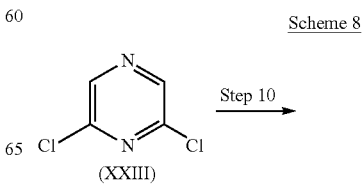

(XXIII)

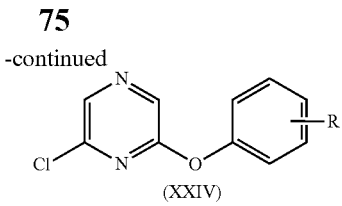

(XXIV)

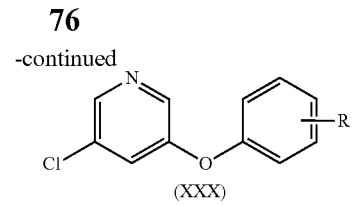

(XXX)

Step 10

Compound of structure XXIV can be obtained via SnAr reaction between compound XXIII, commercially available from Sigma-Aldrich, and a suitable phenol, such as 3-fluorophenol (commercially available from Sigma-Aldrich), the reaction typically proceeds in aprotic solvent, such as DMF, in presence of a suitable base, such as tBuOK, at a temperature of about 90° C. The reaction takes about 2 hours to complete.

Step 13

Compound of structure XXX can be obtained via SnAr reaction between compound XXIX, commercially available from Sigma-Aldrich, and a suitable phenol, such as 3-fluorophenol (commercially available from Sigma-Aldrich), the reaction typically proceeds in aprotic solvent, such as DMF, in presence of a suitable base, such as cesium carbonate, at a temperature of around 80° C. The reaction takes about 48 hours to complete.

Scheme 9

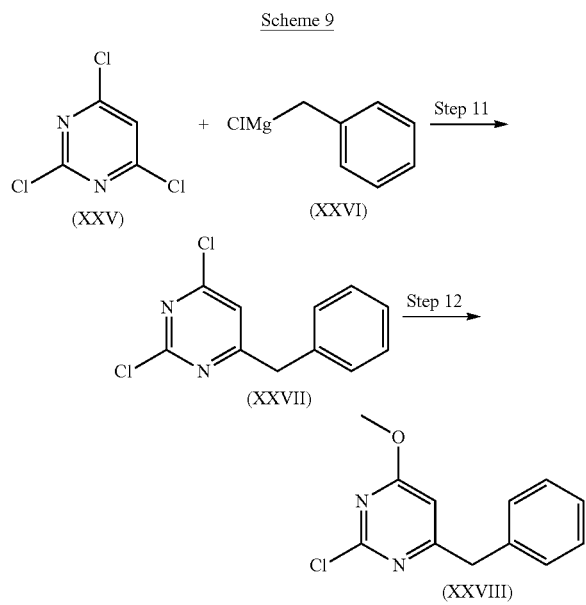

Step 11

Compound XXVII may be obtained by reaction between compound XXV, 2,4,6-trichloropyrimidine (commercially available from Sigma-Aldrich), and a Grignard reagent XXVI, such as benzylmagnesiumchloride, (both commercially available from Sigma-Aldrich). The reaction proceeds at a temperature between −78° C. and 20° C., and takes about 3 hours to complete.

Step 12

Compound XXVIII can be obtained by treatment of compound XXVII with MeONa, freshly obtained in situ by adding NaH in MeOH. The reaction is carried out in MeOH, typically at room temperature and takes about 1 hour to complete.

Scheme 10

EXAMPLES

The invention is further illustrated by the following non-limiting examples. In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar or analogous" procedure, as will be appreciated by those skilled in the art, such procedure may involve minor variation, for example reaction temperature, reagent/solvent amount, reaction time, work-up conditions or chromatographic purification conditions. All temperatures refer to ° C.

Proton Magnetic Resonance (NMR) spectra may be typically recorded either on Varian instruments at 400 or 500 MHz, or on a Bruker instrument at 400 MHz.

Chemical shifts are expressed in parts of million (ppm, δ units). Chemical shifts are reported in ppm downfield (δ) from $Me_4Si$, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions:

DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH conditions. Details of the method operated under low pH conditions were: column, Acquity BEH $C_{18}$, 1.7 μm, 2.1×50 mm or Acquity CSH $C_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the $ES^+/ES^-$ range was 100-1000 amu. Details of the method operated under high pH conditions were the same of those listed above for the low pH method apart from: column Acquity BEH $C_{18}$, 1.7 μm, 2.1×50 mm; mobile phase solvent A was 10 mM aqueous solution of $NH_4HCO_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 m. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 ml/min for columns of internal diameter 19 or 21 mm and 40 or 43 ml/min for columns of internal diameter 30 mm. The trigger for the collection of the target species was the presence of the target m/z ratio value in the TIC MS signal. The gradient timetable was customised on the RT behaviour of the target species.

Purification may also be performed using Biotage® Isolera or Biotage® SP1 flash chromatography (FC) systems, these instruments work with Biotage® KP-SIL cartridges and Biotage® KP-NH cartridges. Unless otherwise stated, all reactions are typically performed under inert atmosphere (for example under Nitrogen).

The following abbreviations are used in the text: EtOAc, AcOEt, EA=ethyl acetate, Et$_2$O=diethyl ether, MeOH=methanol; THF=tetrahydrofuran, Tlc refers to thin layer chromatography on silica plates, and dried refers to a solution dried over anhydrous sodium sulphate, r.t. (RT) refers to room temperature, DMSO=dimethyl sulfoxide; DMF=N,N'-dimethylformamide, DCM=dichloromethane, EtOH=ethanol, DCE=dichloroethane, Cy=cyclohexyl, cHex=cyclohexane, TEA=triethylamine, DIPEA=N,N-Diisopropylethylamine, Boc$_2$O=Di-tert-butyl dicarbonate; LDA=lithium diisopropylamide, LiHMDS=lithium bis(trimethylsilyl)amide, TFA=trifluoroacetic acid, BINAP=(±)-2,2'-Bis(diphenylphosphino)-1,1'-binaphthalene, Pd$_2$(dba)$_3$=Tris(dibenzylideneacetone)dipalladium(0), ACE-Cl=1-chloroethyl chloroformate, SCX Cartridge=Strong Cation Exchange Cartridge, cbz=carboxybenzyl, PG=protecting group.

Preparation 1:
4-(aminomethyl)-1-benzylpiperidin-4-ol (P1)

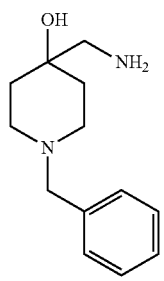 [SMILES: NCC1(O)CCN(Cc2ccccc2)CC1]

Step a:

To an ice-cooled mixture of NaH (60% dispersion in mineral oil, 2.75 g, 68.69 mmol) and trimethylsulfoxonium iodide (12.79 g, 58.12 mmol) DMSO (50 mL) was added keeping the mixture at 10° C. The mixture was stirred for 10 min at 10° C. then it was allowed to reach RT and left stirring at that temperature for 1 h. A solution of 1-benzylpiperidin-4-one (9.79 mL, 52.84 mmol) in DMSO (30 mL) was added via syringe. The mixture was stirred for 1.5 h at RT, diluted with Et$_2$O and quenched by the addition of saturated aqueous NH$_4$Cl. Phases were separated and aqueous one was backextracted with Et$_2$O. Combined organics were dried, filtered and concentrated under reduced pressure affording 6-benzyl-1-oxa-6-azaspiro[2.5]octane (11.3 g) as crude material that was used as such in the next step.

Step b:

To a stirred solution of 6-benzyl-1-oxa-6-azaspiro[2.5]octane (from step a, 11.3 g) in MeOH (69 mL), at 0° C., 28% aq. NH$_4$OH (140 mL) was added portionwise. Once the addition was complete, the ice-bath was removed and the resulting reaction mixture was stirred at RT overnight. The reaction mixture was concentrated under reduced pressure, residue was taken up with DCM and 1N NaOH. Phases were separated and the aqueous phase was backextracted with DCM. Combined organics were dried and concentrated under reduced pressure. The crude material was purified by FC on NH column (eluent: DCM/MeOH from 100/0 to 95/5) affording 4-(aminomethyl)-1-benzylpiperidin-4-ol (p1, 8 g, y=68%).

MS (ES) (m/z): 221.2 [M+H]$^+$

Preparation 2: N-[(1-benzyl-4-hydroxypiperidin-4-yl)methyl]-2-chloroacetamide (P2)

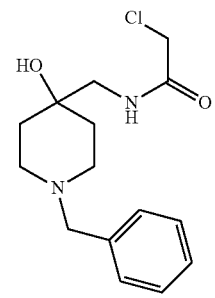

To a stirred solution of 4-(aminomethyl)-1-benzylpiperidin-4-ol (8 g, 36.31 mmol, p1) in DCM (50 mL), at 0° C. and under a nitrogen atmosphere, TEA (10.12 mL, 72.62 mmol) was added followed by a solution of chloroacetylchloride (2.89 mL, 36.31 mmol) in 25 mL of DCM dropwise over 45 min.

Once the addition was completed, the reaction mixture was left stirring at that temperature for 10 min, then diluted with DCM and saturated NH$_4$Cl and allowed to reach RT. Phases were separated and the organic one was washed with brine, dried and concentrated under reduced pressure. The crude material was purified by FC on silica gel (eluent: DCM/MeOH from 100/0 to 95/5) affording N-[(1-benzyl-4-hydroxypiperidin-4-yl)methyl]-2-chloroacetamide (p2, 6 g, y=56%).

MS (ES) (m/z): 297.1 [M+H]$^+$

Preparation 3: tert-butyl 9-benzyl-1-oxa-4,9-diazaspiro[5.5]undecane-4-carboxylate (P3)

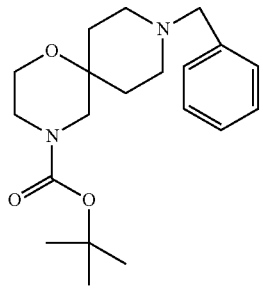 [SMILES: CC(C)(C)OC(=O)N1CCOC2(CCN(Cc3ccccc3)CC2)C1]

Step a:

To a stirred solution of N-[(1-benzyl-4-hydroxypiperidin-4-yl)methyl]-2-chloroacetamide (6 g, 20.22 mmol) in THF (150 mL), at 0° C. and under a nitrogen atmosphere, NaH 60% dispersion in mineral oil (1.6 g, 40.43 mmol) was added portionwise and then the ice-bath was removed. After 1 h at RT, the reaction mixture was concentrated under vacuum. The residue was diluted with AcOEt and water, and neutralized with 1N HCl. Phases were separated and the organic layer was dried, filtered and concentrated under reduced pressure affording 9-benzyl-1-oxa-4,9-diazaspiro[5.5]undecan-3-one (5.7 g) that was used as such in next step.

Step b:

LiAlH$_4$ 1M in THF (28.5 mL, 28.5 mmol) was added to solution of 9-benzyl-1-oxa-4,9-diazaspiro[5.5]undecan-3-one (5.7 g) in THF (100 mL) at 0° C. Once the addition was complete, the mixture was heated to reflux and stirred at that temperature for 40 min, then cooled down to −20° C. and quenched with Na$_2$SO$_4$*10H$_2$O. After quench, the mixture was left stirring at RT for 30 min, then filtered washing the solid with AcOEt. Solvent was concentrated under reduced pressure affording 9-benzyl-1-oxa-4,9-diazaspiro[5.5]undecane (4.5 g) that was used as such in next step.

Step c:

9-benzyl-1-oxa-4,9-diazaspiro[5.5]undecane (4.5 g) was suspended in H$_2$O (120 mL) at RT then cooled at 0° C. Na$_2$CO$_3$ (1.88 g, 18.63 mmol) was added followed by the dropwise addition of a solution of Boc$_2$O (3.99 g, 18.27 mmol) in THF (100 mL). The mixture was stirred at 0° C. for 1 h, then worked up extracting with EtOAc. The organic phase was dried, filtered and concentrated under reduced pressure. Crude was purified by FC on silica gel (eluent: Cy to Cy/AcOEt 50/50) affording tert-butyl 9-benzyl-1-oxa-4,9-diazaspiro[5.5]undecane-4-carboxylate as clear oil (p3, 2.26 g, y=36%)

MS (ES) (m/z): 347.3 [M+H]$^+$

Preparation 4: tert-butyl 1-oxa-4,9-diazaspiro[5.5]undecane-4-carboxylate (P4)

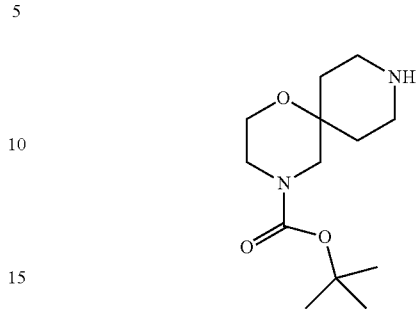

To a solution of tert-butyl 9-benzyl-1-oxa-4,9-diazaspiro[5.5]undecane-4-carboxylate (2.26 g, 6.52 mmol, p3) in MeOH (45 mL) ammonium formate (2.47 g, 39.14 mmol) and 10% Pd/C (650 mg) were added at RT then the mixture was stirred under reflux for 1 h. The mixture was cooled down to RT and filtered through a pad of celite washing with MeOH. Solvent was eliminated under reduced pressure affording tert-butyl 1-oxa-4,9-diazaspiro[5.5]undecane-4-carboxylate (p4, 1.6 g, y=96%) as white wax.

MS (ES) (m/z): 257.2 [M+H]$^+$

Preparation 5: tert-butyl 9-benzyl-1-oxa-4,9-diazaspiro[5.5]undecane-4-carboxylate (P5)

Step a:

To an ice-cooled mixture of NaH (60% dispersion in mineral oil, 11 g, 274.76 mmol) and trimethylsulfoxonium iodide (51.16 g, 232.48 mmol) DMSO (240 mL) was added keeping the mixture at 10° C. The mixture was stirred for 10 min at 10° C. then it was allowed to reach r.t. and left stirring at that temperature for 1 h. A solution of 1-benzylpiperidin-4-one (39.16 mL, 211.36 mmol) in DMSO (130 mL) was added via syringe. The mixture was stirred for 1.5 h at RT, diluted with Et$_2$O and quenched by the addition of saturated aqueous NH$_4$Cl. Phases were separated and aqueous one was backextracted with Et$_2$O. Combined organics were dried, filtered and concentrated under reduced pressure affording 6-benzyl-1-oxa-6-azaspiro[2.5]octane (50.7 g) as crude material that was used as such in the next step.

Step b:

To a stirred solution of 6-benzyl-1-oxa-6-azaspiro[2.5]octane (from step a, 50.7 g) in MeOH (350 mL)/H$_2$O (64 mL), at RT, 2-aminoethylhydrogensulfate (60 g, 422.8 mmol), was added followed by TEA (58.8 mL, 422.8 mmol) and the solution was stirred at 50° C. for 36 hrs. The day after, solid was filtered off and solvent was eliminated under reduced pressure. The residue was triturated with DCM/MeOH (95:5) affording (2-{[(1-benzyl-4-hydroxypiperidin-4-yl)methyl]amino}ethoxy)sulfonic acid as white solid (71.5 g). Presence of desired product and 2-aminoethylhydrogensulfate.

Step c:

To a stirred solution of (2-{[(1-benzyl-4-hydroxypiperidin-4-yl)methyl]amino}ethoxy)sulfonic acid (from step b, 71.5 g) in THF (503.3 mL) and EtOH (15.1 mL) at RT, NaOH (24.87 g, 621.75 mmol), was added and the resulting reaction mixture was stirred at reflux for 5 hrs. The mixture was cooled down to RT, concentrated under reduced pressure and diluted with water and AcOEt. Phases were separated and organic one was dried and concentrated under reduced pressure affording 9-benzyl-1-oxa-4,9-diazaspiro[5.5]undecane (29 g). Used as such in next step.

Step d:

To a solution of 9-benzyl-1-oxa-4,9-diazaspiro[5.5]undecane (from step c, 29 g) in DCM (230 mL) a solution of Boc2O (25.75 g, 117.75 mmol) in DCM (115 mL) was added and the mixture was stirred at rt for 1.5 hr. The mixture was washed with water and brine, organic phase was dried and concentrated. Crude was purified by FC on silica gel (eluent: Cy to Cy/AcOEt 50:50) affording tert-butyl 9-benzyl-1-oxa-4,9-diazaspiro[5.5]undecane-4-carboxylate (p5, 16.88 g, y=23%)

MS (ES) (m/z): 347.2 [M+H]$^+$

Preparation 6: tert-butyl 1-oxa-4,9-diazaspiro[5.5]undecane-4-carboxylate (P6)

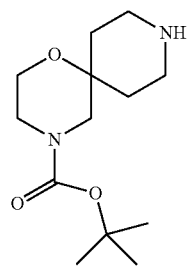 [SMILES: CC(C)(C)OC(=O)N1CCOC2(CCNCC2)C1]

To a solution of tert-butyl 9-benzyl-1-oxa-4,9-diazaspiro[5.5]undecane-4-carboxylate (p5, 16.88 g, 48.72 mmol) in MeOH (280 mL) ammonium formate (18.45 g, 292.41 mmol) and 10% Pd/C (1.67 g) were added at RT then the mixture was stirred under reflux for 1 h. The mixture was cooled down to RT and filtered through a pad of celite washing with MeOH. Solvent was eliminated under reduced pressure affording tert-butyl 1-oxa-4,9-diazaspiro[5.5]undecane-4-carboxylate (p6, 11.3 g, y=90%) as white wax.

MS (ES) (m/z): 257.2 [M+H]$^+$

Preparation 7: 1-bromo-4,5-difluoro-2-(3-fluorophenoxy)benzene (P7)

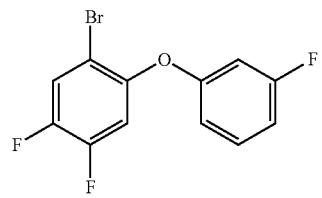 [SMILES: Fc1cccc(Oc2cc(F)c(F)cc2Br)c1]

3-fluorophenol (3.4 mL, 36.78 mmol) and KOH (2.06 g, 36.78 mmol) were stirred at 50° C. for 30 min before the addition of 1,2-dibromo-4,5-difluorobenzene (10.0 g, 36.78 mmol) and Cu powder (2.34 g, 36.78 mmol). The reaction mixture was heated to 150° C. for 2 hrs and then 100° C. overnight. Crude material was purified by FC on silica gel (eluent: cyclohexane), affording 1-bromo-4,5-difluoro-2-(3-fluorophenoxy)benzene (p7, 2.50 g, y=22%).

$^1$H NMR (CHLOROFORM-d): δ ppm 7.47-7.57 (m, 1H) 7.27-7.39 (m, 1H) 6.83-6.97 (m, 2H) 6.75 (d, 1H) 6.70 (dd, 1H)

Preparation 8: 1-bromo-2-phenoxybenzene (P8)

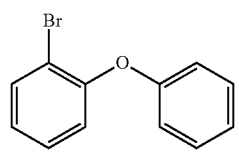 [SMILES: Brc1ccccc1Oc1ccccc1]

phenol (18.5 mg, 1.97 mmol) and KOH (110 mg, 1.97 mmol) were stirred at 50° C. for 30 min before the addition of 1-bromo-2-iodobenzene (557 mg, 1.97 mmol) and Cu powder (125 mg, 1.97 mmol). The reaction mixture was heated to 150° C. for 2 hrs and then 100° C. overnight. Crude material was purified by FC on silica gel (eluent: cyclohexane), affording 1-bromo-2-phenoxybenzene (p8, 179 mg, y=36%) as an oil.

$^1$H NMR (CHLOROFORM-d): δ ppm 7.86-7.93 (m, 1H) 7.33-7.42 (m, 3H) 7.15 (t, 1H) 7.01 (d, 2H) 6.87-6.96 (m, 2H)

Preparation 9: 1-bromo-2-(3-fluorophenoxy)benzene (P9)

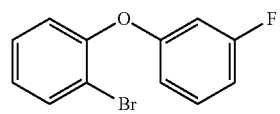 [SMILES: Fc1cccc(Oc2ccccc2Br)c1]

3-fluorophenol (0.16 mL, 1.77 mmol) and KOH (99 mg, 1.77 mmol) were stirred at 50° C. for 30 min before the addition of 1-bromo-2-iodobenzene (500 mg, 1.77 mmol) and Cu powder (113 mg, 1.77 mmol). The reaction mixture was heated to 150° C. for 4 hrs and then shaken at 100° C. overnight. Crude material was purified by FC on silica gel Preparation 10: 3-bromo-4-phenoxybenzonitrile (P10)

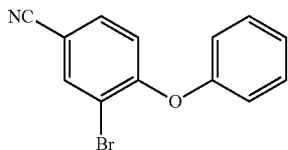 [SMILES: N#Cc1ccc(Oc2ccccc2)c(Br)c1]

To a solution of 3-bromo-4-fluorobenzonitrile (0.5 g, 2.5 mmol) and phenol (0.25 g, 2.62 mmol) in DMSO (2 mL), at RT, K₂CO₃ (0.69 g, 5 mmol) was added and the reaction mixture was stirred at RT overnight. Water and Et₂O were added to the reaction mixture, the organic phase was washed with water, dried and the solvent removed under reduced pressure. The crude material was purified by FC on silica gel (eluent: Cy/EA from 100/0 to 90/10) to give 3-bromo-4-phenoxybenzonitrile (p10, 0.52 g, y=76%) as white wax.

$^1$H NMR (CHLOROFORM-d): δ ppm 7.95 (d, 1H) 7.52 (dd, 1H) 7.40-7.49 (m, 2H) 7.24-7.31 (m, 1H) 7.09 (d, 2H) 6.85 (d, 1H)

Preparation 11: 1-(3-fluorophenoxy)-3-iodobenzene (P11)

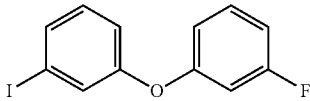 [SMILES: Fc1cccc(Oc2cccc(I)c2)c1]

3-fluorophenol (0.686 mL, 7.58 mmol) and KOH (425 mg, 7.58 mmol) were stirred at 50° C. for 30 min before the addition of 1,3-diiodobenzene (2.5 g, 7.58 mmol) and Cu powder (482 mg, 7.58 mmol). The reaction mixture was heated to 150° C. for 5 hrs and then shaken at 100° C. overnight. Crude material was purified by FC on silica gel (eluent: cyclohexane) affording 1-(3-fluorophenoxy)-3-iodobenzene (p11, 500 mg, y=21%)

$^1$H NMR (CHLOROFORM-d): δ ppm 7.51 (d, 1H) 7.41 (t, 1H) 7.30-7.37 (m, 1H) 7.11 (t, 1H) 7.03 (dd, 1H) 6.87 (td, 1H) 6.81 (dd, 1H) 6.71-6.77 (dt, 1H).

Preparation 12: 1-bromo-3-fluoro-5-(3-fluorophenoxy)benzene (P12)

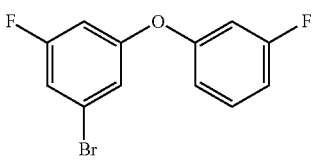 [SMILES: Fc1cccc(Oc2cc(F)cc(Br)c2)c1]

3-fluorophenol (0.178 mL, 1.97 mmol) and KOH (110 mg, 1.97 mmol) were stirred at 50° C. for 30 min before the addition of 1,3-dibromo-5-fluorobenzene (500 mg, 1.97 mmol) and Cu powder (125 mg, 1.97 mmol). The reaction mixture was heated to 150° for 2 hrs and then shaken at 100° C. overnight. Crude material was purified twice by FC on silica gel (eluent: cyclohexane), affording 1-bromo-3-fluoro-5-(3-fluorophenoxy)benzene (p12, 834 mg, y=22%).

$^1$H NMR (CHLOROFORM-d): δ ppm 7.33-7.42 (m, 1H) 7.05 (dt, 1H) 6.98 (s, 1H) 6.93 (td, 1H) 6.86 (dd, 1H) 6.79 (dt, 1H) 6.70 (dt, 1H)

Preparation 13: mixture of 2-bromo-1-fluoro-4-(3-fluorophenoxy)benzene and 4-bromo-1-fluoro-2-(3-fluorophenoxy)benzene (P 13)

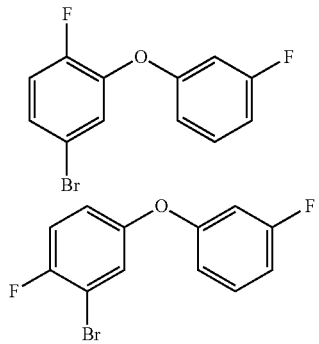

3-fluorophenol (0.333 mL, 3.68 mmol) and KOH (206 mg, 3.68 mmol) were stirred at 50° C. for 30 min before the addition of 2,4-dibromo-1-fluorobenzene (934 mg, 3.68 mmol) and Cu powder (234 mg, 3.68 mmol). The reaction mixture was heated to 150° C. for 4 hrs and then shaken at 100° C. overnight. Crude material was purified by FC on silica gel (eluent: cyclohexane), affording a mixture ~1:1 of 2-bromo-1-fluoro-4-(3-fluorophenoxy)benzene and 4-bromo-1-fluoro-2-(3-fluorophenoxy)benzene (p13, 280 mg, y=26%).

$^1$H NMR (CHLOROFORM-d): δ ppm 7.29-7.35 (m, 1H) 7.21-7.27 (m, 1H) 7.07-7.17 (m, 1H) 6.96-7.01 (m, 1H) 6.81-6.89 (m, 1H) 6.75-6.80 (m, 1H) 6.67-6.74 (m, 1H)

Preparation 14: 1-bromo-2,4-difluoro-5-(3-fluorophenoxy)benzene (P14)

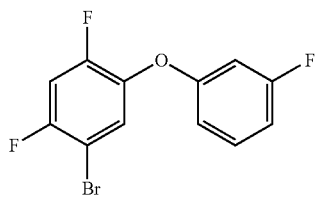 [SMILES: Fc1cccc(Oc2cc(Br)c(F)cc2F)c1]

3-fluorophenol (0.333 mL, 3.68 mmol) and KOH (206 mg, 3.68 mmol) were stirred at 50° C. for 30 min before the addition of 1,5-dibromo-2,4-difluorobenzene (1 g, 3.68 mmol) and Cu powder (234 mg, 3.68 mmol). The reaction mixture was heated to 150° C. for 5 hrs and then shaken at 100° C. overnight. Crude material was purified by FC on silica gel (eluent: cyclohexane), affording 1-bromo-2,4-difluoro-5-(3-fluorophenoxy)benzene (p14, 140 mg, y=12%)

¹H NMR (CHLOROFORM-d): δ ppm 7.30-7.40 (m, 2H) 7.09 (dd, 1H) 6.82-6.89 (m, 1H) 6.76 (d, 1H) 6.67-6.73 (m, 1H)

Preparation 15: 1-bromo-2,3-difluoro-5-(3-fluorophenoxy)benzene and 5-bromo-1,2-difluoro-3-(3-fluorophenoxy)benzene (P15)

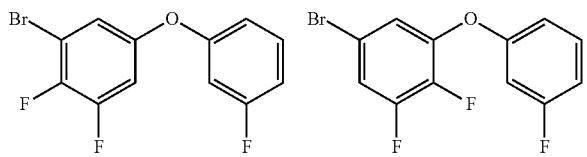

3-fluorophenol (0.117 mL, 1.29 mmol) and KOH (73 mg, 1.29 mmol) were stirred at 50° C. for 30 min before the addition of 1,5-dibromo-2,3-difluorobenzene (350 mg, 1.29 mmol) and Cu powder (82 mg, 1.29 mmol). The reaction mixture was heated to 150° C. for 2 hrs and then shaken at 100° C. overnight. Crude material was purified by FC on silica gel (eluent: cyclohexane), affording a mixture ~1:1 of 1-bromo-2,3-difluoro-5-(3-fluorophenoxy)benzene and 5-bromo-1,2-difluoro-3-(3-fluorophenoxy)benzene (p15, 68 mg, y=17%) as an oil.

¹H NMR (CHLOROFORM-d): δ ppm 7.35 (q, 2H) 7.16-7.23 (m, 1H) 6.97-7.04 (m, 2H) 6.87-6.95 (m, 2H) 6.84-6.87 (m, 1H) 6.79-6.84 (m, 2H) 6.76 (ddt, 2H).

Preparation 16:
1-bromo-2-fluoro-3-phenoxybenzene (P16)

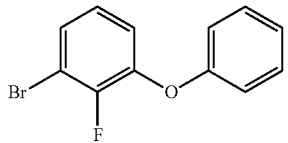 [SMILES: Fc1c(Br)cccc1Oc1ccccc1]

Method A

TEA (2.66 mL, 19.1 mmol) was added to a mixture of 3-bromo-2-fluorophenol (730 mg, 3.82 mmol), phenyl boronic acid (932 mg, 7.64 mmol), Cu(OAc)₂ (1.04 mg, 5.73 mmol), molecular sieves and DCM (35 mL). The mixture was stirred at RT overnight and then filtered through Celite washing with DCM. The filtrate was concentrated and the crude material was purified by FC on silica gel (eluent: Cy) to afford 1-bromo-2-fluoro-3-phenoxybenzene (p16, 40 mg, y=4%) as colourless oil.

Method B

Step a

3-Chloroperbenzoic acid (640 mg, 3 mmol) was dissolved in DCM (10 mL). To the solution iodobenzene (0.31 mL, 2.7 mmol) was added followed by slow addition of BF₃OEt₂ (0.850 mL, 6.8 mmol) at RT. The resulting yellow solution was stirred at RT for 30 min, cooled down to 0° C. and then phenyl boronic acid (370 mg, 3 mmol) was added in one portion. After 15 min at RT the crude reaction mixture was charged on SiO₂ (6 g) and eluted with DCM (60 mL) followed by DCM/MeOH 20/1 (120 mL). The latter solution was concentrated and Et₂O was added to precipitate the product which was further triturated with Et₂O. After decantation the white off solid was dried to afford diphenyliodonium tetrafluoroborate (1 g).

Step b

To a suspension of tBuOK (43 mg, 0.37 mmol) in THF (1.5 mL), 3-bromo-2-fluorophenol (65 mg, 0.34 mmol) was added at 0° C. and the reaction mixture was left stirring for 15 min. Diphenyliodonium tetrafluoroborate (from step a, 145 mg, 0.4 mmol) was added in one portion and the mixture was stirred at 40° C. for 1 h. The reaction was quenched with H₂O and the product was extracted with DCM. Organic phase was evaporated and crude material purified by FC on silica gel (eluent: pentane) to afford 1-bromo-2-fluoro-3-phenoxybenzene (p16, 69 mg, y=76%)

¹H NMR (CHLOROFORM-d): δ ppm 7.42-7.31 (m, 3H), 7.19-7.12 (m, 1H), 7.06-6.94 (m, 4H)

Preparation 17:
1-bromo-2-fluoro-3-(3-fluorophenoxy)benzene (P17)

Method A 3-fluorophenol (0.107 mL, 1.18 mmol) and KOH (66 mg, 1.18 mmol) were stirred at 50° C. for 30 min before the addition of 1,3-dibromo-2-fluorobenzene (300 mg, 1.18 mmol) and Cu powder (75 mg, 1.18 mmol). The reaction mixture was heated to 100° C. overnight. The crude material was purified by FC on silica gel (eluent: Cy), giving 1-bromo-2-fluoro-3-(3-fluorophenoxy)benzene (p17, 12 mg, y=3.5%) as oil.

Method B

Step a

3-Chloroperbenzoic acid (640 mg, 3 mmol) was dissolved in DCM (10 mL). To the solution 3-fluoro-iodobenzene (0.317 mL, 2.7 mmol) was added followed by slow addition of BF₃OEt₂ (0.850 mL, 6.8 mmol) at RT. The resulting yellow solution was stirred at RT for 30 min, then cooled down to 0° C. and 3-fluoro-phenylboronic acid (420 mg, 3 mmol) was added in one portion. After 15 min at RT the crude reaction mixture was charged on SiO₂ (6 g) and eluted with DCM (60 mL) followed by DCM/MeOH 20/1 (120 mL). The latter solution was concentrated and Et₂O was added to triturate the product. After decantation the pale yellow solid was dried to afford bis(3-fluoro-phenyl)iodonium tetrafluoroborate (820 mg).

Step b

To a suspension of tBuOK (97 mg, 1.1 eq) in THF (3.5 mL), 3-bromo-2-fluorophenol (150 mg, 0.785 mmol) was added at 0° C. and the reaction was left stirring for 15 min at that temperature. Bis(3-Fluoro-phenyl)iodonium tetrafluoroborate (from step a, 381 mg, 0.942 mmol) was added in one portion and the mixture was stirred at 40° C. for 1 h. The reaction was quenched with H₂O and the product was extracted with DCM. Organic phase was evaporated and the crude material was purified by FC on silica gel (eluent: pentane) affording 1-bromo-2-fluoro-3-(3-fluorophenoxy)benzene (p17, 160 mg, y=71%).

¹H NMR (DMSO-d₆): δ ppm 7.59 (td, 1H), 7.49-7.40 (m, 1H), 7.30-7.19 (m, 2H), 7.07-6.94 (m, 2H), 6.86 (dd, 1H)

Preparation 18:
1-bromo-2,5-difluoro-3-(3-fluorophenoxy)benzene
(P18)

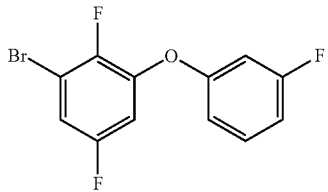 [SMILES: Fc1cccc(Oc2cc(F)cc(Br)c2F)c1]

3-fluorophenol (0.099 mL, 1.1 mmol) and KOH (62 mg, 1.1 mmol) were stirred at 50° C. for 30 min before the addition of 1,3-dibromo-2,5-difluorobenzene (300 mg, 1.1 mmol) and Cu powder (70 mg, 1.1 mmol). The reaction mixture was heated to 100° C. overnight. Crude material was purified by FC on silica gel (eluent: cyclohexane), affording 1-bromo-2,5-difluoro-3-(3-fluorophenoxy)benzene (p18, 61 mg, y=18%).

$^1$H NMR (METHANOL-d$_4$): δ ppm 7.38-7.49 (m, 1H), 7.33 (ddd, 1H), 6.93-7.02 (m, 2H), 6.82-6.90 (m, 2H)

Preparation 19: 1-bromo-2,4-difluoro-3-(3-fluorophenoxy)benzene and 2-bromo-1,3-difluoro-4-(3-fluorophenoxy)benzene (P19)

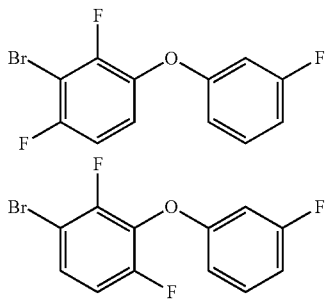

3-fluorophenol (0.333 mL, 3.68 mmol) and KOH (206 mg, 3.68 mmol) were stirred at 50° C. for 30 min before the addition of 1,3-Dibromo-2,4-difluorobenzene (1 g, 3.68 mmol) and Cu powder (234 mg, 3.68 mmol). The reaction mixture was heated to 100° C. overnight. Crude material was purified by FC on silica gel (eluent: cyclohexane) affording a mixture of 1-bromo-2,4-difluoro-3-(3-fluorophenoxy)benzene and 2-bromo-1,3-difluoro-4-(3-fluorophenoxy)benzene (p19, 65 mg, y=6%).

$^1$H NMR (CHLOROFORM-d): δ ppm 7.23-7.33 (m, 2H), 6.94-7.04 (m, 1H), 6.78-6.86 (m, 1H), 6.69-6.76 (m, 1H), 6.64-6.69 (m, 1H)

Preparation 20: 3-bromo-5-phenoxybenzonitrile
(P20)

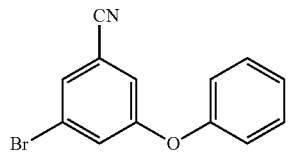 [SMILES: N#Cc1cc(Br)cc(Oc2ccccc2)c1]

A mixture of 3-bromo-5-fluorobenzonitrile (50 mg, 0.25 mmol), phenol (25 mg, 0.26 mmol) and K$_2$CO$_3$ (69 mg, 0.5 mmol) in DMSO (0.6 mL) was heated in a microwave apparatus at 135° C., 2 cycles of 20 min. In parallel a mixture of 3-bromo-5-fluorobenzonitrile (100 mg, 0.5 mmol), phenol (83 mg, 0.85 mmol) and K$_2$CO$_3$ (138 mg, 1 mmol) in DMSO (1 mL) was heated in a microwave apparatus at 160° C. for 20 min. The reactions were worked up together diluting with Et$_2$O and water. Phases were separated and organic phase was washed with water, dried and concentrated under reduced pressure. The crude material was purified by FC on silica gel (eluent: Cy/EA from 100/0 to 95/5) to give 3-bromo-5-phenoxybenzonitrile (p20, 86 mg, y=42%).

$^1$H NMR (CHLOROFORM-d): δ ppm 7.42-7.53 (m, 3H) 7.37 (t, 1H) 7.25-7.32 (m, 1H) 7.13-7.19 (m, 1H) 7.07 (d, 2H)

Preparation 21: 2-bromo-4-phenoxybenzonitrile
(P21)

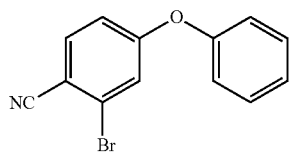 [SMILES: N#Cc1ccc(Oc2ccccc2)cc1Br]

To a solution of 2-bromo-4-fluorobenzonitrile (0.5 g, 2.50 mmol) and phenol (0.25 g, 2.62 mmol) in DMSO (2 mL), at RT, K$_2$CO$_3$ (0.69 g, 5 mmol) was added and the reaction mixture was stirred at RT overnight. Water and Et$_2$O were added to the reaction mixture, the organic phase was washed with water and saturated NaHCO$_3$, dried and the solvent removed under reduced pressure. Crude material was purified by FC on silica gel (eluent: Cy/EA from 100/0 to 90/10) to give 2-bromo-4-phenoxybenzonitrile (p21, 220 mg, y=32%).

$^1$H NMR (CHLOROFORM-d): δ ppm 7.60 (d, 1H) 7.42-7.51 (m, 2H) 7.26-7.33 (m, 1H) 7.23 (d, 1H) 7.09 (d, 2H) 6.98 (dd, 1H)

Preparation 22:
2-bromo-1-methyl-4-phenoxybenzene (P22)

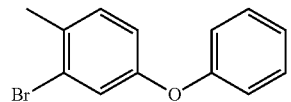

TEA (1.045 mL, 7.5 mmol) was added to a mixture of 3-bromo-4-methylphenol (280 mg, 1.5 mmol), phenyl boronic acid (366 mg, 3 mmol), Cu(OAc)$_2$ (408 mg, 2.25 mmol) and molecular sieves in DCM (12 mL). The mixture was stirred at RT overnight and then filtered through a pad of Celite washing with DCM. The filtrate was concentrated and purified by FC on silica gel (eluent: cHex) to afford 2-bromo-1-methyl-4-phenoxybenzene (p22, 52 mg, y=13%) as colorless oil.

$^1$H NMR (Acetone-d$_6$): δ ppm 7.39-7.46 (m, 2H) 7.35 (d, 1H) 7.17-7.22 (m, 2H) 7.05 (d, 2H) 6.95 (dd, 1H) 2.37 (s, 3H)

Preparation 23: 3-chloro-5-(3-fluorophenoxy)pyridine (P23)

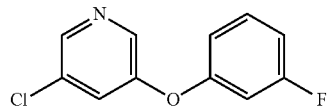 [SMILES: Fc1cccc(Oc2cncc(Cl)c2)c1]

A solution of 3-fluorophenol (0.31 mL, 3.38 mmol) and cesium carbonate (1.21 g, 3.72 mmol) in DMF (7 mL) was stirred at RT for 30 min. 3,5-Dichloropyridine (500 mg, 3.38 mmol) was added and the resulting solution was heated to 80° C. for 2 days. The mixture was filtered and the filtrate was concentrated in vacuo. Crude material was purified by FC on silica gel (eluent: cHex to EtOAc 6%) to obtain 3-chloro-5-(3-fluorophenoxy)pyridine (p23, 140 mg, y=19%) as pale yellow oil.

$^1$H NMR (CHLOROFORM-d): δ ppm 8.40 (s, 1H) 8.34 (s, 1H) 7.33-7.43 (m, 2H) 6.91-6.99 (m, 1H) 6.83-6.89 (m, 1H) 6.80 (dt, 1H)

Preparation 24: 1-benzyl-3-bromobenzene (P24)

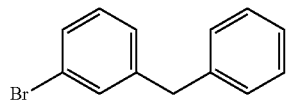 [SMILES: Brc1cccc(Cc2ccccc2)c1]

To stirred TFA (2.2 mL), at 10° C., a solution of (3-bromophenyl)(phenyl)methanone (0.10 g, 0.38 mmol) in DCM (1.1 mL) was added drop-wise followed by addition of NaBH$_4$ (0.17 g, 4.56 mmol) portion-wise. The ice-bath was removed and the reaction mixture was stirred overnight at RT. The mixture was poured into ice, basified with NaOH and extracted with Et$_2$O. The organic phase was washed with water, dried and solvent removed under vacuum to give 1-benzyl-3-bromobenzene (p24, 74 mg, y=79%)

$^1$H NMR (CHLOROFORM-d): δ ppm 7.30-7.41 (m, 4H) 7.23-7.30 (m, 1H) 7.12-7.23 (m, 4H) 3.98 (s, 2H)

Example 1: 9-[4,5-difluoro-2-(3-fluorophenoxy)phenyl]-1-oxa-4,9-diazaspiro[5.5]undecane (E1)

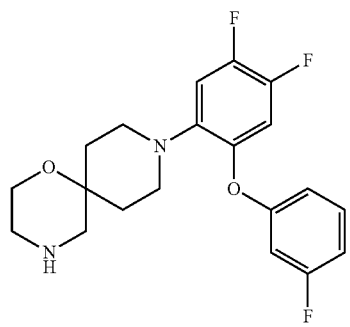 [SMILES: Fc1cccc(Oc2cc(F)c(F)cc2N2CCC3(CC2)CNCCO3)c1]

Step a

To a stirred solution of tert-butyl 1-oxa-4,9-diazaspiro[5.5]undecane-4-carboxylate (p4, 150 mg, 0.585 mmol) in Toluene (5 mL) at RT, BINAP (36 mg, 0.0585 mmol), sodium tert-butoxide (112 mg, 1.17 mmol) and 1-bromo-4,5-difluoro-2-(3-fluorophenoxy)benzene (p7, 178 mg, 0.585 mmol) were added and argon was purged for 10 min. Eventually, Pd$_2$(dba)$_3$ (16 mg, 0.017 mmol) was added and the reaction mixture was shaken at 100° C. overnight. The reaction mixture was concentrated, water was added and then the mixture was extracted with EtOAc. The organic phase was dried, filtered and the solvent was eliminated under reduced pressure. The crude material was purified by FC on silica gel (eluent: Cy to 15% EtOAc) affording tert-butyl 9-[4,5-difluoro-2-(3-fluorophenoxy)phenyl]-1-oxa-4,9diazaspiro[5.5]undecane-4-carboxylate (77 mg) as yellow oil.

Step b tert-butyl 9-[4,5-difluoro-2-(3-fluorophenoxy)phenyl]-1-oxa-4,9diazaspiro[5.5]undecane-4-carboxylate (from step a, 77 mg) was dissolved in DCM (3 mL), treated with TFA (0.5 mL) and left stirring at RT for 1 hr. Solvent and TFA excess were eliminated under reduced pressure and the residue was loaded on a SCX cartridge washing with MeOH and eluting with NH$_3$ 1M in MeOH. Solvent was eliminated under reduced pressure affording 9-[4,5-difluoro-2-(3-fluorophenoxy)phenyl]-1-oxa-4,9-diazaspiro[5.5]undecane (E1, 56.4 mg, y=25%).

MS (ES) (m/z): 379.2 [M+H]$^+$ $^1$H NMR (CHLOROFORM-d): δ ppm 7.20-7.28 (m, 1H), 6.82-6.95 (m, 2H), 6.78 (td, 1H), 6.70 (dd, 1H), 6.60 (dt, 1H), 3.62-3.74 (m, 2H), 3.01-3.12 (m, 2H), 2.90-3.01 (m, 2H), 2.79-2.90 (m, 2H), 2.65 (s, 2H), 1.96 (d, 2H), 1.29-1.44 (m, 2H)

Example 2: 9-[4,5-difluoro-2-(3-fluorophenoxy)phenyl]-1-oxa-4,9-diazaspiro[5.5]undecane hydrochloride (E2)

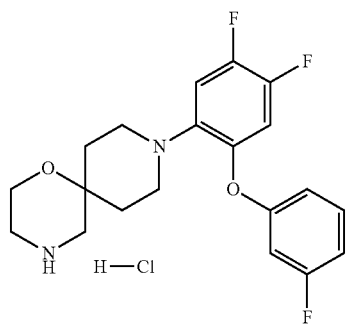

9-[4,5-difluoro-2-(3-fluorophenoxy)phenyl]-1-oxa-4,9-diazaspiro[5.5]undecane (E1, 34.5 mg, 0.091 mmol) was dissolved in DCM (0.5 mL) and 2M HCl in Et$_2$O was added. Solvent was eliminated under reduced pressure and the residue was triturated with Et$_2$O affording 9-[4,5-difluoro-2-(3-fluorophenoxy)phenyl]-1-oxa-4,9-diazaspiro[5.5]undecane hydrochloride (E2, 35.6 mg, y=94%) as off-white solid.

MS (ES) (m/z): 379.2 [M+H]$^+$ $^1$H NMR (DMSO-d$_6$): δ ppm 9.11 (br. s., 2H), 7.32-7.42 (m, 1H), 7.15-7.32 (m, 2H), 6.93 (td, 1H), 6.70-6.82 (m, 2H), 3.71-3.83 (m, 2H), 2.98-3.11 (m, 4H), 2.81-2.98 (m, 4H), 1.84 (s, 1H), 1.88 (s, 1H), 1.43 (t, 2H)

Example 3: 9-(2-phenoxyphenyl)-1-oxa-4,9-diazaspiro[5.5]undecane (E3)

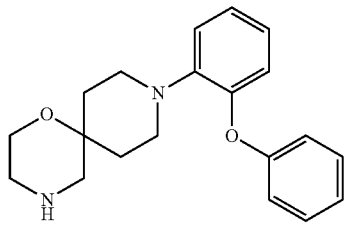 [SMILES: c1ccc(Oc2ccccc2N2CCC3(CC2)CNCCO3)cc1]

The title compound was prepared from tert-butyl 1-oxa-4,9-diazaspiro[5.5]undecane-4-carboxylate (p4, 50 mg, 0.195 mmol) and 1-bromo-2-phenoxybenzene (p8, 97 mg, 0.39 mmol) in analogous manner as described in Example 1. 9-(2-phenoxyphenyl)-1-oxa-4,9-diazaspiro[5.5]undecane (E3, 4 mg, y=4%).

MS (ES) (m/z): 325.13 [M+H]$^+$ $^1$H NMR (CHLOROFORM-d): δ ppm 7.20-7.31 (m, 2H), 7.01-7.16 (m, 3H), 6.89-7.01 (m, 4H), 3.73 (br. s., 2H), 3.18 (d, 2H), 3.03 (t, 2H), 2.89 (br. s., 2H), 2.72 (br. s., 2H), 1.97 (d, 2H), 1.48 (t, 2H)

Example 4: 9-[2-(3-fluorophenoxy)phenyl]-1-oxa-4,9-diazaspiro[5.5]undecane (E4)

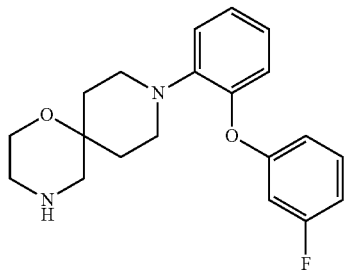 [SMILES: Fc1cccc(Oc2ccccc2N2CCC3(CC2)CNCCO3)c1]

The title compound was prepared from tert-butyl 1-oxa-4,9-diazaspiro[5.5]undecane-4-carboxylate (p4, 50 mg, 0.195 mmol) and 1-(2-bromophenoxy)-3-fluorobenzene (p9, 52 mg, 0.195 mmol) in analogous manner as described in Example 1. 9-[2-(3-fluorophenoxy)phenyl]-1-oxa-4,9-diazaspiro[5.5]undecane (E4, 13 mg, y=19%).

MS (ES) (m/z): 343.2 [M+H]$^+$ $^1$H NMR (CHLOROFORM-d): δ ppm 7.13-7.27 (m, 2H), 7.06-7.13 (m, 1H), 6.98-7.06 (m, 2H), 6.68-6.78 (m, 2H), 6.61 (dt, 1H), 3.64-3.73 (m, 2H), 3.08-3.18 (m, 2H), 2.99-3.08 (m, 2H), 2.82-2.89 (m, 2H), 2.66 (s, 2H), 1.95 (d, 2H), 1.36-1.51 (m, 2H)

Example 5: 3-{1-oxa-4,9-diazaspiro[5.5]undecan-9-yl}-4-phenoxybenzonitrile (E5)

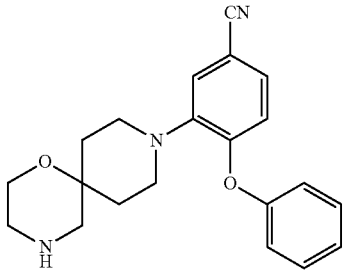 [SMILES: N#Cc1ccc(Oc2ccccc2)c(N2CCC3(CC2)CNCCO3)c1]

The title compound was prepared from tert-butyl 1-oxa-4,9-diazaspiro[5.5]undecane-4-carboxylate (p4, 47 mg, 0.18 mmol) and 3-bromo-4-phenoxybenzonitrile (p10, 60 mg, 0.22 mmol) in analogous manner as described in Example 1. 3-{1-oxa-4,9-diazaspiro[5.5]undecan-9-yl}-4-phenoxybenzonitrile (E5, 16 mg, y=25%).

MS (ES) (m/z): 350.2 [M+H]$^+$ $^1$H NMR (CHLOROFORM-d): δ ppm 7.32-7.43 (m, 2H), 7.29 (s, 1H), 7.11-7.26 (m, 2H), 7.00 (d, 2H), 6.87 (d, 1H), 3.64-3.78 (m, 2H), 3.17-3.30 (m, 2H), 2.98-3.14 (m, 2H), 2.82-2.94 (m, 2H), 2.70 (s, 2H), 2.04 (d, 2H), 1.48-1.62 (m, 2H)

Example 6: 9-(3-phenoxyphenyl)-1-oxa-4,9-diazaspiro[5.5]undecane (E6)

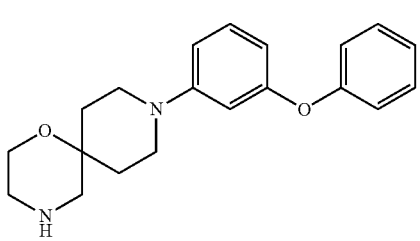 [SMILES: c1ccc(Oc2cccc(N3CCC4(CC3)CNCCO4)c2)cc1]

The title compound was prepared from tert-butyl 1-oxa-4,9-diazaspiro[5.5]undecane-4-carboxylate (p4, 50 mg, 0.195 mmol) and 1-bromo-3-phenoxybenzene (97 mg, 0.39 mmol) in analogous manner as described in Example 1. 9-(3-phenoxyphenyl)-1-oxa-4,9-diazaspiro[5.5]undecane (E6, 36 mg, y=57%).

MS (ES) (m/z): 325.2 [M+H]$^+$ $^1$H NMR (CHLOROFORM-d): δ ppm 7.32-7.39 (m, 2H), 7.21 (t, 1H), 7.10 (t, 1H), 7.04 (d, 2H), 6.72 (d, 1H), 6.65 (s, 1H), 6.47 (dd, 1H), 3.70-3.78 (m, 2H), 3.29-3.43 (m, 2H), 3.09-3.23 (m, 2H), 2.87-2.95 (m, 2H), 2.78 (s, 2H), 2.09 (d, 2H), 1.68-1.76 (m, 2H)

Example 7: 9-[3-(3-fluorophenoxy)phenyl]-1-oxa-4,9-diazaspiro[5.5]undecane (E7)

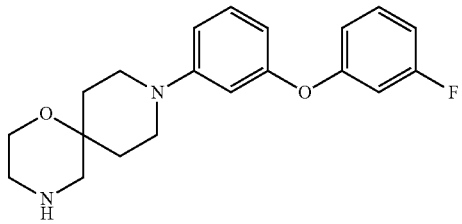 [SMILES: Fc1cccc(Oc2cccc(N3CCC4(CC3)CNCCO4)c2)c1]

The title compound was prepared from tert-butyl 1-oxa-4,9-diazaspiro[5.5]undecane-4-carboxylate (p4, 50 mg, 0.195 mmol) and 1-fluoro-3-(3-iodophenoxy)benzene (p11, 61.3 mg, 0.195 mmol) in analogous manner as described in Example 1. 9-[3-(3-fluorophenoxy)phenyl]-1-oxa-4,9-diazaspiro[5.5]undecane (E7, 16 mg, y=24%).

MS (ES) (m/z): 343.2 [M+H]$^+$ $^1$H NMR (CHLOROFORM-d): δ ppm 7.17-7.27 (m, 2H), 6.66-6.82 (m, 4H), 6.64 (s, 1H), 6.48 (d, 1H), 3.70-3.81 (m, 2H), 3.37 (d, 2H), 3.08-3.20 (m, 2H), 2.86-2.96 (m, 2H), 2.79 (s, 2H), 2.09 (d, 2H), 1.81-1.73 (m, 2H)

Example 8: 9-[3-fluoro-5-(3-fluorophenoxy)phenyl]-1-oxa-4,9-diazaspiro[5.5]undecane (E8)

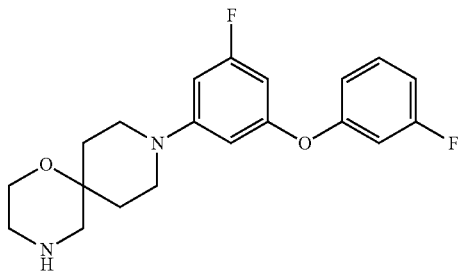 [SMILES: Fc1cccc(Oc2cc(F)cc(N3CCC4(CC3)CNCCO4)c2)c1]

The title compound was prepared from tert-butyl 1-oxa-4,9-diazaspiro[5.5]undecane-4-carboxylate (p4, 50 mg, 0.195 mmol) and 1-bromo-3-fluoro-5-(3-fluorophenoxy)benzene (p12, 55.6 mg, 0.195 mmol) in analogous manner as described in Example 1. 9-[3-fluoro-5-(3-fluorophenoxy)phenyl]-1-oxa-4,9-diazaspiro[5.5]undecane (E8, 44 mg, y=63%).

MS (ES) (m/z): 361.2 [M+H]$^+$ $^1$H NMR (CHLOROFORM-d): δ ppm 7.26-7.35 (m, 1H), 6.80-6.87 (m, 2H), 6.75 (dt, 1H), 6.37-6.47 (m, 2H), 6.17 (d, 1H), 3.68-3.79 (m, 2H), 3.32-3.43 (m, 2H), 3.09-3.24 (m, 2H), 2.86-2.96 (m, 2H), 2.76 (s, 2H), 2.09 (d, 2H), 1.57-1.70 (m, 2H)

Example 9: 9-[3-fluoro-5-(3-fluorophenoxy)phenyl]-1-oxa-4,9-diazaspiro[5.5]undecane hydrochloride (E9)

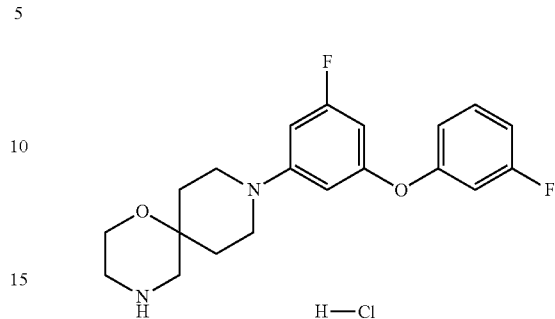

9-[3-fluoro-5-(3-fluorophenoxy)phenyl]-1-oxa-4,9-diazaspiro[5.5]undecane (E8, 37 mg, 0.102 mmol) was dissolved in DCM (0.5 mL) and 2M HCl in Et$_2$O (1 eq) was added. After evaporation, 9-[3-fluoro-5-(3-fluorophenoxy)phenyl]-1-oxa-4,9-diazaspiro[5.5]undecane hydrochloride (E9, 36.6 mg, y=90%) was obtained as white solid.

MS (ES) (m/z): 361.2 [M+H]$^+$ $^1$H NMR (CHLOROFORM-d): δ ppm 7.26-7.35 (m, 1H), 6.80-6.87 (m, 2H), 6.75 (dt, 1H), 6.37-6.47 (m, 2H), 6.17 (d, 1H), 3.68-3.79 (m, 2H), 3.32-3.43 (m, 2H), 3.09-3.24 (m, 2H), 2.86-2.96 (m, 2H), 2.76 (s, 2H), 2.09 (d, 2H), 1.57-1.70 (m, 2H)

Example 10: 9-[2-fluoro-5-(3-fluorophenoxy)phenyl]-1-oxa-4,9-diazaspiro[5.5]undecane (E10)

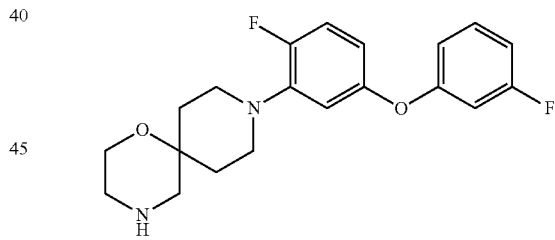

The title compound was prepared from tert-butyl 1-oxa-4,9-diazaspiro[5.5]undecane-4-carboxylate (p4, 50 mg, 0.195 mmol) and a mixture of 2-bromo-1-fluoro-4-(3-fluorophenoxy)benzene and 4-bromo-1-fluoro-2-(3-fluorophenoxy)benzene (p13, 55.6 mg, 0.195 mmol) in analogous manner as described in Example 1. 9-[2-fluoro-5-(3-fluorophenoxy)phenyl]-1-oxa-4,9-diazaspiro[5.5]undecane (E10, 15 mg, y=21%).

MS (ES) (m/z): 361.19 [M+H]$^+$ $^1$H NMR (CHLOROFORM-d): δ ppm 7.22-7.29 (m, 1H), 6.99 (dd, 1H), 6.75-6.79 (m, 1H), 6.71-6.75 (m, 1H), 6.65 (dt, 1H), 6.56 (dt, 1H), 3.70-3.73 (m, 2H), 3.14-3.21 (m, 2H), 3.01 (td, 2H), 2.86-2.91 (m, 2H), 2.77 (s, 2H), 2.11 (d, 2H), 1.66-1.75 (m, 2H)

Example 11: 9-[4-fluoro-3-(3-fluorophenoxy)phenyl]-1-oxa-4,9-diazaspiro[5.5]undecane (E11)

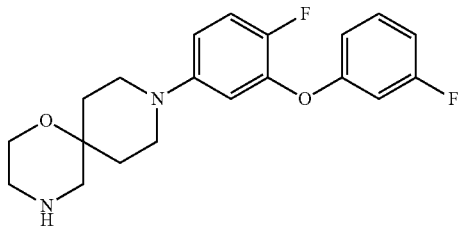 [SMILES: Fc1cccc(Oc2cc(N3CCC4(CC3)CNCCO4)ccc2F)c1]

The title compound was prepared from tert-butyl 1-oxa-4,9-diazaspiro[5.5]undecane-4-carboxylate (p4, 50 mg, 0.195 mmol) and a mixture of 2-bromo-1-fluoro-4-(3-fluorophenoxy)benzene and 4-bromo-1-fluoro-2-(3-fluorophenoxy)benzene (p13, 55.6 mg, 0.195 mmol) in analogous manner as described in Example 1. 9-[4-fluoro-3-(3-fluorophenoxy)phenyl]-1-oxa-4,9-diazaspiro[5.5]undecane (E11, 21.8 mg, y=31%).

MS (ES) (m/z): 361.14 [M+H]$^+$ $^1$H NMR (CHLOROFORM-d): δ ppm 7.21-7.27 (m, 1H), 7.07 (dd, 1H), 6.63-6.79 (m, 5H), 3.70-3.75 (m, 2H), 3.25 (dt, 2H), 3.01-3.10 (m, 2H), 2.87-2.92 (m, 2H), 2.75-2.79 (s, 2H), 2.09 (d, 2H), 1.60-1.70 (m, 2H)

Example 12: 9-[2,4-difluoro-5-(3-fluorophenoxy)phenyl]-1-oxa-4,9-diazaspiro[5.5]undecane (E12)

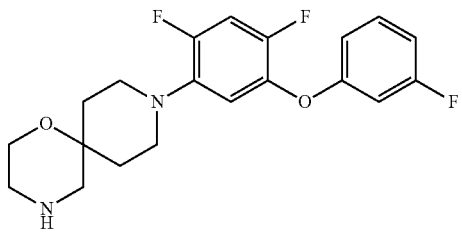 [SMILES: Fc1cccc(Oc2cc(N3CCC4(CC3)CNCCO4)c(F)cc2F)c1]

The title compound was prepared from tert-butyl 1-oxa-4,9-diazaspiro[5.5]undecane-4-carboxylate (p4, 50 mg, 0.195 mmol) and 1-bromo-2,4-difluoro-5-(3-fluorophenoxy)benzene (p14, 59 mg, 0.195 mmol) in analogous manner as described in Example 1. 9-[2,4-difluoro-5-(3-fluorophenoxy)phenyl]-1-oxa-4,9-diazaspiro[5.5]undecane (E12, 24 mg, y=32%).

MS (ES) (m/z): 379.16 [M+H]$^+$ $^1$H NMR (CHLOROFORM-d): δ ppm 7.22-7.29 (m, 1H), 6.97 (dd, 1H), 6.76-6.86 (m, 2H), 6.73 (dd, 1H), 6.65 (dt, 1H), 3.67-3.79 (m, 2H), 3.05-3.18 (m, 2H), 2.93-3.05 (m, 2H), 2.84-2.93 (m, 2H), 2.77 (s, 2H), 2.13 (d, 2H), 1.64-1.83 (m, 4H)

Example 13: 9-[2,3-difluoro-5-(3-fluorophenoxy)phenyl]-1-oxa-4,9-diazaspiro[5.5]undecane (E13)

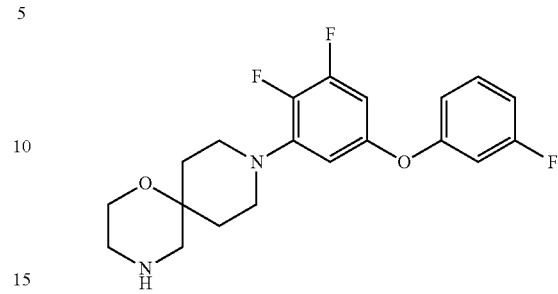

The title compound was prepared from tert-butyl 1-oxa-4,9-diazaspiro[5.5]undecane-4-carboxylate (p4, 50 mg, 0.195 mmol) and a mixture of 1-bromo-2,3-difluoro-5-(3-fluorophenoxy)benzene and 5-bromo-1,2-difluoro-3-(3-fluorophenoxy)benzene1-bromo-3-fluoro-5-(3-fluorophenoxy)benzene (p15, 68 mg, 0.224 mmol) in analogous manner as described in Example 1. 9-[2,3-difluoro-5-(3-fluorophenoxy)phenyl]-1-oxa-4,9-diazaspiro[5.5]undecane (E13, 20 mg, y=27%).

MS (ES) (m/z): 379.14 [M+H]$^+$ $^1$H NMR (CHLOROFORM-d): δ ppm 7.28-7.32 (m, 1H), 6.82 (td, 1H), 6.76 (dd, 1H), 6.69 (dt, 1H), 6.38-6.47 (m, 2H), 3.67-3.82 (m, 2H), 3.19 (m, 2H), 3.03 (t, 2H), 2.93-2.98 (m, 2H), 2.83 (s, 2H), 2.14 (d, 2H), 1.68-1.76 (m, 2H)

Example 14: 9-[2,3-difluoro-5-(3-fluorophenoxy)phenyl]-1-oxa-4,9-diazaspiro[5.5]undecane hydrochloride (E14)

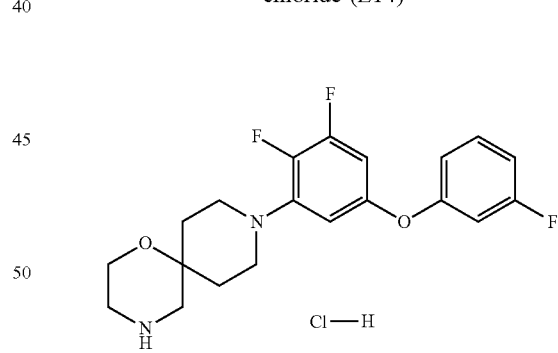

9-[2,3-difluoro-5-(3-fluorophenoxy)phenyl]-1-oxa-4,9-diazaspiro[5.5]undecane (E13, 20 mg, 0.053 mmol) was dissolved in DCM and treated with 1.1 eq of HCl 2M in Et$_2$O, concentrated under reduced pressure and triturated with Et$_2$O affording 9-[2,3-difluoro-5-(3-fluorophenoxy)phenyl]-1-oxa-4,9-diazaspiro[5.5]undecane hydrochloride (E14, 21 mg, y=95%).

MS (ES) (m/z): 379.2 [M+H]$^+$ $^1$H NMR (DMSO-d$_6$): δ ppm 9.14 (br. s., 2H) 7.37-7.47 (m, 1H) 6.99 (td, 1H) 6.81-6.94 (m, 2H) 6.69-6.79 (m, 1H) 6.59 (d, 1H) 3.77-3.85 (m, 2H) 3.15 (s, 1H) 3.18 (s, 1H) 3.04 (br. s., 4H) 2.95 (t, 2H) 2.00 (s, 1H) 2.03 (s, 1H) 1.73 (t, 2H)

Example 15: 9-[3,4-difluoro-5-(3-fluorophenoxy)phenyl]-1-oxa-4,9-diazaspiro[5.5]undecane (E15)

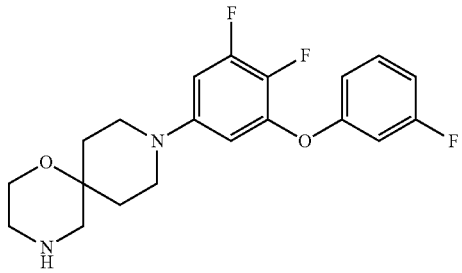 [SMILES: Fc1cccc(Oc2cc(N3CCC4(CC3)CNCCO4)cc(F)c2F)c1]

The title compound was prepared from tert-butyl 1-oxa-4,9-diazaspiro[5.5]undecane-4-carboxylate (p4, 50 mg, 0.195 mmol) and a mixture of 1-bromo-2,3-difluoro-5-(3-fluorophenoxy)benzene and 5-bromo-1,2-difluoro-3-(3-fluorophenoxy)benzene1-bromo-3-fluoro-5-(3-fluorophenoxy)benzene (p15, 68 mg, 0.224 mmol) in analogous manner as described in Example 1. 9-[3,4-difluoro-5-(3-fluorophenoxy)phenyl]-1-oxa-4,9-diazaspiro[5.5]undecane (E15, 22 mg, y=30%).

MS (ES) (m/z): 379.16 [M+H]$^+$ $^1$H NMR (CHLOROFORM-d): δ ppm 7.24-7.31 (m, 1H), 6.74-6.84 (m, 1H), 6.70 (dt, 1H), 6.56 (m, 1H), 6.35-6.43 (m, 1H), 3.78 (s, 2H), 3.20-3.30 (m, 2H), 3.05 (td, 2H), 2.96 (s, 2H), 2.82 (s, 2H), 2.12 (d, 2H), 1.60-1.67 (m, 2H)

Example 16: 9-[3,4-difluoro-5-(3-fluorophenoxy)phenyl]-1-oxa-4,9-diazaspiro[5.5]undecane hydrochloride (E16)

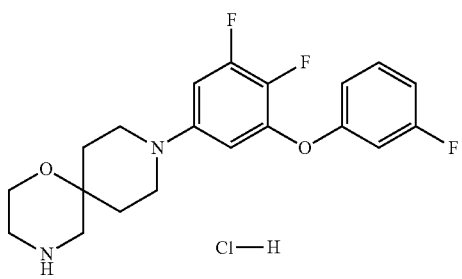 [SMILES: Fc1cccc(Oc2cc(N3CCC4(CC3)CNCCO4)cc(F)c2F)c1 ; Cl]

9-[3,4-difluoro-5-(3-fluorophenoxy)phenyl]-1-oxa-4,9-diazaspiro[5.5]undecane (E15, 22 mg, 0.058 mmol) was dissolved in DCM and treated with 1.1 eq of HCl 2M in Et$_2$O, concentrated under reduced pressure and triturated with Et$_2$O affording 9-[3,4-difluoro-5-(3-fluorophenoxy)phenyl]-1-oxa-4,9-diazaspiro[5.5]undecane hydrochloride (E16, 24 mg, y=quant).

MS (ES) (m/z): 379.2 [M+H]$^+$ $^1$H NMR (DMSO-d$_6$): δ ppm 9.15 (br. s., 2H) 7.35-7.46 (m, 1H), 6.86-7.01 (m, 3H), 6.82 (dd, 1H), 6.60-6.68 (m, 1H), 3.74-3.84 (m, 2H), 3.33-3.45 (m, 2H), 2.90-3.09 (m, 6H), 1.94 (s, 1H), 1.97 (s, 1H), 1.59-1.72 (m, 2H)

Example 17: 9-(2-fluoro-3-phenoxyphenyl)-1-oxa-4,9-diazaspiro[5.5]undecane (E17)

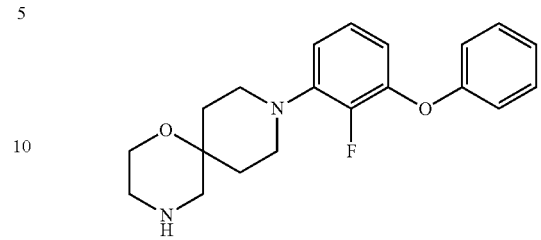

The title compound was prepared from tert-butyl 1-oxa-4,9-diazaspiro[5.5]undecane-4-carboxylate (p6, 38 mg, 0.15 mmol) and 1-bromo-2-fluoro-3-phenoxybenzene (p16, 40 mg, 0.15 mmol) in analogous manner as described in Example 1. 9-(2-fluoro-3-phenoxyphenyl)-1-oxa-4,9-diazaspiro[5.5]undecane (E17, 25 mg, y=49%).

MS (ES) (m/z): 343.15 [M+H]$^+$ $^1$H NMR (CHLOROFORM-d): δ ppm 7.30-7.37 (m, 2H), 7.06-7.13 (m, 1H), 6.97-7.04 (m, 3H), 6.82 (t, 1H), 6.66-6.74 (m, 1H), 3.70-3.79 (m, 2H), 3.17-3.26 (m, 2H), 3.05-3.16 (m, 2H), 2.87-2.94 (m, 2H), 2.79 (s, 2H), 2.11 (s, 1H), 2.15 (s, 1H), 1.69-1.80 (m, 2H)

Example 18: 9-(2-fluoro-3-phenoxyphenyl)-1-oxa-4,9-diazaspiro[5.5]undecane hydrochloride (E18)

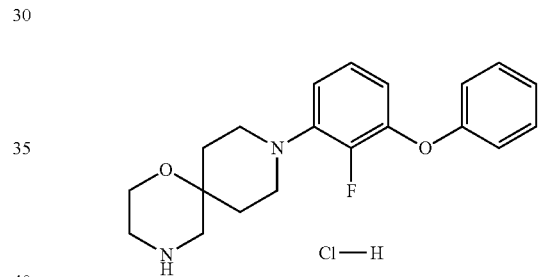

9-(2-fluoro-3-phenoxyphenyl)-1-oxa-4,9-diazaspiro[5.5]undecane (E17, 25 mg, 0.073 mmol) was dissolved in DCM and treated with 1.1 eq of HCl 2M in Et$_2$O, concentrated under reduced pressure and triturated with Et$_2$O affording 9-(2-fluoro-3-phenoxyphenyl)-1-oxa-4,9-diazaspiro[5.5]undecane hydrochloride (E18, 27 mg, y=98%).

MS (ES) (m/z): 343.15 [M+H]$^+$ $^1$H NMR (DMSO-d$_6$): δ ppm 9.21 (br. s., 2H), 7.38 (t, 2H), 7.08-7.18 (m, 2H), 6.88-7.01 (m, 3H), 6.75 (t, 1H), 3.15 (d, 2H), 3.06 (br. s., 4H), 2.92-3.02 (m, 2H), 2.05 (d, 2H), 1.67-1.84 (m, 2H)

Example 19: 9-[2-fluoro-3-(3-fluorophenoxy)phenyl]-1-oxa-4,9-diazaspiro[5.5]undecane (E19)

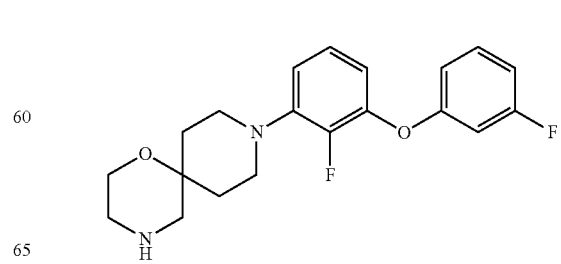

The title compound was prepared from tert-butyl 1-oxa-4,9-diazaspiro[5.5]undecane-4-carboxylate (p6, 144 mg, 0.561 mmol) and 1-bromo-2-fluoro-3-(3-fluorophenoxy)benzene (p17, 160 mg, 0.561 mmol) in analogous manner as described in Example 1. 9-[2-fluoro-3-(3-fluorophenoxy)phenyl]-1-oxa-4,9-diazaspiro[5.5]undecane (E19, 139 mg, y=69%).

MS (ES) (m/z): 361.2 [M+H]$^+$ $^1$H NMR (CHLOROFORM-d): δ ppm 7.22-7.28 (m, 1H) 7.00-7.08 (m, 1H) 6.85 (t, 1H) 6.65-6.81 (m, 4H) 3.73-3.82 (m, 2H) 3.15-3.26 (m, 2H) 3.03-3.14 (m, 2H) 2.92-2.98 (m, 2H) 2.83 (s, 2H) 2.13 (s, 1H) 2.16 (s, 1H) 1.69-1.80 (m, 2H)

Example 20: 9-[2-fluoro-3-(3-fluorophenoxy)phenyl]-1-oxa-4,9-diazaspiro[5.5]undecane hydrochloride (E20)

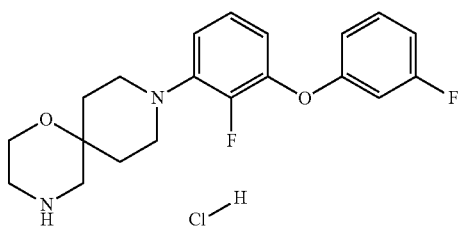

9-[2-fluoro-3-(3-fluorophenoxy)phenyl]-1-oxa-4,9-diazaspiro[5.5]undecane (E19, 24 mg, 0.066 mmol) was dissolved in DCM and treated with 1.1 eq of HCl 2M in Et$_2$O, concentrated under reduced pressure and triturated with Et$_2$O affording 9-[2-fluoro-3-(3-fluorophenoxy)phenyl]-1-oxa-4,9-diazaspiro[5.5]undecane hydrochloride (E20, 26 mg, y=98%).

MS (ES) (m/z): 361.2 [M+H]$^+$ $^1$H NMR (DMSO-d$_6$): δ ppm 9.04 (br. s., 2H), 7.37-7.45 (m, 1H), 7.15 (t, 1H), 6.93-7.01 (m, 2H), 6.80-6.87 (m, 2H), 6.77 (d, 1H), 3.83 (br. s., 2H), 3.15 (d, 2H), 3.07 (br. s., 4H), 2.98 (t, 2H), 2.04 (d, 2H), 1.70-1.82 (m, 2H)

Example 21: 9-[2,5-difluoro-3-(3-fluorophenoxy)phenyl]-1-oxa-4,9-diazaspiro[5.5]undecane (E21)

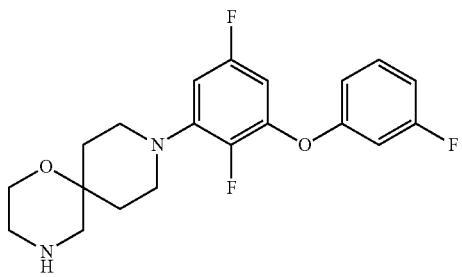 [SMILES: Fc1cccc(Oc2cc(F)cc(N3CCC4(CC3)CNCCO4)c2F)c1]

The title compound was prepared from tert-butyl 1-oxa-4,9-diazaspiro[5.5]undecane-4-carboxylate (p6, 51 mg, 0.197 mmol) and 1-bromo-2,5-difluoro-3-(3-fluorophenoxy)benzene (p18, 60 mg, 0.197 mmol) in analogous manner as described in Example 1. 9-[2,5-difluoro-3-(3-fluorophenoxy)phenyl]-1-oxa-4,9-diazaspiro[5.5]undecane (E21, 44 mg, y=60%).

MS (ES) (m/z): 379.2 [M+H]$^+$ $^1$H NMR (CHLOROFORM-d): δ ppm 7.30 (m, 1H) 6.76-6.87 (m, 2H) 6.70-6.73 (dt, 1H) 6.54 (d, 1H) 6.37-6.44 (m, 1H) 3.72-3.79 (m, 2H) 3.17-3.26 (m, 2H) 3.02-3.15 (m, 2H) 2.87-2.95 (m, 2H) 2.79 (s, 2H) 2.12 (s, 1H) 2.15 (s, 1H) 1.66-1.78 (m, 2H)

Example 22: 9-[2,5-difluoro-3-(3-fluorophenoxy)phenyl]-1-oxa-4,9-diazaspiro[5.5]undecane hydrochloride (E22)

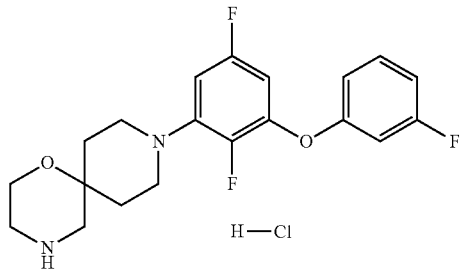

9-[2,5-difluoro-3-(3-fluorophenoxy)phenyl]-1-oxa-4,9-diazaspiro[5.5]undecane (E21, 44 mg, 0.116 mmol) was dissolved in DCM and treated with 1.1 eq of HCl 2M in Et$_2$O, concentrated under reduced pressure and triturated with Et$_2$O affording 9-[2,5-difluoro-3-(3-fluorophenoxy)phenyl]-1-oxa-4,9-diazaspiro[5.5]undecane hydrochloride (E22, 46 mg, y=95%).

MS (ES) (m/z): 379.17 [M+H]$^+$ $^1$H NMR (DMSO-d$_6$): δ ppm 9.13 (br. s., 2H), 7.37-7.47 (m, 1H), 7.00 (td, 1H), 6.91 (dt, 1H), 6.82 (d, 2H), 6.73 (ddd, 1H), 3.81 (br. s., 2H), 3.12-3.26 (m, 2H), 2.91-3.12 (m, 6H), 2.03 (d, 2H), 1.73 (t, 2H)

Example 23: 9-[2,6-difluoro-3-(3-fluorophenoxy)phenyl]-1-oxa-4,9-diazaspiro[5.5]undecane (E23)

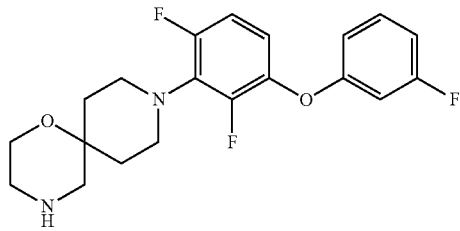 [SMILES: Fc1cccc(Oc2ccc(F)c(N3CCC4(CC3)CNCCO4)c2F)c1]

The title compound was prepared from tert-butyl 1-oxa-4,9-diazaspiro[5.5]undecane-4-carboxylate (p6, 55 mg, 0.214 mmol) and 2-bromo-1,3-difluoro-4-(3-fluorophenoxy)benzene (p19, 65 mg, 0.214 mmol) in analogous manner as described in Example 1. 9-[2,6-difluoro-3-(3-fluorophenoxy)phenyl]-1-oxa-4,9-diazaspiro[5.5]undecane (E23, 19 mg, y=23%).

MS (ES) (m/z): 379.2 [M+H]$^+$ $^1$H NMR (CHLOROFORM-d): δ ppm 7.23-7.27 (m, 1H), 6.70-6.87 (m, 4H), 6.64-6.66 (dt, 1H), 3.74-3.81 (m, 2H), 3.36-3.46 (m, 2H), 3.09-3.12 (d, 2H), 2.90-2.96 (m, 2H), 2.82 (s, 2H), 2.03-2.13 (m, 2H), 1.65-1.75 (m, 2H)

Example 24: 9-[2,6-difluoro-3-(3-fluorophenoxy)phenyl]-1-oxa-4,9-diazaspiro[5.5]undecane hydrochloride (E24)

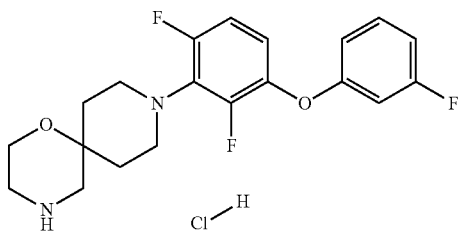

9-[2,6-difluoro-3-(3-fluorophenoxy)phenyl]-1-oxa-4,9-diazaspiro[5.5]undecane (E23, 19 mg, 0.05 mmol) was dissolved in DCM and treated with 1.1 eq of HCl 2M in Et$_2$O, concentrated under reduced pressure and triturated with Et$_2$O affording 9-[2,6-difluoro-3-(3-fluorophenoxy)phenyl]-1-oxa-4,9-diazaspiro[5.5]undecane hydrochloride (E24, 20 mg, y=96%).

MS (ES) (m/z): 379.18 [M+H]$^+$ $^1$H NMR (DMSO-d$_6$): δ ppm 9.00 (br. s, 2H), 7.33-7.44 (m, 1H), 7.05-7.13 (m, 1H), 6.91-7.00 (m, 2H), 6.84 (dt, 1H), 6.77 (dd, 1H), 3.77-3.84 (m, 2H), 3.20-3.31 (m, 2H), 3.00-3.10 (m, 6H), 1.93-2.03 (m, 2H), 1.62-1.76 (m, 2H)

Example 25: 3-{1-oxa-4,9-diazaspiro[5.5]undecan-9-yl}-5-phenoxybenzonitrile (E25)

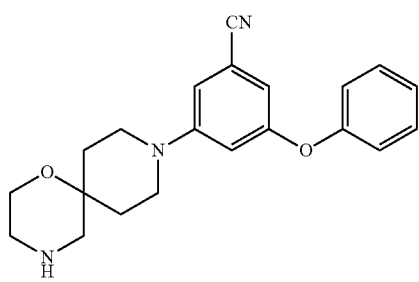 [SMILES: N#Cc1cc(Oc2ccccc2)cc(N2CCC3(CC2)CNCCO3)c1]

The title compound was prepared from tert-butyl 1-oxa-4,9-diazaspiro[5.5]undecane-4-carboxylate (p4, 50 mg, 0.195 mmol) and 3-bromo-5-phenoxybenzonitrile (p20, 53.5 mg, 0.195 mmol) in analogous manner as described in Example 1. 3-{1-oxa-4,9-diazaspiro[5.5]undecan-9-yl}-5-phenoxybenzonitrile (E25, 45 mg, y=66%).

MS (ES) (m/z): 350.2 [M+H]$^+$ $^1$H NMR (CHLOROFORM-d): δ ppm 7.40 (t, 2H), 7.20 (t, 1H), 7.04 (d, 2H), 6.90 (s, 1H), 6.80 (s, 1H), 6.60 (s, 1H), 3.68-3.78 (m, 2H), 3.34-3.46 (m, 2H), 3.12-3.25 (m, 2H), 2.87-2.97 (m, 2H), 2.78 (s, 2H), 2.10 (s, 1H), 2.14 (s, 1H), 1.57-1.67 (m, 2H)

Example 26: 3-{1-oxa-4,9-diazaspiro[5.5]undecan-9-yl}-5-phenoxybenzonitrile hydrochloride (E26)

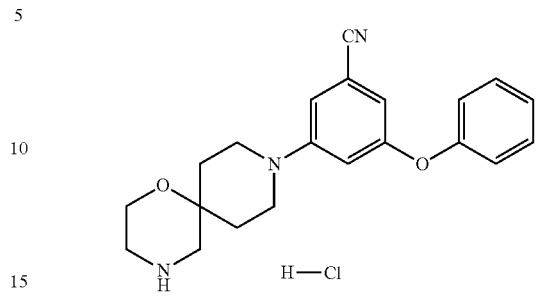

3-{1-oxa-4,9-diazaspiro[5.5]undecan-9-yl}-5-phenoxybenzonitrile (E25, 45 mg, 0.129 mmol) was dissolved in DCM and treated with 1.1 eq of HCl 2M in Et$_2$O, concentrated under reduced pressure and triturated with Et$_2$O affording 3-{1-oxa-4,9-diazaspiro[5.5]undecan-9-yl}-5-phenoxybenzonitrile hydrochloride (E26, 51 mg, y=quantitative).

MS (ES) (m/z): 379.18 [M+H]$^+$ $^1$H NMR (DMSO-d$_6$): δ ppm 9.19 (br. s., 2H), 7.38-7.49 (m, 2H), 7.11-7.25 (m, 2H), 7.06 (d, 2H), 6.94 (s, 1H), 6.66 (s, 1H), 3.76-3.86 (m, 2H), 3.51 (br. s., 2H), 2.97-3.13 (m, 6H), 1.97 (d, 2H), 1.62-1.75 (m, 2H)

Example 27: 2-{1-oxa-4,9-diazaspiro[5.5]undecan-9-yl}-4-phenoxybenzonitrile (E27)

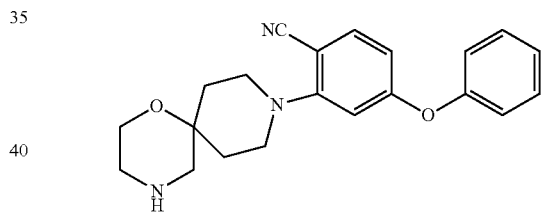

The title compound was prepared from tert-butyl 1-oxa-4,9-diazaspiro[5.5]undecane-4-carboxylate (p4, 54 mg, 0.21 mmol) and 2-bromo-4-phenoxybenzonitrile (p21, 69 mg, 0.25 mmol) in analogous manner as described in Example 1. 2-{1-oxa-4,9-diazaspiro[5.5]undecan-9-yl}-4-phenoxybenzonitrile (E27, 8 mg, y=11%).

MS (ES) (m/z): 350.2 [M+H]$^+$

Example 28: 2-{1-oxa-4,9-diazaspiro[5.5]undecan-9-yl}-4-phenoxybenzonitrile hydrochloride (E28)

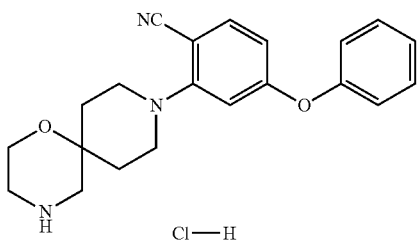 [SMILES: N#Cc1ccc(Oc2ccccc2)cc1N1CCC2(CC1)CNCCO2 ; Cl]

2-{1-oxa-4,9-diazaspiro[5.5]undecan-9-yl}-4-phenoxybenzonitrile (E27, 8 mg, 0.023 mmol) was dissolved in DCM (0.1 mL) and HCl 2N in Et₂O (0.012 mL) was added. The mixture was concentrated under reduced pressure; the residue was triturated with ether and dried under vacuum to give 2-{1-oxa-4,9-diazaspiro[5.5]undecan-9-yl}-4-phenoxybenzonitrile hydrochloride (E28, 8 mg, y=90%).

MS (ES) (m/z): 350.19 [M+H]⁺

¹H NMR (DMSO-d₆): δ ppm 10.00 (br. s., 2H), 7.79 (s, 5H), 7.49 (d, 1H), 7.27 (t, 2H), 7.05 (t, 1H), 6.96 (d, 2H), 6.55 (s, 1H), 6.37 (d, 1H), 3.77 (br. s., 2H), 3.12 (d, 2H), 3.00 (br. s., 4H), 2.88 (t, 2H), 2.63-2.73 (m, 6H), 2.06 (d, 2H), 1.68 (t, 2H)

Example 29: 9-(2-methyl-5-phenoxyphenyl)-1-oxa-4,9-diazaspiro[5.5]undecane (E29)

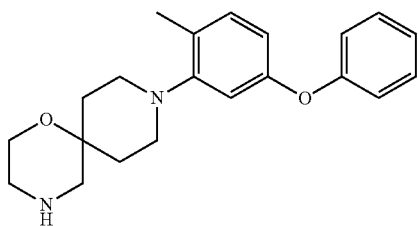

The title compound was prepared from tert-butyl 1-oxa-4,9-diazaspiro[5.5]undecane-4-carboxylate (p4, 50.8 mg, 0.198 mmol) and 2-bromo-1-methyl-4-phenoxybenzene (p22, 52 mg, 0.198 mmol) in analogous manner as described in Example 1. 9-(2-methyl-5-phenoxyphenyl)-1-oxa-4,9-diazaspiro[5.5]undecane (E29, 35 mg, y=52%).

MS (ES) (m/z): 339.2 [M+H]⁺

¹H NMR (CHLOROFORM-d): δ ppm 7.34 (t, 2H) 7.05-7.17 (m, 2H) 7.01 (d, 2H) 6.79 (d, 1H) 6.64 (dd, 1H) 3.72-3.81 (m, 2H) 2.79-3.00 (m, 8H) 2.29 (s, 3H) 2.09 (s, 1H) 2.13 (s, 1H) 1.67-1.80 (m, 2H)

Example 30: 9-(2-methyl-5-phenoxyphenyl)-1-oxa-4,9-diazaspiro[5.5]undecane hydrochloride (E30)

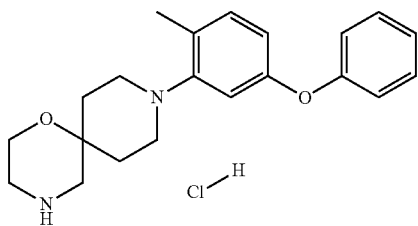 [SMILES: Cc1ccc(Oc2ccccc2)cc1N1CCC2(CC1)CNCCO2 ; Cl]

9-(2-methyl-5-phenoxyphenyl)-1-oxa-4,9-diazaspiro[5.5]undecane (E29, 35 mg, 0.103 mmol) was dissolved in DCM (0.1 mL) and HCl 2N in Et₂O (0.012 mL) was added. The mixture was concentrated under reduced pressure; the residue was triturated with ether and dried under vacuum to give 9-(2-methyl-5-phenoxyphenyl)-1-oxa-4,9-diazaspiro[5.5]undecane hydrochloride (E30, 37 mg, y=96%).

MS (ES) (m/z): 339.17 [M+H]⁺

¹H NMR (DMSO-d₆): δ ppm 9.03 (br. s., 2H), 7.38 (t, 2H), 7.06-7.23 (m, 2H), 6.97 (d, 2H), 6.71 (br. s., 1H), 6.61 (dd, 1H), 3.75-3.86 (m, 2H), 3.07 (br. s., 4H), 2.73-2.91 (m, 4H), 2.23 (s, 3H), 2.01 (d, 2H), 1.76 (br. s., 2H)

Example 31: 9-[5-(3-fluorophenoxy)pyridin-3-yl]-1-oxa-4,9-diazaspiro[5.5]undecane (E31)

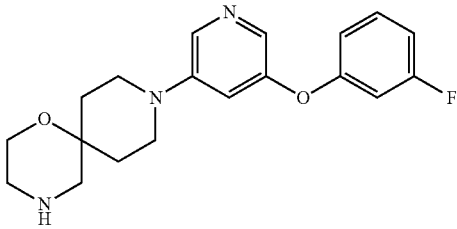 [SMILES: Fc1cccc(Oc2cncc(N3CCC4(CC3)CNCCO4)c2)c1]

The title compound was prepared from tert-butyl 1-oxa-4,9-diazaspiro[5.5]undecane-4-carboxylate (p6, 50 mg, 0.195 mmol) and 3-chloro-5-(3-fluorophenoxy)pyridine (p23, 44 mg, 0.195 mmol) in analogous manner as described in Example 1. 9-[5-(3-fluorophenoxy)pyridin-3-yl]-1-oxa-4,9-diazaspiro[5.5]undecane (E31, 24 mg, y=36%).

MS (ES) (m/z): 344.1 [M+H]⁺

¹H NMR (CHLOROFORM-d): δ ppm 8.17 (d, 1H), 7.86 (d, 1H), 7.30-7.35 (m, 1H), 6.79-6.90 (m, 3H), 6.73-6.76 (dt, 1H), 3.70-3.79 (m, 2H), 3.37-3.47 (m, 2H), 3.13-3.24 (m, 2H), 2.86-2.97 (m, 2H), 2.78 (s, 2H), 2.12 (s, 1H), 2.15 (s, 1H), 1.59-1.71 (m, 2H)

Example 32: 9-[5-(3-fluorophenoxy)pyridin-3-yl]-1-oxa-4,9-diazaspiro[5.5]undecane hydrochloride (E32)

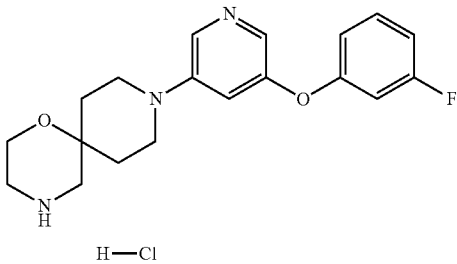 [SMILES: Fc1cccc(Oc2cncc(N3CCC4(CC3)CNCCO4)c2)c1 ; Cl]

9-[5-(3-fluorophenoxy)pyridin-3-yl]-1-oxa-4,9-diazaspiro[5.5]undecane (E31, 24 mg, 0.07 mmol) was dissolved in DCM and treated with HCl 2M in Et₂O. The mixture was concentrated under reduced pressure; the residue was triturated with ether and dried under vacuum to give 9-[5-(3-fluorophenoxy)pyridin-3-yl]-1-oxa-4,9-diazaspiro[5.5]undecane hydrochloride (E32, 28 mg, y=quant).

MS (ES) (m/z): 344.0 [M+H]⁺

¹H NMR (DMSO-d₆): δ ppm 9.04 (br. s., 2H), 8.25 (d, 1H), 7.82 (s, 1H), 7.40-7.50 (m, 1H), 7.23 (br. s., 1H), 7.02 (t, 1H), 6.95 (d, 1H), 6.89 (d, 1H), 3.77-3.85 (m, 3H), 3.56 (d, 2H), 3.00-3.19 (m, 5H), 1.99 (d, 2H), 1.70 (t, 2H)

Example 33: 9-(3-benzylphenyl)-1-oxa-4,9-diazaspiro[5.5]undecane (E33)

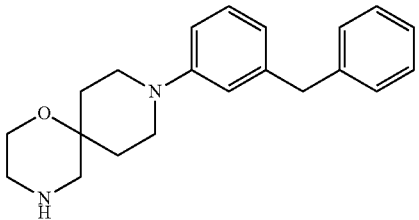 [SMILES: c1ccc(Cc2cccc(N3CCC4(CC3)CNCCO4)c2)cc1]

The title compound was prepared from tert-butyl 1-oxa-4,9-diazaspiro[5.5]undecane-4-carboxylate (p4, 64 mg, 0.25 mmol) and 1-benzyl-3-bromobenzene (p24, 74 mg, 0.3 mmol) in analogous manner as described in Example 1. 9-(3-benzylphenyl)-1-oxa-4,9-diazaspiro[5.5]undecane (E33, 55 mg, y=68%).

MS (ES) (m/z): 323.2 [M+H]$^+$

Example 34: 9-(3-benzylphenyl)-1-oxa-4,9-diazaspiro[5.5]undecane hydrochloride (E34)

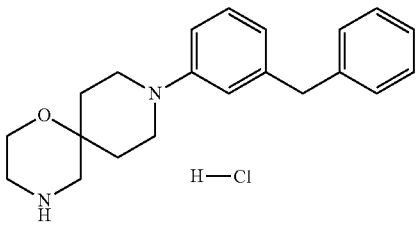

9-(3-benzylphenyl)-1-oxa-4,9-diazaspiro[5.5]undecane (E33, 55 mg, 0.17 mmol) was dissolved in DCM and treated with HCl 2M in Et$_2$O. The mixture was concentrated under reduced pressure; the residue was triturated with ether and dried under vacuum to give 9-(3-benzylphenyl)-1-oxa-4,9-diazaspiro[5.5]undecane hydrochloride (E34, 59 mg, y=97%).

MS (ES) (m/z): 323.22 [M+H]$^+$ $^1$H NMR (DMSO-d$_6$): δ ppm 9.56 (br. s., 2H), 7.11-7.35 (m, 9H), 3.93 (br. s., 2H), 3.84 (br. s., 2H), 3.41 (br. s., 2H), 3.23 (br. s., 2H), 3.06 (d, 4H), 2.18 (br. s., 2H), 2.00 (br. s., 2H)

Preparation 25: tert-butyl 9-[3-cyano-5-(3-fluorophenoxy)-4-methylphenyl]-1-oxa-4,9-diazaspiro[5.5]undecane-4-carboxylate (P25)

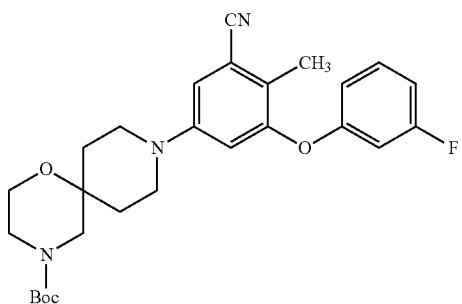 [SMILES: Cc1c(C#N)cc(N2CCC3(CC2)CN(C(=O)OC(C)(C)C)CCO3)cc1Oc1cccc(F)c1]

Step a

A mixture of 3,5-difluoro-2-methylbenzonitrile (50 mg, 0.33 mmol), 3-fluorophenol (33 mg, 0.3 mmol) and K$_2$CO$_3$ (91 mg, 0.66 mmol) in DMSO (0.8 mL) was heated in a microwave apparatus at 120° C., 3 cycles of 20 min each and at 130° C., 3 cycles of 30 min each. Ether and water were added, the organic phase was washed with water, dried over Na$_2$SO$_4$ and the solvent removed under reduced pressure. The crude material was purified by FC on silica gel (eluent: Cy to Cy/EA 95/5) to give 5-fluoro-3-(3-fluorophenoxy)-2-methylbenzonitrile (27 mg).

Step b

A mixture of 5-fluoro-3-(3-fluorophenoxy)-2-methylbenzonitrile (from step a, 27 mg, 0.11 mmol), tert-butyl 1-oxa-4,9-diazaspiro[5.5]undecane-4-carboxylate (prepared according to p6, 56 mg, 0.22 mmol) and K$_2$CO$_3$ (30 mg, 0.22 mmol) in DMSO (0.7 mL) in a sealed vial was heated at 110° C. and shaken overnight. An additional amount of tert-butyl 1-oxa-4,9-diazaspiro[5.5]undecane-4-carboxylate (28 mg) was added; the reaction temperature was brought to 115° C. and the mixture was shaken for further 48 hrs. Ether and water were added, the organic phase was washed with water, dried and solvent removed under reduced pressure. The crude material was purified by FC on silica gel (eluent: Cy/EA from 100/0 to 90/10) to give tert-butyl 9-[3-cyano-5-(3-fluorophenoxy)-4-methylphenyl]-1-oxa-4,9-diazaspiro[5.5]undecane-4-carboxylate (p25, 11 mg, y=21%).

MS (ES) (m/z): 482.3 [M+H]$^+$

Example 35: 3-(3-fluorophenoxy)-2-methyl-5-{1-oxa-4,9-diazaspiro[5.5]undecan-9-yl}benzonitrile hydrochloride (E35)

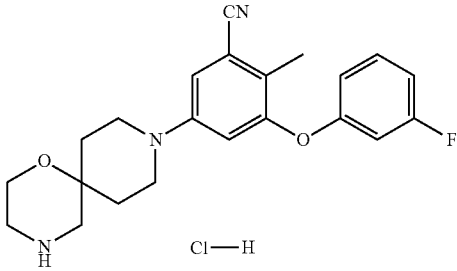 [SMILES: Cc1c(C#N)cc(N2CCC3(CC2)CNCCO3)cc1Oc1cccc(F)c1 ; Cl]

Step a

To a solution of tert-butyl 9-[3-cyano-5-(3-fluorophenoxy)-4-methylphenyl]-1-oxa-4,9-diazaspiro[5.5]undecane-4-carboxylate (p25, 11 mg, 0.023 mmol) in DCM (0.1 mL), at RT, TFA (0.052 mL) was added. After 2 hrs the reaction mixture was concentrated under vacuum. The residue was taken up with DCM and sodium bicarbonate saturated solution, the organic phase was dried and solvent removed under vacuum to give 3-(3-fluorophenoxy)-2-methyl-5-{1-oxa-4,9-diazaspiro[5.5]undecan-9-yl}benzonitrile (6 mg).

Step b 3-(3-fluorophenoxy)-2-methyl-5-{1-oxa-4,9-diazaspiro[5.5]undecan-9-yl}benzonitrile (from step a, 6 mg, 0.021 mmol) was dissolved in DCM (0.1 mL) and HCl 2M in ether (0.021 mL) was added. The mixture was concentrated under reduced pressure; the residue was triturated with ether and dried under vacuum to give 3-(3-fluorophenoxy)-2-methyl-5-{1-oxa-4,9-diazaspiro[5.5]undecan-9-yl}benzonitrile (E35, 6 mg, y=62%)

MS (ES) (m/z): 382.18 [M+H]$^+$

¹H NMR (DMSO-d₆): δ ppm 9.18 (br. s, 2H), 7.34-7.42 (m, 1H), 7.27 (d, 1H), 6.95 (d, 1H), 6.90-6.94 (m, 1H), 6.77 (dt, 1H), 6.70 (dd, 1H), 3.78 (d, 2H), 3.37-3.50 (m, 2H), 3.01 (br. s, 6H), 2.16 (s, 3H), 1.88-2.00 (m, 2H), 1.57-1.69 (m, 2H)

Preparation 26:
2-chloro-6-(3-fluorophenoxy)pyridine (P26)

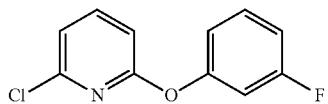 [SMILES: Fc1cccc(Oc2cccc(Cl)n2)c1]

To a solution of 2,6-dichloropyridine (250 mg, 1.65 mmol) and 3 fluorophenol (0.17 mL, 1.98 mmol) in DMSO (2 mL), at RT, K₂CO₃ (350 mg, 2.48 mmol) was added and the reaction mixture was shaken at 90° C. for 24 hrs. The reaction mixture was heated to 103° C. and shaken for further 24 hrs. Ether and water were added to the reaction mixture; the organic phase was washed with water, dried and the solvent removed under reduced pressure. The crude material was combined with the crude from analogous preparation and purified by FC on NH column (eluent: Cy) to give 2-chloro-6-(3-fluorophenoxy)pyridine (p26, 310 mg, y=59%) as colourless oil.
MS (ES) (m/z): 223.9 [M+H]⁺

Preparation 27: 2-chloro-6-(3-fluorophenoxy)-4-(trifluoromethyl)pyridine (P27)

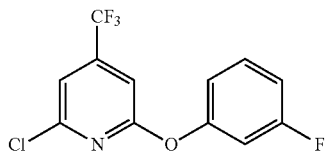 [SMILES: Fc1cccc(Oc2cc(C(F)(F)F)cc(Cl)n2)c1]

To a solution of 2,6-dichloro-4-(trifluoromethyl)pyridine (200 mg, 0.93 mmol) and 3 fluorophenol (0.074 mL, 0.88 mmol) in DMSO (2 mL), at RT, K₂CO₃ (193 mg, 1.4 mmol) was added and the reaction mixture was shaken at 90° C. overnight. Ether and water were added to the reaction mixture, the organic phase was washed with water, dried and solvent removed under reduced pressure to give 2-chloro-6-(3-fluorophenoxy)-4-(trifluoromethyl)pyridine (p27, 226 mg, y=88%) as colourless oil.
MS (ES) (m/z): 292.0 [M+H]⁺

Preparation 28: 2-chloro-6-(3-fluorophenoxy)pyridine-4-carbonitrile (P28)

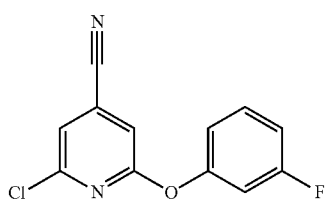 [SMILES: N#Cc1cc(Cl)nc(Oc2cccc(F)c2)c1]

A mixture of 2,6-dichloropyridine-4-carbonitrile (100 mg, 0.58 mmol), 3-fluorophenol (0.053 mL, 0.63 mmol) and K₂CO₃ (120 mg, 0.87 mmol) in DMSO (0.7 mL) in a sealed vial was stirred at RT for 36 hrs. Ether and water were added, the organic phase was washed with water, dried and solvent removed under reduced pressure to give 2-chloro-6-(3-fluorophenoxy)pyridine-4-carbonitrile (p28, 128 mg, y=88%).
MS (ES) (m/z): 248.9 [M+H]⁺

Preparation 29: 2-chloro-6-(3-fluorophenoxy)-4-(trifluoromethyl)pyridine-3-carbonitrile and 6-chloro-2-(3-fluorophenoxy)-4-(trifluoromethyl)pyridine-3-carbonitrile (P29)

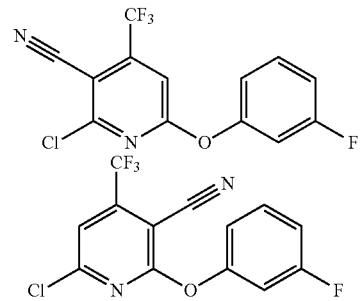

To a solution of 2,6-dichloro-4-(trifluoromethyl)pyridine-3-carbonitrile (75 mg, 0.311 mmol) in DMSO (1 mL) K₂CO₃ (52 mg, 0.373 mmol) and 3-fluorophenol (28 μL, 0.311 mmol) were added and the mixture was heated to 70° C. and shaken at that temperature for 2 hrs. The mixture was cooled down to RT, diluted with DCM and washed with water. Organic phase was dried and evaporated under reduced pressure. Crude material was purified by FC on silica gel (eluent: Cy to Cy/AcOEt 7:3) affording a mixture of the 2 regioisomers 2-chloro-6-(3-fluorophenoxy)-4-(trifluoromethyl)pyridine-3-carbonitrile and 6-chloro-2-(3-fluorophenoxy)-4-(trifluoromethyl)pyridine-3-carbonitrile (p29, 53 mg, y=54%).
MS (ES) (m/z): 316.9 [M+H]⁺

Preparation 30:
2-chloro-6-(3-fluorophenoxy)pyrazine (P30)

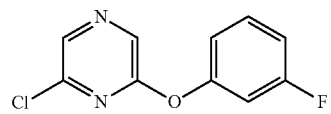 [SMILES: Fc1cccc(Oc2cncc(Cl)n2)c1]

A mixture of 2,6-Dichloropyrazine (250 mg, 1.69 mmol), 3-fluorophenol (0.166 ml, 1.86 mmol) and tBuOK (205 mg, 1.5 mmol) in DMF (4 mL) was heated at 90° C. for 2 hrs. After cooling at RT, EtOAc and water were added and the product was extracted in organic phase. The organic phase was dried and evaporated and crude material was purified by FC on silica gel (eluent:Cy to Cy/AcOEt 85/15) affording 2-chloro-6-(3-fluorophenoxy)pyrazine (p30, 340 mg, y=89%) as white solid.
¹H NMR (CHLOROFORM-d): δ ppm 8.34 (d, 2H), 7.42 (dt, 1H), 7.06-6.91 (m, 3H)

Preparation 31:
2-chloro-4-(3-fluorophenoxy)pyrimidine (P31)

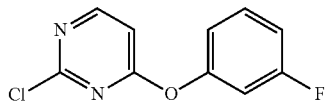 [SMILES: Fc1cccc(Oc2ccnc(Cl)n2)c1]

To a solution of 2,4-dichloropyrimidine (332 mg, 2.23 mmol) in DMSO (1 mL) K$_2$CO$_3$ (462 mg, 3.34 mmol) and 3-fluorophenol (202 μL, 2.23 mmol) were added and the mixture was heated to 70° C. and shaken at that temperature overnight. The mixture was then diluted with AcOEt and washed with water. Organic phase was dried and evaporated under reduced pressure. The crude material was purified by FC on silica gel (eluent: Cy to Cy/AcOEt 7:3) affording 2-chloro-4-(3-fluorophenoxy)pyrimidine (p31, 265 mg, y=52%) as yellowish wax.
MS (ES) (m/z): 225.0 [M+H]$^+$ Preparation 32:
2-chloro-4-methyl-6-phenoxypyrimidine (P32)

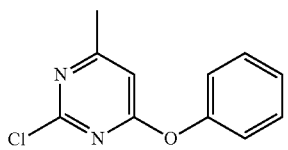

A mixture of 2,4-dichloro-6-methylpyrimidine (150 mg, 0.92 mmol), phenol (86 mg, 0.92 mmol) and K$_2$CO$_3$ (165 mg, 1.2 mmol) in DMSO (1 mL) was heated at 100° C. for 2 hrs.
After cooling at RT, EtOAc and water were added and the product was extracted in organic phase. The organic phase was dried and evaporated; the crude material was purified by FC on silica gel (eluent: Cy to Cy/AcOEt 6:4) affording 2-chloro-4-methyl-6-phenoxypyrimidine as pale yellow oil (p32, 197 mg, y=95%).
MS (ES) (m/z): 221.0 [M+H]$^+$ Preparation 33:
2-chloro-4-(3-fluorophenoxy)-6-methylpyrimidine (P33)

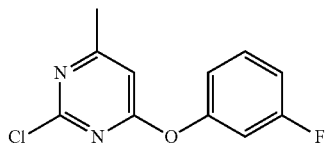 [SMILES: Cc1cc(Oc2cccc(F)c2)nc(Cl)n1]

To a solution of 2,4-dichloro-6-methylpyrimidine 363 mg, 2.23 mmol) in DMSO (2 mL) K$_2$CO$_3$ (370 mg, 2.67 mmol) and 3-fluorophenol (202 μL, 2.23 mmol) were added and the mixture was heated to 70° C. and shaken at that temperature for 2 hrs. The mixture was cooled down to RT, diluted with DCM and washed with water. Organic phase was dried and evaporated under reduced pressure. The crude material was purified by FC on silica gel (eluent: Cy to Cy/AcOEt 7:3) affording 2-chloro-4-(3-fluorophenoxy)-6-methylpyrimidine as a white solid (p33, 413 mg, y=78%)
MS (ES) (m/z): 239.1 [M+H]$^+$ Preparation 34:
2-chloro-4-methyl-6-(3-methylphenoxy)pyrimidine (P34)

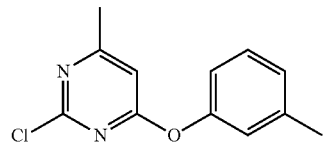 [SMILES: Cc1cccc(Oc2cc(C)nc(Cl)n2)c1]

To a solution of 2,4-dichloro-6-methylpyrimidine (100 mg, 0.61 mmol) and m-cresol (0.058 mL, 0.55 mmol) in DMSO (0.6 mL), at RT, K$_2$CO$_3$ (126 mg, 0.92 mmol) was added and the reaction mixture was stirred at RT overnight. Water and ether were added to the reaction mixture, the organic phase was washed with water and saturated NaHCO$_3$, dried and the solvent removed under reduced pressure to give 2-chloro-4-methyl-6-(3-methylphenoxy)pyrimidine (p34, 108 mg, y=83%) as pale yellow oil.
MS (ES) (m/z): 235.1 [M+H]$^+$ Preparation 35: 3-[(2-chloro-6-methylpyrimidin-4-yl)oxy]benzonitrile (P35)

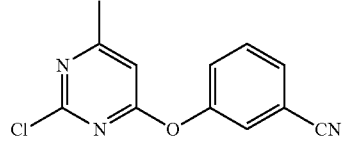 [SMILES: Cc1cc(Oc2cccc(C#N)c2)nc(Cl)n1]

To a solution of 2,4-dichloro-6-methylpyrimidine (100 mg, 0.61 mmol) and 3-cyano phenol (66 mg, 0.55 mmol) in DMSO (0.6 mL), at RT, K$_2$CO$_3$ (126 mg, 0.92 mmol) was added and the reaction mixture was stirred at RT overnight. Water and ether were added to the reaction mixture, the organic phase was washed with water, dried and the solvent removed under reduced pressure to give 3-[(2-chloro-6-methylpyrimidin-4-yl)oxy]benzonitrile (p35, 120 mg, y=88%).
MS (ES) (m/z): 246.0 [M+H]$^+$ Preparation 36: 2-chloro-4-methyl-6-[3-(trifluoromethoxy)phenoxy]pyrimidine (P36)

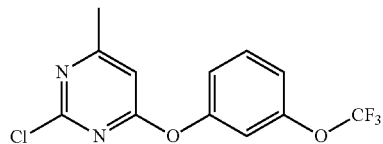 [SMILES: Cc1cc(Oc2cccc(OC(F)(F)F)c2)nc(Cl)n1]

To a solution of 2,4-dichloro-6-methylpyrimidine (100 mg, 0.61 mmol) and 3-(trifluoromethoxy)phenol (0.071 mL, 0.55 mmol) in DMSO (0.6 mL), at RT, K$_2$CO$_3$ (126 mg, 0.92 mmol) was added and the reaction mixture was stirred at RT overnight. Water and ether were added to the reaction mixture, the organic phase was washed with water, dried and the solvent removed under reduced pressure to give 2-chloro-4-methyl-6-[3-(trifluoromethoxy)phenoxy]pyrimidine (p36, 158 mg, y=94%).

MS (ES) (m/z): 305.0 [M+H]+

Preparation 37: 2-chloro-4-methyl-6-[3-(trifluoromethyl)phenoxy]pyrimidine (P37)

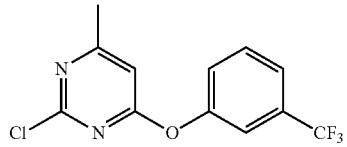 [SMILES: Cc1cc(Oc2cccc(C(F)(F)F)c2)nc(Cl)n1]

To a solution of 2,4-dichloro-6-methylpyrimidine (100 mg, 0.61 mmol) and 3-(trifluoromethyl)phenol (0.067 mL, 0.55 mmol) in DMSO (0.6 mL), at RT, $K_2CO_3$ (126 mg, 0.92 mmol) was added and the reaction mixture was stirred at RT overnight. Ether and water were added to the reaction mixture, the organic phase was washed with water, dried and the solvent removed under reduced pressure. This material was purified by FC on silica gel (eluent: Cy to Cy/EA 92/8) to give 2-chloro-4-methyl-6-[3-(trifluoromethyl)phenoxy]pyrimidine (p37, 73 mg, y=46%) as colourless oil.

MS (ES) (m/z): 289.0 [M+H]+

Preparation 38: 2-chloro-4-(3,5-difluorophenoxy)-6-methylpyrimidine (P38)

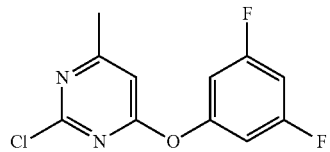 [SMILES: Cc1cc(Oc2cc(F)cc(F)c2)nc(Cl)n1]

A mixture of 2,4-dichloro-6-methylpyrimidine (150 mg, 0.92 mmol), 3,5 difluorophenol (95 mg, 0.736 mmol) and $K_2CO_3$ (165 mg, 1.2 mmol) in DMSO (1 mL) was heated at 100° C. for 2 hrs. After cooling at RT, EtOAc and water were added and the product was extracted in organic phase. The organic phase was dried and evaporated, the crude material was purified by FC on silica gel (eluent: Cy to Cy/EtOAc 80/20) affording 2-chloro-4-(3,5-difluorophenoxy)-6-methylpyrimidine (p38, 150 mg, y=79%). as white solid MS (ES) (m/z): 257.0 [M+H]+

Preparation 39: 2-chloro-4-(3-methoxyphenoxy)-6-methylpyrimidine (P39)

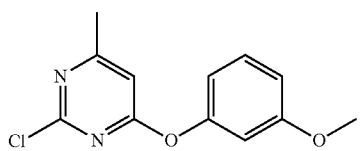 [SMILES: COc1cccc(Oc2cc(C)nc(Cl)n2)c1]

To a solution of 2,4-dichloro-6-methylpyrimidine (100 mg, 0.61 mmol) and 3-methoxyphenol (68 mg, 0.55 mmol) in DMSO (0.6 mL), at RT, $K_2CO_3$ (126 mg, 0.92 mmol) was added and the reaction mixture was stirred at RT overnight. Water and ether were added to the reaction mixture, the organic phase was washed with water, dried and the solvent removed under reduced pressure. The crude material was purified by FC on silica gel (eluent: Cy to Cy/EA 90/10) to give 2-chloro-4-(3-methoxyphenoxy)-6-methylpyrimidine (p39, 114 mg, y=82%).

MS (ES) (m/z): 251.0 [M+H]+

Preparation 40: 2-chloro-4-methyl-6-(2-methylphenoxy)pyrimidine (P40)

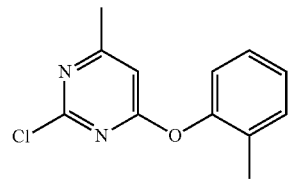 [SMILES: Cc1cc(Oc2ccccc2C)nc(Cl)n1]

To a solution of 2,4-dichloro-6-methylpyrimidine (363 mg, 2.23 mmol) in DMSO (2 mL) $K_2CO_3$ (370 mg, 2.67 mmol) and o-cresol (241 mg, 2.23 mmol) were added and the mixture was heated to 70° C. and shaken at that temperature for 2 hrs. The mixture was cooled down to RT, diluted with DCM and washed with water. Organic phase was dried and evaporated under reduced pressure. The crude material was purified by FC on silica gel (eluent: Cy to Cy/AcOEt 8/2) affording 2-chloro-4-methyl-6-(2-methylphenoxy)pyrimidine (p40, 468 mg, y=89%)

MS (ES) (m/z): 235.1 [M+H]+

Preparation 41: 2-chloro-4-(2-methoxyphenoxy)-6-methylpyrimidine (P41)

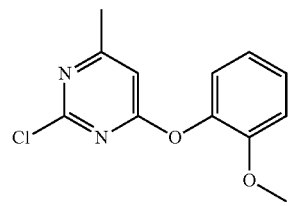 [SMILES: COc1ccccc1Oc1cc(C)nc(Cl)n1]

To a solution of 2,4-dichloro-6-methylpyrimidine (363 mg, 2.23 mmol) in DMSO (2 mL) $K_2CO_3$ (370 mg, 2.67 mmol) and guaiacol (245 µl, 2.23 mmol) were added; the mixture was heated to 70° C. and shaken at that temperature for 2 hrs. Then it was cooled down to RT, diluted with DCM and washed with water. Organic phase was dried and evaporated under reduced pressure. The crude material was purified by FC on silica gel (eluent: Cy to Cy/AcOEt 9/1) affording 2-chloro-4-(2-methoxyphenoxy)-6-methylpyrimidine (p41, 360 mg, y=64%) as a white solid.

MS (ES) (m/z): 251.1 [M+H]+

Preparation 42: 2-chloro-4-methyl-6-(pyridin-3-yloxy)pyrimidine (P42)

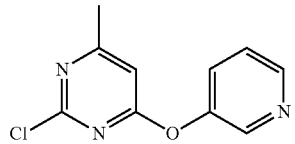

To a solution of 2,4-dichloro-6-methylpyrimidine (150 mg, 0.92 mmol) and pyridin-3-ol (79 mg, 0.83 mmol) in DMSO (1.0 mL), at RT, K$_2$CO$_3$ (191 mg, 1.38 mmol) was added and the reaction mixture was stirred at RT overnight. Water and EA were added to the reaction mixture, the organic phase was washed with water, dried and the solvent removed under reduced pressure. The crude material was combined with the crude from analogous preparation and purified by FC on silica gel (eluent: Cy to Cy/EA 20/80) to give 2-chloro-4-methyl-6-(pyridin-3-yloxy)pyrimidine (p42, 109 mg)

MS (ES) (m/z): 222.0 [M+H]$^+$

Preparation 43: 2-chloro-4-(3-fluorophenoxy)-5-methylpyrimidine (P43)

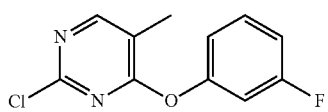 [SMILES: Cc1cnc(Cl)nc1Oc1cccc(F)c1]

A mixture of 2,4-dichloro-5-methylpyrimidine (500 mg, 3.06 mmol), 3-fluorophenol (0.277 ml, 3.06 mmol) and K$_2$CO$_3$ (551 mg, 3.98 mmol) in DMSO (2 mL) was heated at 100° C. for 2 hrs. After cooling at RT, EtOAc and water were added and the product was extracted in organic phase. The organic phase was dried and evaporated affording 2-chloro-4-(3-fluorophenoxy)-5-methylpyrimidine as white off solid (p43, 690 mg, y=94%).

MS (ES) (m/z): 239.0 [M+H]$^+$

Preparation 44: 2,4-dichloro-6-(trifluoromethyl)pyrimidine (P44)

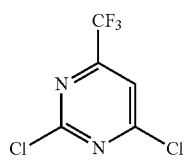 [SMILES: FC(F)(F)c1cc(Cl)nc(Cl)n1]

A mixture of 6-(Trifluoromethyl)uracil (3 g, 16.66 mmol), SOCl$_2$ (8 mL) and DMF (1 mL) was stirred at 80° C. for 4 hrs and then cooled down to 0° C. n-Hexane and crushed ice were added to the resulting mixture, followed by careful addition of NaHCO$_3$ until CO$_2$ had stopped evolving. The organic layer was separated, dried and carefully concentrated under reduced pressure with bath temperature below 35° C., giving 2,4-dichloro-6-(trifluoromethyl)pyrimidine (p44, 3.2 g, y=88%) as pale yellow oil used in the next stage without additional purification.

$^1$H NMR (CHLOROFORM-d): δ ppm 7.67 (s, 1H)

Preparation 45: 2-chloro-4-phenoxy-6-(trifluoromethyl)pyrimidine (P45)

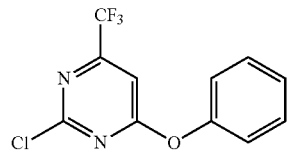 [SMILES: FC(F)(F)c1cc(Oc2ccccc2)nc(Cl)n1]

A mixture of 2,4-dichloro-6-(trifluoromethyl)pyrimidine (p44, 150 mg, 0.69 mmol), phenol (52 mg, 0.55 mmol) and K$_2$CO$_3$ (123 mg, 0.897 mmol) in DMSO (1 mL) was heated at 100° C. for 2 hrs. After cooling at RT, EtOAc and water were added and the product was extracted in organic phase. The organic phase was dried and evaporated, the crude material was purified by FC on silica gel (eluent: Cy to Cy/AcOEt 85/15) affording 2-chloro-4-phenoxy-6-(trifluoromethyl)pyrimidine (p45, 120 mg, y=73%) as pale yellow oil.

MS (ES) (m/z): 275.0 [M+H]$^+$

Preparation 46: 2-chloro-4-(3-fluorophenoxy)-6-(trifluoromethyl)pyrimidine (P46)

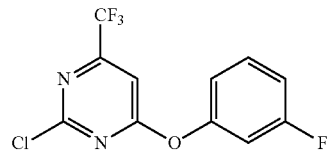 [SMILES: Fc1cccc(Oc2cc(C(F)(F)F)nc(Cl)n2)c1]

A mixture of 2,4-dichloro-6-(trifluoromethyl)pyrimidine (p44, 2 g, 9.2 mmol), 3-fluorophenol (0.75 mL, 8.2 mmol) and K$_2$CO$_3$ (1.66 g, 12 mmol) in DMSO (2 mL) was heated at 60° C. for 20 min. After cooling at RT, EtOAc and water were added and the product was extracted in organic phase. The organic phase was dried and evaporated, the crude material was purified by FC on silica gel (eluent: Cy to Cy/AcOEt 9/1) affording 2-chloro-4-(3-fluorophenoxy)-6-(trifluoromethyl)pyrimidine (p46, 2.26 g, y=94%) as pale yellow oil.

$^1$H NMR (CHLOROFORM-d): δ ppm 7.47 (td, 1H), 7.22 (s, 1H), 7.09 (td, 1H), 7.03-6.93 (m, 2H)

Preparation 47: 2-chloro-4-(2-fluorophenoxy)-6-(trifluoromethyl)pyrimidine (P47)

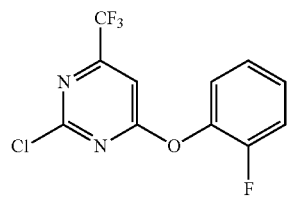 [SMILES: Fc1ccccc1Oc1cc(C(F)(F)F)nc(Cl)n1]

A mixture of 2,4-dichloro-6-(trifluoromethyl)pyrimidine (P44, 150 mg, 0.69 mmol), 2-fluorophenol (0.049 mL, 0.55 mmol) and K$_2$CO$_3$ (123 mg, 0.897 mmol) in DMSO (1 mL) was heated at 100° C. for 2 hrs. After cooling at RT, EtOAc and water were added and the product was extracted in organic phase. The organic phase was dried and evaporated, the crude material was purified by FC on silica gel (eluent: Cy to Cy/AcOEt 85/15) affording 2-chloro-4-(2-fluorophenoxy)-6-(trifluoromethyl)pyrimidine (p47, 115 mg, y=65%) as pale yellow oil.

MS (ES) (m/z): 292.9 [M+H]$^+$

Preparation 48: 2-chloro-4-(4-fluorophenoxy)-6-(trifluoromethyl)pyrimidine (P48)

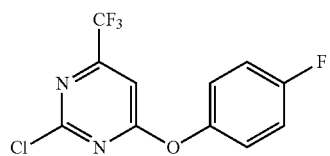 [SMILES: Fc1ccc(Oc2cc(C(F)(F)F)nc(Cl)n2)cc1]

A mixture of 2,4-dichloro-6-(trifluoromethyl)pyrimidine (p44, 150 mg, 0.6 mmol), 4-fluorophenol (61 mg, 0.55 mmol) and K$_2$CO$_3$ (108 mg, 0.78 mmol) in DMSO (1 mL) was heated at 100° C. for 2 hrs. After cooling at RT, EtOAc and water were added and the product was extracted in organic phase. The organic phase was dried and evaporated; the crude material was purified by FC on silica gel (eluent: Cy to Cy/EtOAc 85/15) affording 2-chloro-4-(4-fluorophenoxy)-6-(trifluoromethyl)pyrimidine (p48, 110 mg, y=65%) as pale yellow oil.

MS (ES) (m/z): 293.0 [M+H]$^+$

Preparation 49: 3-{[2-chloro-6-(trifluoromethyl)pyrimidin-4-yl]oxy}benzonitrile (P49)

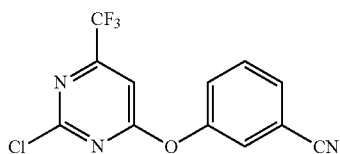 [SMILES: N#Cc1cccc(Oc2cc(C(F)(F)F)nc(Cl)n2)c1]

A mixture of 2,4-dichloro-6-(trifluoromethyl)pyrimidine (p44, 250 mg, 0.92 mmol), 3-cyanophenol (111 mg, 0.92 mmol) and K$_2$CO$_3$ (165 mg, 1.2 mmol) in DMSO (0.5 mL) was stirred at RT for 1 h. EtOAc and water were added and the product was extracted in organic phase. The organic phase was dried and evaporated, the residue triturate with cHex to afford 3-{[2-chloro-6-(trifluoromethyl)pyrimidin-4-yl]oxy}benzonitrile (p49, 257 mg, y=93%) as white solid.

MS (ES) (m/z): 299.9 [M+H]$^+$

Preparation 50: 2-chloro-4-(thiophen-2-yloxy)-6-(trifluoromethyl)pyrimidine (P50)

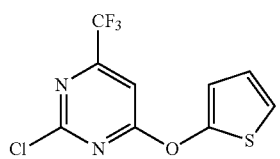 [SMILES: FC(F)(F)c1cc(Oc2cccs2)nc(Cl)n1]

To a solution of 2,4-dichloro-6-(trifluoromethyl)pyrimidine (p44, 100 mg, 0.46 mmol) and 2,5-dihydrothiophen-2-one (44 mg, 0.44 mmol) in DMSO (0.9 mL), at RT, K$_2$CO$_3$ (95 mg, 0.69 mmol) was added and the reaction mixture was stirred at RT for 4 hrs. Ether and water were added to the reaction mixture, the organic phase was washed with water, dried and the solvent removed under reduced pressure. The crude material was purified by FC on silica gel (eluent: Cy to Cy/EtOAc 92/8) to give 2-chloro-4-(thiophen-2-yloxy)-6-(trifluoromethyl)pyrimidine (p50, 66 mg, crude material)

MS (ES) (m/z): 280.9 [M+H]$^+$

Preparation 51: 4-benzyl-2,6-dichloropyrimidine (P51)

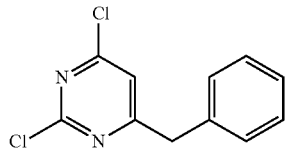 [SMILES: Clc1cc(Cc2ccccc2)nc(Cl)n1]

To a solution of 2,4,6-trichloropyrimidine (936 mg, 5 mmol) in THF (30 mL) 1M benzylmagnesiumchloride in Et$_2$O (5 mL, 5 mmol) was added dropwise at −78° C. The reaction was allowed to warm up to 20° C. over 3 hrs. EtOAc and H$_2$O were added, the product was extracted twice in organic phase, which was dried and evaporated. The crude material was purified by FC on silica (eluent: Cy to Cy/EA 90/10) affording 4-benzyl-2,6-dichloropyrimidine (p51, 1.1 g, y=92%) as pale yellow oil.

$^1$H NMR (CHLOROFORM-d): δ ppm 7.44-7.32 (m, 3H), 7.30-7.24 (m, 2H), 7.04 (s, 1H), 4.12 (s, 2H)

Preparation 52: 4-benzyl-2-chloro-6-methoxypyrimidine (P52)

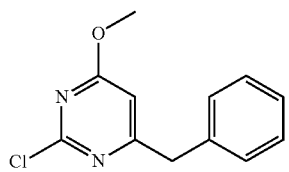 [SMILES: COc1cc(Cc2ccccc2)nc(Cl)n1]

NaH 60% dispersion in mineral oil (25 mg, 0.627 mmol) was dissolved in MeOH (1 mL) and stirred for 30 min, then a solution of 4-benzyl-2,6-dichloropyrimidine (p51, 150 mg, 0.627 mmol) dissolved in MeOH (2 mL) was added dropwise. The resulting mixture was stirred for 1 h at RT. EtOAc and water were added, the product was extracted in organic phase which was dried and evaporated. The crude material was purified by FC on silica gel (eluent: Cy to Cy/EA 90/10) to afford 4-benzyl-2-chloro-6-methoxypyrimidine (p52, 110 mg, y=75%) as white solid.

$^1$H NMR (CHLOROFORM-d): δ ppm 7.40-7.34 (m, 2H), 7.33-7.24 (m, 3H), 6.38 (s, 1H), 4.04 (s, 2H), 3.98 (s, 3H)

Preparation 53: 2-chloro-6-(3-fluorophenoxy)pyrimidine-4-carbonitrile (P53)

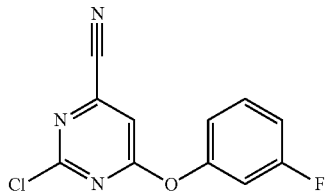 [SMILES: N#Cc1cc(Oc2cccc(F)c2)nc(Cl)n1]

A mixture 2,6-Dichloropyrimidine-4-carbonitrile (50 mg, 0.287 mmol), 3-fluorophenol (0.023 mL, 0.258 mmol) and K$_2$CO$_3$ (52 mg, 0.373 mmol) in DMSO (0.3 mL) was stirred at RT for 2 hrs. EtOAc and water were added and the product was extracted in organic phase. The organic phase was dried and evaporated, the crude material was purified by FC on silica gel (eluent: cHex to cHex/EtOAc 8/2) affording 2-chloro-6-(3-fluorophenoxy)pyrimidine-4-carbonitrile as pale yellow oil (p53, 54 mg, y=75%)

$^1$H NMR (CHLOROFORM-d): δ ppm 7.47 (dt, 1H), 7.24 (s, 1H), 7.10 (dt, 1H), 7.02-6.92 (m, 2H)

Preparation 54: 2,4-dichloro-6-(methylsulfanyl)pyrimidine (P54)

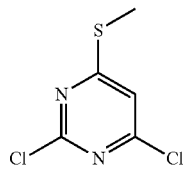

2-chloro-4-(methylthio)pyrimidine (320 mg, 2 mmol) in THF (4 mL) was added dropwise at RT to 2,2,6,6-Tetramethylpiperidinylmagnesium chloride lithium chloride complex 1M solution in THF/Toluene (2.2 mL, 2.2 mmol) and stirred for 5 min. A solution of N-Chlorosuccinimide (400 mg, 3 mmol) in THF (4 mL) was added dropwise and the mixture was stirred at RT for 4 hrs. The reaction mixture was quenched with saturated NH$_4$Cl, extracted whit Et$_2$O (3×) and dried. After evaporation the crude material was purified by FC on silica gel (eluent: cHex to DCM) affording 2,4-dichloro-6-(methylsulfanyl)pyrimidine (p54, 40 mg, y=10%) as white solid.

$^1$H NMR (CHLOROFORM-d): δ ppm 7.17 (s, 1H), 2.63 (s, 3H)

Preparation 55: 2-chloro-4-(3-fluorophenoxy)-6-(methylsulfanyl)pyrimidine and 4-chloro-2-(3-fluorophenoxy)-6-(methylsulfanyl)pyrimidine (P55)

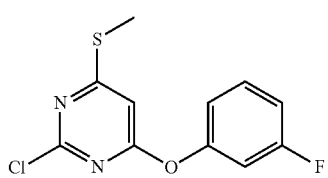

-continued

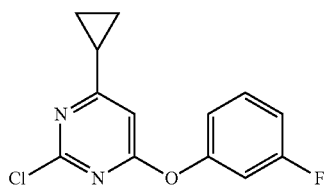 [SMILES: Fc1cccc(Oc2cc(C3CC3)nc(Cl)n2)c1]

A mixture of 2,4-dichloro-6-(methylsulfanyl)pyrimidine (p54, 40 mg, 0.17 mmol), 3 fluorophenol (0.014 mL, 0.153 mmol) and K$_2$CO$_3$ (30 mg, 0.221 mmol) in DMSO (0.3 mL) was stirred at RT for 2 hrs. EtOAc and water were added and the product was extracted in organic phase. The organic phase was dried and evaporated, the crude material was purified by FC on silica gel (eluent: Cy to Cy/EtOAc 7/3) affording 2-chloro-4-(3-fluorophenoxy)-6-(methylsulfanyl)pyrimidine and 4-chloro-2-(3-fluorophenoxy)-6-(methylsulfanyl)pyrimidine as white off solid (p55, 54 mg, y=quant) as mixture of regioisomers.

MS (ES) (m/z): 270.9 [M+H]$^+$

Preparation 56: 2-chloro-4-cyclopropyl-6-(3-fluorophenoxy)pyrimidine (P56)

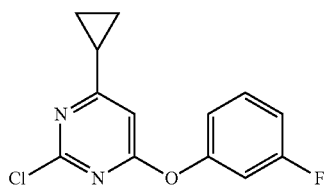 [SMILES: Fc1cccc(Oc2cc(C3CC3)nc(Cl)n2)c1]

A mixture of 2,4-dichloro-6-cyclopropylpyrimidine (25 mg, 0.132 mmol), 3-fluorophenol (0.012 mL, 0.132 mmol) and K$_2$CO$_3$ (24 mg, 0.17 mmol) in DMSO (0.3 mL) was stirred at RT for 1 h. EtOAc and water were then added and the product was extracted in organic phase. The organic phase was dried and evaporated, the crude material was purified by FC on silica gel (eluent: Cy to Cy/EtOAc 75/25) affording 2-chloro-4-cyclopropyl-6-(3-fluorophenoxy)pyrimidine (p56, 38 mg, y=quant) as yellow oil.

MS (ES) (m/z): 265.0 [M+H]$^+$

Preparation 57: tert-butyl 9-[6-(3-fluorophenoxy)pyridin-2-yl]-1-oxa-4,9-diazaspiro[5.5]undecane-4-carboxylate (P57)

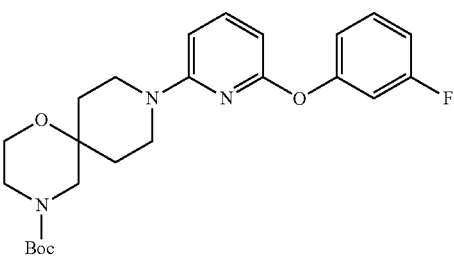 [SMILES: CC(C)(C)OC(=O)N1CCOC2(CCN(c3cccc(Oc4cccc(F)c4)n3)CC2)C1]

A mixture of tert-butyl 1-oxa-4,9-diazaspiro[5.5]undecane-4-carboxylate (p6, 60 mg, 0.23 mmol), 2-chloro-6-(3-fluorophenoxy)pyridine (p26, 47 mg, 0.21 mmol) and K$_2$CO$_3$ (38 mg, 0.27 mmol) in DMSO (0.8 mL) in a sealed vessel was heated at 90° C. and shaken 2.5 hrs at this temperature. The mixture was then shaken at 100° C. for 48 hrs. After cooling to RT, Et₂O and water were added, the organic phase was washed with water, dried and evaporated; crude product was purified by FC on silica gel (eluent: Cy/EA from 100/0 to 80/20) to give tert-butyl 9-[6-(3-fluorophenoxy)pyridin-2-yl]-1-oxa-4,9-diazaspiro[5.5]undecane-4-carboxylate (p57, 19 mg, y=20%).

MS (ES) (m/z): 444.2 [M+H]⁺

Preparation 58: tert-butyl 9-[6-(3-fluorophenoxy)-4-(trifluoromethyl)pyridin-2-yl]-1-oxa-4,9-diazaspiro[5.5]undecane-4-carboxylate (P58)

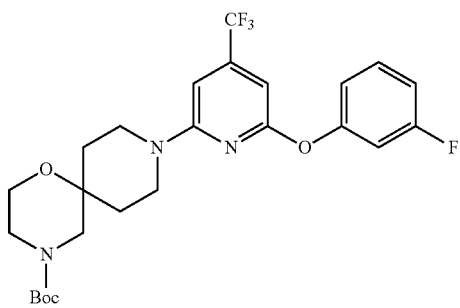

The title compound was prepared from tert-butyl 1-oxa-4,9-diazaspiro[5.5]undecane-4-carboxylate (p6, 60 mg, 0.23 mmol) and 1-benzyl-3-bromobenzene (p27, 68 mg, 0.23 mmol) in analogous manner as described in Preparation 57 (T=90° C., t=2 hrs). tert-butyl 9-[6-(3-fluorophenoxy)-4-(trifluoromethyl)pyridin-2-yl]-1-oxa-4,9-diazaspiro[5.5]undecane-4-carboxylate (p58, 75 mg, y=64%).

MS (ES) (m/z): 512.2 [M+H]⁺

Preparation 59: tert-butyl 9-[4-cyano-6-(3-fluorophenoxy)pyridin-2-yl]-1-oxa-4,9-diazaspiro[5.5]undecane-4-carboxylate (P59)

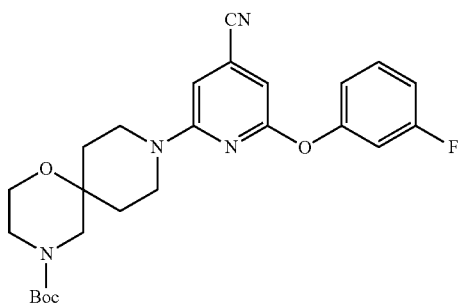 [SMILES: CC(C)(C)OC(=O)N1CCOC2(CCN(c3cc(C#N)cc(Oc4cccc(F)c4)n3)CC2)C1]

The title compound was prepared from tert-butyl 1-oxa-4,9-diazaspiro[5.5]undecane-4-carboxylate (p6, 65 mg, 0.26 mmol) and 2-chloro-6-(3-fluorophenoxy)pyridine-4-carbonitrile (p28, 128 mg, 0.51 mmol) in analogous manner as described in Preparation 57 (T=80° C., t=18 hrs). tert-butyl 9-[4-cyano-6-(3-fluorophenoxy)pyridin-2-yl]-1-oxa-4,9-diazaspiro[5.5]undecane-4-carboxylate (p59, 82 mg, y=67%).

MS (ES) (m/z): 469.1 [M+H]⁺

Preparation 60: tert-butyl 9-[5-cyano-6-(3-fluorophenoxy)-4-(trifluoromethyl)pyridin-2-yl]-1-oxa-4,9-diazaspiro[5.5]undecane-4-carboxylate (P60)

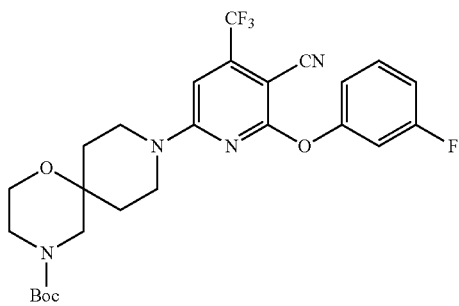 [SMILES: CC(C)(C)OC(=O)N1CCOC2(CCN(c3cc(C(F)(F)F)c(C#N)c(Oc4cccc(F)c4)n3)CC2)C1]

The title compound was prepared from tert-butyl 1-oxa-4,9-diazaspiro[5.5]undecane-4-carboxylate (p4, 36 mg, 0.139 mmol) and a mixture of 2-chloro-6-(3-fluorophenoxy)-4-(trifluoromethyl)pyridine-3-carbonitrile and 6-chloro-2-(3-fluorophenoxy)-4-(trifluoromethyl)pyridine-3-carbonitrile (p29, 53 mg, 0.167 mmol) in analogous manner as described in Preparation 57 (T=100° C., t=2 hrs). tert-butyl 9-[5-cyano-6-(3-fluorophenoxy)-4-(trifluoromethyl)pyridin-2-yl]-1-oxa-4,9-diazaspiro[5.5]undecane-4-carboxylate (p60, 27 mg, y=36%).

MS (ES) (m/z): 537.3 [M+H]⁺

Preparation 61: tert-butyl 9-[3-cyano-6-(3-fluorophenoxy)-4-(trifluoromethyl)pyridin-2-yl]-1-oxa-4,9-diazaspiro[5.5]undecane-4-carboxylate (P61)

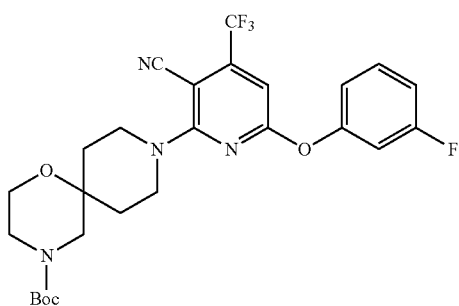 [SMILES: CC(C)(C)OC(=O)N1CCOC2(CCN(c3nc(Oc4cccc(F)c4)cc(C(F)(F)F)c3C#N)CC2)C1]

The title compound was prepared from tert-butyl 1-oxa-4,9-diazaspiro[5.5]undecane-4-carboxylate (p4, 36 mg, 0.139 mmol) and a mixture of 2-chloro-6-(3-fluorophenoxy)-4-(trifluoromethyl)pyridine-3-carbonitrile and 6-chloro-2-(3-fluorophenoxy)-4-(trifluoromethyl)pyridine-3-carbonitrile (p29, 53 mg, 0.167 mmol) in analogous manner as described in Preparation 57 (T=100° C., t=2 hrs). tert-butyl 9-[3-cyano-6-(3-fluorophenoxy)-4-(trifluoromethyl)pyridin-2-yl]-1-oxa-4,9-diazaspiro[5.5]undecane-4-carboxylate (p61, 11 mg, y=15%).

MS (ES) (m/z): 537.3 [M+H]⁺

Preparation 62: tert-butyl 9-[6-(3-fluorophenoxy)pyrazin-2-yl]-1-oxa-4,9-diazaspiro[5.5]undecane-4-carboxylate (P62)

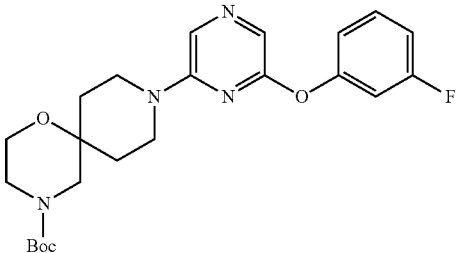 [SMILES: CC(C)(C)OC(=O)N1CCOC2(CCN(c3cncc(Oc4cccc(F)c4)n3)CC2)C1]

The title compound was prepared from tert-butyl 1-oxa-4,9-diazaspiro[5.5]undecane-4-carboxylate (p4, 50 mg, 0.195 mmol) and 2-chloro-6-(3-fluorophenoxy)pyrazine (p30, 44 mg, 0.195 mmol) in analogous manner as described in Preparation 57 (T=100° C., t=1 h). tert-butyl 9-[6-(3-fluorophenoxy)pyrazin-2-yl]-1-oxa-4,9-diazaspiro[5.5]undecane-4-carboxylate (p62, 37 mg, y=42%).

MS (ES) (m/z): 445.3 [M+H]$^+$

Preparation 63: tert-butyl 9-[4-(3-fluorophenoxy)pyrimidin-2-yl]-1-oxa-4,9-diazaspiro[5.5]undecane-4-carboxylate (P63)

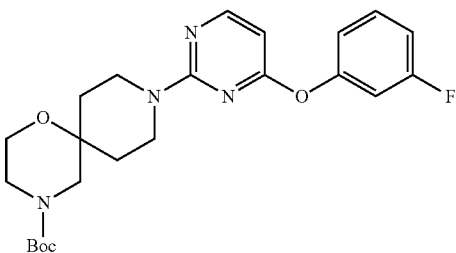 [SMILES: CC(C)(C)OC(=O)N1CCOC2(CCN(c3nccc(Oc4cccc(F)c4)n3)CC2)C1]

The title compound was prepared from tert-butyl 1-oxa-4,9-diazaspiro[5.5]undecane-4-carboxylate (p4, 50 mg, 0.195 mmol) and 2-chloro-4-(3-fluorophenoxy)pyrimidine (p31, 44 mg, 0.195 mmol) in analogous manner as described in Preparation 57 (T=100° C., t=18 hrs). tert-butyl 9-[4-(3-fluorophenoxy)pyrimidin-2-yl]-1-oxa-4,9-diazaspiro[5.5]undecane-4-carboxylate (p63, 38 mg, y=42%).

MS (ES) (m/z): 445.2 [M+H]$^+$

Preparation 64: tert-butyl 9-(4-methyl-6-phenoxypyrimidin-2-yl)-1-oxa-4,9-diazaspiro[5.5]undecane-4-carboxylate (P64)

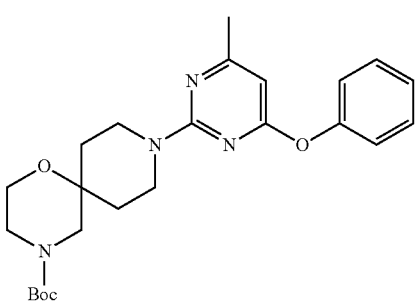 [SMILES: Cc1cc(Oc2ccccc2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 2-chloro-4-methyl-6-phenoxypyrimidine (p32, 44 mg, 0.195 mmol) in analogous manner as described in Preparation 57 (T=100° C., t=2 hrs). tert-butyl 9-(4-methyl-6-phenoxypyrimidin-2-yl)-1-oxa-4,9-diazaspiro[5.5]undecane-4-carboxylate (p64, 53 mg, y=62%).

MS (ES) (m/z): 445.2 [M+H]$^+$

Preparation 65: tert-butyl 9-[4-(3-fluorophenoxy)-6-methylpyrimidin-2-yl]-1-oxa-4,9-diazaspiro[5.5]undecane-4-carboxylate (P65)

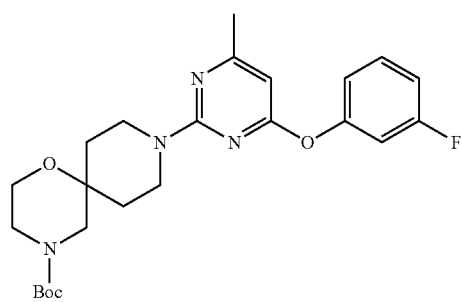 [SMILES: Cc1cc(Oc2cccc(F)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 2-chloro-4-(3-fluorophenoxy)-6-methylpyrimidine (p33, 47 mg, 0.195 mmol) in analogous manner as described in Preparation 57 (T=100° C., t=18 hrs). tert-butyl 9-[4-(3-fluorophenoxy)-6-methylpyrimidin-2-yl]-1-oxa-4,9-diazaspiro[5.5]undecane-4-carboxylate (p65, 45 mg, y=50%).

MS (ES) (m/z): 459.1 [M+H]$^+$

Preparation 66: tert-butyl 9-[4-methyl-6-(3-methylphenoxy)pyrimidin-2-yl]-1-oxa-4,9-diazaspiro[5.5]undecane-4-carboxylate (P66)

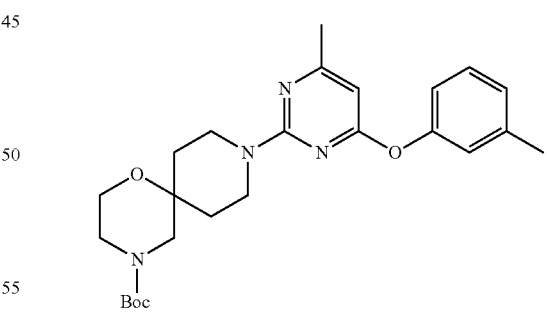

The title compound was prepared from tert-butyl 1-oxa-4,9-diazaspiro[5.5]undecane-4-carboxylate (p4, 53 mg, 0.21 mmol) and 2-chloro-4-methyl-6-(3-methylphenoxy)pyrimidine (p34, 54 mg, 0.23 mmol) in analogous manner as described in Preparation 57 (T=90° C., t=18 hrs). tert-butyl 9-[4-methyl-6-(3-methylphenoxy)pyrimidin-2-yl]-1-oxa-4,9-diazaspiro[5.5]undecane-4-carboxylate (p66, 51 mg, y=54%).

MS (ES) (m/z): 455.3 [M+H]$^+$

Preparation 67: tert-butyl 9-[4-(3-cyanophenoxy)-6-methylpyrimidin-2-yl]-1-oxa-4,9-diazaspiro[5.5]undecane-4-carboxylate (P67)

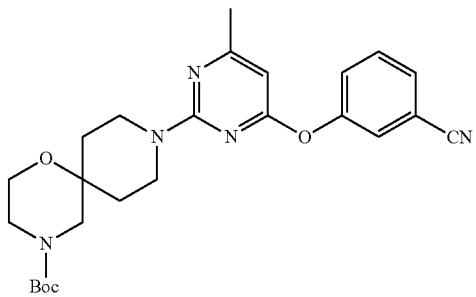 [SMILES: Cc1cc(Oc2cccc(C#N)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 55 mg, 0.21 mmol) and 3-[(2-chloro-6-methylpyrimidin-4-yl)oxy]benzonitrile (p35, 57 mg, 0.23 mmol) in analogous manner as described in Preparation 57 (T=100° C., t=3 hrs). tert-butyl 9-[4-(3-cyanophenoxy)-6-methylpyrimidin-2-yl]-1-oxa-4,9-diazaspiro[5.5]undecane-4-carboxylate (p67, 47 mg, y=48%).

MS (ES) (m/z): 466.1 [M+H]$^+$

Preparation 68: tert-butyl 9-{4-methyl-6-[3-(trifluoromethoxy)phenoxy]pyrimidin-2-yl}-1-oxa-4,9-diazaspiro[5.5]undecane-4-carboxylate (P68)

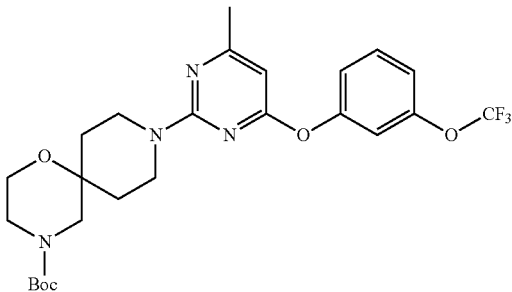 [SMILES: Cc1cc(Oc2cccc(OC(F)(F)F)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 60 mg, 0.23 mmol) and 2-chloro-4-methyl-6-[3-(trifluoromethoxy)phenoxy]pyrimidine (p36, 86 mg, 0.28 mmol) in analogous manner as described in Preparation 57 (T=100° C., t=3 hrs). tert-butyl 9-{4-methyl-6-[3-(trifluoromethoxy)phenoxy]pyrimidin-2-yl}-1-oxa-4,9-diazaspiro[5.5]undecane-4-carboxylate (p68, 56 mg, y=46%).

MS (ES) (m/z): 525.3 [M+H]$^+$

Preparation 69: tert-butyl 9-{4-methyl-6-[3-(trifluoromethyl)phenoxy]pyrimidin-2-yl}-1-oxa-4,9-diazaspiro[5.5]undecane-4-carboxylate (P69)

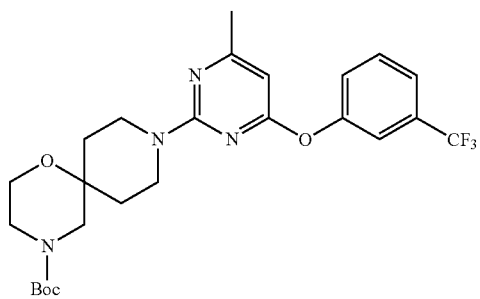 [SMILES: Cc1cc(Oc2cccc(C(F)(F)F)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 53 mg, 0.21 mmol) and 2-chloro-4-methyl-6-[3-(trifluoromethyl)phenoxy]pyrimidine (p37, 65 mg, 0.22 mmol) in analogous manner as described in Preparation 57 (T=90° C., t=18 hrs). tert-butyl 9-{4-methyl-6-[3-(trifluoromethyl)phenoxy]pyrimidin-2-yl}-1-oxa-4,9-diazaspiro[5.5]undecane-4-carboxylate (p69, 60 mg, y=56%).

MS (ES) (m/z): 509.3 [M+H]$^+$

Preparation 70: tert-butyl 9-[4-(3-methoxyphenoxy)-6-methylpyrimidin-2-yl]-1-oxa-4,9-diazaspiro[5.5]undecane-4-carboxylate (P70)

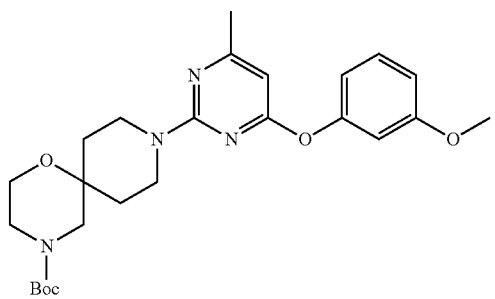 [SMILES: COc1cccc(Oc2cc(C)nc(N3CCC4(CC3)CN(C(=O)OC(C)(C)C)CCO4)n2)c1]

The title compound was prepared from tert-butyl 1-oxa-4,9-diazaspiro[5.5]undecane-4-carboxylate (p4, 45 mg, 0.18 mmol) and 2-chloro-4-(3-methoxyphenoxy)-6-methylpyrimidine (p39, 42 mg, 0.17 mmol) in analogous manner as described in Preparation 57 (T=100° C., t=3 hrs). tert-butyl 9-[4-(3-methoxyphenoxy)-6-methylpyrimidin-2-yl]-1-oxa-4,9-diazaspiro[5.5]undecane-4-carboxylate (p70, 59 mg, y=73%).

MS (ES) (m/z): 471.0 [M+H]$^+$

Preparation 71: tert-butyl 9-[4-(3,5-difluorophenoxy)-6-methylpyrimidin-2-yl]-1-oxa-4,9-diazaspiro[5.5]undecane-4-carboxylate (P71)

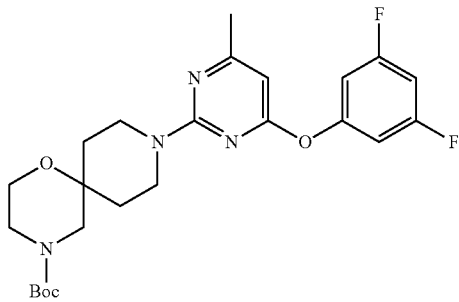 [SMILES: Cc1cc(Oc2cc(F)cc(F)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 2-chloro-4-(3,5-difluorophenoxy)-6-methylpyrimidine (p38, 50 mg, 0.195 mmol) in analogous manner as described in Preparation 57 (T=100° C., t=1 h). tert-butyl 9-[4-(3,5-difluorophenoxy)-6-methylpyrimidin-2-yl]-1-oxa-4,9-diazaspiro[5.5]undecane-4-carboxylate (p71, 40 mg, y=43%).

MS (ES) (m/z): 477.3 [M+H]$^+$

Preparation 72: tert-butyl 9-[4-methyl-6-(2-methyl phenoxy)pyrimidin-2-yl]-1-oxa-4,9-diazaspiro[5.5]undecane-4-carboxylate (P72)

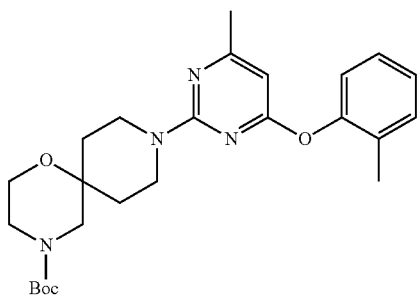 [SMILES: Cc1cc(Oc2ccccc2C)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 2-chloro-4-methyl-6-(2-methylphenoxy)pyrimidine (p40, 55 mg, 0.234 mmol) in analogous manner as described in Preparation 57 (T=100° C., t=1.5 h). tert-butyl 9-[4-methyl-6-(2-methylphenoxy)pyrimidin-2-yl]-1-oxa-4,9-diazaspiro[5.5]undecane-4-carboxylate (p72, 33 mg, y=37%).

MS (ES) (m/z): 455.3 [M+H]$^+$

Preparation 73: tert-butyl 9-[4-(2-methoxyphenoxy)-6-methylpyrimidin-2-yl]-1-oxa-4,9-diazaspiro[5.5]undecane-4-carboxylate (P73)

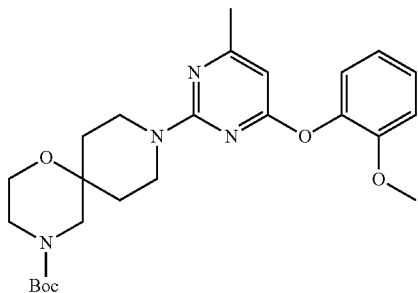 [SMILES: COc1ccccc1Oc1cc(C)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 2-chloro-4-(2-methoxyphenoxy)-6-methylpyrimidine (p41, 49 mg, 0.195 mmol) in analogous manner as described in Preparation 57 (T=100° C., t=1.5 h). tert-butyl 9-[4-(2-methoxyphenoxy)-6-methylpyrimidin-2-yl]-1-oxa-4,9-diazaspiro[5.5]undecane-4-carboxylate (p73, 60 mg, y=65%).

MS (ES) (m/z): 471.3 [M+H]$^+$

Preparation 74: tert-butyl 9-[4-methyl-6-(pyridin-3-yloxy)pyrimidin-2-yl]-1-oxa-4,9-diazaspiro[5.5]undecane-4-carboxylate (P74)

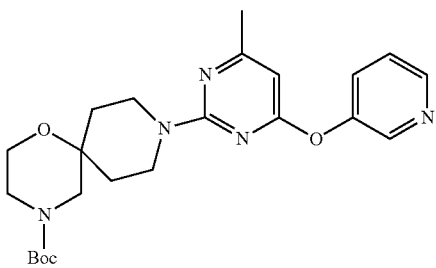 [SMILES: Cc1cc(Oc2cccnc2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 55 mg, 0.21 mmol) and 2-chloro-4-methyl-6-(pyridin-3-yloxy)pyrimidine (p42, 52 mg, 0.24 mmol) in analogous manner as described in Preparation 57 (T=100° C., t=3 hrs). tert-butyl 9-[4-methyl-6-(pyridin-3-yloxy)pyrimidin-2-yl]-1-oxa-4,9-diazaspiro[5.5]undecane-4-carboxylate (p74, 44 mg, y=47%).

MS (ES) (m/z): 442.1 [M+H]$^+$

Preparation 75: tert-butyl 9-[4-(3-fluorophenoxy)-5-methylpyrimidin-2-yl]-1-oxa-4,9-diazaspiro[5.5]undecane-4-carboxylate (P75)

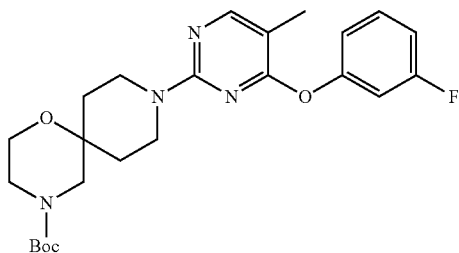 [SMILES: Cc1cnc(N2CCC3(CC2)CN(C(=O)OC(C)(C)C)CCO3)nc1Oc1cccc(F)c1]

The title compound was prepared from tert-butyl 1-oxa-4,9-diazaspiro[5.5]undecane-4-carboxylate (p4, 50 mg, 0.195 mmol) and 2-chloro-4-(3-fluorophenoxy)-5-methylpyrimidine (p43, 47 mg, 0.195 mmol) in analogous manner as described in Preparation 57 (T=100° C., t=1 h). tert-butyl 9-[4-(3-fluorophenoxy)-5-methylpyrimidin-2-yl]-1-oxa-4,9-diazaspiro[5.5]undecane-4-carboxylate (p75, 43 mg, y=48%).

MS (ES) (m/z): 459.3 [M+H]$^+$

Preparation 76: tert-butyl 9-[4-phenoxy-6-(trifluoromethyl)pyrimidin-2-yl]-1-oxa-4,9-diazaspiro[5.5]undecane-4-carboxylate (P76)

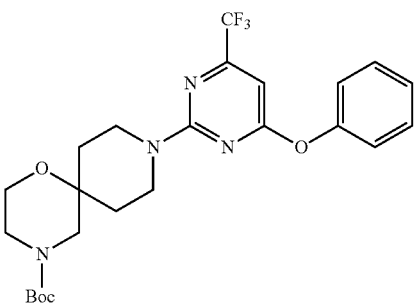 [SMILES: CC(C)(C)OC(=O)N1CCOC2(CCN(c3nc(Oc4ccccc4)cc(C(F)(F)F)n3)CC2)C1]

The title compound was prepared from tert-butyl 1-oxa-4,9-diazaspiro[5.5]undecane-4-carboxylate (p4, 50 mg, 0.195 mmol) and 2-chloro-4-phenoxy-6-(trifluoromethyl)pyrimidine (p45, 53 mg, 0.195 mmol) in analogous manner as described in Preparation 57 (T=100° C., t=2 hrs). tert-butyl 9-[4-phenoxy-6-(trifluoromethyl)pyrimidin-2-yl]-1-oxa-4,9-diazaspiro[5.5]undecane-4-carboxylate (p76, 75 mg, y=77%).

MS (ES) (m/z): 495.3 [M+H]+

Preparation 77: tert-butyl 9-[4-(3-fluorophenoxy)-6-(trifluoromethyl)pyrimidin-2-yl]-1-oxa-4,9-diazaspiro[5.5]undecane-4-carboxylate (P77)

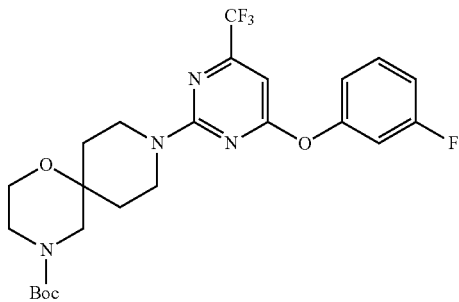 [SMILES: CC(C)(C)OC(=O)N1CCOC2(CCN(c3nc(Oc4cccc(F)c4)cc(C(F)(F)F)n3)CC2)C1]

The title compound was prepared from tert-butyl 1-oxa-4,9-diazaspiro[5.5]undecane-4-carboxylate (p6, 160 mg, 0.624 mmol) and 2-chloro-4-(3-fluorophenoxy)-6-(trifluoromethyl)pyrimidine (p46, 182 mg, 0.624 mmol) in analogous manner as described in Preparation 57 (T=100° C., t=1 h). tert-butyl 9-[4-(3-fluorophenoxy)-6-(trifluoromethyl)pyrimidin-2-yl]-1-oxa-4,9-diazaspiro[5.5]undecane-4-carboxylate (p77, 280 mg, y=87%).

MS (ES) (m/z): 513.2 [M+H]+

Preparation 78: tert-butyl 9-[4-(2-fluorophenoxy)-6-(trifluoromethyl)pyrimidin-2-yl]-1-oxa-4,9-diazaspiro[5.5]undecane-4-carboxylate (P78)

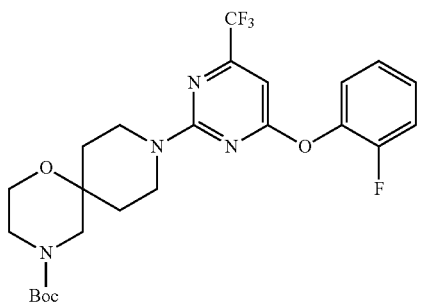 [SMILES: CC(C)(C)OC(=O)N1CCOC2(CCN(c3nc(Oc4ccccc4F)cc(C(F)(F)F)n3)CC2)C1]

The title compound was prepared from tert-butyl 1-oxa-4,9-diazaspiro[5.5]undecane-4-carboxylate (p4, 50 mg, 0.195 mmol) and 2-chloro-4-(2-fluorophenoxy)-6-(trifluoromethyl)pyrimidine (p47, 57 mg, 0.195 mmol) in analogous manner as described in Preparation 57 (T=100° C., t=2 hrs). tert-butyl 9-[4-(2-fluorophenoxy)-6-(trifluoromethyl)pyrimidin-2-yl]-1-oxa-4,9-diazaspiro[5.5]undecane-4-carboxylate (p78, 60 mg, y=60%).

MS (ES) (m/z): 513.3 [M+H]+

Preparation 79: tert-butyl 9-[4-(4-fluorophenoxy)-6-(trifluoromethyl)pyrimidin-2-yl]-1-oxa-4,9-diazaspiro[5.5]undecane-4-carboxylate (P79)

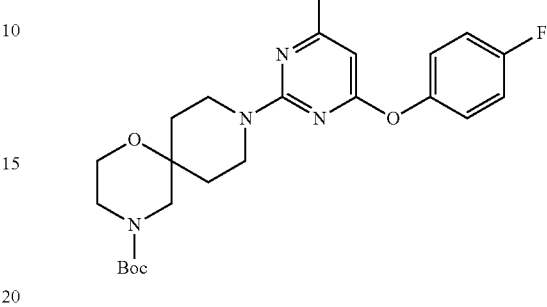

The title compound was prepared from tert-butyl 1-oxa-4,9-diazaspiro[5.5]undecane-4-carboxylate (p4, 50 mg, 0.195 mmol) and 2-chloro-4-(4-fluorophenoxy)-6-(trifluoromethyl)pyrimidine (p48, 57 mg, 0.195 mmol) in analogous manner as described in Preparation 57 (T=100° C., t=2 hrs). tert-butyl 9-[4-(4-fluorophenoxy)-6-(trifluoromethyl)pyrimidin-2-yl]-1-oxa-4,9-diazaspiro[5.5]undecane-4-carboxylate (p79, 79 mg, y=79%).

MS (ES) (m/z): 513.2 [M+H]+

Preparation 80: tert-butyl 9-[4-(3-cyanophenoxy)-6-(trifluoromethyl)pyrimidin-2-yl]-1-oxa-4,9-diazaspiro[5.5]undecane-4-carboxylate (P80)

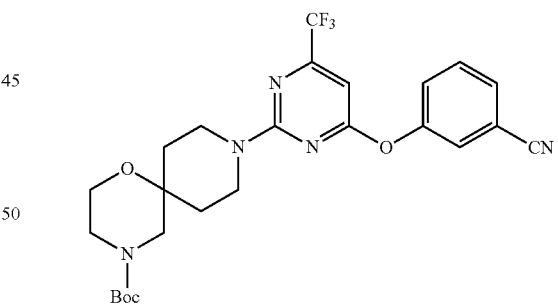

The title compound was prepared from tert-butyl 1-oxa-4,9-diazaspiro[5.5]undecane-4-carboxylate (p4, 50 mg, 0.195 mmol) and 3-{[2-chloro-6-(trifluoromethyl)pyrimidin-4-yl]oxy}benzonitrile (p49, 59 mg, 0.195 mmol) in analogous manner as described in Preparation 57 (T=100° C., t=1 h). tert-butyl 9-[4-(3-cyanophenoxy)-6-(trifluoromethyl)pyrimidin-2-yl]-1-oxa-4,9-diazaspiro[5.5]undecane-4-carboxylate (p80, 56 mg, y=55%).

MS (ES) (m/z): 520.2 [M+H]+

Preparation 81: tert-butyl 9-[4-(thiophen-2-yloxy)-6-(trifluoromethyl)pyrimidin-2-yl]-1-oxa-4,9-diazaspiro[5.5]undecane-4-carboxylate (P81)

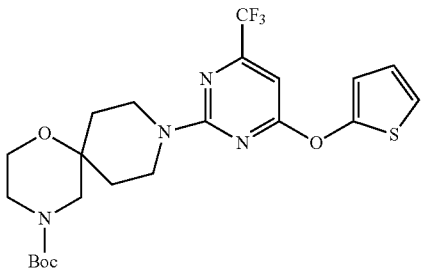 [SMILES: CC(C)(C)OC(=O)N1CCOC2(CCN(c3nc(Oc4cccs4)cc(C(F)(F)F)n3)CC2)C1]

The title compound was prepared from tert-butyl 1-oxa-4,9-diazaspiro[5.5]undecane-4-carboxylate (p6, 41 mg, 0.16 mmol) and 2-chloro-4-(thiophen-2-yloxy)-6-(trifluoromethyl)pyrimidine (p50, 66 mg, 0.27 mmol) in analogous manner as described in Preparation 57 (T=80° C., t=18 hrs). tert-butyl 9-[4-(thiophen-2-yloxy)-6-(trifluoromethyl)pyrimidin-2-yl]-1-oxa-4,9-diazaspiro[5.5]undecane-4-carboxylate (p81, 12 mg, y=15%).
MS (ES) (m/z): 501.2 [M+H]$^+$ Preparation 82: tert-butyl 9-(4-benzyl-6-methoxypyrimidin-2-yl)-1-oxa-4,9-diazaspiro[5.5]undecane-4-carboxylate (P82)

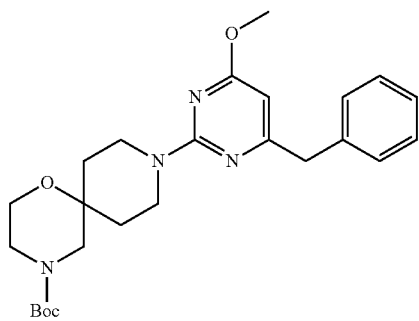 [SMILES: COc1cc(Cc2ccccc2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and 4-benzyl-2-chloro-6-methoxypyrimidine (p51, 69 mg, 0.165 mmol) in analogous manner as described in Preparation 57 (T=100° C., t=1 h). tert-butyl 9-(4-benzyl-6-methoxypyrimidin-2-yl)-1-oxa-4,9-diazaspiro[5.5]undecane-4-carboxylate (p82, 55 mg, y=67%).
MS (ES) (m/z): 455.3 [M+H]$^+$ Preparation 83: tert-butyl 9-[4-cyano-6-(3-fluorophenoxy)pyrimidin-2-yl]-1-oxa-4,9-diazaspiro[5.5]undecane-4-carboxylate (P83)

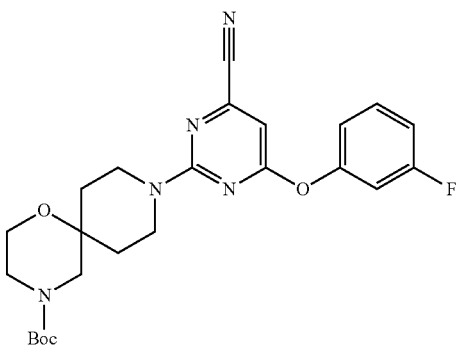 [SMILES: CC(C)(C)OC(=O)N1CCOC2(CCN(c3nc(C#N)cc(Oc4cccc(F)c4)n3)CC2)C1]

The title compound was prepared from tert-butyl 1-oxa-4,9-diazaspiro[5.5]undecane-4-carboxylate (p4, 50 mg, 0.195 mmol) and 2-chloro-6-(3-fluorophenoxy)pyrimidine-4-carbonitrile (p53, 54 mg, 0.195 mmol) in analogous manner as described in Preparation 57 (T=100° C., t=1 h). tert-butyl 9-[4-cyano-6-(3-fluorophenoxy)pyrimidin-2-yl]-1-oxa-4,9-diazaspiro[5.5]undecane-4-carboxylate (p83, 52 mg, y=56%).
MS (ES) (m/z): 470.3 [M+H]$^+$ Preparation 84: tert-butyl 9-[4-(3-fluorophenoxy)-6-(methylsulfanyl)pyrimidin-2-yl]-1-oxa-4,9-diazaspiro[5.5]undecane-4-carboxylate (P84)

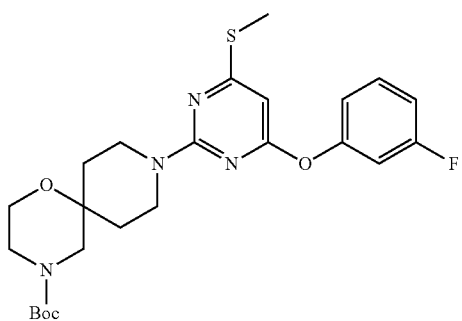 [SMILES: CSc1cc(Oc2cccc(F)c2)nc(N2CCC3(CC2)CN(C(=O)OC(C)(C)C)CCO3)n1]

The title compound was prepared from tert-butyl 1-oxa-4,9-diazaspiro[5.5]undecane-4-carboxylate (p4, 50 mg, 0.195 mmol) and a mixture of 2-chloro-4-(3-fluorophenoxy)-6-(methylsulfanyl)pyrimidine and 4-chloro-2-(3-fluorophenoxy)-6-(methylsulfanyl)pyrimidine (p55, 54 mg, 0.195 mmol) in analogous manner as described in Preparation 57 (T=100° C., t=1 h). tert-butyl 9-[4-(3-fluorophenoxy)-6-(methylsulfanyl)pyrimidin-2-yl]-1-oxa-4,9-diazaspiro[5.5]undecane-4-carboxylate (p84, 48 mg, y=50%).
MS (ES) (m/z): 491.2 [M+H]$^+$ Preparation 85: tert-butyl 9-[2-(3-fluorophenoxy)-6-(methylsulfanyl)pyrimidin-4-yl]-1-oxa-4,9-diazaspiro[5.5]undecane-4-carboxylate (P85)

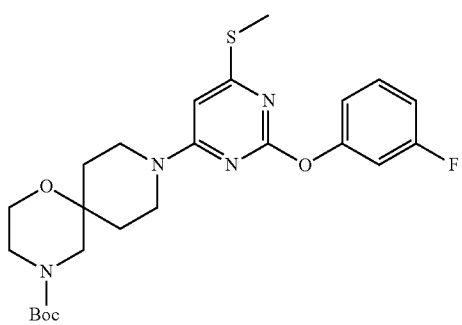 [SMILES: CSc1cc(N2CCC3(CC2)CN(C(=O)OC(C)(C)C)CCO3)nc(Oc2cccc(F)c2)n1]

The title compound was prepared from tert-butyl 1-oxa-4,9-diazaspiro[5.5]undecane-4-carboxylate (p4, 50 mg, 0.195 mmol) and a mixture of 2-chloro-4-(3-fluorophenoxy)-6-(methylsulfanyl)pyrimidine and 4-chloro-2-(3-fluorophenoxy)-6-(methylsulfanyl)pyrimidine (p55, 54 mg, 0.195 mmol) in analogous manner as described in Preparation 57 (T=100° C., t=1 h). tert-butyl 9-[2-(3-fluorophenoxy)-6-(methylsulfanyl)pyrimidin-4-yl]-1-oxa-4,9-diazaspiro[5.5]undecane-4-carboxylate (p85, 24 mg, y=25%).

MS (ES) (m/z): 491.2 [M+H]+

Preparation 86: tert-butyl 9-[4-cyclopropyl-6-(3-fluorophenoxy)pyrimidin-2-yl]-1-oxa-4,9-diazaspiro[5.5]undecane-4-carboxylate (P86)

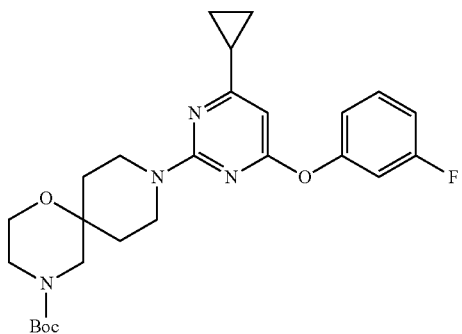 [SMILES: CC(C)(C)OC(=O)N1CCOC2(CCN(c3nc(Oc4cccc(F)c4)cc(C4CC4)n3)CC2)C1]

The title compound was prepared from tert-butyl 1-oxa-4,9-diazaspiro[5.5]undecane-4-carboxylate (p4, 50 mg, 0.195 mmol) and chloro-4-cyclopropyl-6-(3-fluorophenoxy)pyrimidine (p56, 38 mg, 0.132 mmol) in analogous manner as described in Preparation 57 (T=100° C., t=1 h). tert-butyl 9-[4-cyclopropyl-6-(3-fluorophenoxy)pyrimidin-2-yl]-1-oxa-4,9-diazaspiro[5.5]undecane-4-carboxylate (p86, 38 mg, y=59%).

MS (ES) (m/z): 485.0 [M+H]+

Example 36: 9-[6-(3-fluorophenoxy)pyridin-2-yl]-1-oxa-4,9-diazaspiro[5.5]undecane hydrochloride

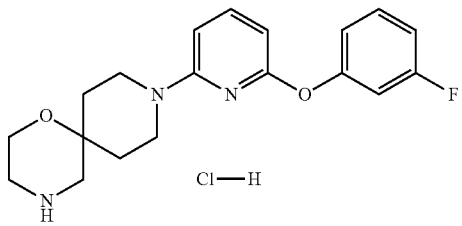 [SMILES: Fc1cccc(Oc2cccc(N3CCC4(CC3)CNCCO4)n2)c1 ; Cl]

Step a
To a solution of tert-butyl 9-[6-(3-fluorophenoxy)pyridin-2-yl]-1-oxa-4,9-diazaspiro[5.5]undecane-4-carboxylate (p57, 19 mg, 0.043 mmol) in DCM (0.2 mL), at RT, TFA (0.098 mL) was added. After 2 hrs the reaction mixture was concentrated under vacuum. The residue was taken up with DCM and sodium bicarbonate saturated solution, the organic phase was dried and the solvent removed under vacuum to give 9-[6-(3-fluorophenoxy)pyridin-2-yl]-1-oxa-4,9-diazaspiro[5.5]undecane (11 mg).
Step b
9-[6-(3-fluorophenoxy)pyridin-2-yl]-1-oxa-4,9-diazaspiro[5.5]undecane (11 mg, 0.032 mmol) was dissolved in DCM (0.1 mL) and HCl 2M in ether (0.016 mL) was added. The mixture was concentrated under reduced pressure; the residue was triturated with ether and dried under vacuum to give 9-[6-(3-fluorophenoxy)pyridin-2-yl]-1-oxa-4,9-diazaspiro[5.5]undecane hydrochloride (E36, 11 mg, y=67%).

MS (ES) (m/z): 344.17 [M+H]+
1H NMR (DMSO-d6): δ ppm 9.19 (br. s., 2H), 7.59 (t, 1H), 7.43 (q, 1H), 6.90-7.09 (m, 3H), 6.59 (d, 1H), 6.19 (d, 1H), 3.67-3.86 (m, 4H), 3.10 (t, 2H), 2.92-3.05 (m, 4H), 1.87 (d, 2H), 1.47-1.60 (m, 2H)

Example 37: 9-[6-(3-fluorophenoxy)-4-(trifluoromethyl)pyridin-2-yl]-1-oxa-4,9-diazaspiro[5.5]undecane hydrochloride (E37)

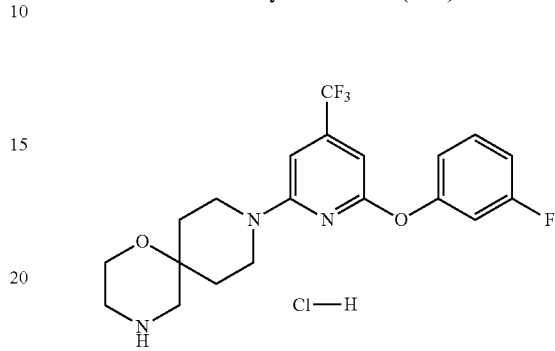

The title compound was prepared from tert-butyl 9-[6-(3-fluorophenoxy)-4-(trifluoromethyl)pyridin-2-yl]-1-oxa-4,9-diazaspiro[5.5]undecane-4-carboxylate (p58, 75 mg, 0.15 mmol) in analogous manner as described in Example 36. 9-[6-(3-fluorophenoxy)-4-(trifluoromethyl)pyridin-2-yl]-1-oxa-4,9-diazaspiro[5.5]undecane hydrochloride (E37, 18 mg, y=27%).

MS (ES) (m/z): 412.17 [M+H]+
1H NMR (DMSO-d6): δ ppm 9.23 (br. s., 2H), 7.40-7.53 (m, 1H), 7.05-7.17 (m, 2H), 6.98-7.05 (m, 1H), 6.86 (s, 1H), 6.43 (s, 1H), 3.73-3.87 (m, 4H), 3.14 (t, 2H), 2.92-3.07 (m, 4H), 1.88 (d, 2H), 1.45-1.60 (m, 2H)

Example 38: 2-(3-fluorophenoxy)-6-{1-oxa-4,9-diazaspiro[5.5]undecan-9-yl}pyridine-4-carbonitrile hydrochloride (E38)

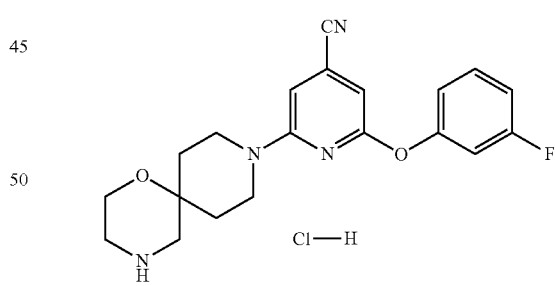

The title compound was prepared from tert-butyl 9-[4-cyano-6-(3-fluorophenoxy)pyridin-2-yl]-1-oxa-4,9-diazaspiro[5.5]undecane-4-carboxylate (p59, 82 mg, 0.175 mmol) in analogous manner as described in Example 36. 2-(3-fluorophenoxy)-6-{1-oxa-4,9-diazaspiro[5.5]undecan-9-yl}pyridine-4-carbonitrile hydrochloride (E38, 28 mg, y=39%).

MS (ES) (m/z): 369.2 [M+H]+
1H NMR (DMSO-d6): δ ppm 9.27 (br. s., 2H), 7.39-7.52 (m, 1H), 7.04-7.16 (m, 3H), 6.96-7.04 (m, 1H), 6.58 (s, 1H), 3.69-3.88 (m, 4H), 3.13 (t, 2H), 2.89-3.06 (m, 4H), 1.89 (s, 1H), 1.86 (s, 1H), 1.46-1.61 (m, 2H)

Example 39: 2-(3-fluorophenoxy)-6-{1-oxa-4,9-diazaspiro[5.5]undecan-9-yl}-4-(trifluoromethyl)pyridine-3-carbonitrile hydrochloride (E39)

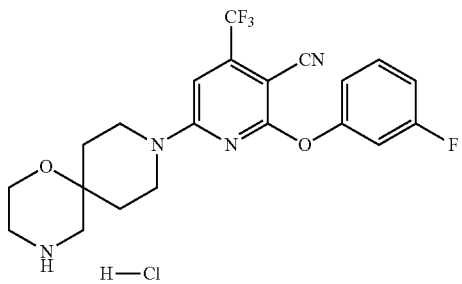

The title compound was prepared from tert-butyl 9-[5-cyano-6-(3-fluorophenoxy)-4-(trifluoromethyl)pyridin-2-yl]-1-oxa-4,9-diazaspiro[5.5]undecane-4-carboxylate (p60, 27 mg, 0.05 mmol) in analogous manner as described in Example 36. 2-(3-fluorophenoxy)-6-{1-oxa-4,9-diazaspiro[5.5]undecan-9-yl}-4-(trifluoromethyl)pyridine-3-carbonitrile hydrochloride (E39, 20 mg, y=84%).

MS (ES) (m/z): 437.22 [M+H]$^+$ $^1$H NMR (DMSO-d$_6$): δ ppm 9.03 (br. s., 2H) 7.47-7.60 (m, 1H) 7.26 (s, 1H) 7.28 (s, 1H) 7.11-7.23 (m, 2H) 7.09 (s, 1H) 3.90 (br. s., 3H) 3.79 (br. s., 2H) 2.98 (s, 2H) 3.03 (s, 2H) 1.88 (br. s., 2H) 1.53 (br. s., 3H)

Example 40: 6-(3-fluorophenoxy)-2-{1-oxa-4,9-diazaspiro[5.5]undecan-9-yl}-4-(trifluoromethyl)pyridine-3-carbonitrile hydrochloride (E40)

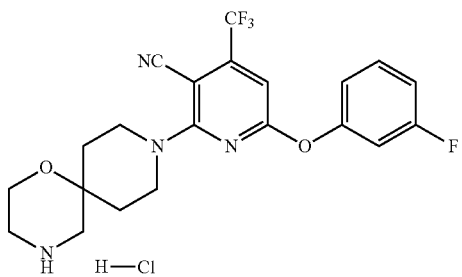

The title compound was prepared from tert-butyl 9-[3-cyano-6-(3-fluorophenoxy)-4-(trifluoromethyl)pyridin-2-yl]-1-oxa-4,9-diazaspiro[5.5]undecane-4-carboxylate (p61, 11 mg, 0.02 mmol) in analogous manner as described in Example 36. 6-(3-fluorophenoxy)-2-{1-oxa-4,9-diazaspiro[5.5]undecan-9-yl}-4-(trifluoromethyl)pyridine-3-carbonitrile hydrochloride (E40, 9 mg, y=95%).

MS (ES) (m/z): 437.2 [M+H]$^+$ $^1$H NMR (DMSO-d$_6$): δ ppm 8.99 (br. s., 2H), 7.53 (d, 1H), 7.27 (d, 1H), 7.09-7.22 (m, 2H), 6.97 (s, 1H), 3.73-3.89 (m, 4H), 3.21-3.30 (m, 2H), 3.02 (br. s., 4H), 1.88 (s, 1H), 1.91 (s, 1H), 1.63 (s, 1H), 1.66 (s, 1H)

Example 41: 9-[6-(3-fluorophenoxy)pyrazin-2-yl]-1-oxa-4,9-diazaspiro[5.5]undecane hydrochloride (E41)

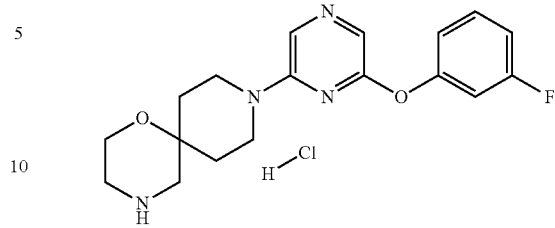

The title compound was prepared from tert-butyl 9-[6-(3-fluorophenoxy)pyrazin-2-yl]-1-oxa-4,9-diazaspiro[5.5]undecane-4-carboxylate (p62, 37 mg, 0.08 mmol) in analogous manner as described in Example 36. 9-[6-(3-fluorophenoxy)pyrazin-2-yl]-1-oxa-4,9-diazaspiro[5.5]undecane hydrochloride (E41, 30 mg, y=95%).

MS (ES) (m/z): 345.19 [M+H]$^+$ $^1$H NMR (DMSO-d$_6$): δ ppm 9.28 (br. s., 2H), 8.11 (s, 1H), 7.61 (s, 1H), 7.41-7.51 (m, 1H), 6.97-7.18 (m, 3H), 3.74-3.85 (m, 4H), 3.15 (t, 2H), 3.01 (d, 4H), 1.92 (d, 2H), 1.49-1.68 (m, 2H)

Example 42: 9-[4-(3-fluorophenoxy)pyrimidin-2-yl]-1-oxa-4,9-diazaspiro[5.5]undecane hydrochloride (E42)

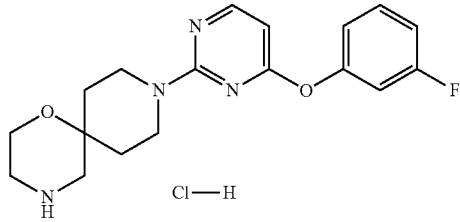 [SMILES: Fc1cccc(Oc2ccnc(N3CCC4(CC3)CNCCO4)n2)c1 ; Cl]

The title compound was prepared from tert-butyl 9-[4-(3-fluorophenoxy)pyrimidin-2-yl]-1-oxa-4,9-diazaspiro[5.5]undecane-4-carboxylate (p63, 38 mg, 0.08 mmol) in analogous manner as described in Example 36. 9-[4-(3-fluorophenoxy)pyrimidin-2-yl]-1-oxa-4,9-diazaspiro[5.5]undecane hydrochloride (E42, 31 mg, y=95%).

MS (ES) (m/z): 345.13 [M+H]$^+$ $^1$H NMR (DMSO-d$_6$): δ ppm 8.98 (br. s., 2H), 8.27 (d, 1H), 7.39-7.57 (m, 1H), 7.10-7.21 (m, 2H), 6.98-7.10 (m, 1H), 6.21 (d, 1H), 4.04 (br. s., 2H), 3.79 (t, 2H), 3.09-3.26 (m, 2H), 3.03 (s, 2H), 2.98 (s, 2H), 1.88 (s, 1H), 1.84 (s, 1H), 1.39-1.59 (m, 2H)

Example 43: 9-(4-methyl-6-phenoxypyrimidin-2-yl)-1-oxa-4,9-diazaspiro[5.5]undecane hydrochloride (E43)

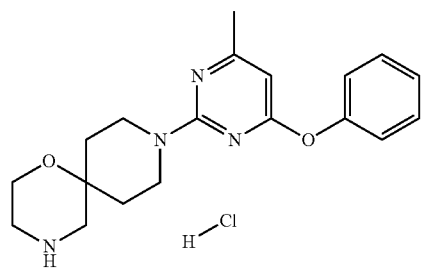 [SMILES: Cc1cc(Oc2ccccc2)nc(N2CCC3(CC2)CNCCO3)n1 ; Cl]

The title compound was prepared from tert-butyl 9-(4-methyl-6-phenoxypyrimidin-2-yl)-1-oxa-4,9-diazaspiro[5.5]undecane-4-carboxylate (p64, 53 mg, 0.12 mmol) in analogous manner as described in Example 36. 9-(4-methyl-6-phenoxypyrimidin-2-yl)-1-oxa-4,9-diazaspiro[5.5]undecane hydrochloride (E43, 47 mg, y=quant).

MS (ES) (m/z): 341.22 [M+H]+

$^1$H NMR (DMSO-d$_6$): δ ppm 9.18 (br. s., 2H), 7.46 (t, 2H), 7.29 (t, 1H), 7.19 (d, 2H), 6.07 (br. s., 1H), 3.81 (br. s., 2H), 3.18 (br. s., 2H), 3.01 (d, 4H), 2.28 (s, 2H), 1.90 (d, 2H), 1.51 (t, 2H)

Example 44: 9-[4-(3-fluorophenoxy)-6-methylpyrimidin-2-yl]-1-oxa-4,9-diazaspiro[5.5]undecane hydrochloride (E44)

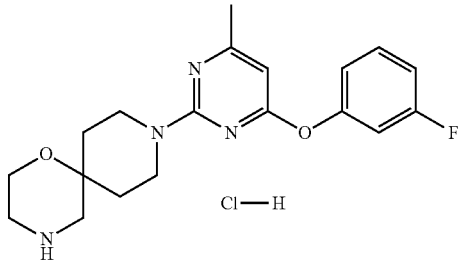 [SMILES: Cc1cc(Oc2cccc(F)c2)nc(N2CCC3(CC2)CNCCO3)n1 ; Cl]

The title compound was prepared from tert-butyl 9-[4-(3-fluorophenoxy)-6-methylpyrimidin-2-yl]-1-oxa-4,9-diazaspiro[5.5]undecane-4-carboxylate (p65, 45 mg, 0.098 mmol) in analogous manner as described in Example 36. 9-[4-(3-fluorophenoxy)-6-methylpyrimidin-2-yl]-1-oxa-4,9-diazaspiro[5.5]undecane hydrochloride (E44, 38 mg, y=98%).

MS (ES) (m/z): 359.20 [M+H]+

$^1$H NMR (DMSO-d$_6$): δ ppm 9.00 (br. s., 2H), 7.44-7.51 (m, 1H), 7.09-7.15 (m, 2H), 7.02-7.07 (m, 1H), 6.08 (s, 1H), 4.07 (br. s., 2H), 3.76-3.83 (m, 2H), 3.16 (t, 2H), 3.00-3.07 (m, 2H), 2.96-3.00 (m, 2H), 2.26 (s, 3H), 1.86 (d, 2H), 1.45-1.53 (m, 2H)

Example 45: 9-[4-methyl-6-(3-methylphenoxy)pyrimidin-2-yl]-1-oxa-4,9-diazaspiro[5.5]undecane hydrochloride (E45)

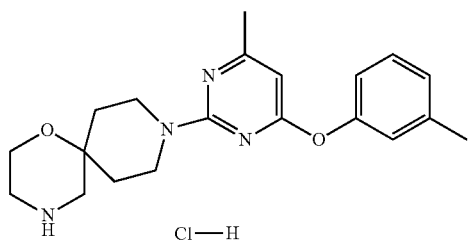 [SMILES: Cc1cccc(Oc2cc(C)nc(N3CCC4(CC3)CNCCO4)n2)c1 ; Cl]

The title compound was prepared from tert-butyl 9-[4-methyl-6-(3-methylphenoxy)pyrimidin-2-yl]-1-oxa-4,9-diazaspiro[5.5]undecane-4-carboxylate (p66, 51 mg, 0.11 mmol) in analogous manner as described in Example 36. 9-[4-methyl-6-(3-methylphenoxy)pyrimidin-2-yl]-1-oxa-4,9-diazaspiro[5.5]undecane hydrochloride (E45, 41 mg, y=95%).

MS (ES) (m/z): 355.14 [M+H]+

$^1$H NMR (DMSO-d$_6$): δ ppm 9.39 (br. s., 2H), 7.22-7.40 (m, 1H), 7.08 (d, 1H), 6.89-7.04 (m, 2H), 6.00 (s, 1H), 4.10 (br. s., 2H), 3.74-3.86 (m, 2H), 3.17 (t, 2H), 2.99 (d, 4H), 2.33 (s, 3H), 2.25 (s, 3H), 1.91 (d, 2H), 1.44-1.60 (m, 2H)

Example 46: 3-[(6-methyl-2-{1-oxa-4,9-diazaspiro[5.5]undecan-9-yl}pyrimidin-4-yl)oxy]benzonitrile hydrochloride (E46)

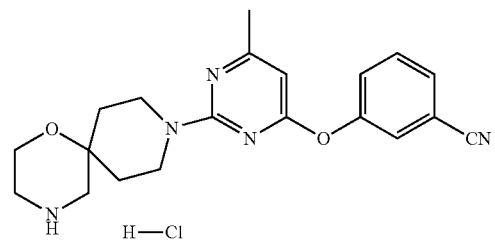

The title compound was prepared from tert-butyl 9-[4-(3-cyanophenoxy)-6-methylpyrimidin-2-yl]-1-oxa-4,9-diazaspiro[5.5]undecane-4-carboxylate (p67, 47 mg, 0.10 mmol) in analogous manner as described in Example 36. 3-[(6-methyl-2-{1-oxa-4,9-diazaspiro[5.5]undecan-9-yl}pyrimidin-4-yl)oxy]benzonitrile hydrochloride (E46, 42 mg, y=quantitative).

MS (ES) (m/z): 366.22 [M+H]+

$^1$H NMR (DMSO-d$_6$): δ ppm 9.30 (br. s., 2H), 7.69-7.81 (m, 2H), 7.65 (t, 1H), 7.53-7.61 (m, 1H), 6.16 (s, 1H), 4.02 (br. s., 2H), 3.74-3.84 (m, 2H), 3.15 (br. s., 2H), 2.99 (d, 4H), 2.28 (s, 3H), 1.88 (d, 2H), 1.49 (t, 2H)

Example 47: 9-{4-methyl-6-[3-(trifluoromethoxy)phenoxy]pyrimidin-2-yl}-1-oxa-4,9-diazaspiro[5.5]undecane hydrochloride (E47)

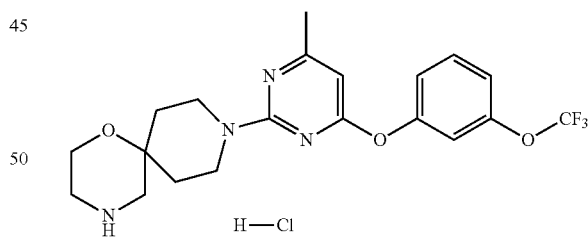

The title compound was prepared from tert-butyl 9-{4-methyl-6-[3-(trifluoromethoxy)phenoxy]pyrimidin-2-yl}-1-oxa-4,9-diazaspiro[5.5]undecane-4-carboxylate (p68, 56 mg, 0.11 mmol) in analogous manner as described in Example 36. 9-{4-methyl-6-[3-(trifluoromethoxy)phenoxy]pyrimidin-2-yl}-1-oxa-4,9-diazaspiro[5.5]undecane hydrochloride (E47, 45 mg, y=89%).

MS (ES) (m/z): 425.14 [M+H]+

$^1$H NMR (DMSO-d$_6$): δ ppm 9.34 (br. s., 2H), 7.57 (t, 1H), 7.20-7.34 (m, 3H), 6.16 (s, 1H), 3.90-4.13 (m, 2H), 3.73-3.84 (m, 2H), 3.14 (br. s., 2H), 2.99 (d, 4H), 2.28 (s, 3H), 1.88 (d, 2H), 1.49 (t, 2H)

Example 48: 9-{4-methyl-6-[3-(trifluoromethyl)phenoxy]pyrimidin-2-yl}-1-oxa-4,9-diazaspiro[5.5]undecane hydrochloride (E48)

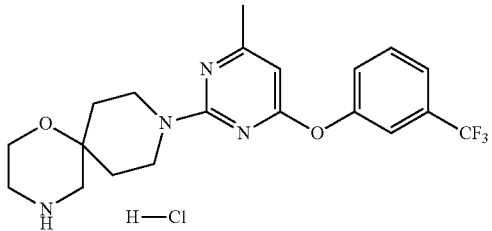

The title compound was prepared from tert-butyl 9-{4-methyl-6-[3-(trifluoromethyl)phenoxy]pyrimidin-2-yl}-1-oxa-4,9-diazaspiro[5.5]undecane-4-carboxylate (p69, 60 mg, 0.12 mmol) in analogous manner as described in Example 36. 9-{4-methyl-6-[3-(trifluoromethyl)phenoxy]pyrimidin-2-yl}-1-oxa-4,9-diazaspiro[5.5]undecane hydrochloride (E48, 44 mg, y=82%).

MS (ES) (m/z): 409.24 [M+H]$^+$ $^1$H NMR (DMSO-d$_6$): δ ppm 9.33 (br. s., 2H), 7.58-7.74 (m, 3H), 7.52 (d, 1H), 6.17 (s, 1H), 4.02 (br. s., 2H), 3.75-3.85 (m, 2H), 3.15 (br. s., 2H), 2.99 (d, 4H), 2.28 (s, 3H), 1.87 (d, 2H), 1.49 (t, 2H)

Example 49: 9-[4-(3-methoxyphenoxy)-6-methylpyrimidin-2-yl]-1-oxa-4,9-diazaspiro[5.5]undecane hydrochloride (E49)

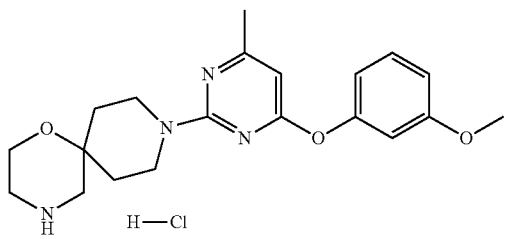

The title compound was prepared from tert-butyl 9-[4-(3-methoxyphenoxy)-6-methylpyrimidin-2-yl]-1-oxa-4,9-diazaspiro[5.5]undecane-4-carboxylate (p70, 59 mg, 0.125 mmol) in analogous manner as described in Example 36. 9-[4-(3-methoxyphenoxy)-6-methyl pyrimidin-2-yl]-1-oxa-4,9-diazaspiro[5.5]undecane hydrochloride (E49, 49 mg, y=96%).

MS (ES) (m/z): 371.22 [M+H]$^+$ $^1$H NMR (DMSO-d$_6$): δ ppm 9.30 (br. s., 2H), 7.34 (t, 1H), 6.84 (dd, 1H), 6.70-6.80 (m, 2H), 6.00 (s, 1H), 4.11 (br. s., 2H), 3.78-3.85 (m, 2H), 3.76 (s, 3H), 3.18 (t, 2H), 3.02 (s, 2H), 2.98 (s, 2H), 2.25 (s, 3H), 1.90 (d, 2H), 1.45-1.61 (m, 2H)

Example 50: 9-[4-(3,5-difluorophenoxy)-6-methylpyrimidin-2-yl]-1-oxa-4,9-diazaspiro[5.5]undecane hydrochloride (E50)

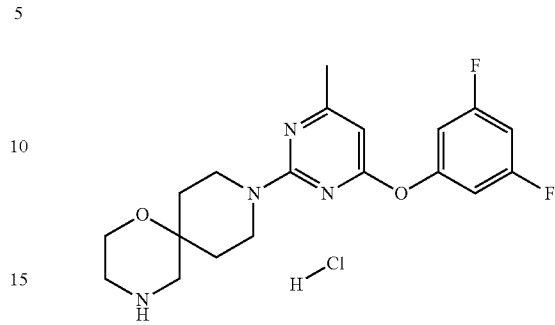

The title compound was prepared from tert-butyl 9-[4-(3,5-difluorophenoxy)-6-methylpyrimidin-2-yl]-1-oxa-4,9-diazaspiro[5.5]undecane-4-carboxylate (p71, 40 mg, 0.084 mmol) in analogous manner as described in Example 36. 9-[4-(3,5-difluorophenoxy)-6-methylpyrimidin-2-yl]-1-oxa-4,9-diazaspiro[5.5]undecane hydrochloride (E50, 49 mg, y=92%).

MS (ES) (m/z): 377.19 [M+H]$^+$ $^1$H NMR (DMSO-d$_6$): δ ppm 9.16 (br. s., 2H), 7.13-7.24 (m, 1H), 7.07 (dd, 2H), 6.16 (s, 1H), 4.08 (br. s., 2H), 3.73-3.89 (m, 2H), 3.18 (br. s., 2H), 3.03 (s, 2H), 2.98 (s, 2H), 2.28 (s, 3H), 1.91 (s, 1H), 1.88 (s, 1H), 1.51 (t, 2H)

Example 51: 9-[4-methyl-6-(2-methylphenoxy)pyrimidin-2-yl]-1-oxa-4,9-diazaspiro[5.5]undecane hydrochloride (E51)

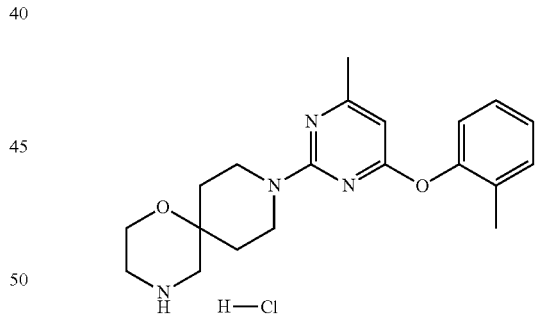

The title compound was prepared from tert-butyl 9-[4-methyl-6-(2-methylphenoxy)pyrimidin-2-yl]-1-oxa-4,9-diazaspiro[5.5]undecane-4-carboxylate (p72, 33 mg, 0.07 mmol) in analogous manner as described in Example 36. 9-[4-methyl-6-(2-methylphenoxy)pyrimidin-2-yl]-1-oxa-4,9-diazaspiro[5.5]undecane hydrochloride (E51, 25 mg, y=91%).

MS (ES) (m/z): 355.21 [M+H]$^+$ $^1$H NMR (DMSO-d$_6$): δ ppm 9.09 (br. s., 2H), 7.33 (d, 1H), 7.17-7.30 (m, 2H), 7.07 (d, 1H), 5.98 (s, 1H), 4.05 (br. s., 2H), 3.79 (br. s., 2H), 3.14 (br. s., 2H), 3.03 (br. s., 2H), 2.98 (br. s., 2H), 2.24 (s, 3H), 2.10 (s, 3H), 1.86 (d, 2H), 1.38-1.58 (m, 2H)

Example 52: 9-[4-(2-methoxyphenoxy)-6-methylpyrimidin-2-yl]-1-oxa-4,9-diazaspiro[5.5]undecane hydrochloride (E52)

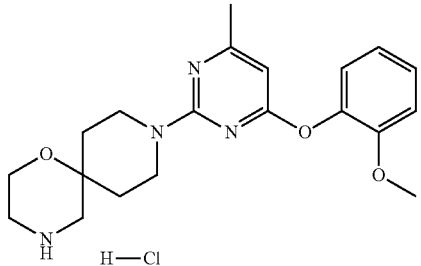

The title compound was prepared from tert-butyl 9-[4-(2-methoxyphenoxy)-6-methylpyrimidin-2-yl]-1-oxa-4,9-diazaspiro[5.5]undecane-4-carboxylate (p73, 60 mg, 0.13 mmol) in analogous manner as described in Example 36. 9-[4-(2-methoxyphenoxy)-6-methyl pyrimidin-2-yl]-1-oxa-4,9-diazaspiro[5.5]undecane hydrochloride (E52, 11 mg, y=20%).

MS (ES) (m/z): 371.24 [M+H]$^+$ $^1$H NMR (DMSO-d$_6$): δ ppm 9.01 (br. s., 2H), 7.22-7.33 (m, 1H), 7.07-7.22 (m, 2H), 6.96-7.05 (m, 1H), 5.95 (s, 1H), 4.04 (br. s., 2H), 3.80 (br. s., 2H), 3.73 (s, 3H), 3.14 (br. s., 2H), 3.04 (br. s., 2H), 2.99 (br. s., 2H), 2.23 (s, 3H), 1.85 (d, 2H), 1.47 (t, 2H)

Example 53: 9-[4-methyl-6-(pyridin-3-yloxy)pyrimidin-2-yl]-1-oxa-4,9-diazaspiro[5.5]undecane hydrochloride (E53)

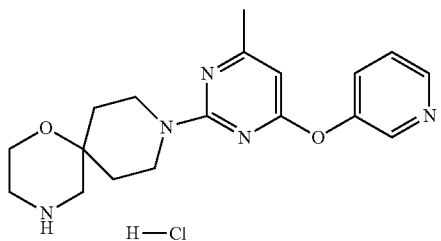

The title compound was prepared from tert-butyl 9-[4-methyl-6-(pyridin-3-yloxy)pyrimidin-2-yl]-1-oxa-4,9-diazaspiro[5.5]undecane-4-carboxylate (p74, 44 mg, 0.10 mmol) in analogous manner as described in Example 36. 9-[4-methyl-6-(pyridin-3-yloxy)pyrimidin-2-yl]-1-oxa-4,9-diazaspiro[5.5]undecane hydrochloride (E53, 32 mg, y=85%).

MS (ES) (m/z): 342.21 [M+H]$^+$ $^1$H NMR (DMSO-d$_6$): δ ppm 9.24 (br. s., 2H), 8.42-8.54 (m, 2H), 7.62-7.74 (m, 1H), 7.50 (dd, 1H), 6.17 (s, 1H), 4.03 (br. s., 2H), 3.74-3.86 (m, 2H), 3.13 (br. s., 2H), 3.02 (br. s., 2H), 2.96 (br. s., 2H), 2.22-2.30 (m, 3H), 1.87 (d, 2H), 1.48 (t, 2H)

Example 54: 9-[4-(3-fluorophenoxy)-5-methylpyrimidin-2-yl]-1-oxa-4,9-diazaspiro[5.5]undecane hydrochloride (E54)

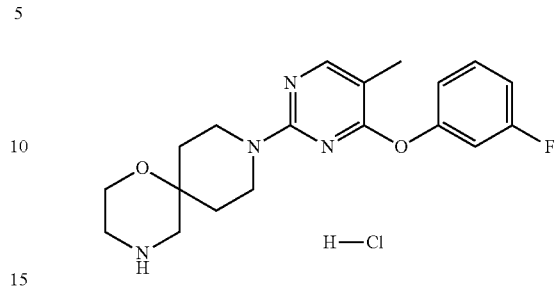

The title compound was prepared from tert-butyl 9-[4-(3-fluorophenoxy)-5-methylpyrimidin-2-yl]-1-oxa-4,9-diazaspiro[5.5]undecane-4-carboxylate (p75, 43 mg, 0.093 mmol) in analogous manner as described in Example 36. 9-[4-(3-fluorophenoxy)-5-methylpyrimidin-2-yl]-1-oxa-4,9-diazaspiro[5.5]undecane hydrochloride (E54, 37 mg, y=quantitative).

MS (ES) (m/z): 359.21 [M+H]$^+$ $^1$H NMR (DMSO-d$_6$): δ ppm 9.19 (br. s., 2H), 8.19 (s, 1H), 7.43-7.56 (m, 1H), 7.01-7.24 (m, 3H), 3.91 (br. s., 2H), 3.73-3.85 (m, 2H), 3.15 (t, 2H), 3.02 (br. s., 2H), 2.97 (br. s., 2H), 2.13 (s, 3H), 1.86 (d, 2H), 1.50 (t, 2H)

Example 55: 9-[4-phenoxy-6-(trifluoromethyl)pyrimidin-2-yl]-1-oxa-4,9-diazaspiro[5.5]undecane hydrochloride (E55)

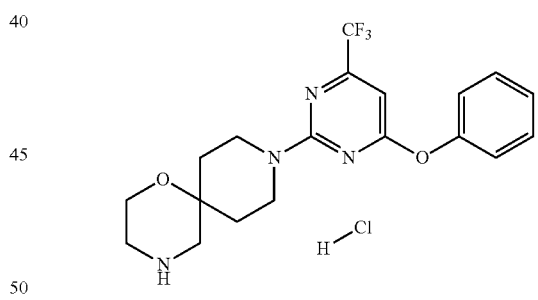

The title compound was prepared from tert-butyl 9-[4-phenoxy-6-(trifluoromethyl)pyrimidin-2-yl]-1-oxa-4,9-diazaspiro[5.5]undecane-4-carboxylate (p76, 75 mg, 0.15 mmol) in analogous manner as described in Example 36. 9-[4-phenoxy-6-(trifluoromethyl)pyrimidin-2-yl]-1-oxa-4,9-diazaspiro[5.5]undecane hydrochloride (E55, 51 mg, y=85%).

MS (ES) (m/z): 395.23 [M+H]$^+$ $^1$H NMR (DMSO-d$_6$): δ ppm 9.04 (br. s., 2H), 7.49 (t, 2H), 7.33 (t, 1H), 7.26 (d, 2H), 6.62 (s, 1H), 4.23 (br. s., 1H), 3.75-3.99 (m, 3H), 3.16 (br. s., 2H), 3.05 (br. s., 2H), 2.98 (br. s., 2H), 1.91 (d, 2H), 1.51 (br. s., 2H)

Example 56: 9-[4-(3-fluorophenoxy)-6-(trifluoromethyl)pyrimidin-2-yl]-1-oxa-4,9-diazaspiro[5.5]undecane hydrochloride (E56)

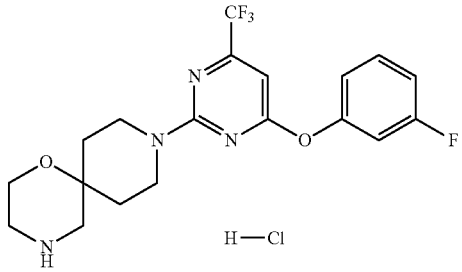 [SMILES: Fc1cccc(Oc2cc(C(F)(F)F)nc(N3CCC4(CC3)CNCCO4)n2)c1 ; Cl]

The title compound was prepared from tert-butyl 9-[4-(3-fluorophenoxy)-6-(trifluoromethyl)pyrimidin-2-yl]-1-oxa-4,9-diazaspiro[5.5]undecane-4-carboxylate (p77, 325 mg, 0.624 mmol) in analogous manner as described in Example 36. 9-[4-(3-fluorophenoxy)-6-(trifluoromethyl)pyrimidin-2-yl]-1-oxa-4,9-diazaspiro[5.5]undecane hydrochloride (E56, 280 mg, y=98%).

MS (ES) (m/z): 413.19 [M+H]$^+$ $^1$H NMR (DMSO-d$_6$): δ ppm 9.07 (br. s., 2H), 7.46-7.61 (m, 1H), 7.08-7.27 (m, 3H), 6.63 (s, 1H), 4.04 (br. s., 2H), 3.77-3.89 (m, 2H), 3.26 (t, 2H), 3.16 (s, 5H), 3.02-3.10 (m, 2H), 3.00 (s, 2H), 1.96 (s, 1H), 1.92 (s, 1H), 1.48-1.66 (m, 2H)

Example 57: 9-[4-(2-fluorophenoxy)-6-(trifluoromethyl)pyrimidin-2-yl]-1-oxa-4,9-diazaspiro[5.5]undecane hydrochloride (E57)

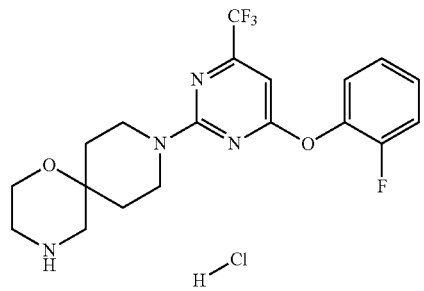 [SMILES: Fc1ccccc1Oc1cc(C(F)(F)F)nc(N2CCC3(CC2)CNCCO3)n1 ; Cl]

The title compound was prepared from tert-butyl 9-[4-(2-fluorophenoxy)-6-(trifluoromethyl)pyrimidin-2-yl]-1-oxa-4,9-diazaspiro[5.5]undecane-4-carboxylate (p78, 60 mg, 0.117 mmol) in analogous manner as described in Example 36. 9-[4-(2-fluorophenoxy)-6-(trifluoromethyl)pyrimidin-2-yl]-1-oxa-4,9-diazaspiro[5.5]undecane hydrochloride (E57, 47 mg, y=89%).

MS (ES) (m/z): 413.22 [M+H]$^+$ $^1$H NMR (DMSO-d$_6$): δ ppm 9.06 (br. s., 2H), 7.36-7.50 (m, 3H), 7.26-7.36 (m, 1H), 6.81 (s, 1H), 4.23 (br. s., 1H), 3.79 (br. s., 3H), 3.40-3.47 (m, 1H), 3.25 (br. s., 1H), 3.04 (br. s., 2H), 2.98 (br. s., 2H), 1.89 (br. s., 2H), 1.51 (br. s., 2H)

Example 58: 9-[4-(4-fluorophenoxy)-6-(trifluoromethyl)pyrimidin-2-yl]-1-oxa-4,9-diazaspiro[5.5]undecane hydrochloride (E58)

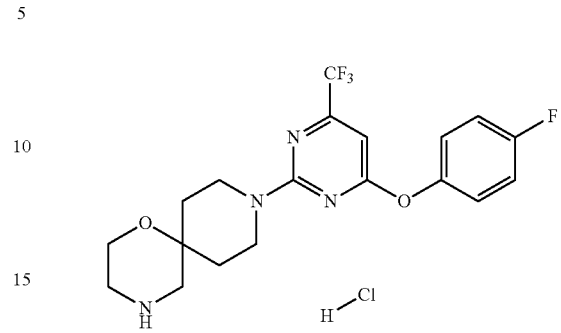

The title compound was prepared from tert-butyl 9-[4-(4-fluorophenoxy)-6-(trifluoromethyl)pyrimidin-2-yl]-1-oxa-4,9-diazaspiro[5.5]undecane-4-carboxylate (p79, 79 mg, 0.154 mmol) in analogous manner as described in Example 36. 9-[4-(4-fluorophenoxy)-6-(trifluoromethyl)pyrimidin-2-yl]-1-oxa-4,9-diazaspiro[5.5]undecane hydrochloride (E58, 55 mg, y=79%).

MS (ES) (m/z): 413.23 [M+H]$^+$ $^1$H NMR (DMSO-d$_6$): δ ppm 8.94 (br. s., 2H), 7.32 (d, 4H), 6.67 (s, 2H), 4.24 (br. s., 2H), 3.81 (br. s., 2H), 3.22 (br. s., 2H), 3.06 (br. s., 2H), 2.99 (br. s., 2H), 1.91 (d, 2H), 1.51 (br. s., 2H)

Example 59: 3-[(2-{1-oxa-4,9-diazaspiro[5.5]undecan-9-yl}-6-(trifluoromethyl)pyrimidin-4-yl)oxy]benzonitrile hydrochloride (E59)

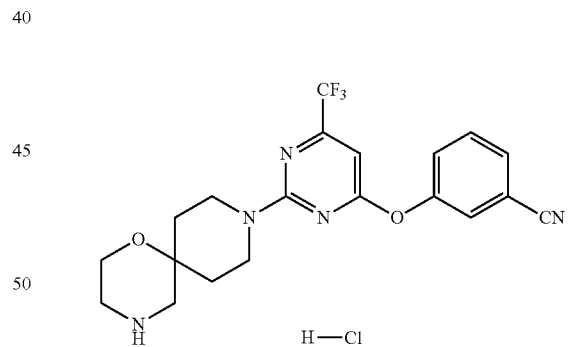

The title compound was prepared from tert-butyl 9-[4-(3-cyanophenoxy)-6-(trifluoromethyl)pyrimidin-2-yl]-1-oxa-4,9-diazaspiro[5.5]undecane-4-carboxylate (p80, 56 mg, 0.107 mmol) in analogous manner as described in Example 36. 3-[(2-{1-oxa-4,9-diazaspiro[5.5]undecan-9-yl}-6-(trifluoromethyl)pyrimidin-4-yl)oxy]benzonitrile hydrochloride (E59, 48 mg, y=98%).

MS (ES) (m/z): 420.20 [M+H]$^+$ $^1$H NMR (DMSO-d$_6$): δ ppm 9.08 (br. s., 2H), 7.88 (s, 1H), 7.81 (d, 1H), 7.60-7.74 (m, 2H), 6.77 (s, 1H), 4.23 (br. s., 1H), 3.79 (br. s., 3H), 3.22-3.34 (br. s., 2H), 3.03 (br. s., 3H), 2.98 (s, 2H), 1.90 (br. s., 2H), 1.51 (br. s., 2H)

Example 60: 9-[4-(thiophen-2-yloxy)-6-(trifluoromethyl)pyrimidin-2-yl]-1-oxa-4,9-diazaspiro[5.5]undecane hydrochloride (E60)

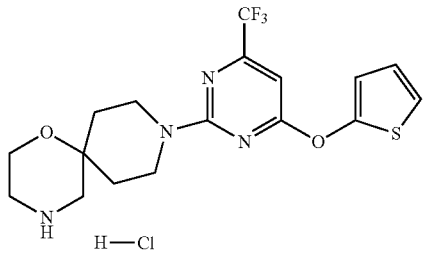

The title compound was prepared from tert-butyl 9-[4-(thiophen-2-yloxy)-6-(trifluoromethyl)pyrimidin-2-yl]-1-oxa-4,9-diazaspiro[5.5]undecane-4-carboxylate (p81, 12 mg, 0.024 mmol) in analogous manner as described in Example 36. 9-[4-(thiophen-2-yloxy)-6-(trifluoromethyl)pyrimidin-2-yl]-1-oxa-4,9-diazaspiro[5.5]undecane hydrochloride (E60, 9 mg, y=86%).

MS (ES) (m/z): 401.11 [M+H]$^+$ $^1$H NMR (DMSO-d$_6$): δ ppm 9.12 (br. s., 2H), 7.24 (dd, 1H), 6.94 (dd, 1H), 6.89 (dd, 1H), 6.77 (s, 1H), 4.14-4.38 (m, 2H), 3.83 (br. s., 2H), 3.28 (br. s., 2H), 2.94-3.09 (m, 4H), 1.93-2.09 (m, 2H), 1.59 (br. s., 2H)

Example 61: 9-(4-benzyl-6-methoxypyrimidin-2-yl)-1-oxa-4,9-diazaspiro[5.5]undecane hydrochloride (E61)

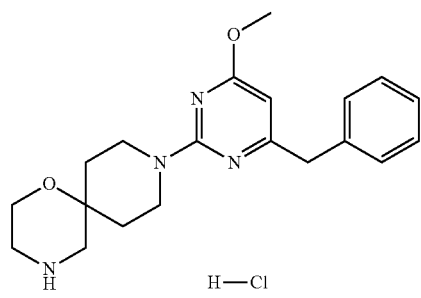 [SMILES: COc1cc(Cc2ccccc2)nc(N2CCC3(CC2)CNCCO3)n1 ; Cl]

The title compound was prepared from tert-butyl 9-(4-benzyl-6-methoxypyrimidin-2-yl)-1-oxa-4,9-diazaspiro[5.5]undecane-4-carboxylate (p82, 55 mg, 0.02 mmol) in analogous manner as described in Example 36. 9-(4-benzyl-6-methoxypyrimidin-2-yl)-1-oxa-4,9-diazaspiro[5.5]undecane hydrochloride (E61, 46 mg, y=98%).

MS (ES) (m/z): 355.2 [M+H]$^+$ $^1$H NMR (DMSO-d$_6$): δ ppm 9.23 (br. s., 2H), 7.31 (d, 4H), 7.18-7.27 (m, 1H), 5.94 (s, 1H), 4.44 (br, 2H), 4.30 (d, 2H), 3.75-3.92 (m, 6H), 3.29 (t, 2H), 3.04 (d, 3H), 1.98 (d, 2H), 1.59 (t, 2H)

Example 62: 6-(3-fluorophenoxy)-2-{1-oxa-4,9-diazaspiro[5.5]undecan-9-yl}pyrimidine-4-carbonitrile hydrochloride (E62)

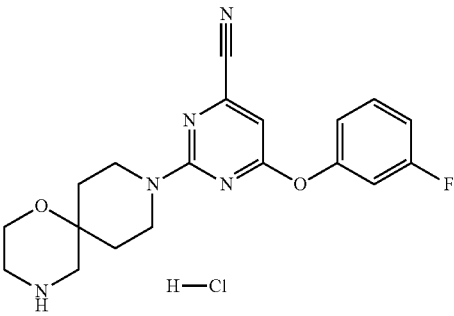 [SMILES: N#Cc1cc(Oc2cccc(F)c2)nc(N2CCC3(CC2)CNCCO3)n1 ; Cl]

The title compound was prepared from tert-butyl 9-[4-cyano-6-(3-fluorophenoxy)pyrimidin-2-yl]-1-oxa-4,9-diazaspiro[5.5]undecane-4-carboxylate (p83, 52 mg, 0.11 mmol) in analogous manner as described in Example 36. 6-(3-fluorophenoxy)-2-{1-oxa-4,9-diazaspiro[5.5]undecan-9-yl}pyrimidine-4-carbonitrile hydrochloride (E62, 41 mg, y=92%).

MS (ES) (m/z): 370.1 [M+H]$^+$ $^1$H NMR (DMSO-d$_6$): δ ppm 9.01 (br. s., 2H), 7.51-7.61 (m, 1H), 7.30 (dt, 1H), 7.24 (td, 1H), 7.17 (dd, 1H), 7.02 (s, 1H), 4.12-4.37 (m, 1H), 3.76-3.99 (m, 3H), 3.13-3.34 (m, 2H), 3.08-3.12 (m, 2H), 3.04 (s, 2H), 1.88-2.02 (m, 2H), 1.47-1.67 (m, 2H)

Example 63: 9-[4-(3-fluorophenoxy)-6-(methylsulfanyl)pyrimidin-2-yl]-1-oxa-4,9-diazaspiro[5.5]undecane hydrochloride (E63)

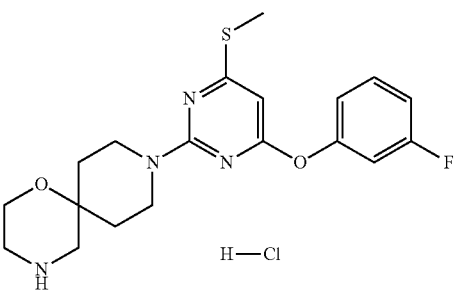 [SMILES: CSc1cc(Oc2cccc(F)c2)nc(N2CCC3(CC2)CNCCO3)n1 ; Cl]

The title compound was prepared from tert-butyl 9-[4-(3-fluorophenoxy)-6-(methylsulfanyl)pyrimidin-2-yl]-1-oxa-4,9-diazaspiro[5.5]undecane-4-carboxylate (p84, 48 mg, 0.098 mmol) in analogous manner as described in Example 36. 9-[4-(3-fluorophenoxy)-6-(methylsulfanyl)pyrimidin-2-yl]-1-oxa-4,9-diazaspiro[5.5]undecane hydrochloride (E63, 40 mg, y=95%).

MS (ES) (m/z): 391.17 [M+H]$^+$ $^1$H NMR (DMSO-d$_6$): δ ppm 8.98 (br. s., 2H), 7.46 (q, 1H), 7.08-7.16 (m, 2H), 7.03 (dd, 1H), 6.11 (s, 1H), 3.88-4.57 (m, 2H), 3.76-3.81 (m, 2H), 3.10-3.24 (m, 2H), 2.90-3.09 (m, 4H), 2.47 (s, 3H), 1.87 (d, 2H), 1.43-1.58 (m, 2H)

145

Example 64: 9-[2-(3-fluorophenoxy)-6-(methylsulfanyl)pyrimidin-4-yl]-1-oxa-4,9-diazaspiro[5.5]undecane hydrochloride (E64)

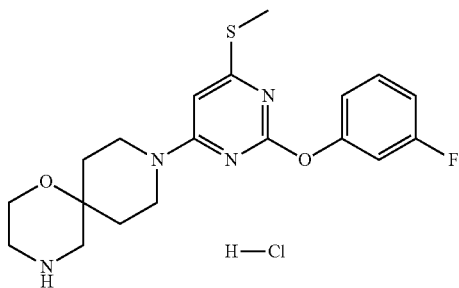 [SMILES: CSc1cc(N2CCC3(CC2)CNCCO3)nc(Oc2cccc(F)c2)n1 ; Cl]

The title compound was prepared from tert-butyl 9-[2-(3-fluorophenoxy)-6-(methylsulfanyl)pyrimidin-4,9-diazaspiro[5.5]undecane-4-carboxylate (p85, 24 mg, 0.049 mmol) in analogous manner as described in Example 36. 9-[2-(3-fluorophenoxy)-6-(methylsulfanyl)pyrimidin-4-yl]-1-oxa-4,9-diazaspiro[5.5]undecane hydrochloride (E64, 20 mg, y=95%).

MS (ES) (m/z): 391.15 [M+H]$^+$ $^1$H NMR (DMSO-d$_6$): δ ppm 9.02 (br. s., 2H), 7.46-7.55 (m, 1H), 7.11-7.21 (m, 2H), 7.09 (dd, 1H), 6.55 (s, 1H), 3.99 (br. s., 2H), 3.81-3.91 (m, 2H), 3.22 (t, 2H), 3.04-3.15 (m, 4H), 2.43 (s, 3H), 1.97 (d, 2H), 1.59 (t, 2H)

Example 65: 9-[4-cyclopropyl-6-(3-fluorophenoxy)pyrimidin-2-yl]-1-oxa-4,9-diazaspiro[5.5]undecane hydrochloride (E65)

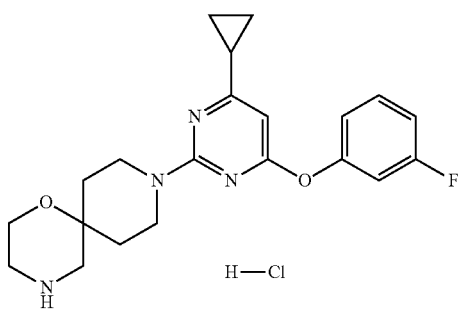 [SMILES: Fc1cccc(Oc2cc(C3CC3)nc(N3CCC4(CC3)CNCCO4)n2)c1 ; Cl]

The title compound was prepared from tert-butyl 9-[4-cyclopropyl-6-(3-fluorophenoxy)pyrimidin-2-yl]-1-oxa-4,9-diazaspiro[5.5]undecane-4-carboxylate (p86, 38 mg, 0.078 mmol) in analogous manner as described in Example 36. 9-[4-cyclopropyl-6-(3-fluorophenoxy)pyrimidin-2-yl]-1-oxa-4,9-diazaspiro[5.5]undecane hydrochloride (E65, 6 mg, y=18%).

MS (ES) (m/z): 385.08 [M+H]$^+$ $^1$H NMR (DMSO-d$_6$): δ ppm 8.96 (br. s., 2H), 7.42-7.51 (m, 1H), 7.07-7.13 (m, 2H), 7.00-7.05 (m, 1H), 6.14 (s, 1H), 3.49-4.21 (m, 4H), 3.07-3.16 (m, 2H), 3.00-3.05 (m, 2H), 2.95-2.99 (m, 2H), 1.89-1.97 (m, 1H), 1.83 (d, 2H), 1.41-1.51 (m, 2H), 0.90-0.98 (m, 4H)

Preparation 87: tert-butyl 9-[4-(3-fluorophenoxy)-6-methoxypyrimidin-2-yl]-1-oxa-4,9-diazaspiro[5.5]undecane-4-carboxylate (P87)

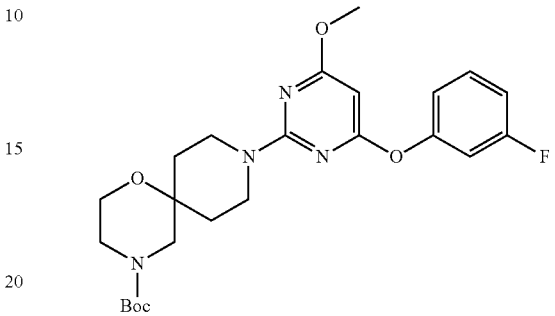

Step a 3-fluorophenol (0.023 mL, 0.251 mmol), 2,4-dichloro-6-methoxypyrimidine (50 mg, 0.279 mmol) and K$_2$CO$_3$ (50.13 mg, 0.363 mmol) were mixed in dry DMSO (0.5 mL) and stirred for 2 hrs at RT. The mixture was diluted with EtOAC and water. The organic phase was washed several times with brine, dried, filtered and evaporated. Crude material was purified by FC on silica gel (eluent: Cy to Cy/EtOAc 90/10) affording a mixture of 2 regioisomers and starting material (65 mg).

Step b

Mixture from step a (62 mg), tert-butyl 1-oxa-4,9-diazaspiro[5.5]undecane-4-carboxylate (p4, 50 mg, 0.195 mmol) and K$_2$CO$_3$ (35 mg, 0.254 mmol) were mixed in dry DMSO (0.5 mL) and stirred for 2 hrs at RT. The mixture was diluted with EtOAc and water. The organic phase was washed several times with brine, dried, filtered and evaporated. Crude was purified by FC on silica gel (eluent: Cy to 10% EtOAc) to give a mixture of desired compound and chlorinated analogue (30 mg).

Step c 3-fluorophenol (7 μL, 0.075 mmol), mixture from step b (30 mg) and K$_2$CO$_3$ (13.54 mg, 0.098 mmol) were mixed in dry DMSO (0.5 mL) and stirred for 12 hrs at RT. Then further 2 eq of K$_2$CO$_3$ were added and the reaction mixture was stirred at 100° C. for 48 hrs. The mixture was diluted with EtOAc and water and the organic phase was washed several times with brine, dried, filtered and evaporated. Crude was purified by FC on silica gel (eluent: Cy to Cy/EtOAc 90/10) affording tert-butyl 9-[4-(3-fluorophenoxy)-6-methoxypyrimidin-2-yl]-1-oxa-4,9-diazaspiro[5.5]undecane-4-carboxylate (p87, 20 mg, y=17%) as colourless oil.

MS (ES) (m/z): 475.3 [M+H]$^+$

Example 66: 9-[4-(3-fluorophenoxy)-6-methoxypyrimidin-2-yl]-1-oxa-4,9 diazaspiro[5.5]undecane hydrochloride (E66)

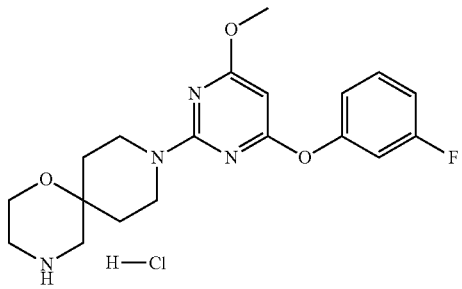

The title compound was prepared from tert-butyl 9-[4-(3-fluorophenoxy)-6-methoxypyrimidin-2-yl]-1-oxa-4,9-diazaspiro[5.5]undecane-4-carboxylate (p87, 20 mg, 0.042 mmol) in analogous manner as described in Example 36. 9-[4-(3-fluorophenoxy)-6-methoxypyrimidin-2-yl]-1-oxa-4,9-diazaspiro[5.5]undecane hydrochloride (E66, 15 mg, y=85%).

MS (ES) (m/z): 375.2 [M+H]$^+$ $^1$H NMR (DMSO-d$_6$): δ ppm 9.11 (br. s., 2H), 7.39-7.53 (m, 1H), 7.06-7.18 (m, 2H), 7.03 (d, 1H), 5.46-5.57 (m, 1H), 4.03 (br. s., 4H), 3.84-3.90 (m, 3H), 3.81 (br. s., 2H), 3.18 (br. s., 2H), 3.05 (s, 1H), 3.00 (s, 1H), 1.92 (s, 1H), 1.89 (s, 1H), 1.52 (br. s., 2H)

Preparation 88: 9-benzyl-1-oxa-4,9-diazaspiro[5.5]undecane (P88)

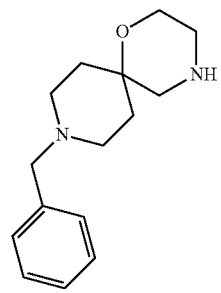 [SMILES: c1ccc(CN2CCC3(CC2)CNCCO3)cc1]

To a solution of tert-butyl 9-benzyl-1-oxa-4,9-diazaspiro[5.5]undecane-4-carboxylate (P3, 100 mg, 0.29 mmol) in DCM (0.8 mL), at RT, TFA (0.40 mL) was added and the mixture was stirred at RT for 2 hrs. The reaction mixture was concentrated under vacuum. The residue was loaded on a SCX cartridge washing with MeOH and eluting with MeOH and 2N NH$_3$ in MeOH to give 9-benzyl-1-oxa-4,9-diazaspiro[5.5]undecane (p88, 58 mg, y=79%).

MS (ES) (m/z): 247.1 [M+H]$^+$

Preparation 89: 9-benzyl-4-[4-(3-fluorophenoxy)-6-(trifluoromethyl)pyrimidin-2-yl]-1-oxa-4,9-diazaspiro[5.5]undecane (P89)

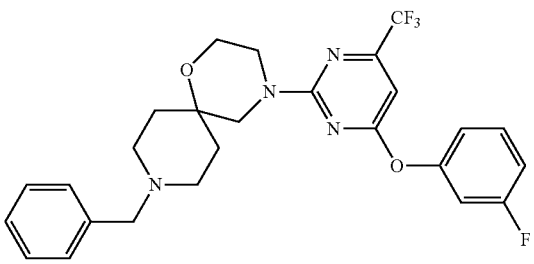 [SMILES: Fc1cccc(Oc2cc(C(F)(F)F)nc(N3CCOC4(CCN(Cc5ccccc5)CC4)C3)n2)c1]

A mixture of 9-benzyl-1-oxa-4,9-diazaspiro[5.5]undecane (p88, 58 mg, 0.24 mol), 2-chloro-4-(3-fluorophenoxy)-6-(trifluoromethyl)pyrimidine (p46, 80 mg, 0.27 mmol) and K$_2$CO$_3$ (43 mg, 0.31 mmol) in DMSO (0.8 mL) was heated at 90° C. and stirred 2 hrs at this temperature. After cooling at RT, EA and water were added, the organic phase was washed with water, dried and evaporated; crude product was purified by FC on silica gel (eluent: Cy to Cy/EA 70/30) affording 9-benzyl-4-[4-(3-fluorophenoxy)-6-(trifluoromethyl)pyrimidin-2-yl]-1-oxa-4,9-diazaspiro[5.5]undecane (p89, 85 mg, y=70%).

MS (ES) (m/z): 503.2 [M+H]$^+$

Example 67: 4-[4-(3-fluorophenoxy)-6-(trifluoromethyl)pyrimidin-2-yl]-1-oxa-4,9-diazaspiro[5.5]undecane hydrochloride (E67)

Step a
To a solution of 9-benzyl-4-[4-(3-fluorophenoxy)-6-(trifluoromethyl)pyrimidin-2-yl]-1-oxa-4,9-diazaspiro[5.5]undecane (p89, 85 mg, 0.17 mmol) in MeOH (5 mL), ammonium formate (64 mg, 1.02 mmol) and 10% Pd/C (22 mg) were added at RT then the mixture was stirred under reflux for 1 h. The reaction mixture was cooled down to RT, filtered through a pad of celite and concentrated under vacuum. The residue was loaded on a SCX cartridge washing with MeOH and eluting with 2N NH$_3$ in MeOH. The crude material was purified by FC on NH column (eluent: DCM to DCM/MeOH 98/2) affording 4-[4-(3-fluorophenoxy)-6-(trifluoromethyl)pyrimidin-2-yl]-1-oxa-4,9-diazaspiro[5.5]undecane (8 mg).

Step b
4-[4-(3-fluorophenoxy)-6-(trifluoromethyl)pyrimidin-2-yl]-1-oxa-4,9-diazaspiro[5.5]undecane (8 mg) was dissolved in DCM (0.1 mL) and 2N HCl in ether (0.001 mL) was added. The mixture was concentrated under vacuum, the white solid was triturated with ether and dried under vacuum to give 4-[4-(3-fluorophenoxy)-6-(trifluoromethyl)pyrimidin-2-yl]-1-oxa-4,9-diazaspiro[5.5]undecane hydrochloride (E67, 8 mg, y=10%)

MS (ES) (m/z): 413.19 [M+H]+

1H NMR (CHLOROFORM-d): δ ppm 7.34-7.47 (m, 1H), 6.87-7.07 (m, 3H), 6.41 (br. s., 1H), 3.89-3.41 (m 6H), 2.98-2.74 (m., 3H), 2.57 (br. s., 1H), 1.77-1.54 (br. s., 4).

Preparation 90:
1-oxa-4,9-diazaspiro[5.5]undecan-3-one (P90)

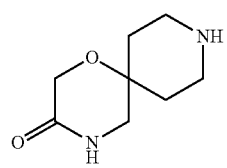 [SMILES: O=C1COC2(CCNCC2)CN1]

Step a:

To a stirred solution of N-[(1-benzyl-4-hydroxypiperidin-4-yl)methyl]-2-chloroacetamide (p2, 6 g, 20.22 mmol) in THF (150 mL), at 0° C. and under a nitrogen atmosphere, NaH 60% dispersion in mineral oil (1.6 g, 40.43 mmol) was added portionwise and then the ice-bath was removed. After 1 h at RT, the reaction mixture was concentrated under vacuum. The residue was diluted with AcOEt and water, and neutralized with 1N HCl. Phases were separated and the organic layer was dried, filtered and concentrated under reduced pressure affording 9-benzyl-1-oxa-4,9-diazaspiro[5.5]undecan-3-one (5.7 g) that was used as such in next step.

Step b:

To a solution of 9-benzyl-1-oxa-4,9-diazaspiro[5.5]undecan-3-one (223 mg, 0.85 mmol) in MeOH (5 mL) ammonium formate (0.324 g, 5.14 mmol) and Pd/C (20 mg) were added at RT then the mixture was stirred under reflux for 1.5 h. The mixture was cooled down to RT and filtered through a pad of celite washing with MeOH. Solvent was eliminated under reduced pressure affording 1-oxa-4,9-diazaspiro[5.5]undecan-3-one (p90, 198 mg, crude material).

MS (ES) (m/z): 171.1 [M+H]+

Example 68: 9-[4-(3-fluorophenoxy)-6-(trifluoromethyl)pyrimidin-2-yl]-1-oxa-4,9-diazaspiro[5.5]undecan-3-one (E68)

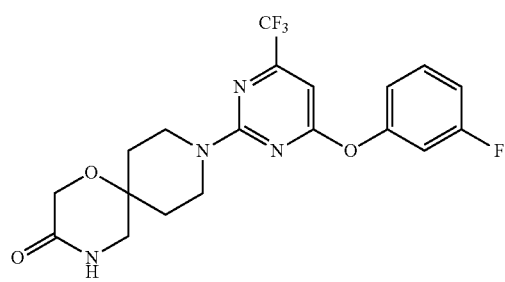 [SMILES: O=C1COC2(CCN(c3nc(Oc4cccc(F)c4)cc(C(F)(F)F)n3)CC2)CN1]

To a solution of 1-oxa-4,9-diazaspiro[5.5]undecan-3-one (p90, 198 mg, 1.16 mmol) in DMSO (2 mL) 2-chloro-4-(3-fluorophenoxy)-6-(trifluoromethyl)pyrimidine (p46, 238 mg, 0.81 mmol) and K2CO3 (240 mg, 1.74 mmol) were added and the mixture was shaken at 50° C. for 1.5 hr. The mixture was diluted with DCM and water, phases were separated, and organic one was dried and concentrated under reduced pressure. Crude material was purified by FC on NH column (eluent: Cy to Cy/AcOEt 50:50), then further purified by FC on silica gel (eluent: Cy to AcOEt 100%) to give a solid that was triturated with Et2O and dried under high vacuum for 1 h affording 9-[4-(3-fluorophenoxy)-6-(trifluoromethyl)pyrimidin-2-yl]-1-oxa-4,9-diazaspiro[5.5]undecan-3-one (E68, 12 mg, y=2.4%).

MS (ES) (m/z): 427.0 [M+H]+

1H NMR (CHLOROFORM-d): δ ppm 7.35-7.46 (m, 1H), 6.88-7.07 (m, 3H), 6.39 (s, 1H), 5.89 (br. s., 1H), 4.60-4.34 (br.s., 2H), 4.22 (s, 2H), 3.15-3.40 (m, 4H), 1.98 (d, 2H), 1.58 (s, 2H)

Preparation 91: N-[(1-benzyl-4-hydroxypiperidin-4-yl)methyl]-2-bromo-2,2-difluoroacetamide (P91)

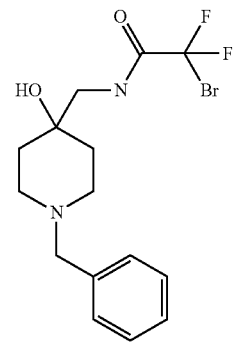

To a solution of 4-(aminomethyl)-1-benzylpiperidin-4-ol (p1, 0.92 g, 4.18 mmol) in DMF (9 mL), ethyl 2-bromo-2,2-difluoroacetate (0.54 mL. 4.18 mmol) was added and the reaction mixture was stirred at RT overnight. The mixture was treated with EA and water, the organic phase was washed with water and brine, dried and the solvent removed under vacuum to give N-[(1-benzyl-4-hydroxypiperidin-4-yl)methyl]-2-bromo-2,2-difluoroacetamide (p91, 1.59 g, y=quant).

MS (ES) (m/z): 379.0 [M+H]+

Preparation 92: 9-benzyl-2,2-difluoro-1-oxa-4,9-diazaspiro[5.5]undecan-3-one (P92)

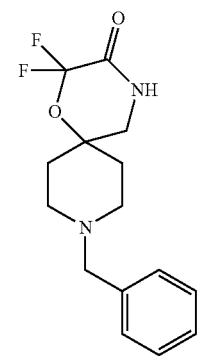 [SMILES: O=C1NCC2(CCN(Cc3ccccc3)CC2)OC1(F)F]

To a stirred mixture of t-BuOK (0.83 g, 7.37 mmol) in THF (25 mL), at 50° C., a solution of N-[(1-benzyl-4- hydroxypiperidin-4-yl)methyl]-2-bromo-2,2-difluoroacetamide (p91, 1.39 g, 3.68 mmol) in THF (10 mL) was added dropwise, then the reaction mixture was heated to 70° C. and stirred at that temperature for 1 h. The mixture was allowed to reach RT then saturated NH₄Cl and EA were added. The organic phase was washed with brine, dried and concentrated under reduced pressure. The crude material was purified by FC on silica gel (eluent: DCM to DCM/MeOH 96/4) to give 9-benzyl-2,2-difluoro-1-oxa-4,9-diazaspiro[5.5]undecan-3-one (p92, 0.58 g, y=53%) as white foam.

MS (ES) (m/z): 297.1 [M+H]⁺

Preparation 93: 9-benzyl-2,2-difluoro-1-oxa-4,9-diazaspiro[5.5]undecane (P93)

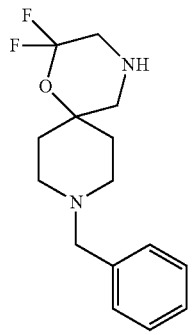 [SMILES: FC1(F)CNCC2(CCN(Cc3ccccc3)CC2)O1]

BH₃Me₂S complex 2M solution in THF (2.4 mL) was added dropwise to a solution of 9-benzyl-2,2-difluoro-1-oxa-4,9-diazaspiro[5.5]undecan-3-one (p92, 0.47 g, 1.59 mmol) in THF (14 mL) at RT. The reaction mixture was heated at 60° C. under nitrogen for 1 h. The mixture was quenched by careful drop-wise addition of methanol (45 mL). N,N'-Dimethylethylenediamine (1 mL) was then added and the mixture heated at 70° C. for 40 minutes. The reaction mixture was concentrated under reduced pressure and the residue was purified by FC on NH column (eluent: DCM to DCM/MeOH 98/2) to give 9-benzyl-2,2-difluoro-1-oxa-4,9-diazaspiro[5.5]undecane (p93, 0.24 g, y=53%).

MS (ES) (m/z): 283.2 [M+H]⁺

Preparation 94: tert-butyl 9-benzyl-2,2-difluoro-1-oxa-4,9-diazaspiro[5.5]undecane-4-carboxylate (P94)

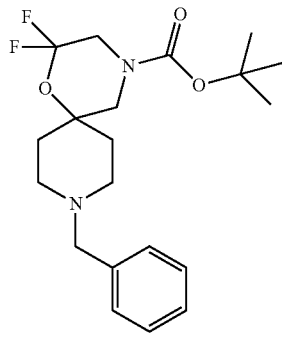 [SMILES: CC(C)(C)OC(=O)N1CC(F)(F)OC2(CCN(Cc3ccccc3)CC2)C1]

To a stirred solution of 9-benzyl-2,2-difluoro-1-oxa-4,9-diazaspiro[5.5]undecane (p93, 240 mg, 0.85 mmol) in DCM (4 mL), at RT, Boc₂O (204 mg, 0.94 mmol) was added portion-wise and the reaction mixture was stirred at RT for 2 hrs. The mixture was washed with concentrated NaHCO₃, brine, then dried and concentrated under reduced pressure to give tert-butyl 9-benzyl-2,2-difluoro-1-oxa-4,9-diazaspiro[5.5]undecane-4-carboxylate (p94, 350 mg, y=quant).

MS (ES) (m/z): 383.2 [M+H]⁺

Preparation 95: tert-butyl 2,2-difluoro-1-oxa-4,9-diazaspiro[5.5]undecane-4-carboxylate (P95)

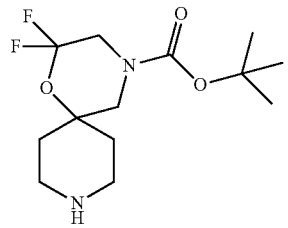 [SMILES: CC(C)(C)OC(=O)N1CC(F)(F)OC2(CCNCC2)C1]

To a solution of tert-butyl 9-benzyl-2,2-difluoro-1-oxa-4,9-diazaspiro[5.5]undecane-4-carboxylate (p94, 350 mg, 0.85 mmol) in MeOH (15 mL), ammonium formate (346 mg, 5.49 mmol) and 10% Pd/C (120 mg) were added at RT then the mixture was stirred under reflux for 1.5 h. The reaction mixture was filtered through a pad of celite and solvent removed under vacuum. The residue was taken up with DCM, the organic solution was washed with water and brine, dried and concentrated under reduced pressure to give tert-butyl 2,2-difluoro-1-oxa-4,9-diazaspiro[5.5]undecane-4-carboxylate (p95, 200 mg, y=80%).

MS (ES) (m/z): 293.2 [M+H]⁺

Preparation 96: tert-butyl 9-[4,5-difluoro-2-(3-fluorophenoxy)phenyl]-2,2-difluoro-1-oxa-4,9-diazaspiro[5.5]undecane-4-carboxylate (P96)

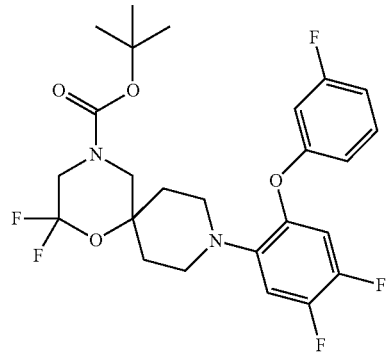 [SMILES: CC(C)(C)OC(=O)N1CC(F)(F)OC2(CCN(c3cc(F)c(F)cc3Oc3cccc(F)c3)CC2)C1]

A stirred mixture of tert-butyl 2,2-difluoro-1-oxa-4,9-diazaspiro[5.5]undecane-4-carboxylate (p95, 80 mg, 0.27 mmol), 1-bromo-4,5-difluoro-2-(3-fluorophenoxy)benzene (p7, 100 mg, 0.33 mmol), BINAP (17 mg, 0.027 mmol) and t-BuONa (52 mg, 0.54 mmol) in toluene (2.5 mL), at RT, was submitted to 3 cycles of nitrogen/vacuum then Pd₂(dba)₃ (8 mg, 0.008 mmol) was added and the reaction mixture was heated to 100° C. and stirred at that temperature overnight. After allowing the reaction mixture to reach RT, EA and water were added; the organic phase was washed with water, dried and the solvent removed under vacuum. The crude material was purified by FC on silica gel (eluent: Cy to Cy/EA 80/20) to give tert-butyl 9-[4,5-difluoro-2-(3-fluorophenoxy)phenyl]-2,2-difluoro-1-oxa-4,9-diazaspiro[5.5]undecane-4-carboxylate (p96, 61 mg, y=44%).

MS (ES) (m/z): 515.3 [M+H]⁺

Example 69: 9-[4,5-difluoro-2-(3-fluorophenoxy)phenyl]-2,2-difluoro-1-oxa-4,9-diazaspiro[5.5]undecane hydrochloride (E69)

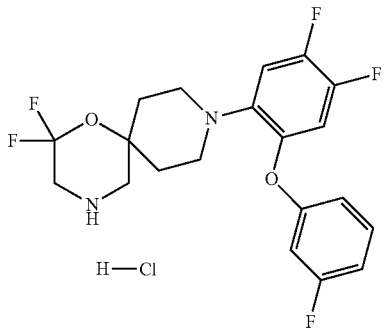 [SMILES: Fc1cccc(Oc2cc(F)c(F)cc2N2CCC3(CC2)CNCC(F)(F)O3)c1 ; Cl]

Step a

To a solution of tert-butyl 9-[4,5-difluoro-2-(3-fluorophenoxy)phenyl]-2,2-difluoro-1-oxa-4,9-diazaspiro[5.5]undecane-4-carboxylate (p96, 61 mg, 0.12 mmol) in DCM (0.5 mL), at RT, TFA (0.28 mL) was added and the mixture was stirred at RT for 1.5 h. The reaction mixture was concentrated under vacuum. The residue was dissolved in MeOH and loaded on a SCX cartridge washing with MeOH and eluting with 2N NH₃ in MeOH to give 9-[4,5-difluoro-2-(3-fluorophenoxy)phenyl]-2,2-difluoro-1-oxa-4,9-diazaspiro[5.5]undecane (40 mg).

Step b

9-[4,5-difluoro-2-(3-fluorophenoxy)phenyl]-2,2-difluoro-1-oxa-4,9-diazaspiro[5.5]undecane (from step a, 40 mg) was dissolved in DCM (0.2 mL) and 2N HCl (0.05 mL) was added dropwise. The mixture was concentrated under reduced pressure, the residue was triturated with ether and dried under vacuum to give 9-[4,5-difluoro-2-(3-fluorophenoxy)phenyl]-2,2-difluoro-1-oxa-4,9-diazaspiro[5.5]undecane hydrochloride (E69, 41 mg, y=76%)

MS (ES) (m/z): 415.0 [M+H]⁺

¹H NMR (DMSO-d₆): δ ppm 10.50 (br. s., 2H), 7.44-7.31 (m, 1H), 7.25 (d, 1H), 7.28 (d, 1H), 6.93 (dt, 1H), 6.85-6.68 (m, 2H), 4.06 (br. s., 2H), 3.64 (t, 2H), 3.14 (d, 2H), 2.94 (t, 2H), 1.91 (d, 2H), 1.62 (t, 2H)

Preparation 97: tert-butyl 2,2-difluoro-9-[4-(3-fluorophenoxy)-6-(trifluoromethyl)pyrimidin-2-yl]-1-oxa-4,9-diazaspiro[5.5]undecane-4-carboxylate (P97)

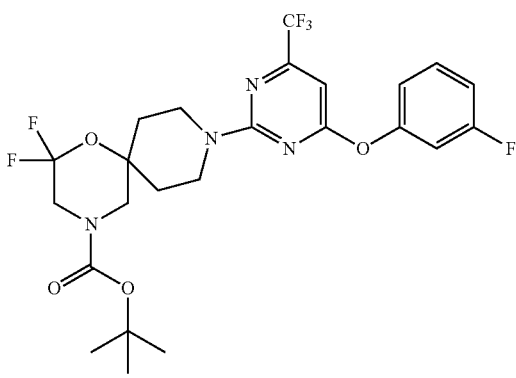 [SMILES: CC(C)(C)OC(=O)N1CC(F)(F)OC2(CCN(c3nc(Oc4cccc(F)c4)cc(C(F)(F)F)n3)CC2)C1]

A mixture of tert-butyl 2,2-difluoro-1-oxa-4,9-diazaspiro[5.5]undecane-4-carboxylate (p95, 60 mg, 0.21 mol), 2-chloro-4-(3-fluorophenoxy)-6-(trifluoromethyl)pyrimidine (p46, 60 mg, 0.21 mmol) and K₂CO₃ (38 mg, 0.27 mmol) in DMSO (0.6 mL) was heated at 100° C. for 2 hrs. After cooling at RT, EA and water were added, the organic phase was washed with water, dried and evaporated; crude product was purified by FC on silica gel (eluent: Cy to Cy/EA 85/15) affording tert-butyl 2,2-difluoro-9-[4-(3-fluorophenoxy)-6-(trifluoromethyl)pyrimidin-2-yl]-1-oxa-4,9-diazaspiro[5.5]undecane-4-carboxylate (p97, 60 mg, y=52%).

MS (ES) (m/z): 549.2 [M+H]⁺

Example 70: 2,2-difluoro-9-[4-(3-fluorophenoxy)-6-(trifluoromethyl)pyrimidin-2-yl]-1-oxa-4,9-diazaspiro[5.5]undecane hydrochloride (E70)

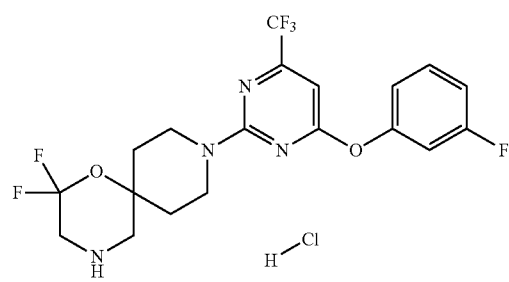 [SMILES: Fc1cccc(Oc2cc(C(F)(F)F)nc(N3CCC4(CC3)CNCC(F)(F)O4)n2)c1 ; Cl]

Step a

To a solution of tert-butyl 2,2-difluoro-9-[4-(3-fluorophenoxy)-6-(trifluoromethyl)pyrimidin-2-yl]-1-oxa-4,9-diazaspiro[5.5]undecane-4-carboxylate (p97, 60 mg, 0.11 mmol) in DCM (0.5 mL), at RT, TFA (0.25 mL) was added and the mixture was stirred at RT for 1.5 h. The reaction mixture was concentrated under vacuum. The residue was dissolved in MeOH and loaded on a SCX cartridge washing with MeOH and eluting with 2N NH₃ in MeOH to give 2,2-difluoro-9-[4-(3-fluorophenoxy)-6-(trifluoromethyl)pyrimidin-2-yl]-1-oxa-4,9-diazaspiro[5.5]undecane (44 mg).

Step b 2,2-difluoro-9-[4-(3-fluorophenoxy)-6-(trifluoromethyl)pyrimidin-2-yl]-1-oxa-4,9-diazaspiro[5.5]undecane (from step a, 44 mg) was dissolved in DCM (0.2 mL) and 2N HCl (0.05 mL) was added drop-wise. The mixture was concentrated under reduced pressure, the residue was triturated with ether and dried under vacuum to give 2,2-difluoro-9-[4-(3-fluorophenoxy)-6-(trifluoromethyl)pyrimidin-2-yl]-1-oxa-4,9-diazaspiro[5.5]undecane hydrochloride (E70, 44 mg, y=82%).

MS (ES) (m/z): 449.13 [M+H]⁺

¹H NMR (DMSO-d₆): δ ppm 10.38 (br. s., 2H), 7.45-7.59 (m, 1H), 7.26 (dt, 1H), 7.05-7.22 (m, 2H), 6.72 (s, 1H), 4.25 (br. s., 1H), 3.86 (br. s., 1H), 3.48-3.71 (m, 4H), 3.28 (s, 2H), 1.95 (br. s., 2H), 1.70 (br. s., 2H)

Preparation 98: 4-bromo-1-[(tert-butoxy)carbonyl]piperidine-4-carboxylic acid (P98)

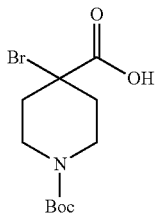

Bromoform (1.74 mL, 20 mmol) was added to a stirred solution of 1-Boc-4 piperidone (1 g, 5 mmol), benzyltriethylammonium chloride (0.125 g, 0.5 mmol) and LiOH H₂O (4.2 g, 100 mmol) in t-BuOH/H₂O (25/5 mL). The resulting mixture was vigorously stirred at RT for 72 hrs. The mixture was diluted with water (75 mL) and extracted with Et₂O (50 mL×2). The organic layer was discarded. The aqueous phase was cooled with an ice bath and the pH was adjusted to 1 with 20% HCl. The resulting precipitated was extracted with Et₂O (50 mL×2). The organic solution was dried and evaporated. The crude material was filtered through a silica cartridge eluting with EtOAc. After evaporation the resulting solid was triturated with hot n-Hexane. The white precipitate was filtered and dried to give 4-bromo-1-[(tert-butoxy)carbonyl]piperidine-4-carboxylic acid (p98, 650 mg, y=42%).

MS (ES) (m/z): 308.0 [M+H]⁺

Preparation 99: tert-butyl 5-oxo-1-thia-4,9-diazaspiro[5.5]undecane-9-carboxylate (P99)

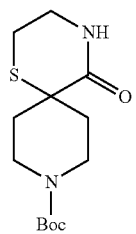 [SMILES: CC(C)(C)OC(=O)N1CCC2(CC1)SCCNC2=O]

Step a:
4-bromo-1-[(tert-butoxy)carbonyl]piperidine-4-carboxylic acid (p98, 650 mg, 2.1 mmol) was dissolved in a mixture of toluene/methanol (15/10 mL) and cooled with an ice bath. Trimethylsilyl-diazomethane (2.73 mL, 5.46 mmol) was added dropwise and then the reaction was stirred at RT for 3 hrs. The mixture was concentrated and Et₂O was added. The organic phase was washed with NH₄Cl and brine, dried and evaporated to afford 1-tert-butyl 4-methyl 4-bromopiperidine-1,4-dicarboxylate (670 mg) as colourless oil.
Step b:
2-amino-ethanthiol (235 mg, 2.07 mmol) was suspended in n-BuOH (15 mL) at 0° C. KOH (232 mg, 4.14 mmol) was added followed by 1-tert-butyl 4-methyl 4-bromopiperidine-1,4-dicarboxylate (from step a, 670 mg, 2.07 mmol). The cooling bath was removed and the reaction mixture was stirred at reflux for 48 hrs. The reaction mixture was cooled down to RT; the solids were removed by filtration. The filtrate was concentrated, re-dissolved with DCM and washed with 1N HCl and brine. Organic phase was then dried and concentrated under reduced pressure. The crude material was purified by FC on silica gel (eluent: cHex to EtOAc) to afford tert-butyl 5-oxo-1-thia-4,9-diazaspiro[5.5]undecane-9-carboxylate (p99, 100 mg, y=17%) as white solid.

MS (ES) (m/z): 287.2 [M+H]⁺

Preparation 100: tert-butyl 1,1,5-trioxo-1λ⁶-thia-4,9-diazaspiro[5.5]undecane-9-carboxylate (P100)

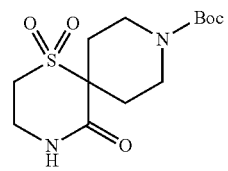 [SMILES: CC(C)(C)OC(=O)N1CCC2(CC1)C(=O)NCCS2(=O)=O]

To a stirred solution of tert-butyl 5-oxo-1-thia-4,9-diazaspiro[5.5]undecane-9-carboxylate (p99, 235 mg, 0.82 mmol) in DCM (5 mL) at 0° C., 3-chloroperbenzoic acid (354 mg, 2.5 mmol) was added. The reaction mixture was stirred at RT for 2 hrs. Water and DCM were then added, phases were separated and the organic one was dried and evaporated. The crude material was purified by FC on silica gel (eluent: Cy to EtOAc/MeOH 90/10) affording tert-butyl 1,1,5-trioxo-1λ⁶-thia-4,9-diazaspiro[5.5]undecane-9-carboxylate (p100, 230 mg, y=88%) as white solid ¹H NMR (CHLOROFORM-d): δ ppm 5.78 (br. s., 1H), 3.94 (br. s., 2H), 3.72 (br. s., 2H), 3.61 (br. s., 1H), 3.52 (br. s., 1H), 3.35 (br. s., 2H), 2.12-2.37 (m, 4H), 1.49 (s, 9H)

Preparation 101: tert-butyl 1,1-dioxo-1λ}-thia-4,9-diazaspiro[5.5]undecane-9-carboxylate (P101)

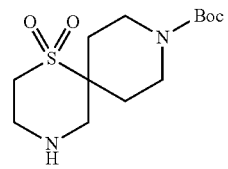 [SMILES: CC(C)(C)OC(=O)N1CCC2(CC1)CNCCS2(=O)=O]

To a stirred solution of tert-butyl 1,1,5-trioxo-1λ⁶-thia-4,9-diazaspiro[5.5]undecane-9-carboxylate (p100, 230 mg, 0.72 mmol) in THF (8 mL) Borane THF complex 1M in THF (7.2 mL, 7.2 mmol) was added. The resulting solution was stirred at 50° C. for 2 hrs. Then the mixture was cooled with an ice bath and MeOH (12 mL) was added dropwise to quench the reaction. The solution was stirred at 40° C. for 2 hrs. After solvent evaporation tert-butyl 1,1-dioxo-1λ}-thia-4,9-diazaspiro[5.5]undecane-9-carboxylate (p101, 220 mg, crude material) was obtained as colourless oil. Used without purification.

MS (ES) (m/z): 249.1 [M−56]+

Preparation 102: 4-benzyl-1λ⁶thia-4,9-diazaspiro[5.5]undecane-1,1-dione (P102)

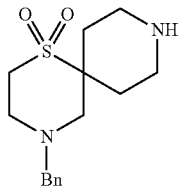 [SMILES: O=S1(=O)CCN(Cc2ccccc2)CC12CCNCC2]

Step a:
To a solution of tert-butyl 1,1-dioxo-1λ}-thia-4,9-diazaspiro[5.5]undecane-9-carboxylate (p101, 230 mg, 0.72 mmol) in DCM (5 mL), benzaldehyde (0.071 mL, 0.72 mmol) was added and the mixture was stirred at RT for 15 min, then NaBH(OAc)₃ (228 mg, 1.08 mmol) was added and the mixture was left stirring at RT overnight. Further 1 eq of NaBH(OAc)₃ was added and the mixture was stirred at RT for further 1 h. The reaction was quenched with NaHCO₃ saturated solution, then phases were separated and aqueous one was back-extracted with DCM twice. Combined organics were washed with brine, dried and concentrated under reduced pressure. The residue was loaded on a SCX cartridge washing with MeOH and eluting with NH₃ 1M in MeOH. Solvent was eliminated under reduced pressure affording tert-butyl 4-benzyl-1,1-dioxo-1λ}-thia-4,9-diazaspiro[5.5]undecane-9-carboxylate (233 mg).

Step b:
Tert-butyl 4-benzyl-1,1-dioxo-1λ}-thia-4,9-diazaspiro[5.5]undecane-9-carboxylate (from step a, 233 mg) was dissolved in DCM (5 mL) and TFA (0.5 mL) was added, the solution was stirred at RT for 1 h, then the solvent was evaporated and the residue was charged on a SCX cartridge washing with MeOH and eluting with NH₃ 1M in MeOH. Solvent was eliminated under reduced pressure affording 4-benzyl-1λ⁶thia-4,9-diazaspiro[5.5]undecane-1,1-dione (p102, 160 mg, y=75%) as white solid.
MS (ES) (m/z): 295.2 [M+H]⁺

Preparation 103: 4-benzyl-9-[4,5-difluoro-2-(3-fluorophenoxy)phenyl]-1λ⁶-thia-4,9-diazaspiro[5.5]undecane-1,1-dione (P103)

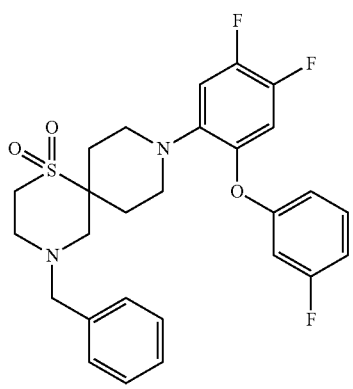 [SMILES: O=S1(=O)CCN(Cc2ccccc2)CC12CCN(c1cc(F)c(F)cc1Oc1cccc(F)c1)CC2]

1-bromo-4,5-difluoro-2-(3-fluorophenoxy)benzene (p7, 197 mg, 0.65 mmol), 4-benzyl-1λ⁶thia-4,9-diazaspiro[5.5]undecane-1,1-dione (p102, 160 mg, 0.543 mmol), BINAP (34 mg, 0.0543 mmol) and sodium t-butoxide (73 mg, 0.76 mmol) were mixed in Toluene (6 mL) and then Argon was bubbled for 10 min. Then Pd₂(dba)₃ (34 mg, 0.016 mmol) was added and the mixture was stirred at 100° C. overnight. The mixture was then cooled down to RT, diluted with EtOAc, dried and concentrated. Crude material was purified by FC on silica gel (eluent: cHex to cHex/EtOAc 50/50) to obtain 4-benzyl-9-[4,5-difluoro-2-(3-fluorophenoxy)phenyl]-1λ⁶-thia-4,9-diazaspiro[5.5]undecane-1,1-dione (p103, 123 mg, y=44%) as white off solid.
MS (ES) (m/z): 517.3 [M+H]⁺

Example 71: 9-[4,5-difluoro-2-(3-fluorophenoxy)phenyl]-1λ⁶-thia-4,9-diazaspiro[5.5]undecane-1,1-dione (E71)

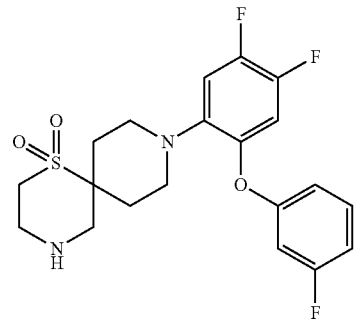 [SMILES: O=S1(=O)CCNCC12CCN(c1cc(F)c(F)cc1Oc1cccc(F)c1)CC2]

To a solution of 4-benzyl-9-[4,5-difluoro-2-(3-fluorophenoxy)phenyl]-1λ⁶-thia-4,9-diazaspiro[5.5]undecane-1,1-dione (p103, 123 mg, 0.238 mmol) in MeOH (8 mL) 10% Pd/C was added (50 mg) and the mixture was stirred under H₂ pressure (1 atm) at RT for 1 h. Then further Pd/C (100 mg) was added and the mixture was stirred in the same condition for further 1.5 h. The mixture was filtered washing with MeOH, solvent was evaporated and the residue was charged on SCX cartridge washing with MeOH and eluting with 1M NH₃ in MeOH. After evaporation 9-[4,5-difluoro-2-(3-fluorophenoxy)phenyl]-1λ⁶-thia-4,9-diazaspiro[5.5]undecane-1,1-dione (E71, 76 mg, y=75%) was obtained as white solid.
MS (ES) (m/z): 427.2 [M+H]⁺
¹H NMR (CHLOROFORM-d): δ ppm 7.24-7.28 (m, 1H), 6.77-6.95 (m, 3H), 6.67-6.76 (m, 1H), 6.58 6.61 (m, 1H), 3.27-3.39 (m, 4H), 3.14 (s, 2H), 3.02-3.10 (m, 2H), 2.85-2.96 (m, 2H), 2.26 (ddd, 2H), 1.84 (s, 1H), 1.81 (s, 1H)

Preparation 104: 9-[4-(3-fluorophenoxy)-6-(trifluoromethyl)pyrimidin-2-yl]-1λ⁶thia-4,9-diazaspiro[5.5]undecane-1,1,5-trione (P104)

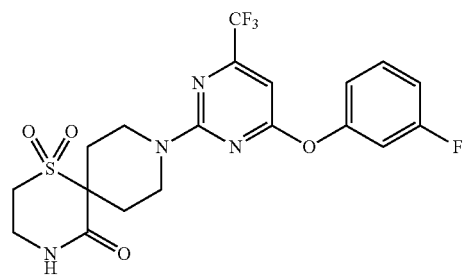 [SMILES: O=C1NCCS(=O)(=O)C12CCN(c1nc(Oc3cccc(F)c3)cc(C(F)(F)F)n1)CC2]

Step a:

To a stirred solution of tert-butyl 1,1,5-trioxo-1λ⁶-thia-4,9-diazaspiro[5.5]undecane-9-carboxylate (p100, 40 mg, 0.139 mmol) in DCM (3 mL) TFA (0.5 mL) was added. The reaction mixture was stirred at RT for 1 h. Solvent was evaporated and the residue was charged on SCX cartridge washing with MeOH and eluting with 1N NH₃ in MeOH. After evaporation 1λ⁶thia-4,9-diazaspiro[5.5]undecane-1,1,5-trione was obtained as white off solid (24 mg).

Step b:

1λ⁶thia-4,9-diazaspiro[5.5]undecane-1,1,5-trione (from step a, 24 mg, 0.11 mmol) was dissolved in DMSO (0.5 mL), K₂CO₃ (20 mg, 0.141 mmol) and 2-chloro-4-(3-fluorophenoxy)-6-(trifluoromethyl)pyrimidine (p46, 32 mg, 0.109 mmol) were added and the mixture was stirred at 100° C. for 1 h. Water and DCM were added, the product was extracted in organic phase that was dried and evaporated. The crude material was purified by FC on silica gel (eluent: Cy to EtOAc) affording 9-[4-(3-fluorophenoxy)-6-(trifluoromethyl)pyrimidin-2-yl]-1λ⁶thia-4,9-diazaspiro[5.5]undecane-1,1,5-trione (p104, 28 mg, y=42%) as white solid.

MS (ES) (m/z): 475.2 [M+H]⁺

Example 72: 9-[4-(3-fluorophenoxy)-6-(trifluoromethyl)pyrimidin-2-yl]-1λ⁶-thia-4,9-diazaspiro[5.5]undecane-1,1-dione (E72)

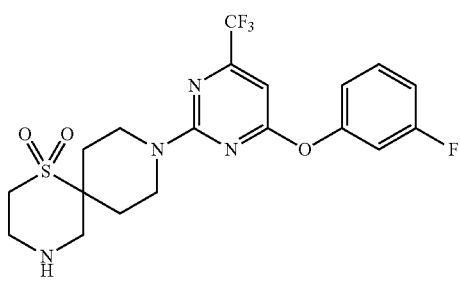 [SMILES: O=S1(=O)CCNCC12CCN(c1nc(Oc3cccc(F)c3)cc(C(F)(F)F)n1)CC2]

To a stirred solution of 9-[4-(3-fluorophenoxy)-6-(trifluoromethyl)pyrimidin-2-yl]-1λ⁶-thia-4,9-diazaspiro[5.5]undecane-1,1,5-trione (p104, 28 mg, 0.059 mmol) in THF (6 mL) Borane THF complex 1M in THF (0.59 mL, 0.59 mmol) was added. The resulting solution was stirred at reflux for 16 hrs. Then it was cooled with an ice bath and MeOH (3 mL) was added dropwise. The solution was stirred at 50° C. for 2 hrs then it was cooled to RT. NaBH₄ (50 mg, 1.3 mmol) was added portionwise to the solution and the mixture was stirred overnight at RT. Water was added, the product was extracted in EtOAc. The organic phase was separated, dried and evaporated. The residue was purified by FC on silica gel (eluent: Cy to EtOAc) affording 9-[4-(3-fluorophenoxy)-6-(trifluoromethyl)pyrimidin-2-yl]-1λ⁶-thia-4,9-diazaspiro[5.5]undecane-1,1-dione (E72, 8.4 mg, y=31%) as white solid.

MS (ES) (m/z): 461.21 [M+H]⁺

¹H NMR (CHLOROFORM-d): δ ppm 7.35-7.45 (m, 1H), 6.88-7.06 (m, 3H), 6.43 (s, 1H), 4.39-3.98 (m, 2H), 3.57-3.37 (m, 2H), 3.36-3.34 (m, 2H)—, 3.23 (s, 2H), 3.10 (d, 2H), 2.16-2.35 (m, 2H), 1.98-1.82 (br. s., 2H)

Preparation 105: tert-butyl 4-amino-4-(nitromethyl)piperidine-1-carboxylate (P105)

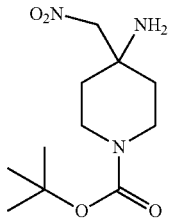 [SMILES: CC(C)(C)OC(=O)N1CCC(N)(C[N+](=O)[O-])CC1]

To a stirred solution of MeNO₂ (1.4 mL, 25.85 mmol) in 28% NH₄OH (11 mL), at RT, tert-butyl 4-oxopiperidine-1-carboxylate (4.0 g, 20.08 mmol) was added portion-wise and the resulting reaction mixture was stirred at RT for 4 hrs. The mixture was diluted with DCM and water, the organic phase was dried and the solvent removed under reduced pressure. The white material was dissolved in MeOH and loaded on a SCX cartridge washing with MeOH and eluting with 2N NH₃ in MeOH to give tert-butyl 4-amino-4-(nitromethyl)piperidine-1-carboxylate (p105, 1.99 g, y=38%)

MS (ES) (m/z): 260.0 [M+H]⁺

Preparation 106: tert-butyl 4-{[(benzyloxy)carbonyl]amino}-4-(nitromethyl)piperidine-1-carboxylate (P106)

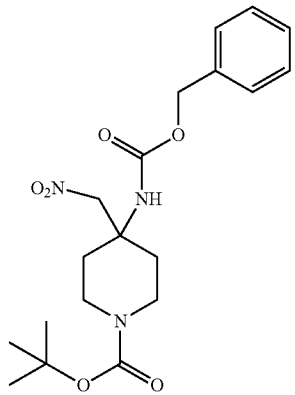 [SMILES: CC(C)(C)OC(=O)N1CCC(C[N+](=O)[O-])(NC(=O)OCc2ccccc2)CC1]

To a solution of tert-butyl 4-amino-4-(nitromethyl)piperidine-1-carboxylate (p105, 1.89 g, 7.29 mmol) in DCM (23 mL) a solution of NaOH (0.41 g, 10.21 mmol) in water (16 mL) was added, then the mixture was cooled to 0° C. and benzyl chloroformate (1.87 mL, 13.12 mmol) was added drop-wise. The reaction mixture was stirred at RT for 3 hrs. The mixture was diluted with DCM, the organic phase was washed with saturated NaHCO₃, dried and the solvent removed under reduced pressure. The crude material was purified by FC on silica gel (eluent: Cy to Cy/EA 80/20) to give tert-butyl 4-{[(benzyloxy)carbonyl]amino}-4-(nitromethyl)piperidine-1-carboxylate (p106, 2.21 g, y=77%).

MS (ES) (m/z): 394.12 [M+H]⁺

Preparation 107: tert-butyl 4-{[(benzyloxy)carbonyl]amino}-4-{[(2-ethoxy-2-oxoethyl)amino]methyl}piperidine-1-carboxylate (P107)

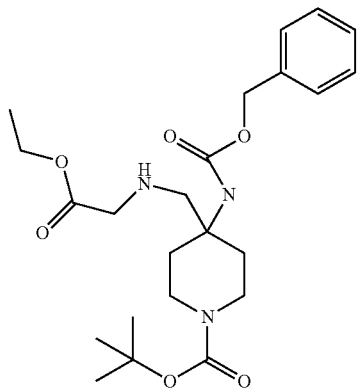 [SMILES: CCOC(=O)CNCC1(NC(=O)OCc2ccccc2)CCN(C(=O)OC(C)(C)C)CC1]

Step a:
To a stirred solution of tert-butyl 4-{[(benzyloxy)carbonyl]amino}-4-(nitromethyl)piperidine-1-carboxylate (p106, 1.96 g, 4.98 mmol) and NiCl$_2$*6H$_2$O (1.18 g, 4.98 mmol) in dry MeOH (35 mL), under a nitrogen atmosphere and at −5° C., NaBH$_4$ (0.94 g, 24.91 mmol) was added portion-wise within 10 min. The ice-bath was removed and the reaction mixture was stirred for 1 h. The reaction was quenched by adding saturated sodium bicarbonate solution and filtered through a pad of Celite. The filtrate was concentrated, the residue was taken up with DCM, the organic phase was washed with water, dried and concentrated under reduced pressure to give tert-butyl 4-(aminomethyl)-4-{[(benzyloxy)carbonyl]amino}piperidine-1-carboxylate (1.48 g) that was used as such.

Step b:
To a stirred solution of tert-butyl 4-(aminomethyl)-4-{[(benzyloxy)carbonyl]amino}piperidine-1-carboxylate (from step a, 1.48 g, 4.07 mmol) and TEA (1.13 mL) in THF (6 mL), at 0° C., ethyl 2-bromoacetate (0.31 mL, 2.8 mmol) was added, and the reaction mixture was stirred for 2 hrs at RT. The reaction mixture was diluted with saturated sodium bicarbonate solution and EA. The organic phase was washed with brine, dried and the solvent removed under reduced pressure. The crude material was purified by FC on silica gel (eluent: DCM to DCM/MeOH 98/2) to give tert-butyl 4-{[(benzyloxy)carbonyl]amino}-4-{[(2-ethoxy-2-oxoethyl)amino]methyl}piperidine-1-carboxylate (p107, 0.88 g, y=39%).
MS (ES) (m/z): 449.81 [M]$^+$ Preparation 108: tert-butyl 2-oxo-1,4,9-triazaspiro[5.5]undecane-9-Carboxylate (P108)

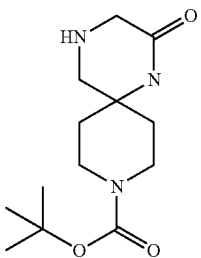 [SMILES: CC(C)(C)OC(=O)N1CCC2(CC1)CNCC(=O)N2]

To a solution of tert-butyl 4-{[(benzyloxy)carbonyl]amino}-4-{[(2-ethoxy-2-oxoethyl)amino]methyl}piperidine-1-carboxylate (p107, 0.88 g, 1.96 mmol) in i-PrOH (28 mL), ammonium formate (0.75 g, 11.76 mmol) and 10% Pd/C (0.25 g) were added at RT then the mixture was stirred under reflux for 2 hrs. The reaction mixture was filtered through a pad of celite and the solvent removed under vacuum. The residue was taken up with DCM, the organic solution was washed with water, brine, dried and the solvent removed under reduced pressure to give tert-butyl 2-oxo-1,4,9-triazaspiro[5.5]undecane-9-Carboxylate (p108, 0.37 g, y=51%).
MS (ES) (m/z): 270.0 [M]$^+$ Example 73: 9-[4-(3-fluorophenoxy)-6-(trifluoromethyl)pyrimidin-2-yl]-1,4,9-triazaspiro[5.5]undecan-2-one (E73)

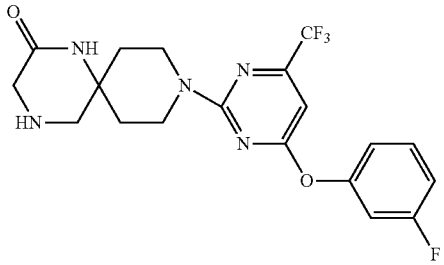 [SMILES: O=C1CNCC2(CCN(c3nc(Oc4cccc(F)c4)cc(C(F)(F)F)n3)CC2)N1]

Step a:
To a solution of tert-butyl 2-oxo-1,4,9-triazaspiro[5.5]undecane-9-Carboxylate (p108, 188 mg, 0.49 mmol) in DCM (1.6 mL), benzaldehyde (0.055 mL, 0.54 mmol) was added and the mixture was stirred at RT for 15 min then NaBH(OAc)$_3$ (208 mg, 0.98 mmol) was added and the mixture was left stirring at RT overnight. Further NaBH(OAc)$_3$ (104 mg, 0.49 mmol) was added and the reaction mixture was stirred overnight at RT. The reaction was quenched with saturated NaHCO$_3$, extracted with DCM, the organic phase was washed with water, dried and the solvent removed under reduced pressure. The crude material was purified by FC on silica gel (eluent: DCM to DCM/MeOH 96/4) to give a mixture of tert-butyl 4-benzyl-2-oxo-1,4,9-triazaspiro[5.5]undecane-9-carboxylate and non reacted tert-butyl 2-oxo-1,4,9-triazaspiro[5.5]undecane-9-Carboxylate (96 mg).

Step b:
To the mixture from step a (96 mg) in DCM (1 mL), at RT, TFA (0.53 mL) was added and the mixture was stirred at RT for 2 hrs. The reaction mixture was concentrated under vacuum. The residue was dissolved in MeOH and loaded on a SCX cartridge (washing with MeOH and eluting with 2N NH$_3$ in MeOH) to give a mixture of 4-benzyl-1,4,9-triazaspiro[5.5]undecan-2-one and 1,4,9-triazaspiro[5.5]undecan-2-one (32 mg) that was used as such.

Step c
The mixture from step b (32 mg), 2-chloro-4-(3-fluorophenoxy)-6-(trifluoromethyl)pyrimidine (p46, 43 mg, 0.148 mmol) and K$_2$CO$_3$ (22 mg, 0.16 mmol) in DMSO (0.6 mL) was heated at 100° C. and stirred 3 hrs at this temperature. After cooling at RT, ether and water were added, the organic phase was washed with water, dried and evaporated; crude product was purified by FC on silica gel (eluent: DCM/MeOH from 100/0 to 90/10) affording 9-[4-(3-fluorophenoxy)-6-(trifluoromethyl)pyrimidin-2-yl]-1,4,9-triazaspiro[5.5]undecan-2-one (E73, 10 mg, y=5%).

MS (ES) (m/z): 426.2 [M+H]+

1H NMR (DMSO-d6): δ ppm 7.74 (s, 1H), 7.47-7.54 (m, 1H), 7.24 (dt, 1H), 7.17 (td, 1H), 7.12 (dd, 1H), 6.64 (s, 1H), 3.19-4.13 (m, 4H), 3.12 (s, 2H), 2.75 (s, 2H), 1.36-1.76 (m, 4H)

Preparation 109: tert-butyl 4-benzyl-1-methyl-1,4,9-triazaspiro[5.5]undecane-9-carboxylate (P109)

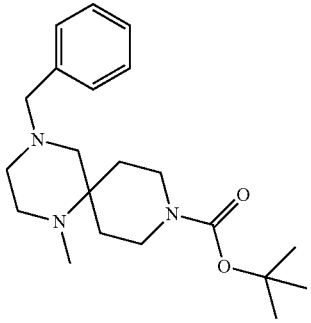 [SMILES: CN1CCN(Cc2ccccc2)CC12CCN(C(=O)OC(C)(C)C)CC2]

To a stirred solution of tert-butyl 1-methyl-1,4,9-triazaspiro[5.5]undecane-9-carboxylate (230 mg, 0.85 mmol) and benzaldehyde (0.077 mL, 0.76 mmol) in DCM (3.1 mL), at RT, AcOH (0.052 mL, 0.92 mmol) and Na(AcO)3BH (259 mg, 1.22 mmol) were subsequently added and the resulting reaction mixture was stirred at RT overnight. The reaction was worked up by adding sodium bicarbonate saturated solution and DCM. The organic phase was dried and the solvent removed under reduced pressure to give tert-butyl 4-benzyl-1-methyl-1,4,9-triazaspiro[5.5]undecane-9-carboxylate (p109, 280 mg, y=quant.) that was used as such.

MS (ES) (m/z): 360.4 [M+H]+

Preparation 110: 4-benzyl-1-methyl-1,4,9-triazaspiro[5.5]undecane (P110)

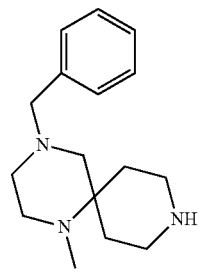 [SMILES: CN1CCN(Cc2ccccc2)CC12CCNCC2]

To a solution of tert-butyl 4-benzyl-1-methyl-1,4,9-triazaspiro[5.5]undecane-9-carboxylate (p109, 280 mg, 0.78 mmol) in DCM (3.5 mL), at RT, TFA (1.79 mL) was added and the mixture was stirred at RT for 2 hrs. The reaction mixture was concentrated under vacuum. The residue was dissolved in MeOH and loaded on a SCX cartridge (washing with MeOH and eluting with 2N NH3 in MeOH) to give 4-benzyl-1-methyl-1,4,9-triazaspiro[5.5]undecane (p110, 143 mg, y=70%).

MS (ES) (m/z): 260.3 [M+H]+

Preparation 111: 4-benzyl-9-[4-(3-fluorophenoxy)-6-(trifluoromethyl)pyrimidin-2-yl]-1-methyl-1,4,9-triazaspiro[5.5]undecane (P111)

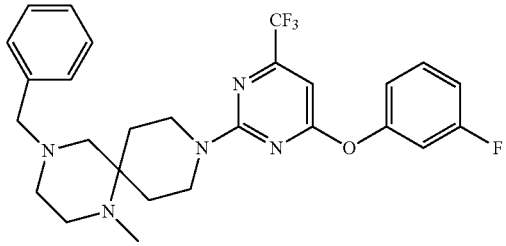 [SMILES: CN1CCN(Cc2ccccc2)CC12CCN(c1nc(Oc3cccc(F)c3)cc(C(F)(F)F)n1)CC2]

A mixture of 4-benzyl-1-methyl-1,4,9-triazaspiro[5.5]undecane (p110, 143 mg, 0.55 mmol), 2-chloro-4-(3-fluorophenoxy)-6-(trifluoromethyl)pyrimidine (p46, 143 mg, 0.49 mmol) and K2CO3 (114 mg, 0.83 mmol) in DMSO (1 mL) was heated at 90° C. and stirred 1.5 h at this temperature. After cooling at RT, EA and water were added, the organic phase was washed with water, dried and evaporated; crude product was purified by FC on silica gel (eluent: Cy to Cy/EA 70/30) affording 4-benzyl-9-[4-(3-fluorophenoxy)-6-(trifluoromethyl)pyrimidin-2-yl]-1-methyl-1,4,9-triazaspiro [5.5]undecane (p111, 175 mg, y=61%).

MS (ES) (m/z): 516.4 [M+H]+

Example 74: 9-[4-(3-fluorophenoxy)-6-(trifluoromethyl)pyrimidin-2-yl]-1-methyl-1,4,9-triazaspiro[5.5]undecane (E74)

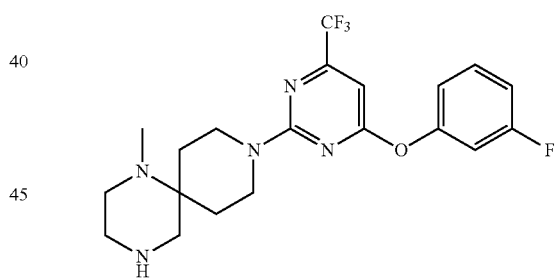

To a solution of 4-benzyl-9-[4-(3-fluorophenoxy)-6-(trifluoromethyl)pyrimidin-2-yl]-1-methyl-1,4,9-triazaspiro [5.5]undecane (p111, 175 mg, 0.34 mmol) in MeOH (30 mL), ammonium formate (128 mg, 2.04 mmol) and 10% Pd/C (80 mg) were added at RT then the mixture was stirred under reflux for 2 hrs. The reaction mixture was filtered through a pad of celite and the solvent removed under vacuum. The crude product was purified by FC on NH column (eluent: Cy to EtOAc) to give 9-[4-(3-fluorophenoxy)-6-(trifluoromethyl)pyrimidin-2-yl]-1-methyl-1,4,9 triazaspiro[5.5]undecane (E74, 19 mg, y=13%).

MS (ES) (m/z): 426.3 [M+H]+

1H NMR (DMSO-d6): δ ppm 7.58-7.46 (m, 1H), 7.25-7.09 (m, 3H), 6.56 (s, 1H), 3.99 (br. s., 2H), 3.18 (m, 2H), 2.78-2.65 (m, 4H), 2.50-2.43 (m, 2H), 2.17 (s, 3H), 1.81-1.62 (m, 2H), 1.55 (d, 2H)

Preparation 112: tert-butyl 4-benzyl-2-oxo-1,4,9-triazaspiro[5.5]undecane-9-carboxylate (P112)

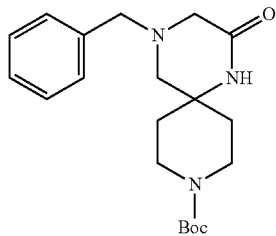 [SMILES: CC(C)(C)OC(=O)N1CCC2(CC1)CN(Cc1ccccc1)CC(=O)N2]

To a stirred solution of tert-butyl 2-oxo-1,4,9-triazaspiro[5.5]undecane-9-Carboxylate (p108, 720 mg, 2.67 mmol) and benzaldehyde (0.30 mL, 2.94 mmol) in DCM (9 mL), at RT, Acetic acid (0.18 mL, 3.20 mmol) and Na(AcO)₃BH (905 mg, 4.27 mmol) were subsequently added and the resulting reaction mixture was stirred at RT for 3 hrs. The reaction was worked up by adding concentrated sodium bicarbonate solution and DCM. The organic phase was dried and the solvent removed under reduced pressure. The crude material was purified by FC on silica gel (eluent: DCM/MeOH from 100/0 to 98/2) affording tert-butyl 4-benzyl-2-oxo-1,4,9-triazaspiro[5.5]undecane-9-carboxylate (p112, 760 mg, y=79%).

MS (ES) (m/z): 360.3 [M]⁺

Preparation 113: 4-benzyl-1,4,9-triazaspiro[5.5]undecan-2-one (P113)

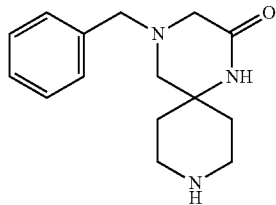 [SMILES: O=C1CN(Cc2ccccc2)CC2(CCNCC2)N1]

To a solution of tert-butyl 4-benzyl-2-oxo-1,4,9-triazaspiro[5.5]undecane-9-carboxylate (p112, 760 mg, 2.11) in DCM (5 mL), at RT, TFA (2.42 mL) was added. After 2 hrs the reaction mixture was concentrated under vacuum. The residue was taken up with MeOH and charged on a SCX cartridge washing with MeOH and eluting with MeOH and 2N NH₃ in MeOH to give 4-benzyl-1,4,9-triazaspiro[5.5]undecan-2-one (p113, 500 mg, y=91%).

MS (ES) (m/z): 260.2 [M]⁺

Preparation 114: 4-benzyl-1,4,9-triazaspiro[5.5]undecane (P114)

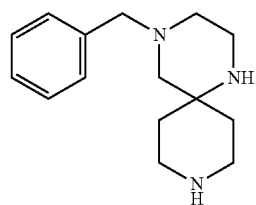 [SMILES: c1ccc(CN2CCNC3(CCNCC3)C2)cc1]

LiAlH₄ 2M solution in THF (1.45 mL, 2.90 mmol) was added drop-wise to a solution of 4-benzyl-1,4,9-triazaspiro[5.5]undecan-2-one (p113, 500 mg, 1.93 mmol) in THF (12 mL) at RT then the mixture was brought to reflux and stirred at that temperature for 8 hrs. The reaction mixture was cooled down to −10° C. and Na₂SO₄*10H₂O was carefully added portion-wise up to fizz end. The mixture was left stirring at RT for 30 min, then it was filtered, the solid was washed with DCM and the solvent concentrated under reduced pressure to give 4-benzyl-1,4,9-triazaspiro[5.5]undecane (p114, 410 mg, y=86%).

MS (ES) (m/z): 246.2 [M]⁺

Preparation 115: 4-benzyl-9-[4-(3-fluorophenoxy)-6-(trifluoromethyl)pyrimidin-2-yl]-1,4,9-triazaspiro[5.5]undecane (P115)

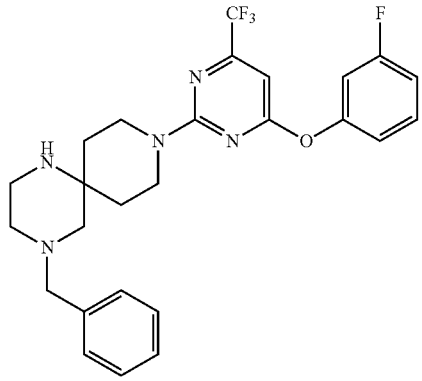 [SMILES: Fc1cccc(Oc2cc(C(F)(F)F)nc(N3CCC4(CC3)CN(Cc3ccccc3)CCN4)n2)c1]

A mixture of 4-benzyl-1,4,9-triazaspiro[5.5]undecane (p114, 191 mg, 0.78 mmol), 2-chloro-4-(3-fluorophenoxy)-6-(trifluoromethyl)pyrimidine (p46, 217 mg, 0.74 mmol) and K₂CO₃ (162 mg, 1.17 mmol) in DMSO (1.3 mL) was heated to 70° C. and stirred 2.5 hrs at this temperature. After cooling at RT, EA and water were added to the reaction mixture; the organic phase was washed with water, dried and evaporated under reduced pressure. The crude product was purified by FC on silica gel (eluent: DCM/MeOH from 100/0 to 97/3) then further purified by FC on NH column (eluent: Cy/EA from 100/0 to 40/60) to give 4-benzyl-9-[4-(3-fluorophenoxy)-6-(trifluoromethyl)pyrimidin-2-yl]-1,4,9-triazaspiro[5.5]undecane (p115, 167 mg, y=45%).

MS (ES) (m/z): 502.3 [M]⁺

Example 75: 9-[4-(3-fluorophenoxy)-6-(trifluoromethyl)pyrimidin-2-yl]-1,4,9-triazaspiro[5.5]undecane (E75)

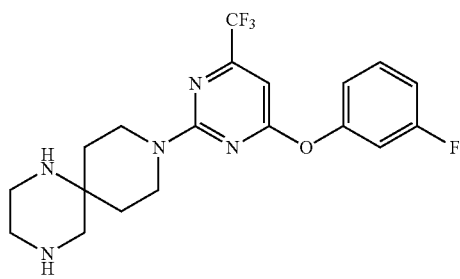 [SMILES: Fc1cccc(Oc2cc(C(F)(F)F)nc(N3CCC4(CC3)CNCCN4)n2)c1]

To a solution of 4-benzyl-9-[4-(3-fluorophenoxy)-6-(trifluoromethyl)pyrimidin-2-yl]-1,4,9-triazaspiro[5.5]undecane (p115, 163 mg, 0.33 mmol) in MeOH (20 mL), ammonium formate (123 mg, 1.95 mmol) and 10% Pd/C (75 mg) were added at RT then the mixture was stirred under reflux for 45 min. The reaction mixture was cooled down to RT, filtered through a pad of celite and the solvent removed under vacuum. Crude material was purified by FC on NH column (eluent: DCM/MeOH from 100/0 to 98/2) to give 9-[4-(3-fluorophenoxy)-6-(trifluoromethyl)pyrimidin-2-yl]-1,4,9-triazaspiro[5.5]undecane (E75, 46 mg, y=34%).

MS (ES) (m/z): 412.2 [M]+

1H NMR (DMSO-d6): δ ppm 7.44-7.60 (m, 1H) 7.22-7.30 (m, 1H) 7.08-7.22 (m, 2H) 6.60 (s, 1H) 3.53 (br. s., 2H) 2.59 (d, 4H) 2.46 (s, 2H) 1.92 (br. s., 2H) 1.59 (br. s., 2H) 1.36 (br. s., 2H)

Example 76: 3-[4-(3-fluorophenoxy)-6-(trifluoromethyl)pyrimidin-2-yl]-7-methyl-3,7,11-triazaspiro[5.6]dodecan-12-one (E76)

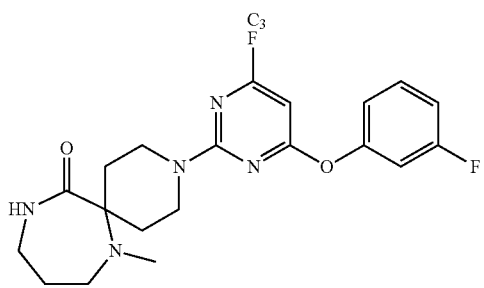

A mixture of 2-chloro-4-(3-fluorophenoxy)-6-(trifluoromethyl)pyrimidine (p46, 300 mg, 1 mmol), 7-methyl-3,7,11-triazaspiro[5.6]dodecan-12-one (200 mg, 1 mmol) and K2CO3 (180 mg, 1.3 mmol) in DMSO (2 mL) was heated at 60° C. overnight. After cooling to RT, EtOAc and water were added and the product was extracted in organic phase. The organic phase was dried and evaporated. The crude material was purified by FC on silica gel (eluent: Cy/EA from 100/0 to 0/100) to give 3-[4-(3-fluorophenoxy)-6-(trifluoromethyl)pyrimidin-2-yl]-7-methyl-3,7,11-triazaspiro[5.6]dodecan-12-one (E76, 140 mg, y=31%) as white solid.

MS (ES) (m/z): 454.2 [M+H]+

1H NMR (DMSO-d6): δ ppm 7.57-7.46 (m, 2H), 7.27 (td, 1H), 7.22-7.11 (m, 2H), 6.64 (s, 1H), 4.04 (q, 1H), 3.70 (br. s., 1H), 3.40 (br. s., 1H), 3.15 (br. s., 3H), 3.08 (br. s., 2H), 2.26 (s, 3H), 2.00 (s, 2H), 1.73 (br. s., 2H), 1.57 (br. s., 2H)

Preparation 116:
7-methyl-3,7,11-triazaspiro[5.6]dodecane (P116)

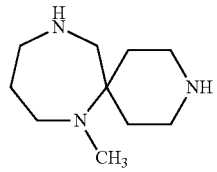

LiAlH4 2M solution in THF (1.64 mL, 3.27 mmol) was added drop-wise to a solution of 7-methyl-3,7,11-triazaspiro[5.6]dodecan-12-one (430 mg, 2.18 mmol) in THF (14 mL) at RT then the mixture was refluxed for 52 hrs. The stirred reaction mixture was cooled down to −10° C. and Na2SO4*10H2O was carefully added portion-wise up to fizz end. The mixture was left stirring at RT for 30 min, then it was filtered, the solid was washed with DCM and the solvent concentrated under reduced pressure to give 7-methyl-3,7,11-triazaspiro[5.6]dodecane (p116, 215 mg, crude material) that was used as such in the next step.

MS (ES) (m/z): 184.2 [M]+

Example 77: 3-[4-(3-fluorophenoxy)-6-(trifluoromethyl)pyrimidin-2-yl]-7-methyl-3,7,11-triazaspiro[5.6]dodecane (E77)

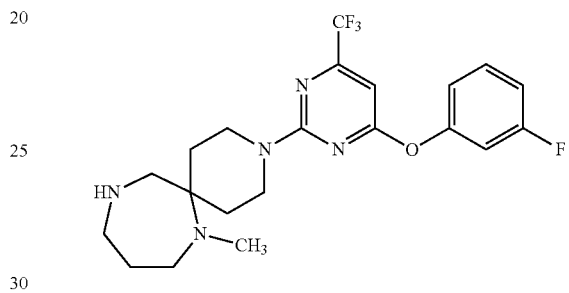

A mixture of 7-methyl-3,7,11-triazaspiro[5.6]dodecane (p116, 210 mg, 1.15 mmol), 2-chloro-4-(3-fluorophenoxy)-6-(trifluoromethyl)pyrimidine (p46, 303 mg, 1.04 mmol) and K2CO3 (238 mg, 1.73 mmol) in DMSO (1.8 mL) was heated at 70° C. and stirred 2 hrs at this temperature. After cooling at RT, EA and water were added, the organic phase was washed with water, dried and evaporated; crude product was purified twice by FC on silica gel (eluent: DCM/MeOH from 100/0 to 97/3) affording 3-[4-(3-fluorophenoxy)-6-(trifluoromethyl)pyrimidin-2-yl]-7-methyl-3,7,11-triazaspiro[5.6]dodecane (E77, 10 mg, y=2%).

MS (ES) (m/z): 440.3 [M+H]+

1H NMR (DMSO-d6): δ ppm 7.50 (m, 1H), 7.05-7.33 (m, 3H), 6.60 (s, 1H), 3.32 (s, 4H), 2.84 (t, 2H), 2.74 (t, 2H), 2.59 (s, 2H), 2.27 (s, 3H), 1.10-1.97 (m, 7H)

Preparation 117:
(4-amino-1-benzylpiperidin-4-yl)methanol (P117)

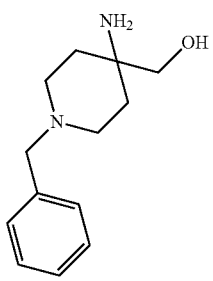 [SMILES: NC1(CO)CCN(Cc2ccccc2)CC1]

LiAlH4 solution 2M in THF (4.3 mL, 2.15 mmol) was added to a solution of 4-amino-1-benzylpiperidine-4-carboxylic acid (0.50 g, 2.13 mmol) in THF (12 mL) at 0° C. then the ice bath was removed and the mixture was refluxed for 2 hrs. The stirred reaction mixture was cooled down to −10° C. and Na$_2$SO$_4$*10H$_2$O was carefully added portion-wise up to fizz end. The mixture was left stirring at RT for 30 min, then it was filtered, the solid was washed with DCM and the solvent concentrated under reduced pressure to give (4-amino-1-benzylpiperidin-4-yl)methanol (p117, 0.35 g, y=74%).

MS (ES) (m/z): 221.2 [M+H]$^+$

Preparation 118: N-[1-benzyl-4-(hydroxymethyl) piperidin-4-yl]-2-chloroacetamide (P118)

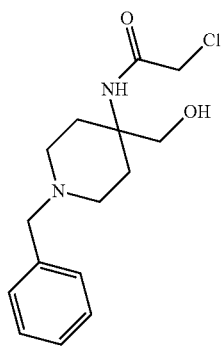 [SMILES: O=C(CCl)NC1(CO)CCN(Cc2ccccc2)CC1]

To a solution of (4-amino-1-benzylpiperidin-4-yl)methanol (p117, 0.35 g, 1.59 mmol) in DCM (5 mL) a solution of NaOH (0.091 g, 2.28 mmol) in water (3 mL) was added, then the mixture was brought to 0° C. and chloro acetyl chloride (0.13 mL, 1.59 mmol) was added drop-wise under vigorous magnetic stirring. The reaction mixture was stirred at RT for 2 hrs. The reaction mixture was diluted with DCM, dried and the solvent removed under reduced pressure. The crude product was purified by FC on silica gel (eluent: DCM to DCM/MeOH 90/10) to give N-[1-benzyl-4-(hydroxymethyl)piperidin-4-yl]-2-chloroacetamide (p118, 0.25 g, y=53%).

MS (ES) (m/z): 297.0 [M+H]$^+$

Preparation 119:
9-benzyl-4-oxa-1,9-diazaspiro[5.5]undecan-2-one (P119)

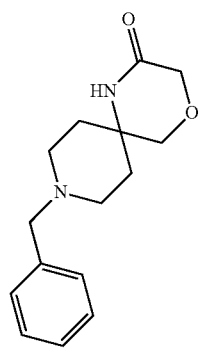 [SMILES: O=C1COCC2(CCN(Cc3ccccc3)CC2)N1]

To a stirred solution of N-[1-benzyl-4-(hydroxymethyl) piperidin-4-yl]-2-chloroacetamide (p118, 250 mg, 0.84 mmol) in THF (18 mL), at RT, t-BuOK (189 mg, 1.68 mmol) was added portion-wise and the resulting reaction mixture was left stirring at RT for 1.5 h. The reaction mixture was concentrated under reduced pressure, the crude material was dissolved in methanol and loaded on a SCX cartridge (washing with MeOH and eluting with 2N NH$_3$ in MeOH) to give 9-benzyl-4-oxa-1,9-diazaspiro[5.5]undecan-2-one (p119, 190 mg, y=87%).

MS (ES) (m/z): 261.2 [M+H]$^+$

Preparation 120:
9-benzyl-4-oxa-1,9-diazaspiro[5.5]undecane (P120)

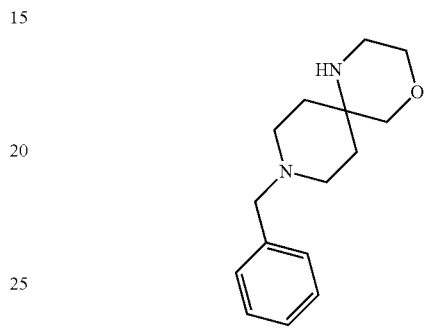

LiAlH$_4$ 2M in THF (0.6 mL, 1.2 mmol) was added to a solution of 9-benzyl-4-oxa-1,9-diazaspiro[5.5]undecan-2-one (p119, 0.19 g, 0.73 mmol) in THF (8 mL) at 0° C., the ice-bath was removed then the mixture was heated to reflux for 2 hrs. The stirred reaction mixture was cooled down to −10° C. and Na$_2$SO$_4$*10H$_2$O was carefully added portion-wise up to fizz end. The mixture was left stirring at RT for 30 min, then it was filtered, the solid was washed with DCM and the solvent concentrated under reduced pressure to give 9-benzyl-4-oxa-1,9-diazaspiro[5.5]undecane (p120, 0.18 g, y=quant.).

MS (ES) (m/z): 247.2 [M+H]$^+$

Preparation 121: tert-butyl 9-benzyl-4-oxa-1,9-diazaspiro[5.5]undecane-1-carboxylate (P121)

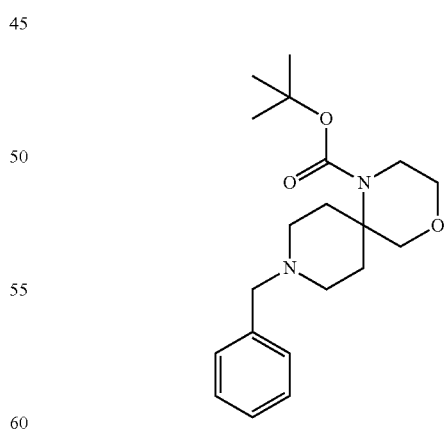

To a stirred solution of 9-benzyl-4-oxa-1,9-diazaspiro[5.5]undecane (p120, 180 mg, 0.73 mmol) in DCM (3 mL), Boc$_2$O (160 mg, 0.73 mmol) was added portion-wise. The ice-bath was removed and the reaction mixture was stirred at RT overnight. The mixture was concentrated under reduced pressure and the residue purified by FC on silica gel (eluent: DCM to DCM/MeOH 98/2) to give tert-butyl 9-benzyl-4-oxa-1,9-diazaspiro[5.5]undecane-1-carboxylate (p121, 75 mg, y=29%).

MS (ES) (m/z): 347.3 [M+H]$^+$

Preparation 122: tert-butyl 4-oxa-1,9-diazaspiro[5.5]undecane-1-carboxylate (P122)

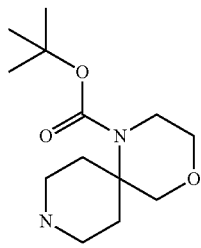 [SMILES: CC(C)(C)OC(=O)N1CCOCC12CCNCC2]

To a solution of tert-butyl 9-benzyl-4-oxa-1,9-diazaspiro[5.5]undecane-1-carboxylate (p121, 75 mg, 0.22 mmol) in MeOH (3.6 mL), ammonium formate (82 mg, 1.3 mmol) and 10% Pd/C (29 mg) were added at RT then the mixture was stirred under reflux for 1 h. The reaction mixture was filtered through a pad of celite and the solvent removed under vacuum to give tert-butyl 4-oxa-1,9-diazaspiro[5.5]undecane-1-carboxylate (p122, 45 mg, y=80%).

MS (ES) (m/z): 257.2 [M+H]$^+$

Preparation 123: tert-butyl 9-[4-(3-fluorophenoxy)-6-(trifluoromethyl)pyrimidin-2-yl]-4-oxa-1,9-diazaspiro[5.5]undecane-1-carboxylate (P123)

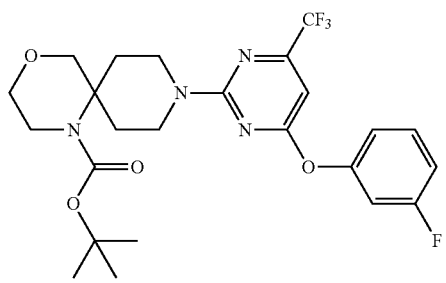 [SMILES: CC(C)(C)OC(=O)N1CCOCC12CCN(c1nc(Oc3cccc(F)c3)cc(C(F)(F)F)n1)CC2]

A mixture of tert-butyl 4-oxa-1,9-diazaspiro[5.5]undecane-1-carboxylate (p122, 45 mg, 0.18 mmol), 2-chloro-4-(3-fluorophenoxy)-6-(trifluoromethyl)pyrimidine (p46, 53 mg, 0.18 mmol) and K$_2$CO$_3$ (37 mg, 0.27 mmol) in DMSO (0.7 mL) was heated at 90° C. and stirred at that temperature for 2 hrs. After cooling at RT, EA and water were added, the organic phase was washed with water, dried and evaporated; crude product was purified by FC on silica gel (eluent: Cy to Cy/EA 83/17) affording tert-butyl 9-[4-(3-fluorophenoxy)-6-(trifluoromethyl)pyrimidin-2-yl]-4-oxa-1,9-diazaspiro[5.5]undecane-1-carboxylate (p123, 59 mg, y=64%).

MS (ES) (m/z): 513.3 [M+H]$^+$

Example 78: 9-[4-(3-fluorophenoxy)-6-(trifluoromethyl)pyrimidin-2-yl]-4-oxa-1,9-diazaspiro[5.5]undecane hydrochloride (E78)

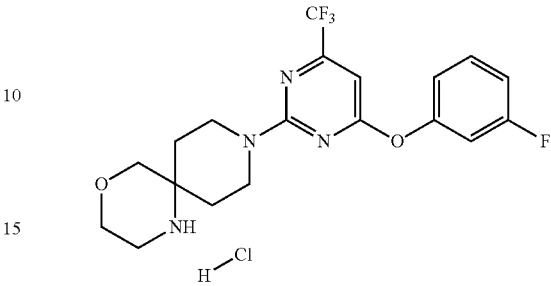

Step a

To a solution of tert-butyl 9-[4-(3-fluorophenoxy)-6-(trifluoromethyl)pyrimidin-2-yl]-4-oxa-1,9-diazaspiro[5.5]undecane-1-carboxylate (p123, 59 mg, 0.11 mmol) in DCM (0.5 mL), at RT, TFA (0.26 mL) was added. The reaction mixture was concentrated under vacuum. The residue was taken up with DCM and sodium bicarbonate saturated solution, the organic phase was dried and the solvent removed under vacuum to give 9-[4-(3-fluorophenoxy)-6-(trifluoromethyl)pyrimidin-2-yl]-4-oxa-1,9-diazaspiro[5.5]undecane (40 mg).

Step b

9-[4-(3-fluorophenoxy)-6-(trifluoromethyl)pyrimidin-2-yl]-4-oxa-1,9diazaspiro[5.5]undecane (40 mg) was dissolved in DCM (0.2 mL) and 2N HCl (0.048 mL) was added. The mixture was concentrated under reduced pressure, the residue was triturated with pentane and dried under vacuum to give 9-[4-(3-fluorophenoxy)-6-(trifluoromethyl)pyrimidin-2-yl]-4-oxa-1,9-diazaspiro[5.5]undecane hydrochloride (E78, 37 mg, y=75%).

MS (ES) (m/z): 413.2 [M+H]$^+$ $^1$H NMR (DMSO-d$_6$): δ ppm 9.56 (br. s., 2H), 7.47-7.58 (m, 1H), 7.27 (dt, 1H), 7.10-7.22 (m, 2H), 6.74 (s, 1H), 4.16 (br. s., 1H), 3.72-3.91 (m, 5H), 3.49 (br. s., 2H), 3.17 (br. s., 2H), 1.94 (br. s., 2H), 1.78 (br. s., 2H)

Preparation 124: 1-tert-butyl 4-ethyl 4-(2-cyanoethyl)piperidine-1,4-dicarboxylate (P124)

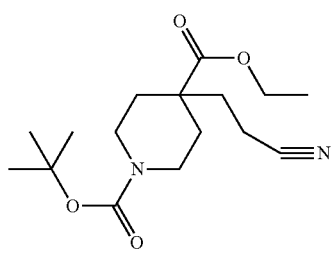 [SMILES: CCOC(=O)C1(CCC#N)CCN(C(=O)OC(C)(C)C)CC1]

To a stirred solution of 1-tert-butyl 4-ethyl piperidine-1,4-dicarboxylate (4.39 g, 17.07 mmol) in THF (70 mL), at −78° C. and under a nitrogen atmosphere, LDA (1.5 M solution in Hexane, 23 mL, 34.14 mmol) was added dropwise and the resulting dark orange solution was stirred 0.5 h at −78° C. 3-bromopropanenitrile (2 mL, 23.90 mmol) was added dropwise, and then the reaction mixture was allowed to reach −30° C. over 4.5 hrs. Saturated NH₄Cl solution and EA were added to the reaction mixture. The organic phase was washed with water, brine and dried. After removal of the solvent under reduced pressure the crude product was purified by FC on silica gel (eluent: Cy to Cy/EA 75/25) to give 1-tert-butyl 4-ethyl 4-(2-cyanoethyl)piperidine-1,4-dicarboxylate (p124, 2.12 g, y=40%) as pale yellow oil.

MS (ES) (m/z): 311.3 [M+H]⁺

Preparation 125: tert-butyl 1-oxo-2,9-diazaspiro[5.5]undecane-9-carboxylate (P125)

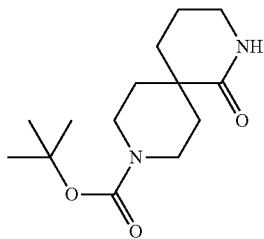 [SMILES: CC(C)(C)OC(=O)N1CCC2(CCCNC2=O)CC1]

Step a:
A mixture of 1-tert-butyl 4-ethyl 4-(2-cyanoethyl)piperidine-1,4-dicarboxylate (p124, 3.91 g, 12.60 mmol) in AcOH (70 mL) and PtO₂ (0.57 g, 2.52 mmol) was hydrogenated at 5.5 atm in autoclave (Parr) under vigorous mechanical stirring, overnight at RT. The mixture was filtered through a pad of celite and the solvent removed under reduced pressure. The residue was dissolved in DCM and the solution washed twice with saturated NaHCO₃, dried and concentrated under reduced pressure affording 4-(3-aminopropyl)-1-[(tert-butoxy)carbonyl]piperidine-4-carboxylic acid (3.61 g).
Step b:
To a stirred solution of 4-(3-aminopropyl)-1-[(tert-butoxy)carbonyl]piperidine-4-carboxylic acid (from step a, 3.61 g, 11.49 mmol) in MeOH/THF (30/5 mL), a solution of LiOH H₂O (1.45 g, 34.47 mmol) in water (10 mL) was added and the reaction mixture was stirred overnight at 50° C. The reaction mixture was allowed to reach RT then it was concentrated under reduced pressure in order to remove the organic solvents and extracted twice with DCM. The organic phase was washed with saturated NaHCO₃, dried and the solvent removed under vacuum. The crude material was purified by FC on silica gel (eluent: DCM to DCM/MeOH 98/2) to give tert-butyl 1-oxo-2,9-diazaspiro[5.5]undecane-9-carboxylate (p125, 1.49 g, y=44%) as white solid.

MS (ES) (m/z): 269.2 [M+H]⁺

Preparation 126: 2,9-diazaspiro[5.5]undecan-1-one hydrochloride (P126)

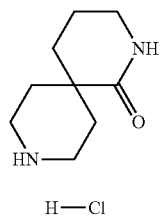

To a solution of tert-butyl 1-oxo-2,9-diazaspiro[5.5]undecane-9-carboxylate (p125, 500 mg, 1.86 mmol) in dioxane (2 mL), at RT, HCl (4N in dioxane) (2.3 mL) was added and the mixture was stirred at RT for 6 hrs. The reaction mixture was concentrated under vacuum to give 2,9-diazaspiro[5.5]undecan-1-one hydrochloride (p126, 380 mg, y=73%).

MS (ES) (m/z): 169.1 [M+H]⁺

Preparation 127: 9-benzyl-2,9-diazaspiro[5.5]undecan-1-one (P127)

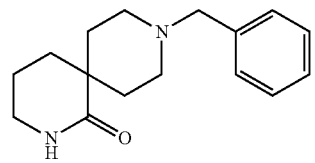 [SMILES: O=C1NCCCC12CCN(Cc1ccccc1)CC2]

To a solution of 2,9-diazaspiro[5.5]undecan-1-one hydrochloride (p126, 320 mg, 1.56 mmol) in DCM (5 mL), benzaldehyde (0.16 mL, 1.56 mmol) was added and the mixture was stirred at RT for 15 min, the NaBH(OAc)₃ (496 mg, 2.34 mmol) was added and the mixture was left stirring at RT overnight. Then, further 1 eq of NaBH(OAc)₃ (330 mg, 1.56 mmol) was added and the mixture stirred at RT for further 1 h. The reaction was quenched with NaHCO3 saturated solution, then phases were separated and aqueous one was backextracted with DCM twice. Combined organics were washed with brine, dried and concentrated under reduced pressure. The residue was loaded on a SCX cartridge washing with MeOH and eluting with NH₃ 1M in MeOH. Solvent was eliminated under reduced pressure affording 9-benzyl-2,9-diazaspiro[5.5]undecan-1-one (p127, 351 mg, y=87%) as white solid MS (ES) (m/z): 259.3 [M+H]⁺

Preparation 128: 9-benzyl-2,9-diazaspiro[5.5]undecane (P128)

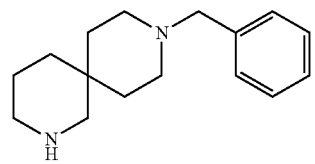 [SMILES: c1ccc(CN2CCC3(CCCNC3)CC2)cc1]

LiAlH₄ 1M in THF (2.72 mL, 2.72 mmol) was added to solution of 9-benzyl-2,9-diazaspiro[5.5]undecan-1-one (p127, 351 mg, 1.36 mmol) in THF (15 mL) at 0° C. then the mixture was refluxed for 1 h, cooled down to −20° C. and quenched with Na₂SO₄*10H₂O. The mixture was left stirring at RT for 10 min, then it was filtered washing with AcOEt and concentrated. Crude material was purified by FC on NH column (eluent: Cy to 70% AcOEt) affording 9-benzyl-2,9-diazaspiro[5.5]undecane (p128, 210 mg, y=63%) as colourless oil.

MS (ES) (m/z): 245.2 [M+H]⁺

Preparation 129: tert-butyl 9-benzyl-2,9-diazaspiro[5.5]undecane-2-carboxylate (P129)

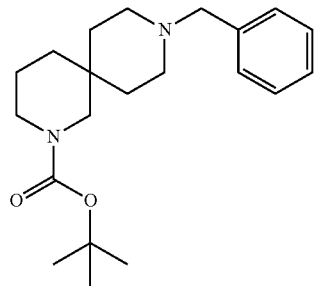 [SMILES: CC(C)(C)OC(=O)N1CCCC2(CCN(Cc3ccccc3)CC2)C1]

9-benzyl-2,9-diazaspiro[5.5]undecane (p128, 100 mg, 0.409 mmol) was dissolved in H₂O (5 mL) at RT then cooled at 0° C. Na$_2$CO$_3$ (42.2 mg, 0.417 mmol) was added followed by the dropwise addiction of Boc$_2$O (89.3 mg, 0.409 mmol) in THF (5 mL). The mixture was stirred at the same temperature for 1 h and then worked up extracting with EtOAc. The organic phase was washed with brine, dried and evaporated. The crude material was purified by FC on Silica gel (eluent: Cy to Cy/EtOAc 50/50) affording tert-butyl 9-benzyl-2,9-diazaspiro[5.5]undecane-2-carboxylate (p129, 100 mg, y=71%) as colourless oil.

MS (ES) (m/z): 345.3 [M+H]⁺

Preparation 130: tert-butyl 2,9-diazaspiro[5.5]undecane-2-carboxylate (P130)

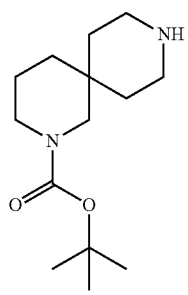 [SMILES: CC(C)(C)OC(=O)N1CCCC2(CCNCC2)C1]

Under a hydrogen atmosphere, a mixture of tert-butyl 9-benzyl-2,9-diazaspiro[5.5]undecane-2-carboxylate (p129, 100 mg, 0.290 mmol) and 10% Pd/C (20 mg, 0.189 mmol) in MeOH (10 mL) was stirred at RT for 2 hrs. Then further 1 eq of Pd/C was added and the mixture stirred under hydrogen atmosphere for further 5 hrs in the same conditions. The Pd/C was filtered off, washed with MeOH, and the filtrate was concentrated under reduced pressure to obtain tert-butyl 2,9-diazaspiro[5.5]undecane-2-carboxylate (p130, 70 mg, y=95%), as colorless oil.

MS (ES) (m/z): 255.23 [M+H]⁺

Preparation 131: tert-butyl 9-[4,5-difluoro-2-(3-fluorophenoxy)phenyl]-2,9-diazaspiro[5.5]undecane-2-carboxylate (P131)

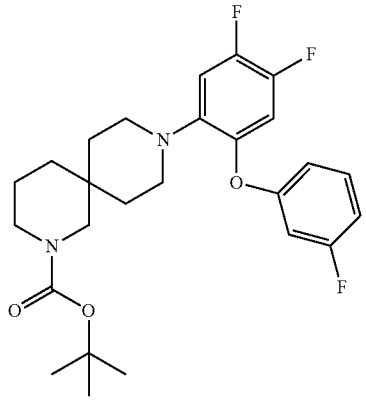 [SMILES: CC(C)(C)OC(=O)N1CCCC2(CCN(c3cc(F)c(F)cc3Oc3cccc(F)c3)CC2)C1]

To a stirred solution of tert-butyl 2,9-diazaspiro[5.5]undecane-2-carboxylate (p131, 70 mg, 0.275 mmol) in Toluene (1.5 mL) at RT, BINAP (17.12 mg, 0.0275 mmol), sodium tert-butoxide (53 mg, 0.55 mmol) and 1-bromo-4,5-difluoro-2-(3-fluorophenoxy)benzene (p7, 83.4 mg, 0.275 mmol) in Toluene (1.5 mL) were added and argon was purged for 10 min. Then Pd$_2$(dba)$_3$ (8 mg, 0.008 mmol) was added and the reaction mixture was stirred at 115° C. overnight under nitrogen atmosphere. The mixture was concentrated, water was added and then mixture was extracted with EtOAc. Solvent was eliminated under reduced pressure and the crude material purified by FC on silica gel (eluent: Cy to CyAcOEt 90/10) affording tert-butyl 9-[4,5-difluoro-2-(3-fluorophenoxy)phenyl]-2,9-diazaspiro [5.5]undecane-2-carboxylate (p131, 46 mg y=35%) as yellow oil.

MS (ES) (m/z): 477.2 [M+H]⁺

Example 79: 9-[4,5-difluoro-2-(3-fluorophenoxy)phenyl]-2,9-diazaspiro[5.5]undecane (E79)

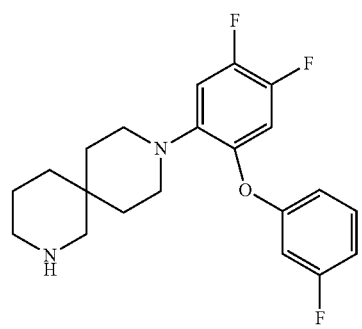 [SMILES: Fc1cccc(Oc2cc(F)c(F)cc2N2CCC3(CCCNC3)CC2)c1]

TFA (0.5 mL) was added to a solution of tert-butyl 9-[4,5-difluoro-2-(3-fluorophenoxy)phenyl]-2,9-diazaspiro [5.5]undecane-2-carboxylate (p131, 46 mg, 0.097 mmol) in DCM (3 mL). The mixture was stirred at RT for 1 h. Then the solvent was removed under reduced pressure. The residue was charged on SCX cartridge eluting with 1M NH$_3$ in MeOH to afford 9-[4,5-difluoro-2-(3-fluorophenoxy)phenyl]-2,9-diazaspiro[5.5]undecane (E79, 14.4 mg, y=39%) as yellow oil.

MS (ES) (m/z): 377.18 [M+H]+

1H NMR (CHLOROFORM-d): δ ppm 7.19-7.28 (m, 1H), 6.85 (d, 1H), 6.88 (d, 1H), 6.78 (td, 1H), 6.70 (dd, 1H), 6.60 (dt, 1H), 2.94 (t, 4H), 2.80 (t, 2H), 2.62 (s, 2H), 1.35-1.57 (m, 8H)

Preparation 132: 9-benzyl-2-[4,5-difluoro-2-(3-fluorophenoxy)phenyl]-2,9-diazaspiro[5.5]undecane (P132)

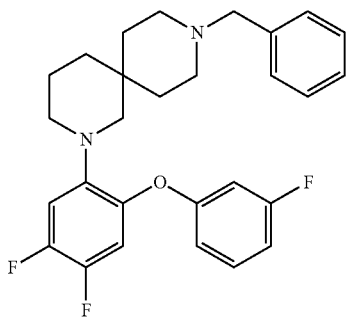 [SMILES: Fc1cccc(Oc2cc(F)c(F)cc2N2CCCC3(CCN(Cc4ccccc4)CC3)C2)c1]

To a stirred solution of 9-benzyl-2,9-diazaspiro[5.5]undecane (p128, 110 mg, 0.450 mmol) in Toluene (2 mL) at RT, BINAP (28 mg, 0.045 mmol), sodium t-butoxide (87 mg, 0.9 mmol) and 1-bromo-4,5-difluoro-2-(3-fluorophenoxy)benzene (p7, 136 mg, 0.450 mmol) in Toluene (2 mL) were added and argon was purged for 10 min. Then Pd2(dba)3 (13 mg, 0.0135 mmol) was added and the reaction mixture was stirred at 115° C. overnight under nitrogen atmosphere. The mixture was concentrated, water was added, and then the mixture was extracted with EtOAc. Solvent was eliminated under reduced pressure and the crude material was purified by FC on silica gel (eluent: Cy to Cy/AcOEt 50/50) affording 9-benzyl-2-[4,5-difluoro-2-(3-fluorophenoxy)phenyl]-2,9-diazaspiro[5.5]undecane (p132, 65 mg, y=31%).

MS (ES) (m/z): 467.3 [M+H]+

Example 80: 2-[4,5-difluoro-2-(3-fluorophenoxy)phenyl]-2,9-diazaspiro[5.5]undecane (E80)

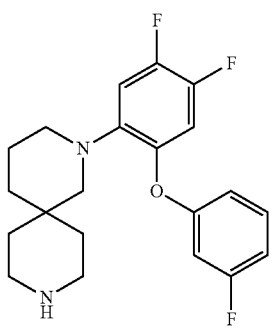 [SMILES: Fc1cccc(Oc2cc(F)c(F)cc2N2CCCC3(CCNCC3)C2)c1]

1-chloroethyl chloroformate (0.015 mL, 0.139 mmol) was added to a solution of 9-benzyl-2-[4,5-difluoro-2-(3-fluorophenoxy)phenyl]-2,9-diazaspiro[5.5]undecane (132, 65 mg, 0.139 mmol) and DIPEA (0.024 mL, 0.139 mmol) in DCM (1 mL). The solution was stirred at reflux for 2 hrs, then solvent was evaporated, the residue was redissolved with MeOH (0.5 mL) and refluxed overnight. The solvent was evaporated; the residue was dissolved with DCM and washed with H2O. The organic phase was dried and evaporated. The crude material was purified by FC on NH column (eluent: EtOAc to EtOAc/MeOH 90/10) affording 2-[4,5-difluoro-2-(3-fluorophenoxy)phenyl]-2,9-diazaspiro[5.5]undecane (E80, 16.5 mg, y=32%) as yellow oil MS (ES) (m/z): 377.2 [M+H]+

1H NMR (Chloroform-d): δ ppm 7.18-7.27 (m, 1H), 6.89 (t, 1H), 6.91 (t, 1H), 6.74 (td, 1H), 6.65 (dd, 1H), 6.52 (dt, 1H), 2.89-2.97 (m, 2H), 2.59-2.77 (m, 6H), 1.54 (dt, 2H), 1.15-1.40 (m, 6H)

Preparation 133: 2-benzyl-8-[4,5-difluoro-2-(3-fluorophenoxy)phenyl]-2,8-diazaspiro[5.5]undecane (P133)

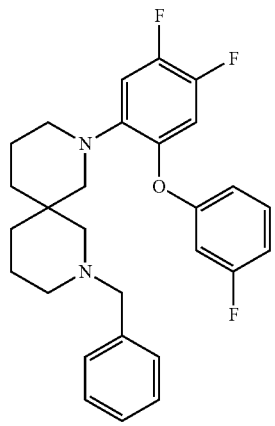 [SMILES: Fc1cccc(Oc2cc(F)c(F)cc2N2CCCC3(CCCN(Cc4ccccc4)C3)C2)c1]

To a suspension of 2-benzyl-2,8-diazaspiro[5.5]undecane hydrochloride (100 mg, 0.356 mmol) in Toluene, 1-bromo-4,5-difluoro-2-(3-fluorophenoxy)benzene (p7, 107 mg, 0.356 mmol) in Toluene (2 mL), BINAP (11 mg, 0.0178 mmol) and sodium t-butoxide (82 mg, 0.85 mmol) were added. Argon was bubbled for 20 min, then Pd2(dba)3 (9.7 mg, 0.0107 mmol) was added and the mixture was stirred at 100° C. overnight. The reaction mixture was concentrated. The residue was charged on SCX cartridge washing with MeOH and eluting with 1M NH3 in MeOH and then solvent was eliminated under reduced pressure. The crude material was purified by FC on silica gel (eluent: Cy to Cy/AcOEt 50/50) affording 2-benzyl-8-[4,5-difluoro-2-(3-fluorophenoxy)phenyl]-2,8-diazaspiro[5.5]undecane (p133, 34.9 mg, y=21%) as yellow oil.

MS (ES) (m/z): 467.3 [M+H]+

Example 81: 2-[4,5-difluoro-2-(3-fluorophenoxy)phenyl]-2,8-diazaspiro[5.5]undecane (E81)

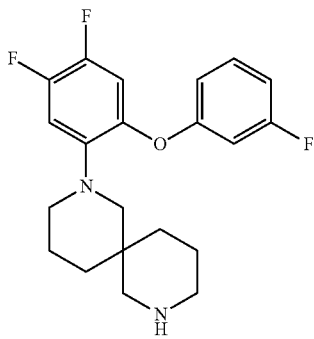 [SMILES: Fc1cccc(Oc2cc(F)c(F)cc2N2CCCC3(CCCNC3)C2)c1]

Under a hydrogen atmosphere, a mixture of 2-benzyl-8-[4,5-difluoro-2-(3-fluorophenoxy)phenyl]-2,8-diazaspiro[5.5]undecane (p133, 34.9 mg, 0.075 mmol), 10% Pd/C (5.19 mg), and MeOH (3 mL) was stirred at RT for 2 hrs. Then further Pd/C (8 mg) was added and the mixture stirred under same conditions overnight. The Pd/C was filtered off, washed with MeOH, and the filtrate was concentrated under reduced pressure. The crude material was purified by FC silica gel (eluent: Cy to Cy/EtOAc 50:50) affording 2-[4,5-difluoro-2-(3-fluorophenoxy)phenyl]-2,8-diazaspiro[5.5]undecane (E81, 17.1 mg, y=61%) as colourless oil.

MS (ES) (m/z): 377.2 [M+H]⁺

¹H NMR (CHLOROFORM-d): δ ppm 7.28-7.20 (m, 1H), 6.95-6.86 (m, 2H), 6.76 (dt, 1H), 6.67 (dd, 1H), 6.55 (td, 1H), 3.01 (dd, 1H), 2.92-2.74 (m, 3H), 2.73-2.58 (m, 2H), 2.50 (d, 1H), 2.34 (d, 1H), 1.51 (td, 2H), 1.46-1.27 (m, 4H), 1.27-1.08 (m, 2H)

Example 82: 3-[4,5-difluoro-2-(3-fluorophenoxy)phenyl]-3,9-diazaspiro[5.5]undecane (E82)

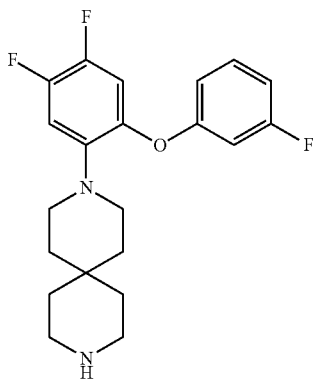 [SMILES: Fc1cccc(Oc2cc(F)c(F)cc2N2CCC3(CCNCC3)CC2)c1]

Step a:

1-bromo-4,5-difluoro-2-(3-fluorophenoxy)benzene (p7, 119 mg, 0.393 mmol), tert-butyl 3,9-diazaspiro[5.5]undecane-3-carboxylate (100 mg, 0.393 mmol), BINAP (12.2 mg, 0.0196 mmol) and sodium t-butoxide (53 mg, 0.55 mmol) were mixed in Toluene (3 mL) and Argon was bubbled for 20 min. Then Pd₂(dba)₃ (11 mg, 0.012 mmol) was added and the mixture was stirred at 100° C. overnight. The mixture was cooled down to RT, diluted with EtOAc, filtered and concentrated. The crude material was purified by FC silica gel (eluent: Cy to Cy/EtOAc 85:15) to obtain tert-butyl 9-[4,5-difluoro-2-(3-fluorophenoxy)phenyl]-3,9-diazaspiro[5.5]undecane-3-carboxylate (45 mg) as yellow oil Step b:

tert-butyl 9-[4,5-difluoro-2-(3-fluorophenoxy)phenyl]-3,9-diazaspiro[5.5]undecane-3-carboxylate (from step a, 45 mg, 0.094 mmol) was diluted with DCM (3 mL), treated with TFA (0.5 mL) and the mixture stirred at RT for 1 h. After solvent evaporation, the residue was charged on SCX washing with MeOH and eluting with 1N NH₃ in MeOH. Crude material was dissolved in MeOH (3 mL), treated with NaBH₄ (19 mg, 0.5 mmol) and the mixture stirred at RT for 3 hrs. Solvent was removed and the residue was dissolved in DCM and washed with H₂O. After evaporation of organic solvent, 3-[4,5-difluoro-2-(3-fluorophenoxy)phenyl]-3,9-diazaspiro[5.5]undecane (E82, 33.3 mg, y=22%) was obtained.

MS (ES) (m/z): 377.2 [M+H]⁺

¹H NMR (CHLOROFORM-d): δ ppm 7.21-7.26 (m, 1H), 6.87-6.81 (m, 2H, 6.76 (td, 1H), 6.70-6.66 (m, 1H), 6.61-6.57 (1H, m), 2.95-2.90 (m, 4H), 2.80-2.74 (m, 4H), 1.46-1.42 (m, 4H), 1.42-1.37 (m, 4H)

Preparation 134: 5-benzyl-1-oxa-5-azaspiro[2.4]heptanes (P134)

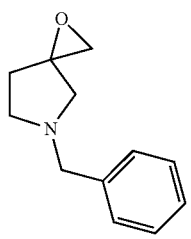 [SMILES: c1ccc(CN2CCC3(CO3)C2)cc1]

To an ice-cooled mixture of NaH (60%, 0.59 g, 14.83 mmol) and trimethylsulfoxonium iodide (2.76 g, 12.55 mmol) DMSO (10 mL) was added keeping the mixture at 10° C. After stirring for 10 min at 10° C., the mixture was allowed to reach RT and left stirring at that temperature for 1 h. A solution of 1-benzylpyrrolidin-3-one (2 g, 11.41 mmol) in DMSO (10 mL) was added via syringe over 10 min. The resulting reaction mixture was stirred for 1.5 h at RT, diluted with Et₂O and quenched by the addition of saturated aqueous NH₄Cl. Phases were separated and aqueous one was backextracted with Et₂O. Combined organics were dried, filtered and concentrated under reduced pressure to give 5-benzyl-1-oxa-5-azaspiro[2.4]heptanes (p134, 2.10 g, y=97%) that was used as such.

MS (ES) (m/z): 190.1 [M+H]⁺

Preparation 135: 3-(aminomethyl)-1-benzylpyrrolidin-3-ol (P135)

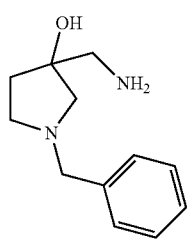 [SMILES: NCC1(O)CCN(Cc2ccccc2)C1]

To a stirred solution of 5-benzyl-1-oxa-5-azaspiro[2.4]heptanes (p134, 2.10 g, 11.1 mmol) in MeOH (12 mL), at 0° C., 28% aq. NH$_4$OH (25 mL), was added portionwise. After 5 min the ice-bath was removed and the resulting reaction mixture was stirred at RT overnight.

The reaction mixture was concentrated under reduced pressure, the residue was taken up with DCM and 1N NaOH, the organic phase was washed with water and brine, dried and concentrated under vacuum. The crude material was purified by FC on NH column (eluting with DCM/MeOH from 100/0 to 95/5) to give 3-(aminomethyl)-1-benzylpyrrolidin-3-ol (p135, 0.94 g, y=41%) as brown oil.

MS (ES) (m/z): 207.2 [M+H]$^+$

Preparation 136: N-[(1-benzyl-3-hydroxypyrrolidin-3-yl)methyl]-2-chloroacetamide (P136)

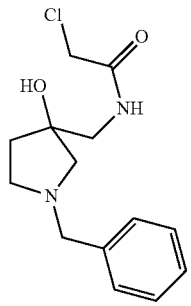 [SMILES: O=C(CCl)NCC1(O)CCN(Cc2ccccc2)C1]

To a stirred solution of 3-(aminomethyl)-1-benzylpyrrolidin-3-ol (p135, 0.84 g, 4.07 mmol) in DCM (9 mL), at 0° C. and under a nitrogen atmosphere, TEA (1.0 mL) was added followed by chloroacetylchloride (0.26 mL, 3.26 mmol) in DCM (2 mL) dropwise over 1 h. The reaction mixture was allowed to reach RT and stirred at that temperature for 4 hrs. The reaction mixture was diluted with DCM and saturated NH$_4$Cl, the organic phase was washed with brine, dried and concentrated under reduced pressure. The crude material was purified by FC on silica gel (eluting with DCM/MeOH from 100/0 to 95/5) to give N-[(1-benzyl-3-hydroxypyrrolidin-3-yl)methyl]-2-chloroacetamide (p136, 0.33 g, y=28.7%).

MS (ES) (m/z): 283.2 [M+H]$^+$

Preparation 137: 2-benzyl-6-oxa-2,9-diazaspiro[4.5]decan-8-one (P137)

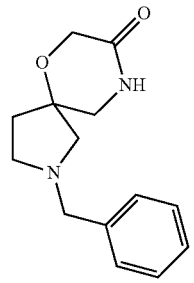 [SMILES: O=C1COC2(CCN(Cc3ccccc3)C2)CN1]

To a stirred solution of N-[(1-benzyl-3-hydroxypyrrolidin-3-yl)methyl]-2-chloroacetamide (p136, 220 mg, 0.778 mmol) in THF (35 mL), at 0° C. and under a nitrogen atmosphere, NaH 60% dispersion in mineral oil (62.25 mg, 1.55 mmol) was added portionwise and then the ice-bath was removed. After 2 hrs at RT, the reaction mixture was concentrated under vacuum. The residue was diluted with DCM and water and neutralized with 1N HCl. The organic layer was dried, filtered and concentrated under reduced pressure to obtain 2-benzyl-6-oxa-2,9-diazaspiro[4.5]decan-8-one (p137, 158 mg, crude material) as colourless oil.

MS (ES) (m/z): 247.2 [M+H]$^+$

Preparation 138: tert-butyl 2-[4,5-difluoro-2-(3-fluorophenoxy)phenyl]-6-oxa-2,9-diazaspiro[4.5]decane-9-carboxylate (P138)

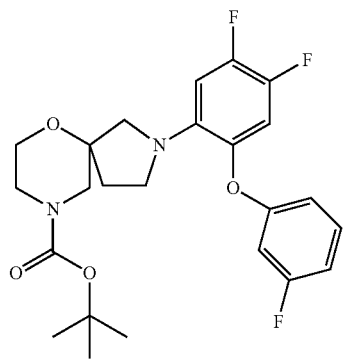 [SMILES: CC(C)(C)OC(=O)N1CCOC2(CCN(c3cc(F)c(F)cc3Oc3cccc(F)c3)C2)C1]

Step a

LiAlH$_4$ 1M in THF (0.664 mL, 0.664 mmol) was added to solution of 2-benzyl-6-oxa-2,9-diazaspiro[4.5]decan-8-one (p137, 109 mg, 0.44 mmol) in THF (10 mL) at 0° C. then the mixture was refluxed for 40 min, cooled down to −20° C. and quenched with Na$_2$SO$_4$*10H$_2$O. The mixture was left stirring at RT for 30 min, and then it was filtered washing with AcOEt. Solvent was eliminated under reduced pressure and crude material was loaded on a SCX cartridge washing with MeOH and eluting with NH$_3$ 2M in MeOH affording 2-benzyl-6-oxa-2,9-diazaspiro[4.5]decane (84 mg).

Step b 2-benzyl-6-oxa-2,9-diazaspiro[4.5]decane (from step a, 84 mg) was suspended in H$_2$O (1 mL) at RT then cooled down to 0° C. Na₂CO₃ (37 mg, 0.37 mmol) was added followed by the dropwise addition of Boc₂O (79 mg, 0.36 mmol) in THF (0.8 mL). The mixture was stirred at the same temperature for 1 h, and then worked up extracting with EtOAc. The organic phase was dried, filtered and concentrated under reduced pressure affording tert-butyl 2-benzyl-6-oxa-2,9-diazaspiro[4.5]decane-9-carboxylate (117 mg) as oil, which was used in the next step without purification.

Step c

To a solution of tert-butyl 2-benzyl-6-oxa-2,9-diazaspiro[4.5]decane-9-carboxylate (from step b, 117 mg) in MeOH (3 mL) ammonium formate (133 mg, 2.11 mmol) and 10% Pd/C (57 mg) were added at RT, then the mixture was stirred under reflux for 1 h. The mixture was cooled down to RT and filtered through a pad of celite washing with MeOH. Solvent was eliminated under reduced pressure affording tert-butyl 6-oxa-2,9-diazaspiro[4.5]decane-9-carboxylate (74 mg), as colorless oil.

Step d tert-butyl 6-oxa-2,9-diazaspiro[4.5]decane-9-carboxylate (from step c, 74 mg), 1-bromo-4,5-difluoro-2-(3-fluorophenoxy)benzene (p7, 144 mg, 0.382 mmol), Johnphos (23 mg, 0.076 mmol) and sodium t-butoxide (41 mg, 0.427 mmol) were mixed in Toluene dry (2.3 mL), then Argon was bubbled for 1 min and Pd(II) acetate (9 mg, 0.038 mmol) was added. The mixture was stirred 100° C. overnight. Then 9 mg more of Pd(II) acetate were added and the mixture stirred at 100° C. for further 3 hrs. The mixture was cooled down to RT, diluted with EtOAc, filtered and concentrated under reduced pressure. Crude material was purified by FC on silica gel (eluent: from cHex to cHex/EtOAc 70/30) affording tert-butyl 2-[4,5-difluoro-2-(3-fluorophenoxy)phenyl]-6-oxa-2,9-diazaspiro[4.5]decane-9-carboxylate (p138, 23 mg, y=11%) as yellow oil.

MS (ES) (m/z): 465.2 [M+H]⁺

Example 83: 2-[4,5-difluoro-2-(3-fluorophenoxy)phenyl]-6-oxa-2,9-diazaspiro[4.5]decane (E83)

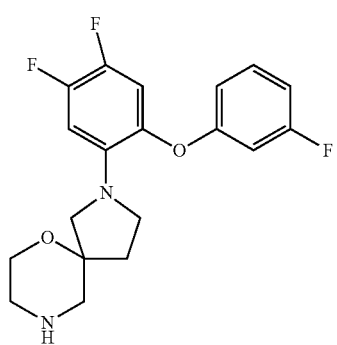 [SMILES: Fc1cccc(Oc2cc(F)c(F)cc2N2CCC3(CNCCO3)C2)c1]

TFA (0.25 mL) was added to a solution of tert-butyl 2-[4,5-difluoro-2-(3-fluorophenoxy)phenyl]-6-oxa-2,9-diazaspiro[4.5]decane-9-carboxylate (p138, 23 mg, 0.049 mmol) in 2 mL of DCM. The mixture was stirred for 1 h at RT, and then the solvent was removed under reduced pressure. The residue was charged on SCX cartridge washing with MeOH and eluting with 1M NH₃ in MeOH affording 2-[4,5-difluoro-2-(3-fluorophenoxy)phenyl]-6-oxa-2,9-diazaspiro[4.5]decane (E83, 5.4 mg, y=30%).

MS (ES) (m/z): 365.2 [M+H]⁺

¹H NMR (CHLOROFORM-d): δ ppm 7.20-7.28 (m, 1H), 6.73-6.86 (m, 2H), 6.69 (dd, 1H), 6.53-6.66 (m, 2H), 3.62-3.81 (m, 2H), 3.43-3.52 (m, 1H), 3.27-3.42 (m, 3H), 2.87 (t, 2H), 2.79 (s, 2H), 2.08-2.18 (m, 1H), 1.89 (dt, 1H)

Preparation 139:
7-benzyl-2,7-diazaspiro[4.5]decan-1-one (P139)

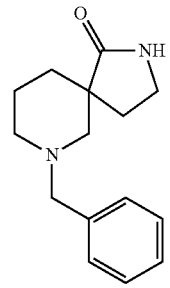 [SMILES: O=C1NCCC12CCCN(Cc1ccccc1)C2]

To a solution of 2,7-diazaspiro[4.5]decan-1-one hydrochloride (1.0 g, 5.26 mmol) in DCM (10 mL), benzaldehyde (0.53 mL, 5.26 mmol) was added and the mixture was stirred at RT for 15 min, then NaBH(OAc)₃ (1.67 g, 7.89 mmol) was added and the mixture was left stirring at RT overnight. The reaction was quenched with saturated NaHCO₃ solution, then phases were separated and aqueous one was backextracted with DCM twice. Combined organics were washed with brine, dried and concentrated under reduced pressure. Crude material was purified by FC on NH column (eluent: Cy to 50% AcOEt) affording 7-benzyl-2,7-diazaspiro[4.5]decan-1-one (p139, 890 mg, y=69%) as white solid.

MS (ES) (m/z): 245.2 [M+H]⁺

Preparation 140: 7-benzyl-2,7-diazaspiro[4.5]decane (P140)

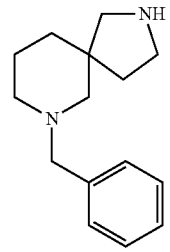 [SMILES: c1ccc(CN2CCCC3(CCNC3)C2)cc1]

LiAlH₄ 1M solution in THF (5.46 mL, 5.46 mmol) was added to a solution of 7-benzyl-2,7-diazaspiro[4.5]decan-1-one (p139, 890 mg, 3.64 mmol) in THF (50 mL) at RT, then the mixture for refluxed for 1 h. The reaction mixture was cooled down to −10° C. and quenched with Na₂SO₄*10H₂O; the mixture was then diluted with EtOAc, filtered and the solvent was evaporated. The crude material was purified by FC on NH column (eluent: cHex to cHex/EtOAc 50/50) affording 7-benzyl-2,7-diazaspiro[4.5]decane (p140, 770 mg, y=92%) as colourless oil.

MS (ES) (m/z): 231.2 [M+H]⁺

Preparation 141: 7-benzyl-2-[4,5-difluoro-2-(3-fluorophenoxy)phenyl]-2,7-diazaspiro[4.5]decane (P141)

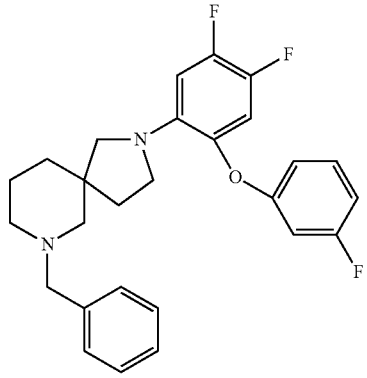 [SMILES: Fc1cccc(Oc2cc(F)c(F)cc2N2CCC3(CCCN(Cc4ccccc4)C3)C2)c1]

To a stirred solution of 1-bromo-4,5-difluoro-2-(3-fluorophenoxy)benzene (p7, 131.6 mg, 0.434 mmol) in Toluene (2 mL) at RT, argon was purged for 30 min. BINAP (27.02 mg, 0.0434 mmol), Pd$_2$(dba)$_3$ (11.90 mg, 0.013 mmol) and sodium tert-butoxide (83.41 mg, 0.868 mmol) were then added and the argon purging was continued for further 20 min; eventually a solution of 7-benzyl-2,7-diazaspiro[4.5]decane (p140, 100 mg, 0.434 mmol) in Toluene (2 mL) was added and the mixture was stirred at 115° C. overnight under nitrogen atmosphere. The reaction mixture was then concentrated and crude material purified by FC on silica gel (eluent: Cy to 10% AcOEt) affording 7-benzyl-2-[4,5-difluoro-2-(3-fluorophenoxy)phenyl]-2,7-diazaspiro[4.5]decane (p141, 160 mg, y=81%) as yellow oil.

MS (ES) (m/z): 453.3 [M+H]$^+$

Example 84: 2-[4,5-difluoro-2-(3-fluorophenoxy)phenyl]-2,7-diazaspiro[4.5]decane (E84)

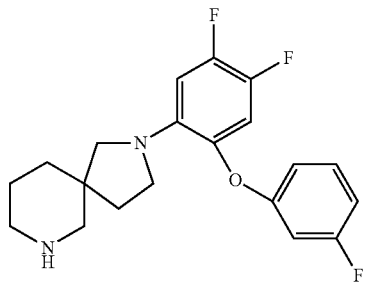 [SMILES: Fc1cccc(Oc2cc(F)c(F)cc2N2CCC3(CCCNC3)C2)c1]

To a solution of 7-benzyl-2-[4,5-difluoro-2-(3-fluorophenoxy)phenyl]-2,7-diazaspiro[4.5]decane (p141, 160 mg, 0.354 mmol) in MeOH (3 mL) ammonium formate (134 mg, 2.12 mmol) and 10% Pd/C (43 mg) were added at RT then the mixture was stirred under reflux for 1 h. The mixture was then cooled down to RT and filtered through a pad of celite washing with MeOH. Solvent was eliminated under reduced pressure and crude material was purified by FC on silica gel (eluent: Cy to 10% AcOEt) affording 2-[4,5-difluoro-2-(3-fluorophenoxy)phenyl]-2,7-diazaspiro[4.5]decane (E84, 42 mg, y=33%) as colourless oil.

MS (ES) (m/z): 363.2 [M+H]$^+$ $^1$H NMR (CHLOROFORM-d): δ ppm 7.23 (q, 1H), 6.80 (dd, 1H), 6.74 (td, 1H), 6.64 (dd, 1H), 6.56 (m, 2H), 3.34 (m, 1H), 3.27 (td, 1H), 3.21 (d, 1H), 3.02 (d, 1H), 2.76 (m, 2H), 2.57 (m, 2H), 1.77 (m, 1H), 1.62 (m, 1H), 1.49 (m, 4H)

Preparation 142: 1-benzyl 3-methyl 4-oxopiperidine-1,3-dicarboxylate (P142)

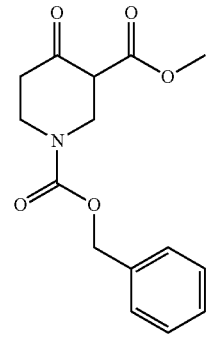 [SMILES: COC(=O)C1CN(C(=O)OCc2ccccc2)CCC1=O]

TEA (17.67 mL, 126.75 mmol) was added to a stirred solution of Methyl 4-oxo-3-piperidinecarboxylate hydrochloride (8.18 g, 42.25 mmol) in DCM (80 mL); the solution was cooled to 0° C. then benzyl chloroformate (6.93 mL, 48.58 mmol) was added dropwise. The resulting mixture was stirred at RT overnight. The mixture was washed with 1N HCl aq then with aq. NaHCO$_3$ saturated solution, organic phase was dried and concentrated under vacuum to give 1-benzyl 3-methyl 4-oxopiperidine-1,3-dicarboxylate (p142, 5.30 g, y=43%) as an orange oil.

MS (ES) (m/z): 292.2 [M+H]$^+$

Preparation 143: 1-benzyl 3-methyl 4-oxo-3-(prop-2-en-1-yl)piperidine-1,3-dicarboxylate (P143)

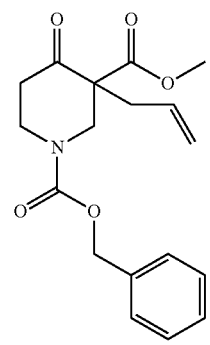 [SMILES: C=CCC1(C(=O)OC)CN(C(=O)OCc2ccccc2)CCC1=O]

To a solution of 1-benzyl 3-methyl 4-oxopiperidine-1,3-dicarboxylate (p142, 5.30 g, 18.19 mmol) in DMF (27 mL) NaH 60% dispersion in mineral oil (0.873 g, 21.83 mmol) was added at 0° C. After vigorous stirring for 1 h at RT, allyl bromide (1.62 mL, 18.74 mmol) was added and the mixture was stirred for 4 hrs. The reaction was quenched by addition of H$_2$O (25 mL) and extracted with EtOAc (3×25 mL). The organic phase was dried and concentrated under reduced pressure. The crude material was purified by FC on silica gel (eluent: cHex to cHex/EtOAc 70/30) affording 1-benzyl 3-methyl 4-oxo-3-(prop-2-en-1-yl)piperidine-1,3-dicarboxylate (p143, 4.7 g, y=78%).

MS (ES) (m/z): 332.2 [M+H]$^+$

Preparation 144: 8-benzyl 6-methyl 6-(prop-2-en-1-yl)-1,4-dioxa-8-azaspiro[4.5]decane-6,8-dicarboxylate (P144)

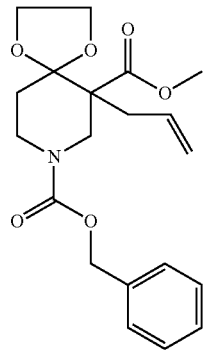 [SMILES: C=CCC1(C(=O)OC)CN(C(=O)OCc2ccccc2)CCC12OCCO2]

A mixture of 1-benzyl 3-methyl 4-oxo-3-(prop-2-en-1-yl)piperidine-1,3-dicarboxylate (p143, 4.70 g, 14.19 mmol), ethylene glycol (7.91 mL, 141.90 mmol) and p-toluensulfonic acid monohydrate (405 mg, 2.13 mmol) in dry Toluene (25 mL) was heated under reflux for 16 hrs using a Dean-Stark apparatus. The mixture was cooled down to RT and concentrated under vacuum. The residue was dissolved in Et$_2$O and washed with water. Phases were separated and organic phase was dried and concentrated under reduced pressure affording 8-benzyl 6-methyl 6-(prop-2-en-1-yl)-1,4-dioxa-8-azaspiro[4.5]decane-6,8-dicarboxylate (p144, 4.90 g, y=92%) as colorless oil.

MS (ES) (m/z): 376.2 [M+H]$^+$

Preparation 145: 8-benzyl 6-methyl 6-(2-oxoethyl)-1,4-dioxa-8-azaspiro[4.5]decane-6,8-dicarboxylate (P145)

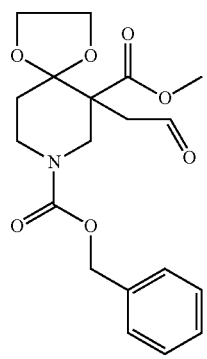 [SMILES: COC(=O)C1(CC=O)CN(C(=O)OCc2ccccc2)CCC12OCCO2]

8-benzyl 6-methyl 6-(prop-2-en-1-yl)-1,4-dioxa-8-azaspiro[4.5]decane-6,8-dicarboxylate (p144, 4.90 g, 13.05 mmol) was dissolved in THF/H$_2$O (25+25 mL). To this stirred mixture a solution of OsO$_4$ 4% in water (3 mL, 0.392 mmol) was added over 30 seconds and the resulting mixture was stirred at RT for 5 min. NaIO$_4$ (6.98 g, 32.63 mmol) was added and the mixture stirred for 1 h. The mixture was partitioned between NaHCO$_3$ (30 mL) and Et$_2$O (3×50 mL). The organic phase was dried and concentrated. The crude material was purified by FC on silica gel (eluent: cHex to cHex/EtOAc 60/40) affording 8-benzyl 6-methyl 6-(2-oxoethyl)-1,4-dioxa-8-azaspiro[4.5]decane-6,8-dicarboxylate (p145, 2.95 g, y=60%) as colorless oil.

MS (ES) (m/z): 378.2 [M+H]$^+$

Preparation 146: benzyl 8-benzyl-7-oxo-1,4-dioxa-8,12-diazadispiro[4.0.4$^6$.4$^5$]tetradecane-12-carboxylate (P146)

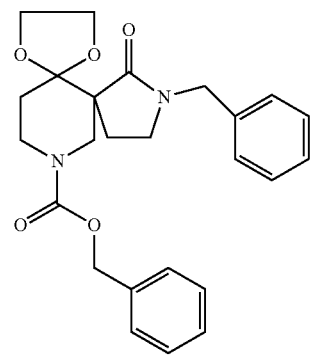 [SMILES: O=C(OCc1ccccc1)N1CCC2(OCCO2)C2(CCN(Cc3ccccc3)C2=O)C1]

To a solution of 8-benzyl 6-methyl 6-(2-oxoethyl)-1,4-dioxa-8-azaspiro[4.5]decane-6,8-dicarboxylate (p145, 2.95 g, 7.82 mmol) and benzylamine (1.11 mL, 10.16 mmol) in THF (30 mL), Na(AcO)$_3$BH (3.31 g, 15.64 mmol) was added. The resulting mixture was stirred at RT overnight. The mixture was partitioned between NaHCO$_3$ saturated solution and EtOAc. The organic phase was dried and concentrated. Crude material was purified by FC on silica gel (eluent: Cy to Cy/AcOEt 40/60) affording benzyl 8-benzyl-7-oxo-1,4-dioxa-8,12-diazadispiro[4.0.4$^6$.4$^5$]tetradecane-12-carboxylate (p146, 2.60 g, y=76%) as colourless oil.

MS (ES) (m/z): 437.3 [M+H]$^+$

Preparation 147: 8-benzyl-1,4-dioxa-8,12-diazadispiro[4.0.4$^6$.4$^5$]tetradecan-7-one (P147)

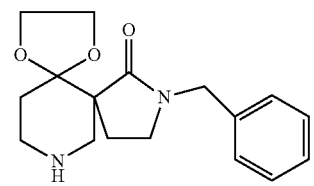 [SMILES: O=C1N(Cc2ccccc2)CCC12CNCCC21OCCO1]

Under a hydrogen atmosphere, a mixture of benzyl 8-benzyl-7-oxo-1,4-dioxa-8,12-diazadispiro[4.0.4$^6$.4$^5$]tetradecane-12-carboxylate (p146, 2.60 g, 5.96 mmol) and 10% Pd/C (412 mg, 3.87 mmol) in MeOH (30 mL) was stirred at RT for 30 min. The Pd/C was filtered off, the mixture was washed with MeOH, and the filtrate was concentrated under reduced pressure affording 8-benzyl-1,4-dioxa-8,12-diazadispiro[4.0.4$^6$.4$^5$.4]tetradecan-7-one (p147, 1.80 g, y=quant.) as colorless oil.

MS (ES) (m/z): 303.2 [M+H]$^+$

Preparation 148: 8-benzyl-1,4-dioxa-8,12-diazadispiro[4.0.4⁶.4⁵]tetradecane (P148)

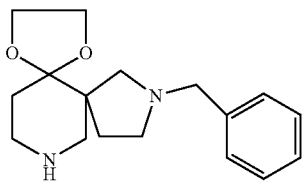 [SMILES: c1ccc(CN2CCC3(CNCCC34OCCO4)C2)cc1]

LiAlH$_4$ 2M solution in THF (4.45 mL, 8.93 mmol) was added to a solution of 8-benzyl-1,4-dioxa-8,12-diazadispiro[4.0.4⁶.4⁵]tetradecan-7-one (p147, 1.80 g, 5.95 mmol) in THF (10 mL), then the mixture was heated to 65° C. and stirred at that temperature for 4 hrs. The reaction was cooled down to 0° C. and quenched with Na$_2$SO$_4$*10H$_2$O, the solid was filtered off, washed with EtOAc and the filtrate was concentrated under reduced pressure affording 8-benzyl-1,4-dioxa-8,12-diazadispiro[4.0.4⁶.4⁵]tetradecane (p148, 1.60 g, y=93%), which was used in the next step without further purification.

MS (ES) (m/z): 289.2 [M+H]⁺

Preparation 149: tert-butyl 8-benzyl-1,4-dioxa-8,12-diazadispiro[4.0.4⁶.4⁵]tetradecane-12-carboxylate (P149)

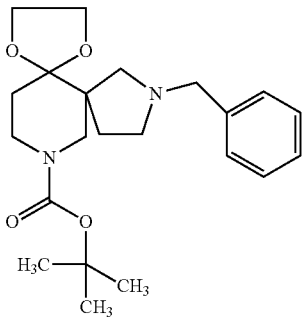 [SMILES: CC(C)(C)OC(=O)N1CCC2(OCCO2)C2(CCN(Cc3ccccc3)C2)C1]

8-benzyl-1,4-dioxa-8,12-diazadispiro[4.0.4⁶.4⁵]tetradecane (p148, 1.60 g, 5.54 mmol) was dissolved in H$_2$O (12 mL) at RT then cooled down to 0° C. Na$_2$CO$_3$ (0.572 g, 5.65 mmol) was added followed by the drop-wise addition of a solution of Boc$_2$O (1.20 g, 5.54 mmol) in THF (10 mL). The mixture was stirred at the same temperature for 1 h, and then worked up extracting with EtOAc. The organic phase was washed with brine, dried and concentrated under reduced pressure affording tert-butyl 8-benzyl-1,4-dioxa-8,12-diazadispiro[4.0.4⁶.4⁵]tetradecane-12-carboxylate (p149, 2.25 g, y=quant.) as colourless oil, which was used in the next step without further purification.

MS (ES) (m/z): 389.3 [M+H]⁺

Preparation 150: tert-butyl 1,4-dioxa-8,12-diazadispiro[4.0.4⁶.4⁵]tetradecane-12-carboxylate (P150)

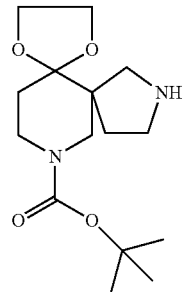 [SMILES: CC(C)(C)OC(=O)N1CCC2(OCCO2)C2(CCNC2)C1]

To a solution of tert-butyl 8-benzyl-1,4-dioxa-8,12-diazadispiro[4.0.4⁶.4⁵]tetradecane-12-carboxylate (p149, 2.25 g, 5.79 mmol) in MeOH (30 mL) ammonium formate (2.19 g, 34.75 mmol) and 10% Pd/C (1.10 g) were added at RT then the mixture was stirred under reflux for 1 h. The mixture was cooled down to RT and filtered through a pad of celite washing with MeOH. Solvent was eliminated under reduced pressure affording tert-butyl 1,4-dioxa-8,12-diazadispiro[4.0.4⁶.4⁵]tetradecane-12-carboxylate (p150, 1.56 g, y=90%) as colorless oil.

MS (ES) (m/z): 299.2 [M+H]⁺

Example 85: 8-[4,5-difluoro-2-(3-fluorophenoxy)phenyl]-1,4-dioxa-8,12-diazadispiro[4.0.4⁶.4⁵]tetradecane (E85)

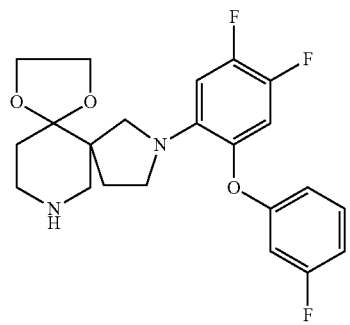 [SMILES: Fc1cccc(Oc2cc(F)c(F)cc2N2CCC3(CNCCC34OCCO4)C2)c1]

Step a 1-bromo-4,5-difluoro-2-(3-fluorophenoxy)benzene (p7, 400 mg, 1.34 mmol), tert-butyl 1,4-dioxa-8,12-diazadispiro[4.0.4⁶.4⁵]tetradecane-12-carboxylate (p150, 400 mg, 1.34 mmol), BINAP (41 mg, 0.067 mmol) and sodium t-butoxide (1.88 g, 1.87 mmol) were mixed in Toluene (5 mL). Argon was bubbled for 20 min, then Pd$_2$(dba)$_3$ (36 mg, 0.04 mmol) was added and the reaction mixture was heated at 100° C. overnight. The mixture was then cooled down to RT, diluted with EtOAc, filtered and concentrated. Crude material was purified by FC on silica gel (eluent: cHex to cHex/EtOAc 85/15) affording tert-butyl 8-[4,5-difluoro-2-(3-fluorophenoxy)phenyl]-1,4-dioxa-8,12-diazadispiro[4.0.4⁶.4⁵]tetradecane-12-carboxylate (133 mg) as yellow oil.

Step b tert-butyl 8-[4,5-difluoro-2-(3-fluorophenoxy)phenyl]-1,4-dioxa-8,12-diazadispiro[4.0.4⁶.4⁵]tetradecane-12-carboxylate (from step a, 133 mg) was dissolved in DCM (4 mL) and TFA (0.5 mL) was added. After stirring for 1 h at RT, the solvent was evaporated and the crude oil was charged on SCX cartridge washing with MeOH and eluting with 1N NH$_3$ in MeOH to obtain 8-[4,5-difluoro-2-(3-fluorophenoxy)phenyl]-1,4-dioxa-8,12-diazadispiro[4.0.4$^6$.4$^5$]tetradecane (E85, 104 mg, y=18%) as yellow oil.

MS (ES) (m/z): 421.23 [M+H]$^+$ $^1$H NMR (CHLOROFORM-d): δ ppm 7.21-7.29 (m, 1H), 6.71-6.87 (m, 2H), 6.55-6.71 (m, 3H), 3.86-4.03 (m, 4H), 3.35-3.47 (m, 1H), 3.30 (d, 1H), 3.22 (td, 1H), 3.13 (d, 1H), 2.84-2.99 (m, 2H), 2.65-2.75 (m, 2H), 2.06 (dt, 1H), 1.49-1.69 (m, 3H)

Preparation 151: benzyl 8-[4,5-difluoro-2-(3-fluorophenoxy)phenyl]-1,4-dioxa-8,12-diazadispiro[4.0.4$^6$.4$^5$]tetradecane-12-carboxylate (P151)

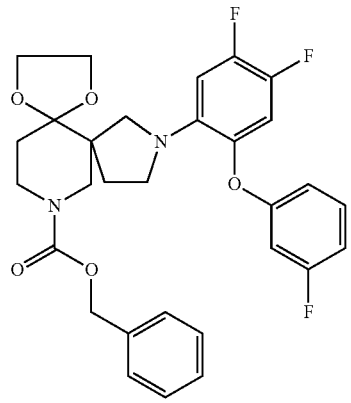 [SMILES: O=C(OCc1ccccc1)N1CCC2(OCCO2)C2(CCN(c3cc(F)c(F)cc3Oc3cccc(F)c3)C2)C1]

TEA (0.082 mL, 0.594 mmol) was added to a stirred solution of 8-[4,5-difluoro-2-(3-fluorophenoxy)phenyl]-1,4-dioxa-8,12-diazadispiro[4.0.4$^6$.4$^5$]tetradecane (E85, 100 mg, 0.2 mmol) in DCM (4 mL); the solution was cooled down to 0° C. and benzyl chloroformate (0.041 mL, 0.289 mmol) was added dropwise. The resulting mixture was stirred at RT for 1 h. The mixture was washed with NaHCO$_3$ (8 mL), dried and concentrated in vacuum. Crude was charged on SCX cartridge washing with MeOH and eluting with 1M NH$_3$ in MeOH to give benzyl 8-[4,5-difluoro-2-(3-fluorophenoxy)phenyl]-1,4-dioxa-8,12-diazadispiro[4.0.4$^6$.4$^5$]tetradecane-12-carboxylate (p151, 111 mg, y=84%) as white foam.

MS (ES) (m/z): 555.2 [M+H]$^+$

Example 86: 2-[4,5-difluoro-2-(3-fluorophenoxy)phenyl]-2,7-diazaspiro[4.5]decan-10-one (E86)

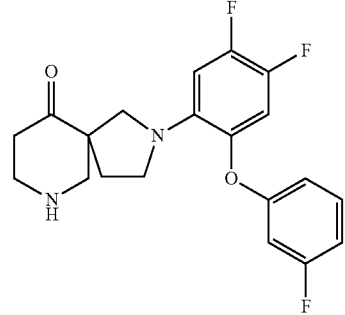 [SMILES: O=C1CCNCC12CCN(c1cc(F)c(F)cc1Oc1cccc(F)c1)C2]

To a solution of benzyl 8-[4,5-difluoro-2-(3-fluorophenoxy)phenyl]-1,4-dioxa-8,12-diazadispiro[4.0.4$^6$.4$^5$]tetra-decane-12-carboxylate (p151, 111 mg, 0.2 mmol) in DCM (4 mL) HClO$_4$ 70% (0.20 mL) was added and the mixture was stirred at RT for 3 hrs. pH was adjusted to ~9 adding Na$_2$CO$_3$, and then the product was extracted with DCM (5 mL×3). The organic phase was dried and concentrated. Crude material was purified by FC on silica gel (eluent: cHex to EtOAc/MeOH 80/20) affording 2-[4,5-difluoro-2-(3-fluorophenoxy)phenyl]-2,7-diazaspiro[4.5]decan-10-one (E86, 14.8 mg, y=20%) as pale yellow oil.

MS (ES) (m/z): 377.15 [M+H]$^+$ $^1$H NMR (CHLOROFORM-d): δ ppm 7.17-7.28 (m, 2H), 6.73-6.91 (m, 2H), 6.54-6.73 (m, 4H), 3.49 (d, 1H), 3.31-3.44 (m, 2H), 3.10-3.26 (m, 3H), 2.78-2.94 (m, 2H), 2.48-2.56 (m, 1H), 2.30-2.47 (m, 2H), 1.72-1.82 (m, 1H)

Preparation 152: tert-butyl 8-[4-(3-fluorophenoxy)-6-(trifluoromethyl)pyrimidin-2-yl]-1,4-dioxa-8,12-diazadispiro[4.0.4$^6$.4$^5$]tetradecane-12-carboxylate (P152)

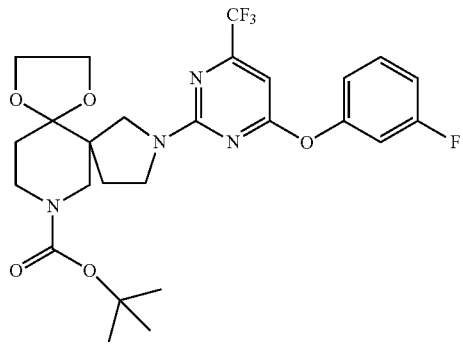 [SMILES: CC(C)(C)OC(=O)N1CCC2(OCCO2)C2(CCN(c3nc(Oc4cccc(F)c4)cc(C(F)(F)F)n3)C2)C1]

A mixture of tert-butyl 1,4-dioxa-8,12-diazadispiro[4.0.4$^6$.4$^5$]tetradecane-12-carboxylate (p150, 300 mg, 1 mmol), 2-chloro-4-(3-fluorophenoxy)-6-(trifluoromethyl)pyrimidine (p46, 300 mg, 1 mmol) and K$_2$CO$_3$ (180 mg, 1.3 mmol) in DMSO (1 mL) was heated at 100° C. for 1 h. After cooling at RT, EtOAc and water were added and phases were separated. The organic phase was dried and evaporated; crude material was purified by FC on silica gel (eluent: cHex to cHex/EtOAc 70/30) affording tert-butyl 8-[4-(3-fluorophenoxy)-6-(trifluoromethyl)pyrimidin-2-yl]-1,4-dioxa-8,12-diazadispiro[4.0.4$^6$.4$^5$]tetradecane-12-carboxylate (p152, 212 mg, y=38%) as white foam.

MS (ES) (m/z): 555.2 [M+H]$^+$

Example 87: 8-[4-(3-fluorophenoxy)-6-(trifluoromethyl)pyrimidin-2-yl]-1,4-dioxa-8,12-diazadispiro[4.0.4$^6$.4$^5$]tetradecane (E87)

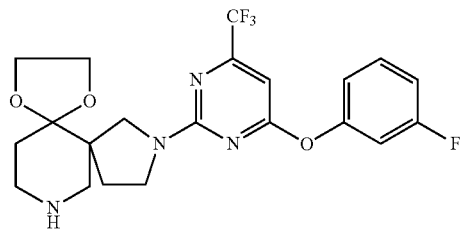 [SMILES: Fc1cccc(Oc2cc(C(F)(F)F)nc(N3CCC4(CNCCC45OCCO5)C3)n2)c1]

TFA (0.7 mL) was added to a solution of tert-butyl 8-[4-(3-fluorophenoxy)-6-(trifluoromethyl)pyrimidin-2-yl]-1,4-dioxa-8,12-diazadispiro[4.0.4⁶.4⁵]tetradecane-12-carboxylate (p152, 212 mg, 0.38 mmol) in DCM (6 mL) and the resulting mixture was stirred at RT for 1 h.

Solvent was removed in vacuo and the residue was charged on SCX cartridge washing with MeOH and eluting with 1M NH₃ in MeOH. After evaporation 8-[4-(3-fluorophenoxy)-6-(trifluoromethyl)pyrimidin-2-yl]-1,4-dioxa-8,12-diazadispiro[4.0.4⁶.4⁵]tetradecane (E87, 170 mg, y=98%) was obtained as white solid.

MS (ES) (m/z): 455.2 [M+H]⁺

¹H NMR (CHLOROFORM-d): δ ppm 7.37 (d,] 1H), 6.97 (br. s., 3H), 6.35 (s, 1H), 3.88-4.07 (m, 4H), 3.42-3.67 (m, 3H), 3.25-3.41 (m, 1H), 2.94 (d, 2H), 2.77-2.89 (m, 2H), 2.05-2.25 (m, 1H), 1.92 (br. s., 1H), 1.83 (br. s., 1H), 1.56 (br. s., 1H)

Preparation 153: benzyl 8-[4-(3-fluorophenoxy)-6-(trifluoromethyl)pyrimidin-2-yl]-1,4-dioxa-8,12-diazadispiro[4.0.4⁶.4⁵]tetradecane-12-carboxylate (P153)

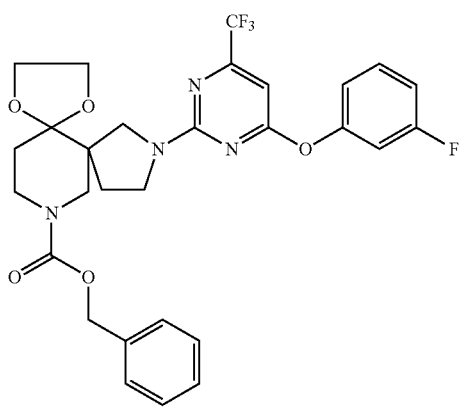 [SMILES: O=C(OCc1ccccc1)N1CCC2(OCCO2)C2(CCN(c3nc(Oc4cccc(F)c4)cc(C(F)(F)F)n3)C2)C1]

To a stirred solution of 8-[4-(3-fluorophenoxy)-6-(trifluoromethyl)pyrimidin-2-yl]-1,4-dioxa-8,12-diazadispiro[4.0.4⁶.4⁵]tetradecane (E87, 150 mg, 0.33 mmol) in DCM (6 mL) at RT under argon atmosphere, TEA (0.1 mL, 0.726 mmol) and benzyl chloroformate (0.06 mL, 0.4 mmol) were added. The reaction solution was stirred for 3 hrs. NaHCO₃ was added and the mixture was extracted with DCM (8 mL×3), the organic solution was dried and concentrated under reduced pressure. The crude material was loaded on a SCX cartridge washing with MeOH and eluting with NH₃ 1M in MeOH. Solvent was eliminated under reduced pressure affording benzyl 8-[4-(3-fluorophenoxy)-6-(trifluoromethyl)pyrimidin-2-yl]-1,4-dioxa-8,12-diazadispiro[4.0.4⁶.4⁵]tetradecane-12-carboxylate (p153, 190 mg, y=98%) as white foam.

MS (ES) (m/z): 589.2 [M+H]⁺

Example 88: 2-[4-(3-fluorophenoxy)-6-(trifluoromethyl)pyrimidin-2-yl]-2,7-diazaspiro[4.5]decan-1-one hydrochloride (E88)

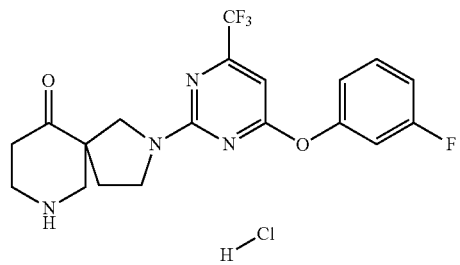 [SMILES: O=C1CCNCC12CCN(c1nc(Oc3cccc(F)c3)cc(C(F)(F)F)n1)C2 ; Cl]

Step a:

To a stirred solution of benzyl 8-[4-(3-fluorophenoxy)-6-(trifluoromethyl)pyrimidin-2-yl]-1,4-dioxa-8,12-diazadispiro[4.0.4⁶.4⁵]tetradecane-12-carboxylate (p153, 190 mg, 0.33 mmol) in DCM (4 mL) at RT, HClO₄ 70% (0.33 mL) was added dropwise; the resulting solution was stirred at RT for 2 hrs. NaHCO₃ saturated solution was added to adjust pH to 8, DCM was added and the phases were separated. The organic phase was dried and evaporated. The crude material was purified by FC on silica gel (eluent: DCM to 20% MeOH), then further purified by FC on NH column and then by Prep HPLC:

LC/MS Conditions:

Columns: Gemini 5 μm C18 110A AXIA (100×30 mm) at RT

Loop volume: 1 mL

Solvents: A=10 mM ammonium bicarbonate aqueous (solution adjusted to pH 10 with ammonia); B=Acetonitrile Gradient:

| Time (min) | Flow rate (mL/min) | % A | % B | Curve |
|---|---|---|---|---|
| Initial | 43.0 | 60.0 | 40.0 | — |
| 10.0 | 43.0 | 20.0 | 80.0 | 6 |
| 10.5 | 43.0 | 0.0 | 100.0 | 6 |
| 14.5 | 43.0 | 0.0 | 100.0 | 6 |
| 15.0 | 43.0 | 60.0 | 40.0 | 6 |

Affording 2-[4-(3-fluorophenoxy)-6-(trifluoromethyl)pyrimidin-2-yl]-2,7-diazaspiro[4.5]decan-10-one (27 mg)

Step b:

2-[4-(3-fluorophenoxy)-6-(trifluoromethyl)pyrimidin-2-yl]-2,7-diazaspiro[4.5]decan-10-one (27 mg, 0.066 mmol) was dissolved in Et₂O and treated with 2M HCl in Et₂O affording 2-[4-(3-fluorophenoxy)-6-(trifluoromethyl)pyrimidin-2-yl]-2,7-diazaspiro[4.5]decan-10-one hydrochloride (E88, 28.7 mg, y=19%) as white off solid.

MS (ES) (m/z): 411.1 [M+H]⁺

¹H NMR (DMSO-d6): δ ppm 9.02 (br. s., 2H), 7.47-7.56 (m, 1H), 7.23 (d, 1H), 7.10-7.20 (m, 2H), 6.65 (br. s., 1H), 3.92 (br. s., 2H), 3.33-3.56 (m, 4H), 2.80 (br. s., 2H), 2.25-2.39 (m, 2H), 2.10 (br. s., 2H)

Preparation 154: tert-butyl N-[(1-benzyl-4-hydroxypiperidin-4-yl)methyl]carbamate (P154)

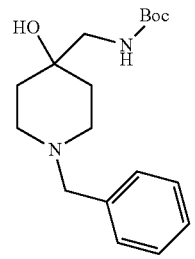 [SMILES: CC(C)(C)OC(=O)NCC1(O)CCN(Cc2ccccc2)CC1]

To a stirred solution of Boc₂O (1.04 g, 4.72 mmol) in DCM (5 mL), at RT, a solution of 4-(aminomethyl)-1-benzylpiperidin-4-ol (p1, 1.03 g, 4.72 mmol) in DCM (4 mL) was added and the reaction mixture was stirred at RT. After 2 hrs, the reaction mixture was concentrated under reduced pressure, the residue was taken up with DCM and NaHCO₃ saturated solution, the organic phase was washed with water, dried and concentrated. Crude material was purified by FC on silica gel (eluent: DCM/MeOH from 100/0 to 99/1) affording tert-butyl N-[(1-benzyl-4-hydroxypiperidin-4-yl)methyl]carbamate (p154, 0.76 g, y=50%).

MS (ES) (m/z): 321.2 [M+H]⁺

Preparation 155: 8-benzyl-1-oxa-3,8-diazaspiro[4.5]decan-2-one (P155)

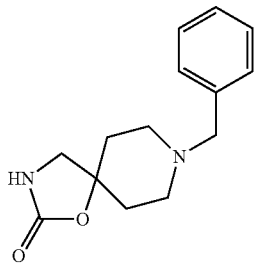 [SMILES: O=C1NCC2(CCN(Cc3ccccc3)CC2)O1]

To a stirred solution of tert-butyl N-[(1-benzyl-4-hydroxypiperidin-4-yl)methyl]carbamate (p154, 0.5 g, 1.56 mmol) in THF (40 mL), at RT, t-BuOK (0.35 g, 3.12 mmol) was added portionwise and the resulting reaction mixture was stirred at RT for 2.5 hrs. The reaction mixture was concentrated under reduced pressure and the residue was loaded on a SCX cartridge washing with MeOH and eluting with 2N NH₃ in MeOH to give 8-benzyl-1-oxa-3,8-diazaspiro[4.5]decan-2-one (p155, 0.33 g, y=86%).

MS (ES) (m/z): 247.1 [M+H]⁺

Preparation 156: 1-oxa-3,8-diazaspiro[4.5]decan-2-one (P156)

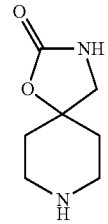 [SMILES: O=C1NCC2(CCNCC2)O1]

To a solution of 8-benzyl-1-oxa-3,8-diazaspiro[4.5]decan-2-one (p155, 170 mg, 0.69 mmol) in MeOH (20 mL), ammonium formate (261 mg) and 10% Pd/C (89 mg) were added at RT then the mixture was stirred under reflux for 1.5 h. The reaction mixture was filtered through a pad of celite and the solvent removed under vacuum. The residue was dissolved in MeOH and the solution was passed through a SCX cartridge washing with MeOH and eluting with 2N NH₃ in MeOH to give 1-oxa-3,8-diazaspiro[4.5]decan-2-one (p156, 80 mg, y=74%).

MS (ES) (m/z): 157.0 [M+H]⁺

Example 89: 8-[4-(3-fluorophenoxy)-6-(trifluoromethyl)pyrimidin-2-yl]-1-oxa-3,8-diazaspiro[4.5]decan-2-one (E89)

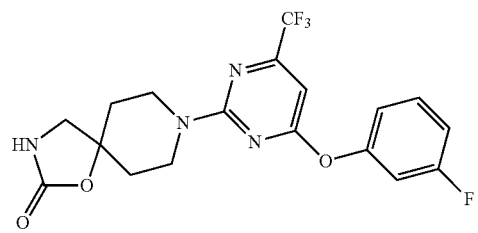 [SMILES: O=C1NCC2(CCN(c3nc(Oc4cccc(F)c4)cc(C(F)(F)F)n3)CC2)O1]

A mixture of 1-oxa-3,8-diazaspiro[4.5]decan-2-one (p156, 24 mg, 0.15 mmol), 2-chloro-4-(3-fluorophenoxy)-6-(trifluoromethyl)pyrimidine (p46, 50 mg, 0.17 mmol) and K₂CO₃ (31 mg, 0.22 mmol) in DMSO (0.8 mL) was heated at 90° C. and stirred 2 hrs at this temperature. After cooling to RT, EA and water were added, the organic phase was washed with water, dried and evaporated; crude product was purified by FC on silica gel (eluent: DCM/MeOH from 100/0 to 98/2) affording 8-[4-(3-fluorophenoxy)-6-(trifluoromethyl)pyrimidin-2-yl]-1-oxa-3,8-diazaspiro[4.5]decan-2-one (E89, 7 mg, y=11%).

MS (ES) (m/z): 413.1 [M+H]⁺

¹H NMR (CHLOROFORM-d): δ ppm 7.34-7.45 (m, 1H), 6.86-7.08 (m, 3H), 6.40 (s, 1H), 5.34 (s, 1H), 4.18-4.47 (m, 2H), 3.46 (br. s., 2H), 3.37 (s, 2H), 1.93-2.08 (m, 2H), 1.70 (br. s., 2H)

Preparation 157: 1-tert-butyl 4-ethyl 4-(prop-2-en-1-yl)piperidine-1,4-dicarboxylate (P157)

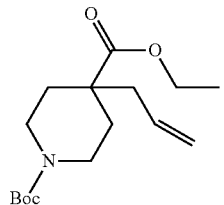 [SMILES: C=CCC1(C(=O)OCC)CCN(C(=O)OC(C)(C)C)CC1]

To a solution of 1-tert-butyl 4-ethyl piperidine-1,4-dicarboxylate (2.0 g, 7.77 mmol) in THF (12 mL), at −78° C. and under a nitrogen atmosphere, 1.0 M in THF LiHMDS (10.1 mL. 10.1 mmol) was added dropwise and the reaction mixture was stirred at this temperature for 30 min. 3-bromoprop-1-ene (1.0 mL, 11.66 mmol) was added dropwise, the reaction mixture was allowed to reach RT and stirred at that temperature overnight. The reaction mixture was treated with concentrated NH$_4$Cl and extracted with EA, the organic phase was washed with water, brine and the solvent removed under reduced pressure. The crude product was purified by FC on silica gel (eluent: Cy to Cy/EA 95/5) to give 1-tert-butyl 4-ethyl 4-(prop-2-en-1-yl)piperidine-1,4-dicarboxylate (p157, 2.05 g, y=89%) as a colourless oil.

$^1$H NMR (CHLOROFORM-d): δ ppm 5.69 (m, 1H), 5.00-5.13 (m, 2H), 4.18 (q, 2H), 3.88 (br. s., 2H), 2.91 (br. s., 2H), 2.28 (d, 2H), 2.08 (s, 2H), 2.11 (s, 2H), 1.46 (s, 9H), 1.23-1.32 (m, 3H)

Preparation 158: 1-tert-butyl 4-ethyl 4-(2-oxoethyl)piperidine-1,4-dicarboxylate (P158)

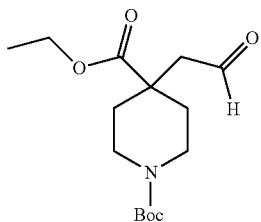 [SMILES: CCOC(=O)C1(CC=O)CCN(C(=O)OC(C)(C)C)CC1]

1-tert-butyl 4-ethyl 4-(prop-2-en-1-yl)piperidine-1,4-dicarboxylate (p157, 1.8 g, 6.06 mmol) was dissolved in THF/water (30/30 mL) and a solution of OsO$_4$ 4% in water (4.5 mL, 0.5 mmol) was added. After 5 min NaIO$_4$ (3.2 g, 15.15 mmol) was added and the mixture was stirred at RT for 3 hrs. EtOAc was added and the organic phase was washed with NaHCO$_3$, the aqueous phase was extracted with EtOAC and the combined organic layers dried and concentrated under reduced pressure affording 1-tert-butyl 4-ethyl 4-(2-oxoethyl)piperidine-1,4-dicarboxylate (p158, 1.98 g, y=quant.) as brown oil.

$^1$H NMR (CHLOROFORM-d): δ ppm 9.76 (s, 1H), 4.15 (q, 2H), 3.70 (br. s., 2H), 3.24 (t, 2H), 2.71 (s, 2H), 2.15 (dt, 2H), 1.50-1.59 (m, 2H), 1.48 (s, 9H), 1.29 (t, 3H)

Preparation 159: tert-butyl 2-benzyl-1-oxo-2,8-diazaspiro[4.5]decane-8-carboxylate (P159)

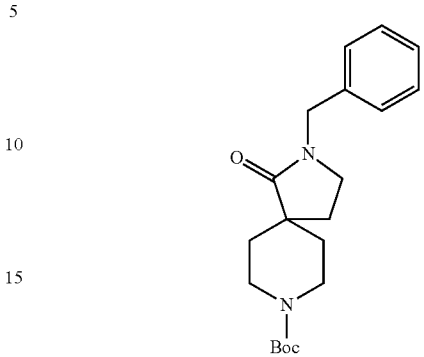

To a solution of 1-tert-butyl 4-ethyl 4-(2-oxoethyl)piperidine-1,4-dicarboxylate (p158, 1.7 g, 5.68 mmol) and Benzylamine (0.81 mL, 7.39 mmol) in THF (30 mL), NaBH(OAc)$_3$ was added (2.4 g, 11.37 mmol) and the mixture was stirred at RT overnight. EtOAc was added and the organic phase was washed with NaHCO$_3$ solution. The aqueous phase was extracted twice with EtOAC. The combined organic phases were concentrated to dryness. The crude material was purified by FC on silica gel (eluent: Cy/EtOAc 50/50 to Cy/EtOAc 30/70) giving tert-butyl 2-benzyl-1-oxo-2,8-diazaspiro[4.5]decane-8-carboxylate (p159, 1.27 g, y=65%).

$^1$H NMR (CHLOROFORM-d): δ ppm 7.30-7.40 (m, 3H), 7.24 (d, 2H), 4.48 (s, 2H), 4.04 (br. s., 2H), 3.21 (t, 2H), 3.01 (t, 2H), 1.87-2.01 (m, 4H), 1.47-1.55 (m, 9H), 1.37-1.47 (m, 2H)

Preparation 160: tert-butyl 2,8-diazaspiro[4.5]decane-8-carboxylate (P160)

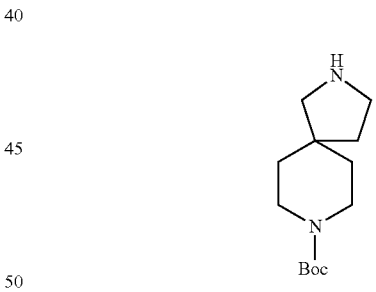

Step a

A solution of LiAlH$_4$ in THF 2M (2.7 mL, 2.7 mmol) was added dropwise to a solution of tert-butyl 2-benzyl-1-oxo-2,8-diazaspiro[4.5]decane-8-carboxylate (p159, 1.2 g, 3.48 mmol) in THF (20 mL) cooled to −20° C. The reaction mixture was stirred at RT for 2 hrs and then quenched by addition of Na$_2$SO$_4$.*10H$_2$O. The suspension was filtered and concentrated to dryness. The crude material was purified by FC on silica gel (DCM/MeOH, from 0 to 10%), giving tert-butyl 2-benzyl-2,8-diazaspiro[4.5]decane-8-carboxylate (0.986 g)

Step b

To a solution of tert-butyl 2-benzyl-2,8-diazaspiro[4.5]decane-8-carboxylate (from step a, 0.78 g, 2.36 mmol) in MeOH (25 mL), ammonium formate (0.9 g, 14.3 mmol) and 10% Pd/C (0.3 g) were added at RT and the mixture was stirred at reflux for 1 h. The mixture was cooled, filtered through a pad of celite washing with MeOH and the solution was concentrated to dryness. The crude material was loaded on a SCX cartridge, washing with MeOH and eluting with NH$_3$ 2M in MeOH, affording tert-butyl 2,8-diazaspiro[4.5]decane-8-carboxylate (p160, 0.56 g).

$^1$H NMR (CHLOROFORM-d): δ ppm 3.33-3.50 (m, 4H), 3.21 (t, 2H), 2.94 (s, 2H), 1.80 (t, 2H), 1.58 (t, 4H), 1.49 (s, 9H)

Preparation 161: tert-butyl 2-[4,5-difluoro-2-(3-fluorophenoxy)phenyl]-2,8-diazaspiro[4.5]decane-8-carboxylate (P161)

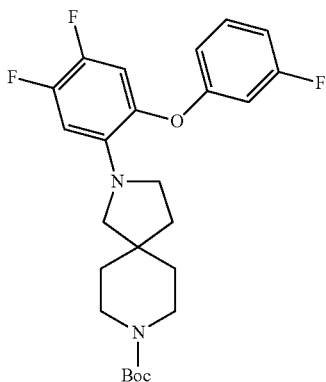 [SMILES: CC(C)(C)OC(=O)N1CCC2(CC1)CCN(c1cc(F)c(F)cc1Oc1cccc(F)c1)C2]

1-bromo-4,5-difluoro-2-(3-fluorophenoxy)benzene (p7, 131 mg, 0.433 mmol), Pd$_2$(dba)$_3$ (12 mg, 0.013 mmol), BINAP (13.5 mg, 0.022 mmol) and sodium t-butoxide (58.3 mg, 0.606 mmol) were added to a solution of tert-butyl 2,8-diazaspiro[4.5]decane-8-carboxylate (p160, 110 mg, 0.433 mmol) in Toluene (1 mL) and the mixture was stirred at 100° C. overnight. Then the mixture was cooled down to RT, diluted with EtOAc, dried and concentrated. Crude material was purified by FC on silica gel (eluent: cHex to cHex/EtOAc 85/15) to obtain tert-butyl 2-[4,5-difluoro-2-(3-fluorophenoxy)phenyl]-2,8-diazaspiro[4.5]decane-8-carboxylate (p161, 45 mg, y=23%) as orange oil.

MS (ES) (m/z): 463.3 [M+H]$^+$

Example 90: 2-[4,5-difluoro-2-(3-fluorophenoxy)phenyl]-2,8-diazaspiro[4.5]decane (E90)

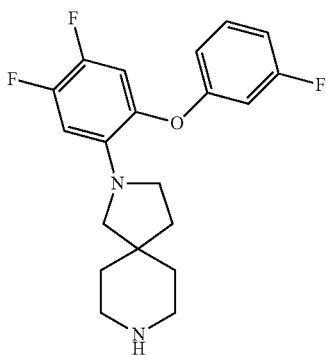 [SMILES: Fc1cccc(Oc2cc(F)c(F)cc2N2CCC3(CCNCC3)C2)c1]

TFA (0.5 mL) was added to a solution of tert-butyl 2-[4,5-difluoro-2-(3-fluorophenoxy)phenyl]-2,8-diazaspiro[4.5]decane-8-carboxylate (p161, 45 mg, 0.315 mmol) in 3 mL of DCM. The mixture was stirred for 1 h at RT, and then the solvent was removed under reduced pressure. The residue was charged on SCX cartridge washing with MeOH and eluting with 2M NH$_3$ in MeOH affording 2-[4,5-difluoro-2-(3-fluorophenoxy)phenyl]-2,8-diazaspiro[4.5]decane (E90, 32 mg, y=91%) as orange oil.

MS (ES) (m/z): 363.2 [M+H]$^+$ $^1$H NMR (CHLOROFORM-d): δ ppm 7.20-7.28 (m, 1H) 6.70-6.86 (m, 2H) 6.66 (dd, 1H) 6.50-6.61 (m, 2H) 3.33 (t, 2H) 3.12 (s, 2H) 2.80-2.90 (m, 2H) 2.67-2.80 (m, 2H) 1.67-1.78 (m, 2H) 1.48 (br. s., 4H)

Preparation 162: 2-benzyl-2,8-diazaspiro[4.5]decan-1-one (P162)

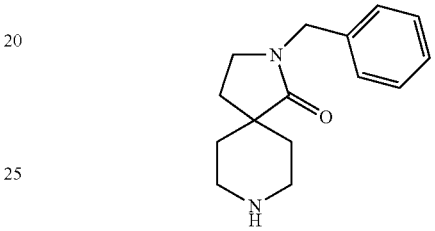

To a stirred solution of tert-butyl 2-benzyl-1-oxo-2,8-diazaspiro[4.5]decane-8-carboxylate (p159, 2.99 g, 8.69 mmol) in DCM (40 mL) at RT, TFA (8 mL) was added and the reaction mixture was stirred at RT for 1 h. The reaction mixture was concentrated, the residue was charged on SCX cartridge washing with MeOH and eluting with 2N NH$_3$ in MeOH affording 2-benzyl-2,8-diazaspiro[4.5]decan-1-one (p162, 2.16 g, y=93%) as pale brown oil.

MS (ES) (m/z): 245.1 [M+H]$^+$

Preparation 163: 2-benzyl-2,8-diazaspiro[4.5]decane (P163)

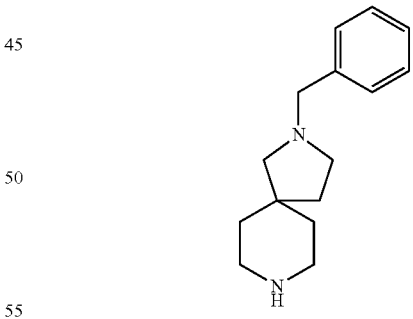

A solution of LiAlH$_4$ 1M in THF (12.18 mL, 12.18 mmol) was added dropwise to a solution of 2-benzyl-2,8-diazaspiro[4.5]decan-1-one (p162, 2.16 g, 8.12 mmol) in THF (35 mL). The reaction mixture was refluxed for 2 hrs, cooled down to 0° C. and quenched by addition of Na$_2$SO$_4$*10H$_2$O. The mixture was stirred at RT for 20 min, then filtered and washed with EtOAc. The filtrate was concentrated under reduced pressure to provide 2-benzyl-2,8-diazaspiro[4.5]decane (p163, 1.37 g, y=73%), which was used in the next step without further purification.

MS (ES) (m/z): 231.2 [M+H]$^+$

Preparation 164: 2-benzyl-8-[4,5-difluoro-2-(3-fluorophenoxy)phenyl]-2,8-diazaspiro[4.5]decane (P164)

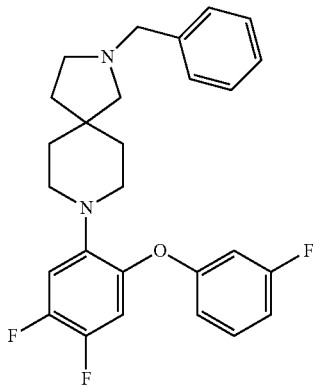 [SMILES: Fc1cccc(Oc2cc(F)c(F)cc2N2CCC3(CCN(Cc4ccccc4)C3)CC2)c1]

To a stirred solution of 2-benzyl-2,8-diazaspiro[4.5]decane (p163, 290 mg, 1.26 mmol) and 1-bromo-4,5-difluoro-2-(3-fluorophenoxy)benzene (p7, 381 mg, 1.26 mmol) in Toluene (15 mL) at RT, BINAP (78 mg, 0.126 mmol), sodium tert-butoxide (242 mg, 2.52 mmol) were added and argon purged for 10 min. Finally, Pd$_2$(dba)$_3$ (34 mg, 0.038 mmol) was added and the reaction mixture was stirred at 100° C. overnight under nitrogen atmosphere. The reaction mixture was concentrated, water was added and then mixture was extracted with EtOAc. The organic phase was dried, filtered and concentrated under reduced pressure. The crude material was purified by FC on silica gel (eluent: Cy/AcOEt 80/20) affording 2-benzyl-8-[4,5-difluoro-2-(3-fluorophenoxy)phenyl]-2,8-diazaspiro[4.5]decane (p164, 244 mg, y=43%).

MS (ES) (m/z): 453.2 [M+H]$^+$

Example 91: 8-[4,5-difluoro-2-(3-fluorophenoxy)phenyl]-2,8-diazaspiro[4.5]decane (E91)

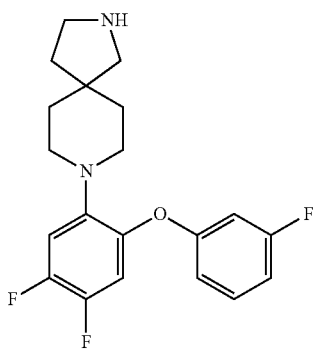 [SMILES: Fc1cccc(Oc2cc(F)c(F)cc2N2CCC3(CCNC3)CC2)c1]

2-benzyl-8-[4,5-difluoro-2-(3-fluorophenoxy)phenyl]-2,8-diazaspiro[4.5]decane (p164, 244 mg, 0.54 mmol) was dissolved in MeOH (70 mL), several vacuum/N$_2$ cycles were done, Pd/C (100 mg) was added and the mixture was stirred under H$_2$ pression (1 atm) at RT overnight. The solution was filtered through a pad of Celite eluting with MeOH. The organic solution was evaporated and the residue was charged on SCX cartridge washing with MeOH and eluting with 1N NH$_3$ in MeOH. After evaporation of opportune fractions the residue was purified by FC on silica gel (eluent: DCM/MeOH 95:5 to 85:15), providing 8-[4,5-difluoro-2-(3-fluorophenoxy)phenyl]-2,8-diazaspiro[4.5]decane (E91, 96.5 mg, y=49%) as colourless oil.

MS (ES) (m/z): 363.1 [M+H]$^+$ $^1$H NMR (CHLOROFORM-d): δ ppm 7.20-7.28 (m, 1H), 6.83-6.95 (m, 2H), 6.79 (td, 1H), 6.70 (dd, 1H), 6.62 (t, 1H), 3.05 (t, 2H), 2.91-3.00 (m, 4H), 2.77 (s, 2H), 1.62 (t, 2H), 1.48-1.56 (m, 4H)

Preparation 165: 2-benzyl-8-[3-fluoro-5-(3-fluorophenoxy)phenyl]-2,8-diazaspiro[4.5]decane (P165)

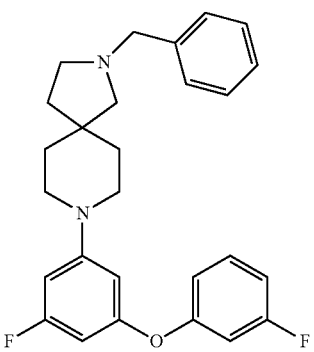 [SMILES: Fc1cccc(Oc2cc(F)cc(N3CCC4(CCN(Cc5ccccc5)C4)CC3)c2)c1]

To a stirred solution of 2-benzyl-2,8-diazaspiro[4.5]decane (p163, 110 mg, 0.48 mmol) and 1-bromo-3-fluoro-5-(3-fluorophenoxy)benzene (p12, 137 mg, 0.48 mmol) in Toluene (5 mL) at RT, BINAP (30 mg, 0.048 mmol) and sodium tert-butoxide (92 mg, 0.96 mmol) were added and Argon was purged for 10 min. Then Pd$_2$(dba)$_3$ (13 mg, 0.0144 mmol) was added and the reaction mixture was stirred at 100° C. overnight under nitrogen atmosphere. The mixture was concentrated, water was added and then the mixture was extracted with EtOAc. The organic phase was dried, filtered and concentrated. The crude material was purified by FC on silica gel (eluent: Cy/AcOEt 80:20) affording 2-benzyl-8-[3-fluoro-5-(3-fluorophenoxy)phenyl]-2,8-diazaspiro[4.5]decane (p165, 200 mg, y=96%).

MS (ES) (m/z): 435.1 [M+H]$^+$

Example 92: 8-[3-fluoro-5-(3-fluorophenoxy)phenyl]-2,8-diazaspiro[4.5]decane (E92)

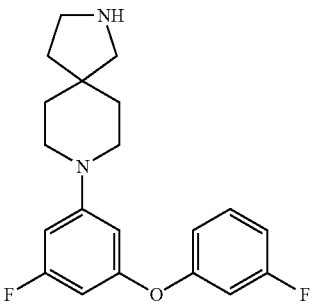 [SMILES: Fc1cccc(Oc2cc(F)cc(N3CCC4(CCNC4)CC3)c2)c1]

2-benzyl-8-[3-fluoro-5-(3-fluorophenoxy)phenyl]-2,8-diazaspiro[4.5]decane (p165, 200 mg, 0.46 mmol) was dissolved in MeOH (15 mL), then ammonium formate (145 mg, 2.30 mmol) and 10% Pd/C (20 mg) were added and the mixture was stirred at 60° C. for 3 hrs. The mixture was cooled down to RT, then filtered through a pad of Celite washing with MeOH. The organic solution was evaporated and the residue was charged on SCX cartridge washing with MeOH and eluting with 1N $NH_3$ in MeOH. Crude material was purified by FC on silica gel (eluent: DCM/MeOH 95:5 to 85:15), affording 8-[3-fluoro-5-(3-fluorophenoxy)phenyl]-2,8-diazaspiro[4.5]decane (E92, 135 mg, y=85%) as colorless oil.

MS (ES) (m/z): 345.1 [M+H]$^+$ $^1$H NMR (CHLOROFORM-d): δ ppm 7.23-7.36 (m, 1H), 6.78-6.87 (m, 2H), 6.69-6.75 (d, 1H), 6.32-6.46 (m, 2H), 6.16 (dt, 1H), 3.12-3.28 (m, 4H), 3.05 (t, 2H), 2.80 (s, 2H), 2.42 (br. s., 2H), 1.59-1.76 (m, 6H)

Preparation 166: Ethyl 1-benzyl-3-oxo-4-(prop-2-en-1-yl)piperidine-4-carboxylate (P166)

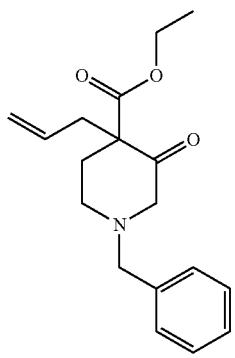 [SMILES: C=CCC1(C(=O)OCC)CCN(Cc2ccccc2)CC1=O]

A mixture of potassium tert-butoxide (3.77 g, 33.58 mmol) in THF (100 mL) was stirred at RT for 0.5 h. The resulting milky solution was cooled to 0° C., and then Ethyl 1-benzyl-3-oxopiperidine-4-carboxylate hydrochloride (5 g, 16.79 mmol) was added portion wise keeping the internal temperature below 5° C. The mixture was then warmed to RT and further stirred for 1 h, resulting in a yellow solution. After cooling to 0° C., allyl bromide (1.6 mL, 18.47 mmol) was added dropwise. The reaction mixture was warmed to RT and stirred overnight. The reaction solution was cooled down to 0° C., and 50 mL of saturated $NH_4Cl$ solution was added. After extraction and phase separation, the aqueous phase was extracted twice with 100 mL of AcOEt. The combined organic phases were washed with 100 mL of saturated NaCl solution and dried; the solvent was evaporated under reduced pressure and the obtained crude material was purified by FC on silica gel (eluent: Cy/AcOEt from 1/0 to 8/2) to give Ethyl 1-benzyl-3-oxo-4-(prop-2-en-1-yl)piperidine-4-carboxylate (p166, 4.23 g, y=84%) as a yellow oil.

MS (ES) (m/z): 302.23 [M+H]$^+$

Preparation 167: Ethyl 3-oxo-4-(prop-2-en-1-yl)piperidine-4-carboxylate (P167)

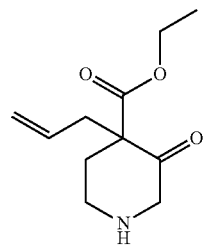

To a solution of Ethyl 1-benzyl-3-oxo-4-(prop-2-en-1-yl)piperidine-4-carboxylate (p166, 4.23 g, 14.04 mmol) in DCE (100 mL) ACE-CI (4.6 mL, 42.12 mmol) was added dropwise. The mixture was heated to reflux and stirred for 2 hrs. Further ACE-CI (10 mL) was added and the mixture was stirred at reflux overnight. Solvent was evaporated; residue was dissolved in MeOH and refluxed for 1.5 h. The solvent was evaporated and the obtained crude material was purified by FC on silica gel (eluent: DCM/MeOH/2M $NH_3$ in MeOH from 98/2/0 to 80/15/5) to give Ethyl 3-oxo-4-(prop-2-en-1-yl)piperidine-4-carboxylate (p167, 2.87 g, y=96%).

MS (ES) (m/z): 212.16 [M+H]$^+$

Preparation 168: 1-benzyl 4-ethyl 3-oxo-4-(prop-2-en-1-yl)piperidine-1,4-dicarboxylate (P168)

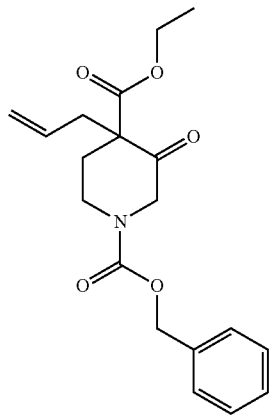 [SMILES: C=CCC1(C(=O)OCC)CCN(C(=O)OCc2ccccc2)CC1=O]

To a solution of Ethyl 3-oxo-4-(prop-2-en-1-yl)piperidine-4-carboxylate (p167, 2.87 g, 13.58 mmol) in DCM (50 mL) at 0° C., benzyl chloroformate (3.86 mL 27.16 mmol) and DIPEA (4.73 mL, 27.16 mmol) were added dropwise. Once the addition was complete the reaction mixture was allowed to reach RT and left stirring at that temperature for 2 hrs. It was quenched with water and phases were separated. Aqueous phase was back extracted with DCM. Organic layers were combined, dried and concentrated. The obtained crude material was purified by FC on silica gel (Eluent: Cy/AcOEt from 95/5 to 8/2) to give 1-benzyl 4-ethyl 3-oxo-4-(prop-2-en-1-yl)piperidine-1,4-dicarboxylate (p168, 3.85 g, y=82%, purity: 65% by UV a/a).

MS (ES) (m/z): 346.2 [M+H]$^+$

Preparation 169: 7-benzyl 10-ethyl 10-(prop-2-en-1-yl)-1,4-dioxa-7-azaspiro[4.5]decane-7,10-dicarboxylate (P169)

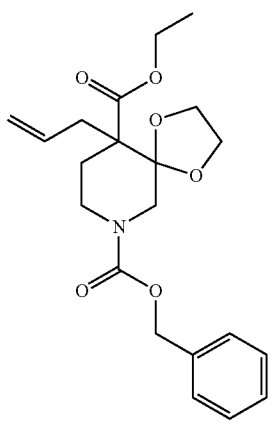 [SMILES: C=CCC1(C(=O)OCC)CCN(C(=O)OCc2ccccc2)CC12OCCO2]

A mixture of 1-benzyl 4-ethyl 3-oxo-4-(prop-2-en-1-yl) piperidine-1,4-dicarboxylate (p168, 4 g, 11.15 mmol), ethylene glycol (6.22 mL, 111.5 mmol) and p-toluensulfonicacid monohydrate (317.77 mg, 1.67 mmol) in dry Toluene (10 mL) was heated under reflux overnight using a Dean-Stark apparatus. The mixture was cooled down to RT and concentrated under vacuum. The residue was dissolved in Et$_2$O and washed with water. After evaporation of the organic phase, the crude material was purified by FC on silica gel (cHex/EtOAc from 9/1 to 6/4) to afford 7-benzyl 10-ethyl 10-(prop-2-en-1-yl)-1,4-dioxa-7-azaspiro[4.5]decane-7,10-dicarboxylate (p169, 2.68 g, y=62%).

MS (ES) (m/z): 390.21 [M+H]$^+$

Preparation 170: 7-benzyl 10-ethyl 10-(2-oxoethyl)-1,4-dioxa-7-azaspiro[4.5]decane-7,10-dicarboxylate (P170)

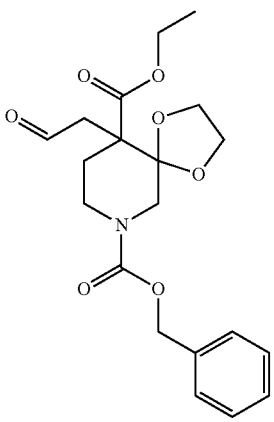 [SMILES: CCOC(=O)C1(CC=O)CCN(C(=O)OCc2ccccc2)CC12OCCO2]

7-benzyl 10-ethyl 10-(prop-2-en-1-yl)-1,4-dioxa-7-azaspiro[4.5]decane-7,10-dicarboxylate (p169, 2.68 g, 6.88 mmol) was dissolved in THF/H$_2$O (30+30 mL). To this stirred mixture a solution of OsO$_4$ 4% in water (3.5 mL, 0.55 mmol) was added over 30 seconds, the resulting mixture was stirred at RT for 5 min. NaIO$_4$ (3.68 g, 17.2 mmol) was added and the mixture stirred for 2 hrs. The mixture was partitioned between NaHCO$_3$ and Et$_2$O, phases were separated and aqueous one was back-extracted with Et$_2$O twice. Combined organic phases were dried and evaporated. The crude material was purified by FC on silica gel (eluent: cHex/EtOAc from 8/2 to 6/4) to give 7-benzyl 10-ethyl 10-(2-oxoethyl)-1,4-dioxa-7-azaspiro[4.5]decane-7,10-dicarboxylate (p170, 2.03 g, y=75%) as a colourless oil.

MS (ES) (m/z): 392.18 [M+H]$^+$

Preparation 171: benzyl 8-benzyl-7-oxo-1,4-dioxa-8,13-diazadispiro[4.0.4$^6$.4$^5$]tetradecane-13-carboxylate (P171)

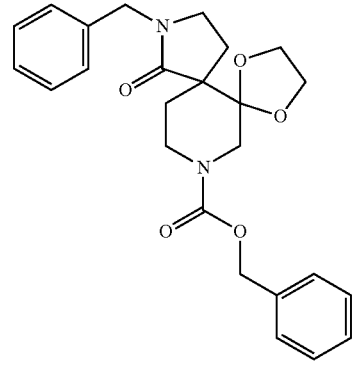 [SMILES: O=C(OCc1ccccc1)N1CCC2(CCN(Cc3ccccc3)C2=O)C2(C1)OCCO2]

To a solution of 7-benzyl 10-ethyl 10-(2-oxoethyl)-1,4-dioxa-7-azaspiro[4.5]decane-7,10-dicarboxylate (p170, 2.03 g, 5.19 mmol) and benzylamine (0.75 mL, 6.75 mmol) in THF (40 mL), Na(AcO)$_3$BH (2.2 g, 10.38 mmol) was added. The resulting mixture was stirred at RT overnight. The mixture was partitioned between NaHCO$_3$ and EtOAc. The organic phase was dried and evaporated. Crude material was purified by FC on silica gel (eluent: Cy/AcOEt from 8/2 to 5/5) to give benzyl 8-benzyl-7-oxo-1,4-dioxa-8,13-diazadispiro[4.0.4$^6$.4$^5$]tetradecane-13-carboxylate (p171, 1.98 g, y=87%) as a colourless oil.

MS (ES) (m/z): 437.3 [M+H]$^+$

Preparation 172: 8-benzyl-1,4-dioxa-8,13-diazadispiro[4.0.4$^6$.4$^5$]tetradecan-7-one (P172)

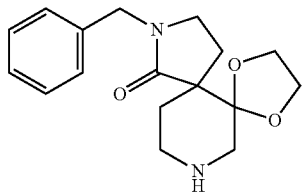 [SMILES: O=C1N(Cc2ccccc2)CCC12CCNCC21OCCO1]

Under a hydrogen atmosphere, a mixture of benzyl 8-benzyl-7-oxo-1,4-dioxa-8,13-diazadispiro[4.0.4$^6$.4$^5$]tetradecane-13-carboxylate (p171, 1.98 g, 4.54 mmol), 10% Pd/C (313 mg), and MeOH (25 mL) was stirred at RT for 1.5 hrs. The Pd/C was filtered off, the mixture was washed with MeOH, and the filtrate was concentrated under reduced pressure to obtain 8-benzyl-1,4-dioxa-8,13-diazadispiro[4.0.4$^6$.4$^5$]tetradecan-7-one (p172, 1.33 g, crude material), as a colorless oil, which was used in the next step without purification.

MS (ES) (m/z): 303.2 [M+H]$^+$

Preparation 173: 8-benzyl-1,4-dioxa-8,13-diazadispiro[4.0.4⁶.4⁵]tetradecane (P173)

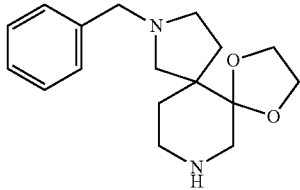 [SMILES: c1ccc(CN2CCC3(CCNCC34OCCO4)C2)cc1]

To a solution of 8-benzyl-1,4-dioxa-8,13-diazadispiro [4.0.4⁶.4⁵]tetradecan-7-one (p172, 1.33 g, 4.4 mmol) in THF (10 mL) LiAlH$_4$ 1M in THF (6.6 mL, 6.6 mmol) was added dropwise at 0° C. The mixture was heated to reflux and stirred for 1.5 hrs. The reaction was quenched with Na$_2$SO$_4$*10H$_2$O, the solid was filtered off, washed with EtOAc and the filtrate was concentrated under reduced pressure affording 8-benzyl-1,4-dioxa-8,13-diazadispiro [4.0.4⁶.4⁵]tetradecane (p173, 1.33 g, crude material) as a colourless oil, which was used in the next step without further purification.

MS (ES) (m/z): 289.2 [M+H]⁺

Preparation 174: tert-butyl 8-benzyl-1,4-dioxa-8,13-diazadispiro[4.0.4⁶.4⁵]tetradecane-13-carboxylate (P174)

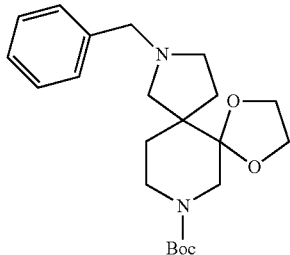 [SMILES: CC(C)(C)OC(=O)N1CCC2(CCN(Cc3ccccc3)C2)C2(C1)OCCO2]

8-benzyl-1,4-dioxa-8,13-diazadispiro[4.0.4⁶.4⁵]tetradecane (p173, 1.33 g, 4.6 mmol) was dissolved in water (12 mL) and cooled to 0° C. Na$_2$CO$_3$ (466 mg, 4.6 mmol) was added followed by the dropwise addition of a solution of Boc$_2$O (1 g, 4.6 mmol) in THF (10 mL). The reaction mixture was stirred at 0° C. for 1 h, then it was extracted with EtOAc (×2). The organic phases were combined, washed with brine, dried and evaporated to dryness to give tert-butyl 8-benzyl-1,4-dioxa-8,13-diazadispiro[4.0.46.45] tetradecane-13-carboxylate (p174, 1.8 g) as a colourless oil which was used in the next step without further purification.

MS (ES) (m/z): 389.3 [M+H]⁺

Preparation 175: tert-butyl 1,4-dioxa-8,13-diazadispiro[4.0.4⁶.4⁵]tetradecane-13-carboxylate (P175)

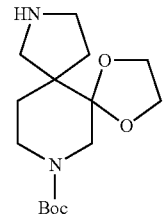 [SMILES: CC(C)(C)OC(=O)N1CCC2(CCNC2)C2(C1)OCCO2]

To a solution of tert-butyl 8-benzyl-1,4-dioxa-8,13-diazadispiro[4.0.46.45]tetradecane-13-carboxylate (p174, 1.8 g, 4.66 mmol) in MeOH (30 mL) ammonium formate (1.76 g, 27.9 mmol) and 10% Pd/C (0.5 g) were added. The reaction mixture was stirred under reflux for 2 hrs then it was cooled down to RT, filtered through a pad of celite and washed with MeOH. The solvent was evaporated and the obtained crude material was purified by SCX (MeOH, 2 M NH$_3$ in MeOH). The fractions eluted with ammonia were combined and evaporated to dryness to give tert-butyl 1,4-dioxa-8,13-diazadispiro[4.0.46.45]tetradecane-13-carboxylate (p175, 1.33 g, y=95.6%) as a colourless oil.

MS (ES) (m/z): 299.2 [M+H]⁺

Preparation 176: tert-butyl 8-[4,5-difluoro-2-(3-fluorophenoxy)phenyl]-1,4-dioxa-8,13-diazadispiro [4.0.4⁶.4⁵]tetradecane-13-carboxylate (P176)

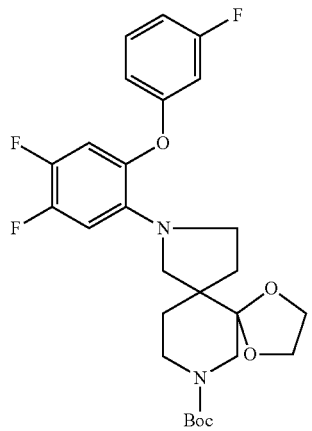 [SMILES: CC(C)(C)OC(=O)N1CCC2(CCN(c3cc(F)c(F)cc3Oc3cccc(F)c3)C2)C2(C1)OCCO2]

To a stirred solution of 1-bromo-4,5-difluoro-2-(3-fluorophenoxy)benzene (p7, 80 mg, 0.27 mmol) in Toluene (2 mL) at RT BINAP (16.8 mg, 0.027 mmol), Pd$_2$(dba)$_3$ (7.36 mg, 0.008 mmol) and sodium tert-butoxide (52 mg, 0.54 mmol) were added and then Argon was purged for 20 min. tert-butyl 1,4-dioxa-8,13-diazadispiro[4.0.46.45]tetradecane-13-carboxylate (p175, 80 mg, 0.27 mmol) was added and the mixture was shaken at 100° C. overnight. The reaction mixture was partitioned between water and DCM, organic phase was separated, dried and concentrated. Crude material was purified by FC on silica gel (eluent: Cy to 20% AcOEt) affording tert-butyl 8-[4,5-difluoro-2-(3-fluorophenoxy)phenyl]-1,4-dioxa-8,13-diazadispiro[4.0.4⁶.4⁵]tetradecane-13-carboxylate (p176, 40 mg, y=28%).

MS (ES) (m/z): 521.3 [M+H]⁺

Example 93: 8-[4,5-difluoro-2-(3-fluorophenoxy)phenyl]-1,4-dioxa-8,13-diazadispiro[4.0.4⁶.4⁵]tetradecane (E93)

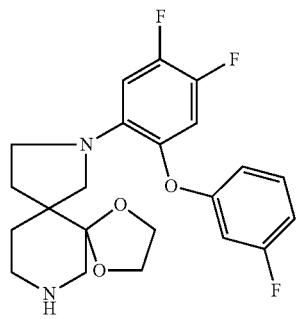 [SMILES: Fc1cccc(Oc2cc(F)c(F)cc2N2CCC3(CCNCC34OCCO4)C2)c1]

To a solution of tert-butyl 8-[4,5-difluoro-2-(3-fluorophenoxy)phenyl]-1,4-dioxa-8,13-diazadispiro[4.0.4⁶.4⁵]tetradecane-13-carboxylate (p176, 40 mg, 0.077 mmol) in DCM (2 mL), TFA (0.2 mL) was added and the solution was stirred at RT for 1 h. Solvent and excess of TFA were removed under reduced pressure, residue dissolved in MeOH and loaded on a SCX cartridge washing with MeOH and eluting with $NH_3$ 2M in MeOH. 8-[4,5-difluoro-2-(3-fluorophenoxy)phenyl]-1,4-dioxa-8,13-diazadispiro[4.0.4⁶.4⁵]tetradecane (E93, 32 mg, y=99%) was recovered as clear oil.

MS (ES) (m/z): 421.3 [M+H]⁺

¹H NMR (CHLOROFORM-d): δ ppm 7.20-7.26 (m, 1H), 6.81 (dd, 1H), 6.74 (td, 1H), 6.65 (dd, 1H), 6.52-6.61 (m, 2H), 3.84-4.01 (m, 4H), 3.31-3.43 (m, 2H), 3.22 (td, 1H), 3.08 (d, 1H), 2.78-2.87 (m, 2H), 2.64-2.77 (m, 2H), 2.05-2.14 (m, 1H), 1.56-1.71 (m, 3H)

Example 94: 8-[4,5-difluoro-2-(3-fluorophenoxy)phenyl]-1,4-dioxa-8,13-diazadispiro[4.0.4⁶.4⁵]tetradecane hydrochloride (E94)

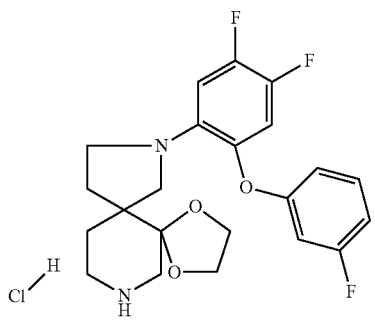

8-[4,5-difluoro-2-(3-fluorophenoxy)phenyl]-1,4-dioxa-8,13-diazadispiro[4.0.4⁶.4⁵]tetradecane (E93, 32 mg, 0.076 mmol) was dissolved in DCM and treated with 1.1 eq of HCl 2M in $Et_2O$, concentrated under reduced pressure and triturated with $Et_2O$ affording 8-[4,5-difluoro-2-(3-fluorophenoxy)phenyl]-1,4-dioxa-8,13-diazadispiro[4.0.4⁶.4⁵]tetradecane hydrochloride (E94, 32 mg, y=92%) as white solid.

MS (ES) (m/z): 421.3 [M+H]⁺

¹H NMR (DMSO-d₆): δ ppm 8.86 (br. s., 1H), 8.70 (br. s., 1H), 7.33-7.43 (m, 1H), 7.22-7.24 (m, 1H), 6.87-6.97 (m, 2H), 6.65-6.77 (m, 2H), 3.94-4.08 (m, 2H), 3.86 (d, 1H), 3.43-3.77 (m, 4H), 3.27-3.42 (m, 2H), 3.17-3.27 (m, 1H), 2.93-3.11 (m, 3H), 1.91-2.06 (m, 1H), 1.68 (br. s., 2H)

Preparation 177: tert-butyl 8-[4-(3-fluorophenoxy)-6-(trifluoromethyl)pyrimidin-2-yl]-1,4-dioxa-8,13-diazadispiro[4.0.4⁶.4⁵]tetradecane-13-carboxylate (P177)

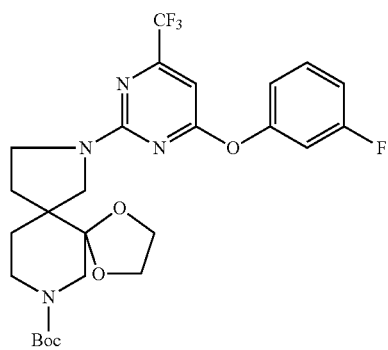 [SMILES: CC(C)(C)OC(=O)N1CCC2(CCN(c3nc(Oc4cccc(F)c4)cc(C(F)(F)F)n3)C2)C2(C1)OCCO2]

To a solution of tert-butyl 1,4-dioxa-8,13-diazadispiro[4.0.46.45]tetradecane-13-carboxylate (p175, 58 mg, 0.195 mmol) in DMSO (2 mL) $K_2CO_3$ (33 mg, 0.234 mmol) and 2-chloro-4-(3-fluorophenoxy)-6-(trifluoromethyl)pyrimidine (p46, 57 mg, 0.195 mmol) were added and the mixture was heated to 100° C. and shaken at that temperature for 2 hrs. The mixture was cooled down to RT, diluted with DCM and washed with water. Organic phase was dried and evaporated under reduced pressure. Crude material was purified by FC on silica gel (eluent: Cy to Cy/AcOEt 7:3) affording tert-butyl 8-[4-(3-fluorophenoxy)-6-(trifluoromethyl)pyrimidin-2-yl]-1,4-dioxa-8,13-diazadispiro[4.0.4⁶.4⁵]tetradecane-13-carboxylate (p177, 41 mg, y=38%).

MS (ES) (m/z): 555.3 [M+H]⁺

Example 95: 8-[4-(3-fluorophenoxy)-6-(trifluoromethyl)pyrimidin-2-yl]-1,4-dioxa-8,13-diazadispiro[4.0.4⁶.4⁵]tetradecane hydrochloride (E95)

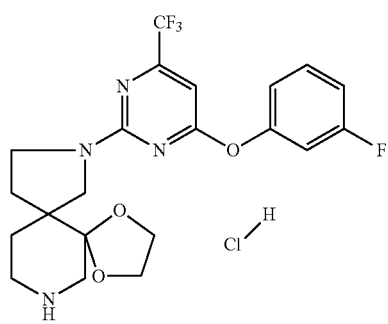 [SMILES: Fc1cccc(Oc2cc(C(F)(F)F)nc(N3CCC4(CCNCC45OCCO5)C3)n2)c1 ; Cl]

Step a

To a solution of tert-butyl 8-[4-(3-fluorophenoxy)-6-(trifluoromethyl)pyrimidin-2-yl]-1,4-dioxa-8,13-diazadispiro[4.0.4⁶.4⁵]tetradecane-13-carboxylate (p177, 41 mg, 0.07 mmol) in DCM (2 mL) TFA was added and the solution was stirred at RT for 1 h. Solvent and excess of TFA were removed under reduced pressure; the residue was dissolved in MeOH and loaded on a SCX cartridge washing with MeOH and eluting with NH₃ 2M in MeOH. 8-[4-(3-fluorophenoxy)-6-(trifluoromethyl)pyrimidin-2-yl]-1,4-dioxa-8,13-diazadispiro[4.0.4⁶.4⁵] tetradecane (31 mg) was recovered as clear oil.

Step b

8-[4-(3-fluorophenoxy)-6-(trifluoromethyl)pyrimidin-2-yl]-1,4-dioxa-8,13-diazadispiro[4.0.4⁶.4⁵]tetradecane (from step a, 31 mg, 0.068 mmol) was dissolved in DCM and treated with 1.1 eq of HCl 2M in Et₂O, concentrated under reduced pressure and triturated with Et₂O affording 8-[4-(3-fluorophenoxy)-6-(trifluoromethyl)pyrimidin-2-yl]-1,4-dioxa-8,13-diazadispiro[4.0.4⁶.4⁵]tetradecane hydrochloride (E95, 28 mg, y=81%) as white solid.

MS (ES) (m/z): 455.3 [M+H]⁺

¹H NMR (DMSO-d₆): δ ppm 8.78 (br. s., 2H), 7.45-7.57 (m, 1H), 7.24-7.35 (m, 1H), 7.11-7.22 (m, 2H), 6.69-6.60 (s, 1H), 4.07 (br. s., 2H), 3.87-4.02 (m, 2H), 3.69 (m, 1H), 3.54-3.57 (m, 1H), 3.35-3.48 (m, 2H), 2.98-3.21 (m, 4H), 2.04-2.22 (m, 1H), 1.92 (m, 1H), 1.86 (m, 2H)

Preparation 178: 1-benzyl 4-ethyl 3-hydroxy-4-(prop-2-en-1-yl)piperidine-1,4-dicarboxylate (P178)

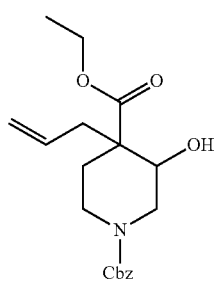 [SMILES: C=CCC1(C(=O)OCC)CCN(C(=O)OCc2ccccc2)CC1O]

To a stirred solution of 1-benzyl 4-ethyl 3-oxo-4-(prop-2-en-1-yl)piperidine-1,4-dicarboxylate (p168, 1.0 g, 2.90 mmol) in MeOH (10 mL), cooled with an ice bath, NaBH₄ (132 mg, 3.48 mmol) was added portionwise. The mixture was stirred at RT for 1 h. The reaction mixture was quenched with 1N NaOH and diluted with EtOAc. The organic layer was separated, washed with brine, dried, filtered and concentrated. Crude material was purified by FC on silica gel (eluent: 0% to 30% EtOAc in cHex) to give 1-benzyl 4-ethyl 3-hydroxy-4-(prop-2-en-1-yl)piperidine-1,4-dicarboxylate (p178, 720 mg, y=71%, mixture of diastereoisomers) as colorless oil.

MS (ES) (m/z): 348.2 [M+H]⁺

Preparation 179: 1-benzyl 4-ethyl 3-hydroxy-4-(2-oxoethyl)piperidine-1,4-dicarboxylate (P179)

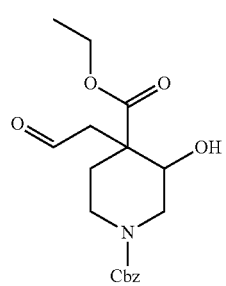 [SMILES: CCOC(=O)C1(CC=O)CCN(C(=O)OCc2ccccc2)CC1O]

1-benzyl 4-ethyl 3-hydroxy-4-(prop-2-en-1-yl)piperidine-1,4-dicarboxylate (p178, 50 mg, 0.144 mmol) was dissolved in THF/H₂O (0.5 mL+0.5 mL). To this stirred mixture a solution of OsO₄ 2.5% in tert-butanol (0.041 mL, 0.004 mmol) was added over 30 seconds, the resulting mixture was stirred at RT for 5 min. NaIO₄ (77 mg, 0.360 mmol) was added and the mixture stirred at the same temperature for 1 h. The mixture was partitioned between NaHCO₃ and Et₂O and phases were separated. Aqueous phase was back-extracted twice with Et₂O, and then combined organics were dried, filtered and evaporated. Crude material was purified by FC on silica gel (eluent: Cy to Cy/AcOEt 1:1) affording 1-benzyl 4-ethyl 3-hydroxy-4-(2-oxoethyl)piperidine-1,4-dicarboxylate (p179, 200 mg, y=44%).

MS (ES) (m/z): 350.2 [M+H]⁺

Preparation 180: benzyl 2-benzyl-6-hydroxy-1-oxo-2,8-diazaspiro[4.5]decane-8-carboxylate (P180)

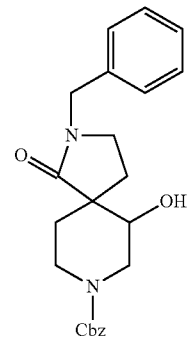 [SMILES: O=C(OCc1ccccc1)N1CCC2(CCN(Cc3ccccc3)C2=O)C(O)C1]

To a solution of 1-benzyl 4-ethyl 3-hydroxy-4-(2-oxoethyl)piperidine-1,4-dicarboxylate (p179, 200 mg, 0.572 mmol) and benzylamine (0.081 mL, 0.744 mmol) in THF (3.5 mL), Na(AcO)₃BH (242 mg, 1.144 mmol) was added. The resulting mixture was stirred at RT for 2 days. The mixture was partitioned between NaHCO₃ and EtOAc. The organic phase was dried and evaporated. Crude material was purified by FC on silica gel (eluent: Cy/AcOEt from 100/0 to 50/50) to give benzyl 2-benzyl-6-hydroxy-1-oxo-2,8-diazaspiro[4.5]decane-8-carboxylate (p180, 80 mg, y=35%, purity 80%) as a colourless oil.

MS (ES) (m/z): 395.1 [M+H]⁺

Preparation 181: 2-benzyl-6-hydroxy-2,8-diazaspiro[4.5]decan-1-one (P181)

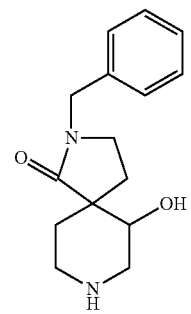

To a solution of benzyl 2-benzyl-6-hydroxy-1-oxo-2,8-diazaspiro[4.5]decane-8-carboxylate (p180, 80 mg, 0.203 mmol) in MeOH (15 mL) 10% Pd/C (140 mg, 0.132 mmol) was added and the mixture was stirred at RT under H₂ atmosphere (1 atm) overnight. The Pd/C was filtered off, washed with MeOH, and the filtrate was concentrated under reduced pressure to obtain 2-benzyl-6-hydroxy-2,8-diazaspiro[4.5]decan-1-one (p181, 40 mg, y=76%, purity 75%) as colourless oil.

MS (ES) (m/z): 361.1 [M+H]⁺

Preparation 182:
2-benzyl-2,8-diazaspiro[4.5]decan-6-ol (P182)

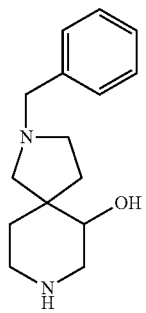 [SMILES: OC1CNCCC12CCN(Cc1ccccc1)C2]

LiAlH₄ 1M in THF (0.230 mL, 0.230 mmol) was added to solution of 2-benzyl-6-hydroxy-2,8-diazaspiro[4.5]decan-1-one (p181, 40 mg, 0.154 mmol) in THF (2 mL) at 0° C. then the mixture was refluxed for 1 h, cooled down to −20° C. and quenched with Na₂SO₄*10H₂O. The mixture was left stirring at RT for 20 min, then it was filtered washing with AcOEt; solvent was concentrated under reduced pressure affording 2-benzyl-2,8-diazaspiro[4.5]decan-6-ol (p182, 30 mg, y=79%). Used as such in next step.

MS (ES) (m/z): 247.2 [M+H]⁺

Preparation 183: tert-butyl 2-benzyl-6-hydroxy-2,8-diazaspiro[4.5]decane-8-carboxylate (P183)

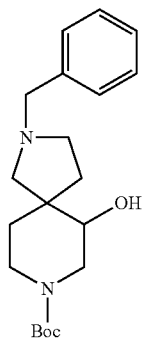 [SMILES: CC(C)(C)OC(=O)N1CCC2(CCN(Cc3ccccc3)C2)C(O)C1]

2-benzyl-2,8-diazaspiro[4.5]decan-6-ol (p182, 30 mg, 0.122 mmol) was dissolved in DCM (0.5 mL), TEA (0.026 mL, 0.183 mmol) was added followed by a solution of Boc₂O (32 mg, 0.146 mmol) in DCM (0.5 mL). The resulting solution was stirred at RT for 2 hrs. NH₄Cl solution was added, the organic phase was separated, dried and concentrated. Crude material was purified by FC on silica gel (eluent: from EtOAc to EtOAc 90%/MeOH 10%) affording tert-butyl 2-benzyl-6-hydroxy-2,8-diazaspiro[4.5]decane-8-carboxylate (p183, 15 mg, y=35%) as colourless oil.

MS (ES) (m/z): 347.2 [M+H]⁺

Preparation 184: tert-butyl 6-hydroxy-2,8-diazaspiro[4.5]decane-8-carboxylate (P184)

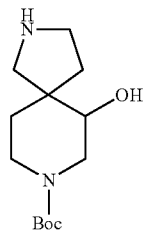

To a solution of tert-butyl 2-benzyl-6-hydroxy-2,8-diazaspiro[4.5]decane-8-carboxylate (p183, 15 mg, 0.043 mmol) in MeOH (5 mL) 10% Pd/C (30 mg, 0.028 mmol) was added and the mixture was stirred at RT under H₂ atmosphere (1 atm) for 1 h. The Pd/C was filtered off, washed with MeOH, and the filtrate was concentrated under reduced pressure to obtain tert-butyl 6-hydroxy-2,8-diazaspiro[4.5]decane-8-carboxylate (p184, 9 mg, y=92%), as colourless oil.

MS (ES) (m/z): 257.2 [M+H]⁺

Example 96: 2-[4-(3-fluorophenoxy)-6-(trifluoromethyl)pyrimidin-2-yl]-2,8-diazaspiro[4.5]decan-6-ol (E96)

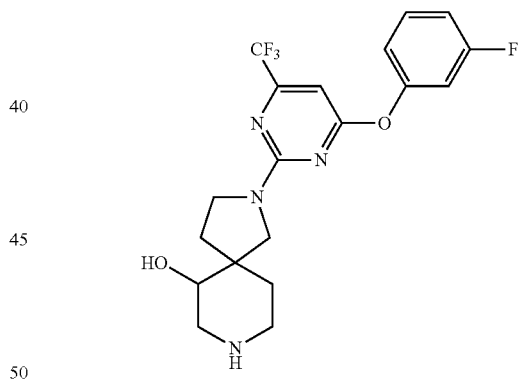

Step a
2-chloro-4-(3-fluorophenoxy)-6-(trifluoromethyl)pyrimidine (p46, 10.2 mg, 0.035 mmol), tert-butyl 6-hydroxy-2,8-diazaspiro[4.5]decane-8-carboxylate (p184, 9 mg, 0.035 mmol) and K₂CO₃ (6.36 mg, 0.046 mmol) were mixed in dry DMSO (0.5 mL) and stirred for 2 hrs at RT. The mixture was diluted with EtOAC and water. The organic phase was washed with brine, dried, filtered and evaporated. Crude material was purified by FC on silica gel (eluent: from Cy to Cy/EtOAc 85/15) affording tert-butyl 2-[4-(3-fluorophenoxy)-6-(trifluoromethyl)pyrimidin-2-yl]-6-hydroxy-2,8-diazaspiro[4.5]decane-8-carboxylate (5 mg).

Step b
tert-butyl 2-[4-(3-fluorophenoxy)-6-(trifluoromethyl)pyrimidin-2-yl]-6-hydroxy-2,8-diazaspiro[4.5]decane-8-carboxylate (5 mg, from step a) was dissolved in DCM (1 mL), treated with TFA (0.1 mL) and left stirring at RT for 1 h. Solvent and TFA excess were eliminated under reduced pressure and the residue was loaded on a SCX cartridge washing with MeOH and eluting with NH₃ 1M in MeOH. Solvent was eliminated under reduced pressure affording 2-[4-(3-fluorophenoxy)-6-(trifluoromethyl)pyrimidin-2-yl]-2,8-diazaspiro[4.5]decan-6-ol (E96, 4 mg, y=28%) as a single diastereoisomer in a mixture of conformers.

MS (ES) (m/z): 413.2 [M+H]⁺

$^1$H NMR (DMSO-d$_6$): δ ppm 7.50-7.60 (m, 1H), 7.26-7.38 (m, 1H), 7.13-7.26 (m, 2H), 6.67 (s, 1H), 5.00 (br. s., 1H), 3.04-3.77 (m, 5H), 2.60-2.91 (m, 4H), 1.99 (d, 2H), 1.54-1.85 (m, 4H), 1.29-1.43 (m, 2H)

Preparation 185: 1-tert-butyl 4-ethyl 3-oxo-4-(prop-2-en-1-yl)piperidine-1,4-dicarboxylate (P185)

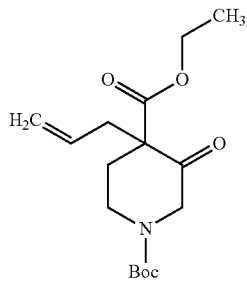 [SMILES: C=CCC1(C(=O)OCC)CCN(C(=O)OC(C)(C)C)CC1=O]

ethyl 3-oxo-4-(prop-2-en-1-yl)piperidine-4-carboxylate (p167, 1.20 g, 3.32 mmol) was dissolved in DCM (15 mL), TEA (0.69 mL, 4.98 mmol) was added followed by a solution of Boc₂O (0.869 mg, 3.98 mmol) in DCM (15 mL). The resulting solution was stirred at RT for 2 hrs. NH₄Cl solution was added, and then phases were separated; the organic phase was dried and concentrated; crude material was purified by FC on silica gel (eluent: cHex to cHex/EtOAc 90/10) affording 1-tert-butyl 4-ethyl 3-oxo-4-(prop-2-en-1-yl)piperidine-1,4-dicarboxylate (p185, 600 mg, y=58%) as colorless oil.

MS (ES) (m/z): 312.2 [M+H]⁺

Preparation 186: 1-tert-butyl 4-ethyl 3-hydroxy-4-(prop-2-en-1-yl)piperidine-1,4-dicarboxylate (P186)

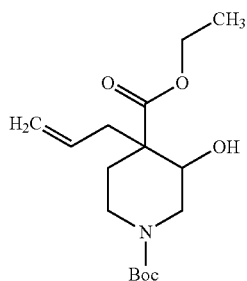 [SMILES: C=CCC1(C(=O)OCC)CCN(C(=O)OC(C)(C)C)CC1O]

To a stirred solution of 1-tert-butyl 4-ethyl 3-oxo-4-(prop-2-en-1-yl)piperidine-1,4-dicarboxylate (p185, 600 mg, 1.93 mmol) in MeOH (6 mL) cooled with an ice bath, NaBH₄ (88 mg, 2.31 mmol) was added portionwise. The mixture was stirred at RT for 1 h. The reaction mixture was quenched with 1N NaOH and diluted with EtOAc. The organic layer was separated, washed with brine, dried, filtered and concentrated. Crude material was purified by FC on silica gel (eluent: Cy to 15% EtOAc in cHex) to give 1-tert-butyl 4-ethyl 3-hydroxy-4-(prop-2-en-1-yl)piperidine-1,4-dicarboxylate (p186, 610 mg, y=quant.) as mixture of diastereoisomers.

MS (ES) (m/z): 314.2 [M+H]⁺

Preparation 187: tert-butyl 2-benzyl-6-hydroxy-1-oxo-2,8-diazaspiro[4.5]decane-8-carboxylate (P187)

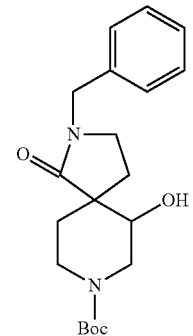 [SMILES: CC(C)(C)OC(=O)N1CCC2(CCN(Cc3ccccc3)C2=O)C(O)C1]

Step a 1-tert-butyl 4-ethyl 3-hydroxy-4-(prop-2-en-1-yl)piperidine-1,4-dicarboxylate (p186, 610 mg, 1.95 mmol) was dissolved in THF/H₂O (7 mL+7 mL). To this stirred mixture, a solution of OsO₄ 4 wt. % in water (0.4 mL, 0.03 mmol) was added over 30 seconds, the resulting mixture was stirred at RT for 5 min. NaIO₄ (1.04 g, 4.88 mmol) was added and the mixture stirred at same temperature for 1 h. The mixture was partitioned between NaHCO₃ and Et₂O (×3). The organic phase was dried, filtered and evaporated. The residue was purified by FC on silica gel (eluent: cHex to 50% EtOAc) affording 1-tert-butyl 4-ethyl 3-hydroxy-4-(2-oxoethyl)piperidine-1,4-dicarboxylate (345 mg) as colorless oil.

Step b

To a solution of 1-tert-butyl 4-ethyl 3-hydroxy-4-(2-oxoethyl)piperidine-1,4-dicarboxylate (from step a, 345 mg) and benzylamine (0.155 mL, 1.42 mmol) in THF (7 mL), Na(AcO)₃BH (462 mg, 2.18 mmol) was added. The resulting mixture was stirred at RT overnight. The mixture was partitioned between NaHCO₃ and EtOAc. Phases were separated, and the organic phase was dried and evaporated. Crude material was purified by FC on silica gel (eluent: Cy/AcOEt from 5/5 to 2/8) to give tert-butyl 2-benzyl-6-hydroxy-1-oxo-2,8-diazaspiro[4.5]decane-8-carboxylate (p187, 325 mg, y=46%) as a mixture of diastereisomers.

MS (ES) (m/z): 361.0 [M+H]⁺

217

Preparation 188:
2-benzyl-6-hydroxy-2,8-diazaspiro[4.5]decan-1-one
(P188)

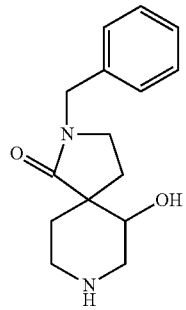 [SMILES: O=C1N(Cc2ccccc2)CCC12CCNCC2O]

TFA (0.35 mL) was added to a solution of tert-butyl 2-benzyl-6-hydroxy-1-oxo-2,8-diazaspiro[4.5]decane-8-carboxylate (p187, 325 mg, 0.902 mmol) in 8 mL of DCM. The mixture was stirred at RT for 1 h, and then the solvent was removed under reduced pressure. The residue was charged on SCX cartridge eluting with 1M $NH_3$ in MeOH to afford 2-benzyl-6-hydroxy-2,8-diazaspiro[4.5]decan-1-one (p188, 160 mg, y=68%) as colorless oil.

MS (ES) (m/z): 261.1 $[M+H]^+$

Preparation 189: tert-butyl 2-benzyl-6-hydroxy-2,8-diazaspiro[4.5]decane-8-carboxylate (P189)

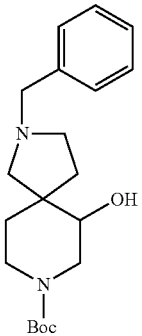 [SMILES: CC(C)(C)OC(=O)N1CCC2(CCN(Cc3ccccc3)C2)C(O)C1]

Step a

LiAlH$_4$ 1M solution in THF (0.922 mL, 0.922 mmol) was added to solution of 2-benzyl-6-hydroxy-2,8-diazaspiro[4.5]decan-1-one (p188, 160 mg, 0.615 mmol) in THF (8 mL) at 0° C. then the mixture was refluxed for 3 hrs, cooled down to −20° C. and quenched with $Na_2SO_4$*$10H_2O$. The mixture was left stirring at RT for 20 min, and then it was filtered washing with AcOEt; Solvent was then concentrated under reduced pressure affording 2-benzyl-2,8-diazaspiro[4.5]decan-6-ol (130 mg).

Step b 2-benzyl-2,8-diazaspiro[4.5]decan-6-ol (from step a, 130 mg) was dissolved in DCM (2.5 mL), TEA (0.11 mL, 0.792 mmol) was added followed by a solution of Boc$_2$O (138 mg, 0.633 mmol) in DCM (2.5 mL). The resulting solution was stirred at RT for 2 hrs. NH$_4$Cl solution was added, phases were separated, and the organic phase was dried and concentrated under reduced pressure. The crude material was purified by FC on silica gel (eluent: Cy to EtOAc 100%) affording tert-butyl 2-benzyl-6-hydroxy-2,8-diazaspiro[4.5]decane-8-carboxylate (p189, 80 mg, y=37%) as colorless oil.

MS (ES) (m/z): 347.2 $[M+H]^+$

218

Preparation 190: tert-butyl 2-[4-(3-fluorophenoxy)-6-(trifluoromethyl)pyrimidin-2-yl]-6-hydroxy-2,8-diazaspiro[4.5]decane-8-carboxylate (P190)

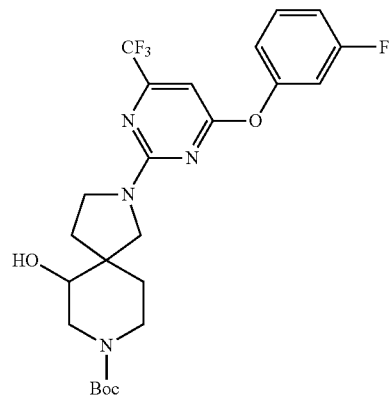 [SMILES: CC(C)(C)OC(=O)N1CCC2(CCN(c3nc(Oc4cccc(F)c4)cc(C(F)(F)F)n3)C2)C(O)C1]

Step a:

To a solution of tert-butyl 2-benzyl-6-hydroxy-2,8-diazaspiro[4.5]decane-8-carboxylate (p189, 80 mg, 0.231 mmol) in MeOH (7 mL), 10% Pd/C (160 mg, 0.150 mmol) was added and the mixture was stirred at RT under H$_2$ atmosphere (1 atm) for 1 h. The Pd/C was filtered through a pad of Celite, washed with MeOH, and the filtrate was concentrated under reduced pressure to obtain tert-butyl 6-hydroxy-2,8-diazaspiro[4.5]decane-8-carboxylate (53 mg) as colorless oil.

Step b:

2-chloro-4-(3-fluorophenoxy)-6-(trifluoromethyl)pyrimidine (p46, 81 mg, 0.207 mmol), tert-butyl 6-hydroxy-2,8-diazaspiro[4.5]decane-8-carboxylate (from step a, 53 mg, 0.207 mmol) and K$_2$CO$_3$ (37 mg, 0.269 mmol) were mixed in dry DMSO (1 mL) and the mixture was shaken at 100° C. for 1 h. The mixture was diluted with EtOAC and water. The organic phase was washed with brine, dried, filtered and evaporated. Crude material was purified by FC on silica gel (eluent: from Cy to Cy/EtOAc 85/15) affording tert-butyl 2-[4-(3-fluorophenoxy)-6-(trifluoromethyl)pyrimidin-2-yl]-6-hydroxy-2,8-diazaspiro[4.5]decane-8-carboxylate (p190, 40 mg, y=34%).

MS (ES) (m/z): 513.2 $[M+H]^+$

Example 97: 2-[4-(3-fluorophenoxy)-6-(trifluoromethyl)pyrimidin-2-yl]-2,8-diazaspiro[4.5]decan-6-ol (E97)

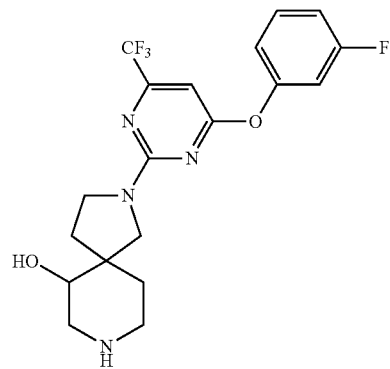 [SMILES: OC1CNCCC12CCN(c1nc(Oc3cccc(F)c3)cc(C(F)(F)F)n1)C2]

TFA (0.3 mL) was added to a solution of tert-butyl 2-[4-(3-fluorophenoxy)-6-(trifluoromethyl)pyrimidin-2-yl]-6-hydroxy-2,8-diazaspiro[4.5]decane-8-carboxylate (p190, 40 mg, 0.078 mmol) in 3 mL of DCM. The mixture was stirred at RT for 1 h and then the solvent was removed under reduced pressure. The residue was charged on SCX cartridge washing with MeOH and eluting with 1M NH$_3$ in MeOH to afford 2-[4-(3-fluorophenoxy)-6-(trifluoromethyl)pyrimidin-2-yl]-2,8-diazaspiro[4.5]decan-6-ol (E97, 30 mg, y=94%) as a mixture ~1:1 of diastereoisomers.

MS (ES) (m/z): 413.2 [M+H]$^+$ $^1$H NMR (CHLOROFORM-d): δ ppm 7.34-7.45 (m, 1H), 6.91-7.06 (m, 3H), 6.29-6.44 (m, 1H), 3.85-3.30 (m, 5H), 3.25 (m, 1H), 2.97 (br. s., 2H), 2.72-2.86 (m, 1H), 2.09-2.24 (m, 1H), 1.59-2.02 (m, 2H), 1.40-1.52 (d, 1H)

Examples 98, 99, 100 and 101: 2-[4-(3-fluorophenoxy)-6-(trifluoromethyl)pyrimidin-2-yl]-2,8-diazaspiro[4.5]decan-6-ol-single enantiomers (E98, E99, E100, E101)

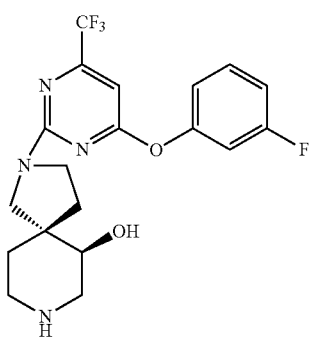

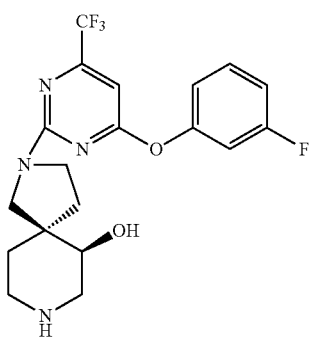

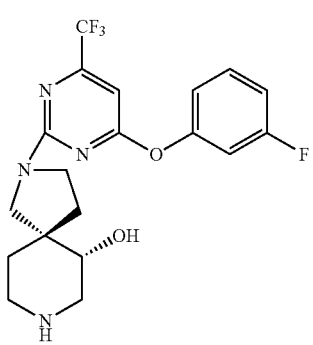

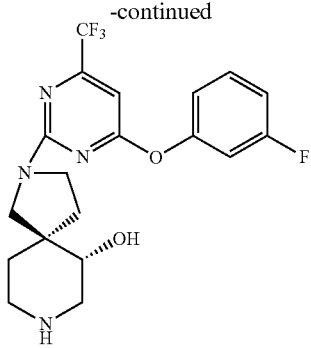

2-[4-(3-fluorophenoxy)-6-(trifluoromethyl)pyrimidin-2-yl]-2,8-diazaspiro[4.5]decan-6-ol (E97, 30 mg, mixture ~1:1 of diastereoisomers) was submitted to 2 subsequent chiral prep HPLC affording: 2-[4-(3-fluorophenoxy)-6-(trifluoromethyl)pyrimidin-2-yl]-2,8-diazaspiro[4.5]decan-6-ol:

Diastereoisomer 1-enantiomer 1: ed 83.7%, ee 100%
Diastereoisomer 1-enantiomer 2: ed 100%, ee 100%
MS (ES) (m/z): 413.2 [M+H]$^+$ $^1$H NMR (DMSO-d$_6$): δ ppm 7.42-7.57 (m, 1H), 7.22-7.34 (m, 1H), 7.06-7.20 (m, 2H), 6.49-6.66 (m, 1H), 4.69-4.87 (m, 2H), 3.31 (s, 5H), 2.50 (br. s., 4H), 1.85-2.12 (m, 1H), 1.45-1.74 (m, 2H), 1.07-1.37 (m, 1H)

Diastereoisomer 2-enantiomer 1: ed 100%, ee 100%
Diastereoisomer 2-enantiomer 2: ed 100%, ee 100%
MS (ES) (m/z): 413.2 [M+H]$^+$ $^1$H NMR (DMSO-d$_6$): δ ppm 7.42-7.56 (m, 1H), 7.22-7.32 (m, 1H), 7.06-7.20 (m, 2H), 6.50-6.65 (m, 1H), 4.64-4.81 (m, 1H), 3.31 (s, 5H), 2.50 (d, 4H), 1.84-2.13 (m, 1H), 1.52-1.76 (m, 2H), 1.00-1.34 (m, 1H)

Preparation 191: 1-(diphenylmethyl)-3-[(trimethylsilyl)oxy]azetidine-3-carbonitrile (P191)

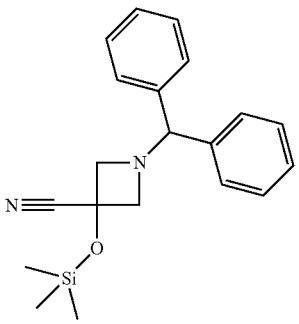 [SMILES: C[Si](C)(C)OC1(C#N)CN(C(c2ccccc2)c2ccccc2)C1]

To a stirred solution of 1-(diphenylmethyl)azetidin-3-one (1.03 g, 4.34 mmol) and trimethylsilanecarbonitrile (1.14 mL, 9.11 mmol) in DCM (22 mL), at RT, a solution of TEBA-CN (116 mg, 0.43 mmol) in DCM (17 mL) was added drop-wise over 10 min, then the resulting reaction mixture was stirred at RT for 1 h. The reaction mixture was washed with water, the organic phase was dried and the solvent evaporated under reduced pressure to give 1-(diphenylmethyl)-3-[(trimethylsilyl)oxy]azetidine-3-carbonitrile (p191, 1.52 g, crude material).

MS (ES) (m/z): 337.2 [M+H]$^+$

Preparation 192: 3-(aminomethyl)-1-(diphenylmethyl)azetidin-3-ol (P192)

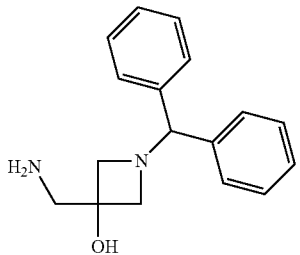 [SMILES: NCC1(O)CN(C(c2ccccc2)c2ccccc2)C1]

To a stirred solution of 1-(diphenylmethyl)-3-[(trimethylsilyl)oxy]azetidine-3-carbonitrile (p191, 1.42 g, 4.22 mmol) and NiCl$_2$.6H$_2$O (1.0 g, 4.22 mmol) in dry MeOH (30 mL), under a nitrogen atmosphere and at −5° C., NaBH$_4$ (0.80 g, 21.10 mmol) was added portion-wise within 10 min. The ice-bath was removed and the reaction mixture was stirred at RT for 1 h. The reaction was quenched by adding aqueous saturated sodium bicarbonate solution and the resulting mixture was filtered through a pad of Celite. The filtrate was concentrated and the residue was purified by FC on NH column (eluent: DCM/MeOH from 100/0 to 96/4) to give 3-(aminomethyl)-1-(diphenylmethyl)azetidin-3-ol (p192, 0.55 g, y=48%).

MS (ES) (m/z): 269.2 [M+H]$^+$

Preparation 193: 2-chloro-N-{[1-(diphenylmethyl)-3-hydroxyazetidin-3-yl]methyl}acetamide (P193)

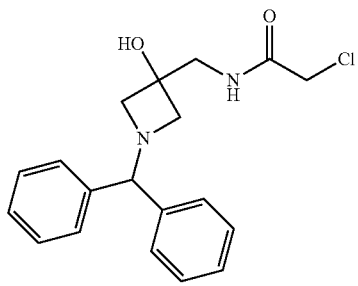 [SMILES: O=C(CCl)NCC1(O)CN(C(c2ccccc2)c2ccccc2)C1]

To a solution of 3-(aminomethyl)-1-(diphenylmethyl)azetidin-3-ol (p192, 0.55 g, 2.05 mmol) in DCM (6 mL) a solution of NaOH (0.098 g) in water (4 mL) was added, then the mixture was brought to 0° C. and chloroacetyl chloride (0.16 mL, 2.05 mmol) was added over 15 min under vigorous magnetic stirring. The ice-bath was removed and the reaction mixture was stirred at RT for 2 h. The reaction mixture was diluted with DCM, the organic phase was washed with water, dried and the solvent removed under vacuum to give 2-chloro-N-{[1-(diphenylmethyl)-3-hydroxyazetidin-3-yl]methyl}acetamide (p193, 0.67 g) used as crude material.

MS (ES) (m/z): 345.2 [M+H]$^+$

Preparation 194: tert-butyl 2-(diphenylmethyl)-5-oxa-2,8-diazaspiro[3.5]nonane-8-carboxylate (P194)

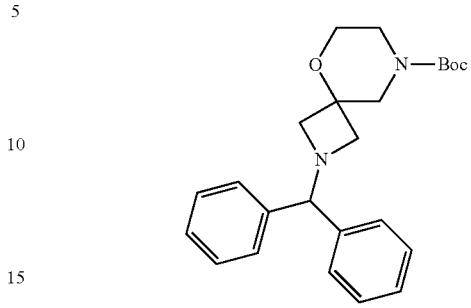

Step a

To a stirred solution of 2-chloro-N-{[1-(diphenylmethyl)-3-hydroxyazetidin-3-yl]methyl}acetamide (p193, 0.67 g, 1.94 mmol) in THF (40 mL), at RT, t-BuOK (0.44 g, 3.89 mmol) was added portion-wise and the resulting reaction mixture was left stirring at RT for 1.5 h. The reaction mixture was concentrated under reduced pressure, the crude material was taken up with DCM, the organic phase was washed with water, dried and the solvent removed under reduced pressure to give 2-(diphenylmethyl)-5-oxa-2,8-diazaspiro[3.5]nonan-7-one (0.59 g).

Step b

LiAlH$_4$ 2M solution in THF (1.43 mL, 2.85 mmol) was added drop-wise to a stirred solution of 2-(diphenylmethyl)-5-oxa-2,8-diazaspiro[3.5]nonan-7-one (from step a, 0.59 g) in THF (18 mL) at 0° C. and under a nitrogen atmosphere; the ice-bath was removed then the mixture was brought to reflux for 2 hrs. The stirred reaction mixture was cooled down to −10° C. and Na$_2$SO$_4$*10H$_2$O was carefully added portion-wise up to fizz end. The mixture was left stirring at RT for 30 min, then it was filtered, the solid was washed with DCM and the organic phase concentrated under reduced pressure to give 2-(diphenylmethyl)-5-oxa-2,8-diazaspiro[3.5]nonane (0.54 g).

Step c

To a stirred solution of 2-(diphenylmethyl)-5-oxa-2,8-diazaspiro[3.5]nonane (from step b, 0.54 g) in DCM (8 mL), Boc$_2$O (0.44 g) was added portion-wise. The ice-bath was removed and the reaction mixture was stirred at RT overnight. The mixture was concentrated under reduced pressure and the residue purified by FC on silica gel (eluent: DCM/MeOH from 100/0 to 99/1) to give tert-butyl 2-(diphenylmethyl)-5-oxa-2,8-diazaspiro[3.5]nonane-8-carboxylate (p194, 0.36 g, y=47%).

MS (ES) (m/z): 395.3 [M+H]$^+$

Preparation 195: tert-butyl 5-oxa-2,8-diazaspiro[3.5]nonane-8-carboxylate (P195)

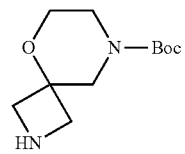

To a solution of tert-butyl 2-(diphenylmethyl)-5-oxa-2,8-diazaspiro[3.5]nonane-8-carboxylate (p194, 360 mg, 0.91 mmol) in EtOH (25 mL), ammonium formate (345 mg, 5.5 mmol) and 10% Pd/C (200 mg) were added at RT then the mixture was stirred at reflux for 30 min. The reaction mixture was filtered through a pad of celite and the solvent removed under vacuum. The crude product was purified by FC on NH column (eluent: DCM/MeOH from 100/0 to 90/10) to give tert-butyl 5-oxa-2,8-diazaspiro[3.5]nonane-8-carboxylate (p195, 151 mg, y=73%).

MS (ES) (m/z): 229.1 [M+H]$^+$

Preparation 196: tert-butyl 2-[4-(3-fluorophenoxy)-6-(trifluoromethyl)pyrimidin-2-yl]-5-oxa-2,8-diazaspiro[3.5]nonane-8-carboxylate (P196)

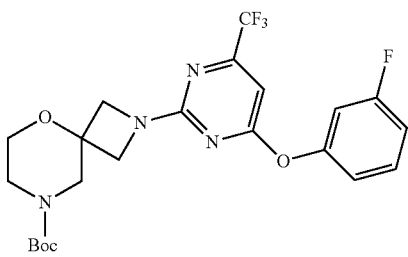 [SMILES: CC(C)(C)OC(=O)N1CCOC2(C1)CN(c1nc(Oc3cccc(F)c3)cc(C(F)(F)F)n1)C2]

A mixture of tert-butyl 5-oxa-2,8-diazaspiro[3.5]nonane-8-carboxylate (p195, 71 mg, 0.31 mmol), 2-chloro-4-(3-fluorophenoxy)-6-(trifluoromethyl)pyrimidine (p46, 100 mg, 0.34 mmol) and $K_2CO_3$ (64 mg, 0.47 mmol) in DMSO (1.2 mL) was heated at 70° C. and stirred 1.5 h at this temperature. After cooling at RT, ether and water were added, the organic phase was washed with water, dried and evaporated; a crude product was purified by FC on silica gel (eluent: Cy/EA from 100/0 to 85/25) affording tert-butyl 2-[4-(3-fluorophenoxy)-6-(trifluoromethyl)pyrimidin-2-yl]-5-oxa-2,8-diazaspiro[3.5]nonane-8-carboxylate (p196, 70 mg, y=47%).

MS (ES) (m/z): 485.3 [M+H]$^+$

Example 102: 2-[4-(3-fluorophenoxy)-6-(trifluoromethyl)pyrimidin-2-yl]-5-oxa-2,8-diazaspiro[3.5]nonane (E102)

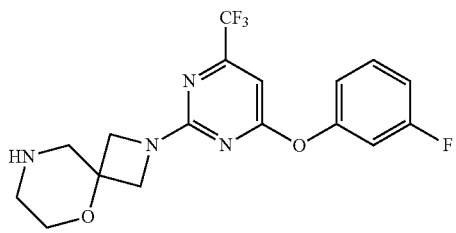 [SMILES: Fc1cccc(Oc2cc(C(F)(F)F)nc(N3CC4(CNCCO4)C3)n2)c1]

To a solution of tert-butyl 2-[4-(3-fluorophenoxy)-6-(trifluoromethyl)pyrimidin-2-yl]-5-oxa-2,8-diazaspiro[3.5]nonane-8-carboxylate (p196, 70 mg, 0.14 mmol) in DCM (0.6 mL), at RT, TFA (0.27 mL) was added and the mixture was stirred at RT for 1 h. The reaction mixture was concentrated under vacuum, the residue was taken up with DCM and aqueous concentrated sodium bicarbonate solution; the organic phase was dried and the solvent removed under vacuum to give 2-[4-(3-fluorophenoxy)-6-(trifluoromethyl)pyrimidin-2-yl]-5-oxa-2,8-diazaspiro[3.5]nonane (E102, 43 mg, y=80%).

MS (ES) (m/z): 385.1 [M+H]$^+$ $^1$H NMR (DMSO-$d_6$): δ ppm 7.46-7.56 (m, 1H) 7.19-7.26 (m, 1H) 7.09-7.19 (m, 2H) 6.64 (s, 1H) 3.88 (d, 2H) 3.78 (d, 2H) 3.49-3.59 (m, 2H) 2.82 (s, 2H) 2.60-2.72 (m, 2H)

Biological Methods

The ability of the compounds of formula (I) to inhibit dopamine transporters may be determined using the following biological assays:

Measure of Affinity to the Human Transporters DAT, NET and SERT

The affinities of the compounds of the invention for the human dopamine transporter (DAT), human norepinephrine transporter (NET) and for the human serotonin transporter (SERT) may be determined by the assays described below. Affinity is expressed in terms of inhibition constant (Ki) of the compounds of the invention for DAT, NET and SERT, and it is typically calculated from the $IC_{50}$ values obtained in competition experiments using Cheng and Prusoff equation (Cheng and Prusoff, *Biochem. Pharmacol.* 22:3099, 1973). In the context of the present invention pKi values (corresponding to the antilogarithm of Ki) are used instead of Ki; pKi are only estimated to be accurate to about 0.3 log unit.

Scintillation Proximity Assay (SPA) for Human DAT, NET and SERT Binding a) Membrane Preparation Chinese Hamster Ovary (CHO) cells stably expressing either human DAT (hDAT-CHO) or human NET (hNET-CHO) or human SERT (hSERT-CHO) are used for the membrane preparations for radioligand binding assays using Scintillation proximity Assay (SPA) technique. Each cell line is cultured independently in F-12K Nutrient Mixture containing 10% of Fetal Bovine Serum (FBS) supplemented with 450 μg/ml G-418. When cells are at 70-80% of confluence 3 mM Na Butyrate was added to the cell culture medium. After 24 h of incubation, the culture medium was removed and the cells detached with Versene (DAT) or by scraping (NET and SERT). Cell suspension is centrifuged at 41,000 g for 10 minutes at 4° C. The resultant pellets are re-suspended in 15 volumes of Ice-cold buffer (20 mM HEPES, 145 mM NaCl, 5 mM KCl, pH7.3), homogenized using an Ultra Turrax homogeniser and centrifuged as before. The resultant membrane pellets are re-suspended in up to 15 volume of ice-cold buffer, incubated for 20 minutes at 37-C and centrifuged as before at 41,000 g. The final membrane pellets are re-suspended into 5-10 volumes of ice-cold buffer, dispensed into 0.5 ml aliquots and stored at −80° C. until use. Protein concentration for each preparation is determined using Bio-Rad Protein Assay kit.

b) Competition Binding Experiments Using Scintillation Proximity Assay (SPA) for Human DAT, NET and SERT The affinity of the compounds of the invention to the human DAT or NET or SERT transporters is assessed by using the [$^3$H]WIN-35,428 or [$^3$H]nisoxetine or [$^3$H]citalopram binding assays in recombinant human DAT, NET and SERT membranes with the SPA technology. The final assay volume is 50 μL in 384 well plates.

Briefly, 0.5 μL of test compound in neat DMSO or 0.5 μL of DMSO for total binding (TB) or 0.5 μL of indatraline 1 mM (10 μM final concentration) for non specific binding (NSB) are added to the assay plate. 50 μL of the SPA mixture is added to each well, containing: 30 μg/mL or 10 μg/mL or 25 μg/mL DAT, NET, SERT membranes, respectively; 5 nM [$^3$H]WIN-35,428 or 5 nM [$^3$H]nisoxetine or 1 nM [$^3$H]

citalopram, for DAT, NET, SERT assay, respectively; 2.5 mg/mL or 1 mg/mL or 4 mg/mL WGA-PVT SPA beads (PerkinElmer RPNQ0001, for DAT, NET, SERT assay, respectively. All components are added to Assay Buffer (20 mM HEPES pH 7.4, 145 mM NaCl, 5 mM KCl, 0.01% Pluronic F-127). 0.02% BSA was used for DAT binding only. Plates are sealed with Topseal A and centrifuged 1 min, 800 rpm. Plates are loaded into a 1450 Microbeta TriLux (Perkin-Elmer) plate reader and the radioactivity counted after at least 4 hrs or overnight incubation at room temperature. Curve fitting and $IC_{50}$ estimations are performed using a four parameter model in XLfit (IDBS, Guilford, UK) for Microdoft Excel (Microsoft, Redmond, Wash.).

Uptake Functional Assay on hDAT-CHO Cells

The potency of the compounds of the invention in blocking the DAT function is measured using an uptake assay in a recombinant CHO cell line expressing human DAT (hDAT-CHO). Potency is measured in terms of $pIC_{50}$ by testing the compounds of invention for the inhibition of [$^3$H]-dopamine uptake in DAT-CHO cells using a SPA technology in 384 well format.

Briefly, on the days of the experiment hDAT-CHO cells are detached using Versene and added (75,000 cells/mL) to the SPA Mixture, which contains the following components in Assay Buffer (20 mM HEPES, 145 mM NaCl, 5 mM KCl, 2 mM $CaCl_2$, 1 mM $MgCl_2$ and 1 g/L glucose, pH 7.3): 0.02% w/v of Pluronic F127, 2 mg/mL SPA Imaging beads (RPNQ0260, PerkinElmer), 10 µM pargyline and 80 nM of [$^3$H]-dopamine. The SPA Mixture is added 50 µl/well to 384 well plates containing 0.5 µL/well of test compound in neat DMSO or 0.51 µL of DMSO (control uptake) or 0.51 µL of the standard inhibitor indatraline (at 10 µM final in the assay). Plates are sealed with a Top-seal A and read using Viewlux instrument (Perkin-Elmer) at 15-30 min time intervals. The first highest signal is used for data analysis.

Measure of the Effect on hERG Channel by Tail Current Recording Using In Vitro Rapid ICE™

The potency of the compounds of the invention in inhibiting human ERG potassium channel (hERG) tail current is assessed in a recombinant HEK293 cell line stably transfected with hERG cDNA using Rapid ICE™ (Rapid Ion Channel Electrophysiology) assay. Rapid ICE™ is an automated patch-clamp assay utilizing the PatchXpress 7000A system (Molecular Devices Corporation) or the QPatch HTX system (Sophion Bioscience A/S).

Briefly cells are cultivated for 24 to 72 hours before recordings in minimum essential medium supplemented with 10% FBS, 1% non-essential amino acids, 1% sodium pyruvate, 2 mM L-glutamine. The day of the experiment cells are detached with TrypLE and prepared to be loaded on the instrument. For PatchXpress cells are finally resuspended in 150 µl of Extracellular Buffer whereas for QPatch cells are resuspended in 7 ml Serum-Free Media containing 25 mM Hepes and Soybean trypsin inhibitor and immediately placed in the cell storage tank of the machine. The composition of the Extracellular Buffer is (mM): NaCl 137; KCl 4; CaCl2 1.8; MgCl2 1.0; D-glucose 10; N 2 hydroxyethylpiperazine-N'-2-ethanesulfonic acid (HEPES) 10; pH 7.4 with 1 M NaOH. The composition of the pipette solution is (mM): KCl 130; MgCl2 1.0; Ethylene glycol-bis(β-aminoethyl ether)-N,N,N',N'-tetraacetic acid (EGTA) 5; MgATP 5; HEPES 10; pH 7.2 with 1 M KOH. The voltage protocol includes the following steps: step from −80 mV to −50 mV for 200 ms, +20 mV for 4.8 s, step to −50 mV for 5 s then step to the holding potential of −80 mV. Compounds of the invention are dissolved in DMSO and diluted in Extracellular Buffer to achieve final test concentrations (0.1, 1 and 10 µM) in 0.1% DMSO. The voltage protocol is run and recorded continuously during the experiment. The vehicle, corresponding to 0.1% DMSO in Extracellular Buffer, is then applied for 3 min followed by the test substance in triplicate. The standard combined exposure time is 5 min. The average of tail current amplitude values recorded from 4 sequential voltage pulses is used to calculate for each cell the effect of the test substance by calculating the residual current (% control) compared with vehicle pre-treatment. Data are reported as % inhibition for each concentration tested and $IC_{50}$ values are estimated using DataXpress or QPatch software. At least two cells are tested, more if results diverge.

Representative compounds of the present invention were tested according to the procedure described above, with results as listed in Table 1 below.

TABLE 1

| Example | pIC$_{50}$ | | | |
| --- | --- | --- | --- | --- |
| | DAT | NET | SERT | hERG |
| 1 | 7.96 | 5.69 | 6.44 | 6.0 |
| 2 | 8.14 | 6.03 | 6.49 | — |
| 3 | 6.09 | 5.28 | 5.02 | — |
| 4 | 7.31 | 6.13 | 6.24 | 5.8 |
| 5 | 6.82 | 6.19 | 7.63 | 6.2 |
| 6 | 7.41 | 5.83 | 6.12 | — |
| 7 | 7.54 | 6.33 | 5.99 | 5.8 |
| 8 | 8.25 | 6.90 | 7.10 | 6.3 |
| 9 | 8.38 | 6.91 | 7.00 | — |
| 10 | 7.56 | 6.07 | 5.32 | 5.6 |
| 11 | 6.78 | 5.72 | 6.22 | 6.5 |
| 12 | 6.78 | 5.75 | 5.97 | — |
| 13 | 8.38 | 6.74 | 6.33 | 5.6 |
| 15 | 7.05 | 6.02 | 7.03 | — |
| 17 | 8.42 | 6.46 | 5.65 | 5.4 |
| 19 | 8.64 | 7.01 | 5.99 | 5.4 |
| 21 | 9.11 | 7.49 | 6.48 | 5.4 |
| 23 | 8.32 | 6.91 | 6.16 | — |
| 25 | 8.66 | 7.19 | 7.43 | 6.1 |
| 27 | 7.54 | 5.69 | 5.15 | — |
| 29 | 7.44 | 6.01 | 5.80 | — |
| 31 | 7.43 | 5.96 | 5.71 | — |
| 33 | 6.42 | 5.54 | 5.73 | — |
| 35 | 8.16 | 6.52 | 8.45 | — |
| 36 | 7.37 | 5.73 | 5.66 | — |
| 37 | 8.86 | 7.07 | 5.33 | 5.9 |
| 38 | 8.61 | 6.75 | 7.27 | — |
| 39 | 6.68 | 5.78 | 4.50 | — |
| 40 | 7.25 | 6.29 | 5.35 | — |
| 41 | 7.44 | 5.33 | 6.02 | 5.9 |
| 42 | 7.33 | 5.64 | 4.69 | 6.4 |
| 43 | 8.01 | 6.11 | 4.42 | 5.7 |
| 44 | 8.29 | 6.65 | 4.80 | 6.0 |
| 45 | 7.59 | 5.54 | 4.83 | 5.7 |
| 46 | 8.03 | 5.85 | 6.11 | 6.6 |
| 47 | 6.59 | 5.51 | 5.27 | — |
| 48 | 6.50 | 5.48 | 5.58 | 5.6 |
| 49 | 6.92 | 5.45 | 4.67 | 5.5 |
| 50 | 8.24 | 6.96 | 5.11 | — |
| 51 | 7.33 | 5.78 | 5.21 | — |
| 52 | 5.96 | 5.30 | <4 | — |
| 53 | 6.63 | 5.21 | 4.56 | — |
| 54 | 6.96 | 5.34 | 5.00 | — |
| 55 | 8.19 | 6.12 | 6.14 | 5.7 |
| 56 | 8.42 | 6.37 | 5.77 | — |
| 57 | 7.89 | 5.94 | 6.18 | 5.7 |
| 58 | 7.53 | 5.52 | 7.31 | — |
| 59 | 8.01 | 5.67 | 5.15 | 7.0 |
| 60 | 7.34 | 5.75 | 5.83 | — |
| 61 | 6.67 | 5.29 | 4.89 | — |
| 62 | 8.01 | 5.86 | 5.83 | 6.5 |
| 63 | 8.07 | 6.34 | 5.15 | — |
| 64 | 6.38 | 5.35 | 4.86 | — |
| 65 | 8.79 | 7.08 | 5.44 | 5.7 |
| 66 | 8.29 | 6.52 | 5.27 | 5.7 |

TABLE 1-continued

| | | pIC$_{50}$ | | |
| Example | DAT | NET | SERT | hERG |
| --- | --- | --- | --- | --- |
| 67 | 7.80 | 6.02 | 5.32 | — |
| 68 | 7.28 | 5.39 | 4.45 | <5 |
| 69 | 5.97 | 5.06 | <4 | — |
| 70 | 6.65 | 5.17 | <4 | 5.0 |
| 71 | 6.22 | 4.82 | 4.55 | 5.1 |
| 72 | 7.08 | 4.92 | <4 | 5.5 |
| 73 | 6.32 | 4.82 | <4 | — |
| 74 | 8.38 | 6.42 | 4.95 | — |
| 75 | 8.88 | 6.54 | 5.18 | — |
| 76 | 7.28 | 4.88 | <4 | — |
| 77 | 8.08 | 6.33 | 5.30 | — |
| 78 | 7.94 | 7.32 | 5.17 | — |
| 79 | 7.86 | 6.31 | 6.49 | 6.1 |
| 80 | 6.64 | 5.84 | 6.49 | — |
| 81 | 7.18 | 6.25 | 6.71 | — |
| 82 | 8.14 | 6.10 | 8.00 | 6.0 |
| 83 | 7.24 | 6.76 | 6.40 | 6.2 |
| 84 | 7.94 | 6.76 | 6.33 | 6.6 |
| 85 | 6.62 | 5.81 | 6.35 | — |
| 86 | 6.87 | 5.81 | 5.65 | — |
| 87 | 8.67 | 6.82 | 5.43 | 6.0 |
| 88 | 8.15 | 6.55 | 4.48 | — |
| 89 | 7.73 | 5.66 | 4.89 | 5.7 |
| 90 | 8.36 | 6.85 | 6.31 | 6.1 |
| 91 | 8.01 | 6.26 | 7.29 | 5.9 |
| 92 | 8.84 | 7.33 | 7.37 | 6.2 |
| 93 | 8.44 | 6.64 | 6.90 | 6.0 |
| 94 | 8.69 | 7.11 | 7.14 | — |
| 95 | 8.16 | 6.09 | 6.29 | 5.6 |
| 96 | 7.95 | 6.62 | 5.25 | — |
| 97 | 8.41 | 6.62 | 5.34 | — |
| 98, 99, 100, 101 | 8.59 | 6.36 | 4.95 | — |
| | 8.06 | 6.61 | 4.95 | — |
| | 7.95 | 6.40 | 5.16 | — |
| | 8.16 | 6.58 | 4.95 | — |
| 102 | 8.00 | 6.22 | 4.00 | — |

While the foregoing specification teaches the principles of the present invention, with examples provided for the purpose of illustration, it will be understood that the practice of the invention encompasses all of the usual variations, adaptations and/or modifications as come within the scope of the following claims.

REFERENCES

1 Wise R A, Annu Rev Neurosci. 1996; 19: 319-340
2 Cohen N J et al., Psychopharmacologia. 1971; 22(3): 282-294
3 Leibowitz S F et al., Brain Res Bull. 1986; 17(5): 681-689.
4 Hartmann E et al., Psychopharmacology (Berl). 1976 10; 50(2): 171-175
5 Lader M H, J Clin Psychiatry. 1996; 57 Suppl 2: 39-44
6 Montejo-González A L et al., J Sex Marital Ther. 1997; 23(3): 176-194
7 Olfson M et al., Arch Gen Psychiatry. 2006 August; 63(8): 865-872
8 Dworkin N, J Am Acad Child Adolesc Psychiatry. 2005; 44(6): 510
9 Denolle T et al., Clin Pharmacol Ther. 1999; 66(3): 282-287
10 Nieoullon A, Prog Neurobiol. 2002; 67(1): 53-83
11 Cornish R S et al., Pharm Res. 2005; 22(4): 603-612
12 Cook E H Jr et al., Am J Hum Genet. 1995; 56(4): 993-998
13 Van Gaalen M M et al., Biol Psychiatry. 2006; 60(1): 66-73
14 Yoon et al., J Neurol Sci. 2007; 255(1-2): 50-56
15 Cheon et al., Psychiatry Res. 2004; 130(1): 85-95
16 Kim C H et al., Eur J Nucl Med Mol Imaging. 2003; 30(12): 1637-1643
17 Grigorenko E L et al., Aggress Behav. 2010; 36(3): 158-176
18 Amsterdam et al., J Affect Disord. 2012; 141(2-3): 425-431
19 Hsiao et al., Psychiatry Res. 2013; 211(1): 72-77
20 Baldwin D S et al., Br J Psychiatry. 2013; 202: 396-397
21 Abler B et al., Neuropsychopharmacology. 2011; 36(9): 1837-1847
22 Segman et al., Mol Psychiatry. 2002; 7(8): 903-7
23 Devos D et al., J Neurol Neurosurg Psychiatry. 2007; 78(5): 470-475
24 Espay et al., Neurology. 2011; 76(14): 1256-1262
25 Auriel et al., Clin Neuropharmacol. 2006; 29(1): 15-17
26 Baumann M H et al., J Pharmacol Exp Ther. 1994; 271(3): 1216-1222
27 Rothman R B et al., Pharmacol Biochem Behav. 1991; 40(2): 387-397
28 Wang G J et al., Obesity (Silver Spring) 2011; 19(8): 1601-1608
29 Michaelides M et al., Int Rev Psychiatry. 2012; 24(3): 211-218
30 Bello et al., Brain Res Bull. 2006; 70(4-6): 422-429
31 Shinohara M et al., J Psychiatry Neurosci. 2004; 29(2): 134-137
32 Slama et al., Diabete Metab. 1978; 4(3): 193-199
33 Remy P et al., Curr Opin Neurol. 2003; 16 Suppl 2: S37-41
34 Berrios G E, Compr Psychiatry 1990; 31(2): 140-151
35 Harris J D, Curr Opin Support Palliat Care 2008; 2(3): 180-186
36 Lacerda et al., J Cardiovasc Electrophysiol. 2010; 21(3): 301-310
37 Campbell V C et al., J Pharmacol Exp Ther. 2005; 315(2): 631-640
38 Zou M F et al., J Med Chem. 2006; 49(21): 6391-6399
39 Li S M et al., J Pharmacol Exp Ther. 2011; 336(2): 575-585

The invention claimed is:
1. A compound according to formula I,

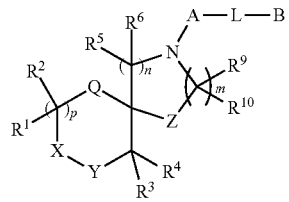

wherein:
Q is O;
X is selected from C=O, CR$^{11}$R$^{12}$, NH and N-alkyl;
Y is selected from CR$^{11}$R$^{12}$, NH and O;
wherein:
X is C=O or CR$^{11}$R$^{12}$ when Y is O or NH;
X is C=O or CR$^{11}$R$^{12}$ when p is 0;
Y is CR$^{11}$R$^{12}$ when X is NH, or N-alkyl; and
at least one of X and Y is NH, N-cycloalkyl or N-alkyl;
wherein Z is CR$^{11}$R$^{12}$;
A is selected from phenyl and heteroaryl;
B is selected from phenyl and heteroaryl;

L is a linker selected from alkylene and O;
R¹ is selected from H, OH, alkyl, F, Cl and alkoxy;
R² is selected from H, OH, alkyl, F, Cl and alkoxy;
or R¹ and R² may together form =O;
R³ and R⁴ are independently selected from H, OH, alkoxy and alkyl;
or R³ and R⁴ may both be O, wherein said O atoms are linked by an alkylene group to form a straight chain or branched alkylenedioxy group;
or R³ and R⁴ may together form =O;
R⁵ and R⁶ are independently selected from H and alkyl;
R⁹ is H or alkyl;
R¹⁰ is H or alkyl;
R¹¹ and R¹² are independently selected from H and alkyl;
R¹³ and R¹⁴ are independently selected from H and alkyl;
n is 0, 1 or 2, wherein n is 0 or 1 when m is 2 and n is 1 or 2 when m is 0;
m is 0, 1 or 2, wherein m is 0 or 1 when n is 2 and m is 1 or 2 when n is 0;
p is 0, 1 or 2, wherein p is 1 or 2 when m is 1 and n is 1 or when n is 2 and m is 0;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents independently selected from S-alkyl, S(O)alkyl, S(O)$_2$alkyl, cycloalkyl, heterocyclyl, alkoxy, OH, —CN, CF$_3$, COOR¹³, CONR¹³R¹⁴, F, Cl, NR¹³COR¹⁴ and NR¹³R¹⁴;
alkylene is a bivalent $C_{1-3}$ straight-chained alkyl radical or a bivalent $C_{3-4}$ branched alkyl radical, wherein alkylene may optionally be substituted with 1 or 2 substituents selected from S-alkyl, S(O)alkyl, S(O)$_2$alkyl, heterocyclyl, alkoxy, OH, —CN, CF$_3$, COOR¹³, CONR¹³R¹⁴, F, Cl, NR¹³COR¹⁴ and NR¹³R¹⁴;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from S-alkyl, S(O)alkyl, S(O)$_2$alkyl, alkyl, OH, —CN, CF$_3$, COOR¹³, CONR¹³R¹⁴, F, Cl, NR¹³COR¹⁴ and NR¹³R¹⁴;
cycloalkyl is a monocyclic saturated hydrocarbon of between 3 and 7 carbon atoms; cycloalkyl may optionally be substituted with 1, 2, 3, 4 or 5 substituents independently selected from S-alkyl, S(O)alkyl, S(O)$_2$alkyl, alkyl, alkoxy, OH, —CN, CF$_3$, COOR¹³, CONR¹³R¹⁴, F, Cl, NR¹³COR¹⁴ and NR¹³R¹⁴;
phenyl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR¹³COR¹⁴ and NR¹³R¹⁴,
heteroaryl is a 5 or 6 membered aromatic ring, containing, where possible, 1, 2 or 3 ring members independently selected from N, NR¹³, S and O; heteroaryl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR¹³COR¹⁴ and NR¹³R¹⁴;
heterocyclyl is a monocyclic ring which is saturated or partially unsaturated, containing, where possible, 1 or 2 ring members independently selected from N, S, O and NR¹³ and 2 to 5 carbon atoms; heterocyclyl may optionally be substituted with 1, 2 or 3 substituents independently selected from alkyl, cycloalkyl, alkoxy, S-alkyl, S(O)alkyl, S(O)$_2$alkyl, oxo, OH, F, Cl, —CN, OCF$_3$, CF$_3$, NR¹³COR¹⁴ and NR¹³R¹⁴;

and tautomers, stereoisomers (including enantiomers, diastereoisomers and racemic and scalemic mixtures thereof), pharmaceutically acceptable salts and solvates thereof;

wherein:
R¹ is not OH or alkoxy when X is NH; and
R² is not OH or alkoxy when X is NH; and
R³ is not OH or alkoxy when Y is O or NH; and
R⁴ is not OH or alkoxy when Y is O or NH.

2. The compound of claim 1 wherein: (i) m is 1 and n is 2; (ii) m is 2 and n is 1; or (iii) m and n are both 1.

3. The compound of claim 1 wherein L is O.

4. The compound of claim 1 wherein R¹, R², R⁵ and R⁶ are all H; and R³ and R⁴ are H, or R³ and R⁴ may both be O, wherein said O atoms are linked by an ethylene group to form an ethylenedioxy group.

5. The compound of claim 1 wherein A is phenyl, pyridyl or pyrimidinyl, optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR¹³COR¹⁴ and NR¹³R¹⁴.

6. The compound of claim 1 wherein A is phenyl, 2-pyridyl or 1,3-pyrimidinyl, optionally substituted with 1, 2 or 3 substituents independently selected from alkyl, F, Cl, —CN and CF$_3$.

7. The compound of claim 1 wherein A is selected from the group consisting of:

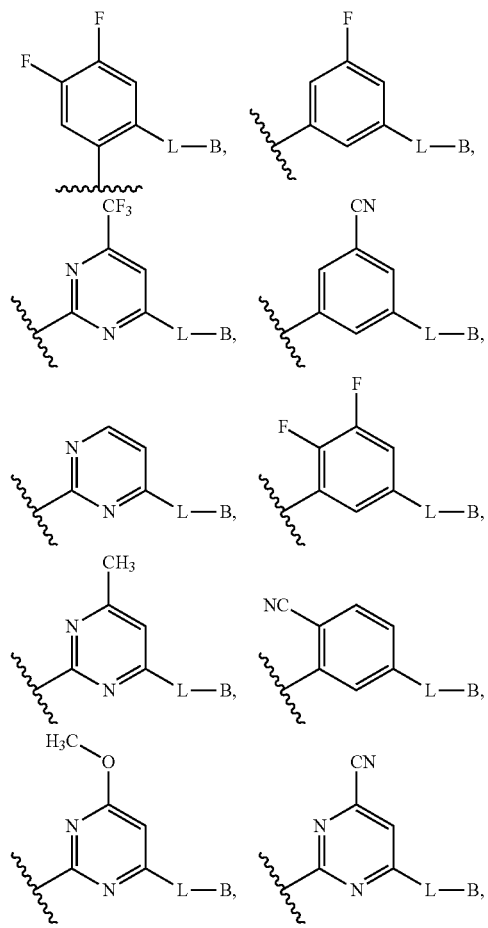

-continued

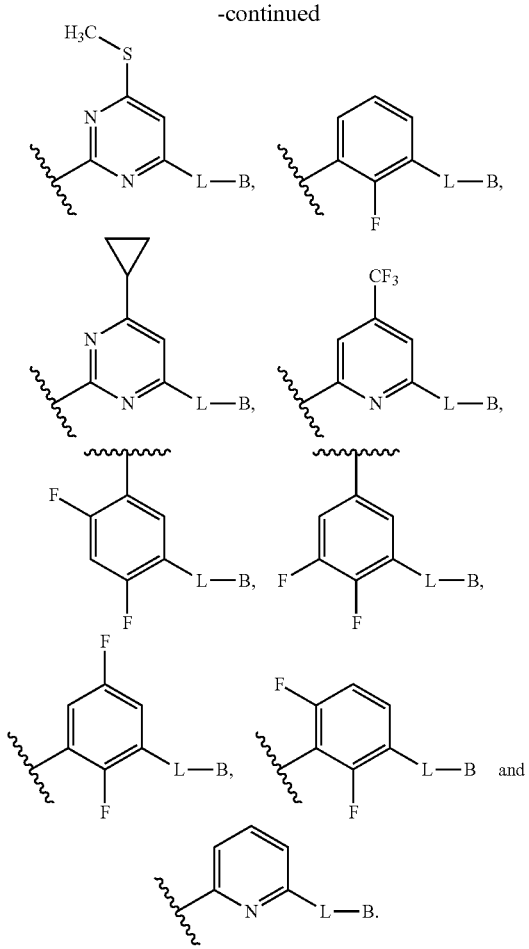

8. The compound of claim 1 wherein B is phenyl, optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR$^{13}$COR$^{14}$ and NR$^{13}$R$^{14}$.

9. The compound of claim 1 wherein B is selected from the group consisting of:

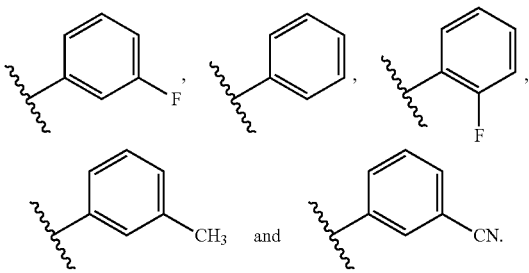

10. A compound selected from:
9-[4,5-difluoro-2-(3-fluorophenoxy)phenyl]-1-oxa-4,9-diazaspiro[5.5]undecane;
9-(2-phenoxyphenyl)-1-oxa-4,9-diazaspiro[5.5]undecane;
9-[2-(3-fluorophenoxy)phenyl]-1-oxa-4,9-diazaspiro[5.5]undecane;
3-{1-oxa-4,9-diazaspiro[5.5]undecan-9-yl}-4-phenoxybenzonitrile;
9-(3-phenoxyphenyl)-1-oxa-4,9-diazaspiro[5.5]undecane;
9-[3-(3-fluorophenoxy)phenyl]-1-oxa-4,9-diazaspiro[5.5]undecane;
9-[3-fluoro-5-(3-fluorophenoxy)phenyl]-1-oxa-4,9-diazaspiro[5.5]undecane;
9-[2-fluoro-5-(3-fluorophenoxy)phenyl]-1-oxa-4,9-diazaspiro[5.5]undecane;
9-[4-fluoro-3-(3-fluorophenoxy)phenyl]-1-oxa-4,9-diazaspiro[5.5]undecane;
9-[2,4-difluoro-5-(3-fluorophenoxy)phenyl]-1-oxa-4,9-diazaspiro[5.5]undecane;
9-[2,3-difluoro-5-(3-fluorophenoxy)phenyl]-1-oxa-4,9-diazaspiro[5.5]undecane;
9-[3,4-difluoro-5-(3-fluorophenoxy)phenyl]-1-oxa-4,9-diazaspiro[5.5]undecane;
9-(2-fluoro-3-phenoxyphenyl)-1-oxa-4,9-diazaspiro[5.5]undecane;
9-[2-fluoro-3-(3-fluorophenoxy)phenyl]-1-oxa-4,9-diazaspiro[5.5]undecane;
9-[2,5-difluoro-3-(3-fluorophenoxy)phenyl]-1-oxa-4,9-diazaspiro[5.5]undecane;
9-[2,6-difluoro-3-(3-fluorophenoxy)phenyl]-1-oxa-4,9-diazaspiro[5.5]undecane;
3-{1-oxa-4,9-diazaspiro[5.5]undecan-9-yl}-5-phenoxybenzonitrile;
2-{1-oxa-4,9-diazaspiro[5.5]undecan-9-yl}-4-phenoxybenzonitrile;
9-(2-methyl-5-phenoxyphenyl)-1-oxa-4,9-diazaspiro[5.5]undecane;
9-[5-(3-fluorophenoxy)pyridin-3-yl]-1-oxa-4,9-diazaspiro[5.5]undecane;
9-(3-benzylphenyl)-1-oxa-4,9-diazaspiro[5.5]undecane;
3-(3-fluorophenoxy)-2-methyl-5-{1-oxa-4,9-diazaspiro[5.5]undecan-9-yl}benzonitrile;
9-[6-(3-fluorophenoxy)pyridin-2-yl]-1-oxa-4,9-diazaspiro[5.5]undecane;
9-[6-(3-fluorophenoxy)-4-(trifluoromethyl)pyridin-2-yl]-1-oxa-4,9-diazaspiro[5.5]undecane;
2-(3-fluorophenoxy)-6-{1-oxa-4,9-diazaspiro[5.5]undecan-9-yl}pyridine-4-carbonitrile;
2-(3-fluorophenoxy)-6-{1-oxa-4,9-diazaspiro[5.5]undecan-9-yl}-4-(trifluoromethyl)pyridine-3-carbonitrile;
6-(3-fluorophenoxy)-2-{1-oxa-4,9-diazaspiro[5.5]undecan-9-yl}-4-(trifluoromethyl)pyridine-3-carbonitrile;
9-[6-(3-fluorophenoxy)pyrazin-2-yl]-1-oxa-4,9-diazaspiro[5.5]undecane;
9-[4-(3-fluorophenoxy)pyrimidin-2-yl]-1-oxa-4,9-diazaspiro[5.5]undecane;
9-(4-methyl-6-phenoxypyrimidin-2-yl)-1-oxa-4,9-diazaspiro[5.5]undecane;
9-[4-(3-fluorophenoxy)-6-methylpyrimidin-2-yl]-1-oxa-4,9-diazaspiro[5.5]undecane;
9-[4-methyl-6-(3-methylphenoxy)pyrimidin-2-yl]-1-oxa-4,9-diazaspiro[5.5]undecane;
3-[(6-methyl-2-{1-oxa-4,9-diazaspiro[5.5]undecan-9-yl}pyrimidin-4-yl)oxy]benzonitrile;
9-{4-methyl-6-[3-(trifluoromethoxy)phenoxy]pyrimidin-2-yl}-1-oxa-4,9-diazaspiro[5.5]undecane;
9-{4-methyl-6-[3-(trifluoromethyl)phenoxy]pyrimidin-2-yl}-1-oxa-4,9-diazaspiro[5.5]undecane;
9-[4-(3-methoxyphenoxy)-6-methylpyrimidin-2-yl]-1-oxa-4,9-diazaspiro[5.5]undecane;
9-[4-(3,5-difluorophenoxy)-6-methylpyrimidin-2-yl]-1-oxa-4,9-diazaspiro[5.5]undecane;
9-[4-methyl-6-(2-methylphenoxy)pyrimidin-2-yl]-1-oxa-4,9-diazaspiro[5.5]undecane;

9-[4-(2-methoxyphenoxy)-6-methylpyrimidin-2-yl]-1-oxa-4,9-diazaspiro[5.5]undecane;
9-[4-methyl-6-(pyridin-3-yloxy)pyrimidin-2-yl]-1-oxa-4,9-diazaspiro[5.5]undecane;
9-[4-(3-fluorophenoxy)-5-methylpyrimidin-2-yl]-1-oxa-4,9-diazaspiro[5.5]undecane;
9-[4-phenoxy-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecane;
9-[4-(2-fluorophenoxy)-6-(trifluoromethyl)pyrimidin-2-yl]-1-oxa-4,9-diazaspiro[5.5]undecane;
9-[4-(4-fluorophenoxy)-6-(trifluoromethyl)pyrimidin-2-yl]-1-oxa-4,9-diazaspiro[5.5]undecane;
3-[(2-{1-oxa-4,9-diazaspiro[5.5]undecan-9-yl}-6-(trifluoromethyl)pyrimidin-4-yl)oxy]benzonitrile;
9-[4-(thiophen-2-yloxy)-6-(trifluoromethyl)pyrimidin-2-yl]-1-oxa-4,9-diazaspiro[5.5]undecane;
9-(4-benzyl-6-methoxypyrimidin-2-yl)-1-oxa-4,9-diazaspiro[5.5]undecane;
6-(3-fluorophenoxy)-2-{1-oxa-4,9-diazaspiro[5.5]undecan-9-yl}pyrimidine-4-carbonitrile;
9-[4-(3-fluorophenoxy)-6-(methyl sulfanyl)pyrimidin-2-yl]-1-oxa-4,9-diazaspiro[5.5]undecane;
9-[2-(3-fluorophenoxy)-6-(methyl sulfanyl)pyrimidin-4-yl]-1-oxa-4,9-diazaspiro[5.5]undecane;
9-[4-cyclopropyl-6-(3-fluorophenoxy)pyrimidin-2-yl]-1-oxa-4,9-diazaspiro[5.5]undecane;
9-[4-(3-fluorophenoxy)-6-methoxypyrimidin-2-yl]-1-oxa-4,9 diazaspiro[5.5]undecane;
4-[4-(3-fluorophenoxy)-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecan-3-one;
9-[4,5-difluoro-2-(3-fluorophenoxy)phenyl]-2,2-difluoro-1-oxa-4,9-diazaspiro[5.5]undecane;
2,2-difluoro-9-[4-(3-fluorophenoxy)-6-(trifluoromethyl)pyrimidin-2-yl]-1-oxa-4,9-diazaspiro[5.5]undecane;
9-[4,5-difluoro-2-(3-fluorophenoxy)phenyl]-1λ6-thia-4,9-diazaspiro[5.5]undecane-1,1-dione;
9-[4-(3-fluorophenoxy)-6-(trifluoromethyl)pyrimidin-2-yl]-1λ6-thia-4,9-diazaspiro[5.5]undecane-1,1-dione;
9-[4-(3-fluorophenoxy)-6-(trifluoromethyl)pyrimidin-2-yl]-1,4,9-triazaspiro[5.5]undecan-2-one;
9-[4-(3-fluorophenoxy)-6-(trifluoromethyl)pyrimidin-2-yl]-1-methyl-1,4,9-triazaspiro[5.5]undecane;
9-[4-(3-fluorophenoxy)-6-(trifluoromethyl)pyrimidin-2-yl]-1,4,9-triazaspiro[5.5]undecane;
3-[4-(3-fluorophenoxy)-6-(trifluoromethyl)pyrimidin-2-yl]-7-methyl-3,7,11-triazaspiro[5.6]dodecan-12-one;
3-[4-(3-fluorophenoxy)-6-(trifluoromethyl)pyrimidin-2-yl]-7-methyl-3,7,11-triazaspiro[5.6]dodecane;
9-[4-(3-fluorophenoxy)-6-(trifluoromethyl)pyrimidin-2-yl]-4-oxa-1,9-diazaspiro[5.5]undecane;
9-[4,5-difluoro-2-(3-fluorophenoxy)phenyl]-2,9-diazaspiro[5.5]undecane;
2-[4,5-difluoro-2-(3-fluorophenoxy)phenyl]-2,9-diazaspiro[5.5]undecane;
2-[4,5-difluoro-2-(3-fluorophenoxy)phenyl]-2,8-diazaspiro[5.5]undecane;
3-[4,5-difluoro-2-(3-fluorophenoxy)phenyl]-3,9-diazaspiro[5.5]undecane;
2-[4,5-difluoro-2-(3-fluorophenoxy)phenyl]-6-oxa-2,9-diazaspiro[4.5]decane;
2-[4,5-difluoro-2-(3-fluorophenoxy)phenyl]-2,7-diazaspiro[4.5]decane;
8-[4,5-difluoro-2-(3-fluorophenoxy)phenyl]-1,4-dioxa-8,12-diazadispiro[4.0.4⁶.4⁵]tetradecane;
2-[4,5-difluoro-2-(3-fluorophenoxy)phenyl]-2,7-diazaspiro[4.5]decan-10-one;
8-[4-(3-fluorophenoxy)-6-(trifluoromethyl)pyrimidin-2-yl]-1,4-dioxa-8,12-diazadispiro[4.0.4⁶.4⁵]tetradecane;
2-[4-(3-fluorophenoxy)-6-(trifluoromethyl)pyrimidin-2-yl]-2,7-diazaspiro[4.5]decan-10-one;
8-[4-(3-fluorophenoxy)-6-(trifluoromethyl)pyrimidin-2-yl]-1-oxa-3,8-diazaspiro[4.5]decan-2-one;
2-[4,5-difluoro-2-(3-fluorophenoxy)phenyl]-2,8-diazaspiro[4.5]decane;
8-[4,5-difluoro-2-(3-fluorophenoxy)phenyl]-2,8-diazaspiro[4.5]decane;
8-[3-fluoro-5-(3-fluorophenoxy)phenyl]-2,8-diazaspiro[4.5]decane;
8-[4,5-difluoro-2-(3-fluorophenoxy)phenyl]-1,4-dioxa-8,13-diazadispiro[4.0.4⁶.4⁵]tetradecane;
8-[4-(3-fluorophenoxy)-6-(trifluoromethyl)pyrimidin-2-yl]-1,4-dioxa-8,13-diazadispiro[4.0.4⁶.4⁵]tetradecane;
2-[4-(3-fluorophenoxy)-6-(trifluoromethyl)pyrimidin-2-yl]-2,8-diazaspiro[4.5]decan-6-ol;
2-[4-(3-fluorophenoxy)-6-(trifluoromethyl)pyrimidin-2-yl]-5-oxa-2,8-diazaspiro[3.5]nonane;
and pharmaceutically acceptable salts and solvates thereof.

11. The compound of claim 10 selected from:
9-[4,5-difluoro-2-(3-fluorophenoxy)phenyl]-1-oxa-4,9-diazaspiro[5.5]undecane;
9-[3-fluoro-5-(3-fluorophenoxy)phenyl]-1-oxa-4, 9-diazaspiro[5.5]undecane;
9-[2,3-difluoro-5-(3-fluorophenoxy)phenyl]-1-oxa-4,9-diazaspiro[5.5]undecane;
9-(2-fluoro-3-phenoxyphenyl)-1-oxa-4, 9-diazaspiro[5.5]undecane;
9-[2-fluoro-3-(3-fluorophenoxy)phenyl]-1-oxa-4, 9-diazaspiro[5.5]undecane;
9-[2, 5-difluoro-3-(3-fluorophenoxy)phenyl]-1-oxa-4,9-diazaspiro[5.5]undecane;
9-[2,6-difluoro-3-(3-fluorophenoxy)phenyl]-1-oxa-4,9-diazaspiro[5.5]undecane;
3-{1-oxa-4,9-diazaspiro[5.5]undecan-9-yl}-5-phenoxybenzonitrile;
2-{1-oxa-4,9-diazaspiro[5.5]undecan-9-yl}-4-phenoxybenzonitrile;
3-(3-fluorophenoxy)-2-methyl-5-{1-oxa-4,9-diazaspiro[5.5]undecan-9-yl}benzonitrile;
9-[6-(3-fluorophenoxy)-4-(trifluoromethyl)pyridin-2-yl]-1-oxa-4,9-diazaspiro[5.5]undecane;
2-(3-fluorophenoxy)-6-{1-oxa-4,9-diazaspiro[5.5]undecan-9-yl}pyridine-4-carbonitrile;
9-[4-(3-fluorophenoxy)pyrimidin-2-yl]-1-oxa-4,9-diazaspiro[5.5]undecane;
9-(4-methyl-6-phenoxypyrimidin-2-yl)-1-oxa-4,9-diazaspiro[5.5]undecane;
9-[4-(3-fluorophenoxy)-6-methylpyrimidin-2-yl]-1-oxa-4,9-diazaspiro[5.5]undecane;
9-[4-methyl-6-(3-methylphenoxy)pyrimidin-2-yl]-1-oxa-4,9-diazaspiro[5.5]undecane;
3-[(6-methyl-2-{1-oxa-4,9-diazaspiro[5.5]undecan-9-yl}pyrimidin-4-yl)oxy]benzonitrile;
9-[4-(3,5-difluorophenoxy)-6-methylpyrimidin-2-yl]-1-oxa-4,9-diazaspiro[5.5]undecane;
9-[4-phenoxy-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecane;

9-[4-(2-fluorophenoxy)-6-(trifluoromethyl)pyrimidin-2-yl]-1-oxa-4,9-diazaspiro[5.5]undecane;
3-[(2-{1-oxa-4,9-diazaspiro[5.5]undecan-9-yl}-6-(trifluoromethyl)pyrimidin-4-yl)oxy]benzonitrile;
6-(3-fluorophenoxy)-2-{1-oxa-4,9-diazaspiro[5.5]undecan-9-yl}pyrimidine-4-carbonitrile;
9-[4-(3-fluorophenoxy)-6-(methyl sulfanyl)pyrimidin-2-yl]-1-oxa-4,9-diazaspiro[5.5]undecane;
9-[4-cyclopropyl-6-(3-fluorophenoxy)pyrimidin-2-yl]-1-oxa-4,9-diazaspiro[5.5]undecane;
9-[4-(3-fluorophenoxy)-6-methoxypyrimidin-2-yl]-1-oxa-4,9 diazaspiro[5.5]undecane;
4-[4-(3-fluorophenoxy)-6-(trifluoromethyl)pyrimidin-2-yl]-1-oxa-4,9-diazaspiro[5.5]undecane;
9-[4-(3-fluorophenoxy)-6-(trifluoromethyl)pyrimidin-2-yl]-1-oxa-4,9-diazaspiro[5.5]undecan-3-one;
9-[4-(3-fluorophenoxy)-6-(trifluoromethyl)pyrimidin-2-yl]-1λ6-thia-4,9-diazaspiro[5.5]undecane-1, 1-dione;
9-[4-(3-fluorophenoxy)-6-(trifluoromethyl)pyrimidin-2-yl]-1-methyl-1,4,9-triazaspiro[5.5]undecane;
9-[4-(3-fluorophenoxy)-6-(trifluoromethyl)pyrimidin-2-yl]-1,4,9-triazaspiro[5.5]undecane;
3-[4-(3-fluorophenoxy)-6-(trifluoromethyl)pyrimidin-2-yl]-7-methyl-3,7,11-triazaspiro[5.6]dodecan-12-one;
3-[4-(3-fluorophenoxy)-6-(trifluoromethyl)pyrimidin-2-yl]-7-methyl-3,7,11-triazaspiro[5.6]dodecane;
9-[4-(3-fluorophenoxy)-6-(trifluoromethyl)pyrimidin-2-yl]-4-oxa-1,9-diazaspiro[5.5]undecane;
9-[4,5-difluoro-2-(3-fluorophenoxy)phenyl]-2,9-diazaspiro[5.5]undecane;
3-[4,5-difluoro-2-(3-fluorophenoxy)phenyl]-3,9-diazaspiro[5.5]undecane;
8-[4-(3-fluorophenoxy)-6-(trifluoromethyl)pyrimidin-2-yl]-1,4-dioxa-8,12-diazadispiro[4.0.4⁶.4⁵]tetradecane;
2-[4-(3-fluorophenoxy)-6-(trifluoromethyl)pyrimidin-2-yl]-2,7-diazaspiro[4.5]decan-10-one;
8-[4-(3-fluorophenoxy)-6-(trifluoromethyl)pyrimidin-2-yl]-1-oxa-3,8-diazaspiro[4.5]decan-2-one;
2-[4,5-difluoro-2-(3-fluorophenoxy)phenyl]-2,8-diazaspiro[4.5]decane;
8-[4,5-difluoro-2-(3-fluorophenoxy)phenyl]-2,8-diazaspiro[4.5]decane;
8-[3-fluoro-5-(3-fluorophenoxy)phenyl]-2,8-diazaspiro[4.5]decane;
8-[4,5-difluoro-2-(3-fluorophenoxy)phenyl]-1,4-dioxa-8, 13-diazadispiro[4.0.4⁶.4⁵]tetradecane;
8-[4-(3-fluorophenoxy)-6-(trifluoromethyl)pyrimidin-2-yl]-1,4-dioxa-8,13-diazadispiro[4.0.4⁶.4⁵]tetradecane;
2-[4-(3-fluorophenoxy)-6-(trifluoromethyl)pyrimidin-2-yl]-2,8-diazaspiro[4.5]decan-6-ol;
2-[4-(3-fluorophenoxy)-6-(trifluoromethyl)pyrimidin-2-yl]-5-oxa-2,8-diazaspiro[3.5]nonane;
and pharmaceutically acceptable salts and solvates thereof.

12. A pharmaceutical composition comprising a compound of claim 1 and a pharmaceutically acceptable excipient.

13. A method of treating a condition, disease or disorder selected from sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, sleep disorders, narcolepsy, conduct disorder, substance abuse, eating disorders, chronic or persistent fatigue, and impulse control disorders, the method comprising administering the compound of claim 1 to a subject in need thereof.

14. The method of claim 13, wherein said condition, disease or disorder is selected from attention deficit disorder (ADD), attention deficit hyperactivity disorder (ADHD), binge eating disorder, alcohol dependence, opioid dependence, cocaine dependence, *cannabis* dependence, amphetamine dependence, dependence on an amphetamine-like substance, hallucinogen dependence, inhalant dependence, polysubstance dependence, phencyclidine dependence, dependence on a phencyclidine-like substance, nicotine dependence, and fatigue associated with a condition selected from the group consisting of chronic fatigue syndrome, post-viral fatigue syndrome, HIV, multiple sclerosis, amyotrophic lateral sclerosis (ALS), myasthenia gravis, sarcoidosis, cancer, chemotherapy treatment, celiac disease, irritable bowel syndrome, spondyloarthropathy, fibromyalgia, arthritis, infectious diseases, diabetes, eating disorders, Parkinson's disease, sleep disorders, stroke, mood disorders, drug abuse and alcohol abuse.

15. The compound of claim 1 wherein X is $CH_2$ and Y is NH.

16. The compound of claim 1 wherein the compound is defined by formula 1C

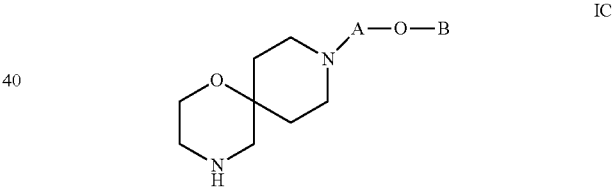

wherein

A is phenyl, optionally substituted with 1 or 2 substituents selected from $CF_3$, F, —CN, $OCH_3$, and $CH_3$; or heteroaryl selected from pyridyl and pyrimidinyl, optionally substituted with 1 or 2 substituents selected from $CF_3$, F, —CN, $OCH_3$, $SCH_3$, $CH_3$; and B is phenyl, optionally substituted with 1 substituent selected from F, —CN and $CH_3$.

* * * * *